US012714778B2

(12) United States Patent
McLoughlin et al.

(10) Patent No.: US 12,714,778 B2
(45) Date of Patent: Aug. 25, 2026

(54) DRUG CARTRIDGE, DRUG DELIVERY DEVICES, AND METHODS FOR PREPARING THEREOF

(71) Applicant: Bristol-Myers Squibb Company, Princeton, NJ (US)

(72) Inventors: Martin John McLoughlin, Hillsborough, NJ (US); Mark Steven Howansky, Basking Ridge, NJ (US); George Tyler Currier, Somerset, NJ (US); Peter William Heyman, Florham Park, NJ (US); Yuhong Wu, Skillman, NJ (US); Erinc Sahin, East Brunswick, NJ (US); Shreya Shashank Kulkarni, North Brunswick, NJ (US); Ankur Sagar Kulshrestha, Hillsborough, NJ (US); Xiaodong Chen, Belle Mead, NJ (US); John Christian Knutsen, Crosswicks, NJ (US); James William Kidner Bradford, Cambridge (GB); Simon Francis Brereton, Baldock (GB); Timothy Donald Barrow-Williams, St Albans (GB); Christopher William Rosier, Cambridge (GB); Jeffrey Nicholas Philippson, Cambridge (GB); Carys Eleri Lee, Cambridge (GB); Paul Antony Merritt, Royston (GB)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

(21) Appl. No.: 18/568,337

(22) PCT Filed: Jun. 13, 2022

(86) PCT No.: PCT/US2022/033249
§ 371 (c)(1),
(2) Date: Dec. 8, 2023

(87) PCT Pub. No.: WO2022/261540
PCT Pub. Date: Dec. 15, 2022

(65) Prior Publication Data

US 2024/0269372 A1 Aug. 15, 2024

Related U.S. Application Data

(60) Provisional application No. 63/209,675, filed on Jun. 11, 2021.

(51) Int. Cl.
*A61M 5/00* (2006.01)
*A61J 1/20* (2006.01)
*A61M 5/14* (2006.01)

(52) U.S. Cl.
CPC ............ *A61M 5/001* (2013.01); *A61J 1/2006* (2015.05); *A61M 5/1408* (2013.01)

(58) Field of Classification Search
CPC ...... A61L 2/10; A61L 2/0047; A61M 5/2448; A61M 2005/3114; A61M 5/001; A61M 5/1408; A61M 2039/268; A61J 1/2006
See application file for complete search history.

(56) References Cited

U.S. PATENT DOCUMENTS 2,696,212 A * 12/1954 Dunmire .............. A61M 5/282 604/199
4,629,159 A * 12/1986 Wellenstam .......... A61M 39/26 604/326

(Continued)

FOREIGN PATENT DOCUMENTS

CA 3118038 A1 * 5/2020 .......... A61M 5/1782
WO 2012158973 A2 11/2012
WO 2017001925 A1 1/2017

OTHER PUBLICATIONS

International Search Report from PCT International Application No. PCT/US2022/033249 dated Feb. 8, 2023.

*Primary Examiner* — Scott J Medway

(74) *Attorney, Agent, or Firm* — Budzyn IP Law, LLC

(57) ABSTRACT

In one aspect, a method is provided herein of preparing a drug delivery device, the drug delivery device having a body with at least one fluid duct being open along a first face of the body, the at least one fluid duct for conveying drug from at least one reservoir to a needle configured for injection into a patient, the method including: providing a barrier across the first face of the body to at least cover the at least one fluid duct, wherein the barrier is ultraviolet transmissive; and, exposing the first face of the body to ultraviolet radiation so as to allow the ultraviolet radiation to pass through the barrier and decontaminate the at least one fluid duct.

24 Claims, 160 Drawing Sheets

(56) References Cited

U.S. PATENT DOCUMENTS

| | | | | | |
|---|---|---|---|---|---|
| 5,222,948 | A * | 6/1993 | Austin | A61M 5/50 | 604/905 |
| 5,637,087 | A * | 6/1997 | O'Neil | A61M 5/284 | 604/82 |
| 8,652,096 | B2 * | 2/2014 | Alvey | A61J 1/2093 | 604/257 |
| 9,849,247 | B2 * | 12/2017 | Taylor | A61M 5/3287 | |
| 9,883,834 | B2 * | 2/2018 | Amirouche | A61M 5/1408 | |
| 9,931,458 | B1 | 4/2018 | Di Naro | | |
| 10,835,678 | B2 * | 11/2020 | Koska | A61M 5/50 | |
| 10,953,217 | B2 * | 3/2021 | Lance | A61M 39/16 | |
| 11,266,777 | B2 * | 3/2022 | Gibson | A61M 5/14248 | |
| 11,382,833 | B2 * | 7/2022 | Koska | A61J 1/14 | |
| 11,439,716 | B2 * | 9/2022 | Etter | A61L 2/26 | |
| 2003/0136932 | A1 * | 7/2003 | Doyle | A61M 39/045 | 251/149.1 |
| 2004/0124389 | A1 * | 7/2004 | Phillips | A61B 5/150389 | 604/905 |
| 2008/0083691 | A1 * | 4/2008 | Poynter | B65D 51/002 | 215/6 |
| 2009/0159813 | A1 | 6/2009 | Kemp et al. | | |
| 2012/0302844 | A1 * | 11/2012 | Schnidrig | C09J 7/20 | 600/309 |
| 2013/0144214 | A1 | 6/2013 | Amirouche et al. | | |
| 2013/0237947 | A1 * | 9/2013 | Amirouche | A61M 5/148 | 604/151 |
| 2014/0008366 | A1 * | 1/2014 | Genosar | A61J 1/2096 | 220/265 |
| 2014/0046270 | A1 * | 2/2014 | Thornton | A61M 5/2033 | 604/244 |
| 2014/0303601 | A1 * | 10/2014 | Fangrow | A61M 39/10 | 604/537 |
| 2015/0073352 | A1 * | 3/2015 | Finke | A61M 5/24 | 29/434 |
| 2016/0158519 | A1 * | 6/2016 | Rhinehart | A61M 39/105 | 604/535 |
| 2016/0262984 | A1 | 9/2016 | Arnott et al. | | |
| 2016/0271312 | A1 * | 9/2016 | Lance | A61M 1/285 | |
| 2017/0080205 | A1 * | 3/2017 | Lauer | A61M 1/362261 | |
| 2021/0069405 | A1 * | 3/2021 | Barbedette | A61L 2/08 | |
| 2021/0301116 | A1 * | 9/2021 | Matsutani | A61L 31/049 | |

* cited by examiner

12

DRUG CARTRIDGE, DRUG DELIVERY DEVICES, AND METHODS FOR PREPARING THEREOF

FIELD OF THE INVENTION

The subject invention relates to methods of preparing drug cartridges and drug delivery devices.

BACKGROUND OF THE INVENTION

Sterilization techniques are well known in the medical arts, particularly for sterilizing drug cartridges and drug delivery devices intended for parenteral drug delivery. Techniques have been developed in the prior art involving sterilization of a drug delivery device, such as an injector, at a manufacturing facility, with the sterilized device being packaged, e.g., in a pouch, to maintain sterility until point of use. Separately, drug is prepared, maintained in a sterile state, and introduced into the drug delivery device at the point of use.

Techniques have also been developed in the prior art for preparing pre-filled drug delivery devices wherein a drug delivery device is preloaded with drug at a manufacturing facility, packaged as a single combination product, and the device and drug are sterilized as a single unit (known as terminal sterilization), with sterility maintained to the point of use. However, the majority of drugs, particularly proteins, cannot withstand the terminal sterilization conditions, so this approach is of limited application.

Lastly, techniques have also been developed in the prior art for preparing pre-filled drug delivery devices wherein a drug delivery device is sterilized, a sterile drug product is separately prepared, the drug product is loaded in a presterilized container using aseptic techniques, and this container is loaded in the device, with sterility maintained individually of the device and container. However, a sterile fluidic connection must be made between the device and container in order to maintain sterility of the drug product and fluid path within the device. This invention describes novel means of accomplishing the sterile connection step in a non-aseptic environment, which can be accomplished either at the time of assembly by the manufacturer or just prior to use.

In addition, further drug preparation steps may be required at the time of use, such as reconstitution of a dry drug product. This invention describes novel means of accomplishing the reconstitution process, immediately prior to use.

It is also desirable from a convenience standpoint for a patient receiving combination drug therapy to be able to receive all of their prescribed drugs from a single injection device. This invention describes a device that can be loaded with one or several drugs in ready-to-use liquid or to-be-reconstituted solid-state format (e.g. lyophilized, spray dried dispersion, spray freeze dried), suspension, or combination thereof, in the prescribed ratio for that particular patient, reconstitute the dry drugs, and then automatically deliver those drugs sequentially to the patient.

SUMMARY OF THE INVENTION

In one aspect, a method is provided herein of preparing a drug cartridge containing lyophilized drug, the method including: providing a reservoir component including a rigid cartridge support body and a collapsible reservoir therewithin for accommodating one or more drug components, wherein the cartridge support body includes a filling port defining an open passageway into the reservoir, the filling port including a tapered section convergently tapered towards the reservoir to define a reduced diameter opening; filling the reservoir, through the filling port, with one or more liquid drug components; providing a plug adapter configured to mount to the reservoir component, the plug adapter including a fluid outlet and an elongated neck which terminates at a neck end, wherein an internal lumen extends from the fluid outlet and through the elongated neck; inserting the elongated neck into the filling port into an open vent position with the neck end being out of contact with the tapered section; with the elongated neck in the open vent position, subjecting the at least one or more liquid drug components in the reservoir to lyophilization conditions to lyophilize the one or more liquid drug components; and, after the one or more liquid drug components have been lyophilized, further inserting the elongated neck into the filling port to a closed vent position with the neck end being received in the reduced diameter opening.

In a further aspect, a method is provided herein of preparing a drug cartridge containing lyophilized drug, the method including: providing a reservoir component including a rigid cartridge support body and a collapsible reservoir therewithin for accommodating one or more drug components, wherein the cartridge support body includes a filling port defining an open passageway into the reservoir, the filling port including an internal surface having at least one venting passageway formed therein; filling the reservoir, through the filling port, with one or more liquid drug components; providing a plug adapter configured to mount to the reservoir component, the plug adapter including a fluid outlet and an elongated neck which terminates at a neck end, at least one seal being formed on an external surface of the elongated neck, wherein an internal lumen extends from the fluid outlet and through the elongated neck; inserting the elongated neck into the filling port into an open vent position, wherein, in the open vent position, the at least one is not located between the at least one venting passageway and the reservoir; with the elongated neck in the open vent position, subjecting the at least one or more liquid drug components in the reservoir to lyophilization conditions to lyophilize the one or more liquid drug components; and, after the one or more liquid drug components have been lyophilized, further inserting the elongated neck into the filling port to a closed vent position with the at least one being located between the at least one venting passageway and the reservoir.

In yet a further aspect, a method is provided herein of preparing a drug delivery device, the method including: pre-filling a reservoir of at least one drug cartridge with one or more drug components, wherein the drug cartridge includes a fluid outlet and an internal lumen for conveying the one or more drug components from the reservoir to the fluid outlet; sterilizing the internal lumen of the drug cartridge; forming a seal across the sterilized internal lumen to limit ingress therein of contaminants; assembling the pre-filled drug cartridge to a body of the drug delivery device such that the fluid outlet is aligned with a fluid duct defined in the body, wherein the seal separates the sterilized internal lumen from the fluid outlet, the fluid duct extending from the fluid outlet to an opening in a first face of the body; providing a barrier across the first face of the body to at least cover the opening, wherein the barrier is ultraviolet transmissive; and, exposing the first face of the body to ultraviolet radiation so as to allow the ultraviolet radiation to pass through the barrier and decontaminate the fluid duct and the fluid outlet through the opening.

In still yet a further aspect, a method is provided herein of preparing a drug delivery device, the method including: pre-filling a reservoir of at least one drug cartridge with one or more drug components, wherein the drug cartridge includes a fluid outlet and an internal lumen for conveying the one or more drug components from the reservoir to the fluid outlet; sterilizing the internal lumen of the drug cartridge; forming a seal across the sterilized internal lumen to limit ingress therein of contaminants; assembling the pre-filled drug cartridge to a body of the drug delivery device such that the fluid outlet is aligned with a fluid duct defined in the body, wherein the seal separates the sterilized internal lumen from the fluid outlet, the fluid duct extending from the fluid outlet to an opening in a first face of the body; providing a barrier across the first face of the body to at least cover the opening, wherein the barrier is electron-beam transmissive; and, exposing the first face of the body to an electron-beam so as to allow the electron-beam to pass through the barrier and decontaminate the fluid duct and the fluid outlet through the opening.

In a further aspect, a method is provided herein of preparing a drug delivery device, the method including: providing a reservoir component including a reservoir for accommodating one or more drug components, and a filling port defining an open passageway into the reservoir; filling the reservoir, through the filling port, with one or more drug components; providing a plug adapter configured to mount to the reservoir component, the plug adapter including a fluid outlet and an internal lumen extending from the fluid outlet; sterilizing the internal lumen of the plug adapter; forming a seal on the plug adapter within the internal lumen to limit ingress therein of contaminants, wherein the seal separates the sterilized internal lumen from the fluid outlet; after forming the seal on the plug adapter, mounting the plug adapter to the reservoir component in forming a drug cartridge, the plug adapter being mounted so that a portion of the sterilized internal lumen extends through the filling port into communication with the reservoir; assembling the drug cartridge to a body of the drug delivery device such that the fluid outlet is aligned with a fluid duct defined in the body, wherein, the fluid duct extends from the fluid outlet to an opening in a first face of the body; providing a barrier across the first face of the body to at least cover the opening, wherein the barrier is ultraviolet transmissive; and, exposing the first face of the body to ultraviolet radiation so as to allow the ultraviolet radiation to pass through the barrier and decontaminate the fluid duct and the fluid outlet through the opening.

In yet a further aspect, a method is provided herein of preparing a drug delivery device, the method including: providing a reservoir component including a reservoir for accommodating one or more drug components, and a filling port defining an open passageway into the reservoir; filling the reservoir, through the filling port, with one or more drug components; providing a plug adapter configured to mount to the reservoir component, the plug adapter including a fluid outlet and an internal lumen extending from the fluid outlet; sterilizing the internal lumen of the plug adapter; forming a seal on the plug adapter within the internal lumen to limit ingress therein of contaminants, wherein the seal separates the sterilized internal lumen from the fluid outlet; after forming the seal on the plug adapter, mounting the plug adapter to the reservoir component in forming a drug cartridge, the plug adapter being mounted so that a portion of the sterilized internal lumen extends through the filling port into communication with the reservoir; assembling the drug cartridge to a body of the drug delivery device such that the fluid outlet is aligned with a fluid duct defined in the body, wherein, the fluid duct extends from the fluid outlet to an opening in a first face of the body; providing a barrier across the first face of the body to at least cover the opening, wherein the barrier is electron-beam transmissive; and, exposing the first face of the body to an electron-beam so as to allow the electron-beam to pass through the barrier and decontaminate the fluid duct and the fluid outlet through the opening.

In still yet a further aspect, a method is provided herein of preparing a drug delivery device, the drug delivery device having a body with at least one fluid duct being open along a first face of the body, the at least one fluid duct for conveying drug from at least one reservoir to a needle configured for injection into a patient, the method including: providing a barrier across the first face of the body to at least cover the at least one fluid duct, wherein the barrier is ultraviolet transmissive; and, exposing the first face of the body to ultraviolet radiation so as to allow the ultraviolet radiation to pass through the barrier and decontaminate the at least one fluid duct.

In a further aspect, a method is provided herein of preparing a drug delivery device, the drug delivery device having a body with at least one fluid duct being open along a first face of the body, the at least one fluid duct for conveying drug from at least one reservoir to a needle configured for injection into a patient, the method included: providing a barrier across the first face of the body to at least cover the at least one fluid duct, wherein the barrier is electron-beam transmissive; and, exposing the first face of the body to an electron-beam so as to allow the electron-beam to pass through the barrier and decontaminate the at least one fluid duct.

Any of the foregoing methods of preparing a drug delivery device may be modified to utilize pulsed light to decontaminate in place of ultraviolet radiation or electron-beam, with a barrier being used configured to be transmissive to the pulsed light. Stated differently, a drug delivery device may be prepared in the same manner as in any of the foregoing methods but with pulsed light causing decontamination (utilizing a pulsed light transmissive barrier).

Advantageously, the subject invention provides a drug cartridge useable in lyophilization.

Also, advantageously, the subject invention allows for pre-filling of a drug cartridge for a drug delivery device, separately from assembly, with subsequent controlled sterilization of drug pathways to limit detrimental effects on the loaded drug. This allows for heightened protection for biologics which may be sensitive to sterilization techniques using radiation.

As used herein, a “drug” or “drug component,” may be used interchangeably, and shall mean any therapeutic agent in any physical state (e.g., solid, liquid, suspension) and/or any component, in any physical state, intended to be mixed with, or otherwise co-act with, any therapeutic agent, such as a diluent and/or any combinations or mixtures thereof (e.g., a mixture of diluent and one or therapeutic agents). The drug may be prepared using any known technique, including, but not limited to, lyophilization, spray-dried dispersion (SDD), spray-freeze drying (SFD), and, melt crystallization (e.g., to form crystallized suspensions).

As used herein, “ultraviolet radiation” shall mean electromagnetic radiation with wavelengths generally found within the ultraviolet portion of the light spectrum, including within the range of 100-315 nm, suitable for decontamination. Ultraviolet radiation includes electromagnetic radiation within the ultraviolet B (UVB) range (280-315 nm) and/or electromagnetic radiation with wavelengths within the ultraviolet C (UVC) range (100-280 nm).

As used herein, an "electron-beam" shall mean a concentrated highly-charged stream of electrons suitable for decontamination. The electron beam may be characterized as "low energy," e.g., as a having a kinetic energy of ≤300 keV.

As used herein, "x-ray radiation" shall mean electromagnetic radiation with energy in the range of up to 10 MeV, possibly being up to 7.5 MeV. The x-ray radiation may be characterized as being within the wavelength range for "soft" x-rays, "hard" x-rays or gamma rays. The x-ray radiation may be applied to reach a dose of up to 25 kGy. Alternatively, a lower dose may be applied to achieve a sufficient sterility assurance level for a relevant bioburden.

Also used herein, "pulsed light" shall mean repeated, short bursts of electromagnetic radiation suitable for decontamination, including electromagnetic radiation within visible and invisible portions of the light spectrum. Each burst of the pulsed light may be characterized as "high energy," e.g., on the order of 300 J, with a high-power flash, e.g., on the order of 1 mW, delivered over a short duration on the order of 0.3 milliseconds. Pulsed light may include ultraviolet radiation, where ultraviolet radiation is applied in repeated short bursts, including ultraviolet radiation in the UVB and UVC ranges, as well as the ultraviolet A (UVA) range (315-400 nm). Additionally, pulsed light may include any electromagnetic radiation effective in decontamination, including, but, not limited to, x-ray radiation, light in the visible spectrum (400-770 nm) and/or infrared radiation within the infrared portion of the light spectrum (770-1100 nm). As will be understood by those skilled in the art, pulses of pulsed light may include a mix of different types of electromagnetic radiation, e.g., including visible light with ultraviolet radiation, e.g., UVC.

As used herein, "decontamination," and variants thereof, shall mean removal of germs, bacteria or other living microorganisms. High levels of such removal are achievable, including levels acceptable for sterilization.

These and other features of the subject invention shall be better understood through a study of the following detailed description and accompanying drawings.

BRIEF DESCRIPTION OF THE DRAWINGS

FIG. 40A-1 shows the initial, sealed, state of a system for accessing a drug cartridge by shifting two seals, in accordance with the subject invention.

FIG. 40A-2 shows the final, opened, state of a system of FIG. 40A-1.

FIG. 73C shows the UV threshold dose achieved after thirty seconds of ultraviolet radiation exposure.

FIG. 74 shows a drug delivery device with a further alternate barrel-configured drug cartridge, in accordance with the subject invention.

FIG. 75 shows plunger actuation in the drug delivery device of FIG. 74.

FIG. 76 shows plunger actuation in the opposing direction, following the action shown in FIG. 75.

FIG. 77 shows plunger rotation to another barrel, following the action shown in FIG. 76.

FIG. 78 shows plunger actuation, following the action shown in FIG. 77.

FIG. 79A shows a drug delivery device worn via a clip on a patient's clothing, in accordance with the subject invention.

FIG. 79B is a side view of the drug delivery device of FIG. 79A.

FIG. 80A shows a drug delivery device worn via adhesive on a patient's abdomen, in accordance with the subject invention.

FIG. 80B is a side view of the drug delivery device of FIG. 80A.

FIG. 81A shows a drug delivery device worn via a strap or belt across a patient's waist, in accordance with the subject invention.

FIG. 81B is a side view of the drug delivery device of FIG. 81A.

Figure 82B:
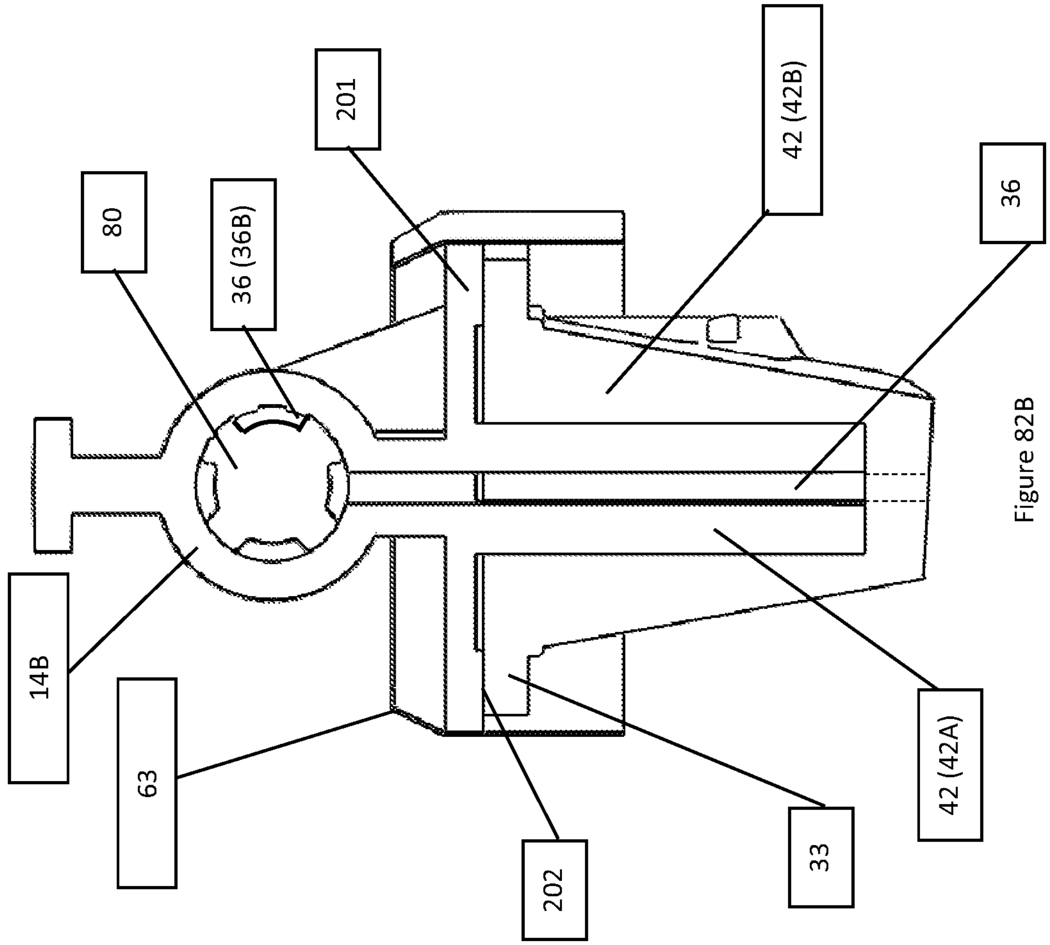
Figure 82A:
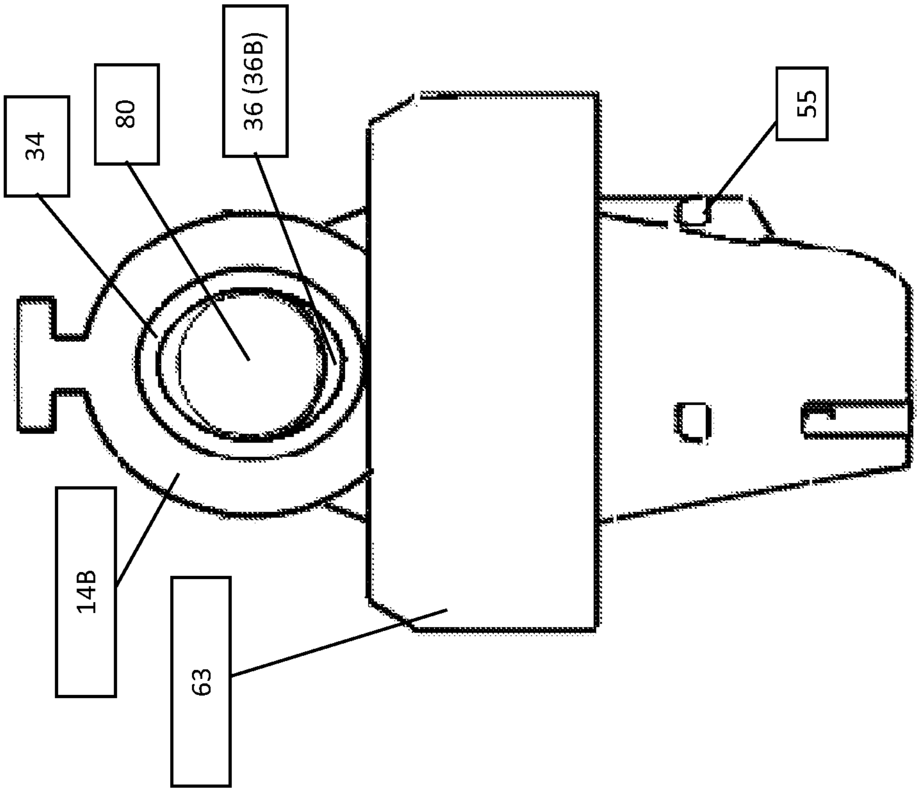

FIG. 82A is a top view of an alternative plug adapter useable with the subject invention.

FIG. 82B is a section view of the plug adapter of FIG. 82A.

Figure 83B:
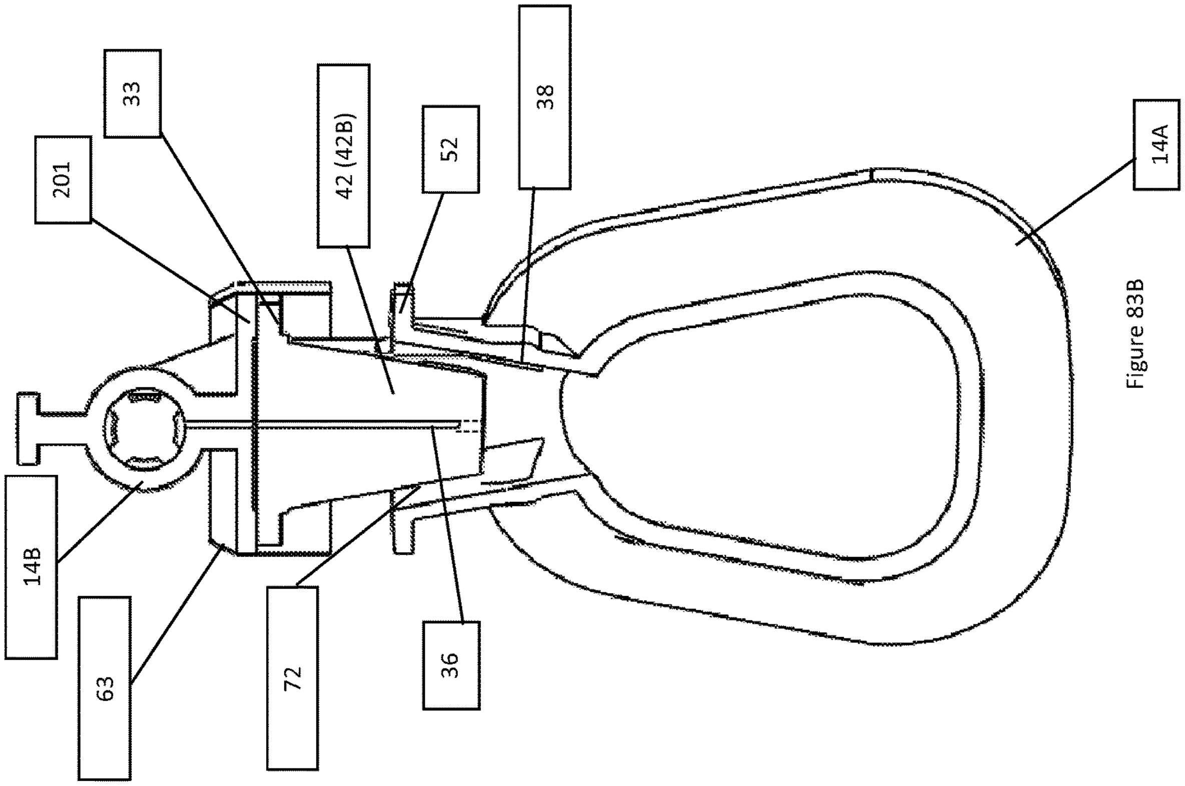
Figure 83A:
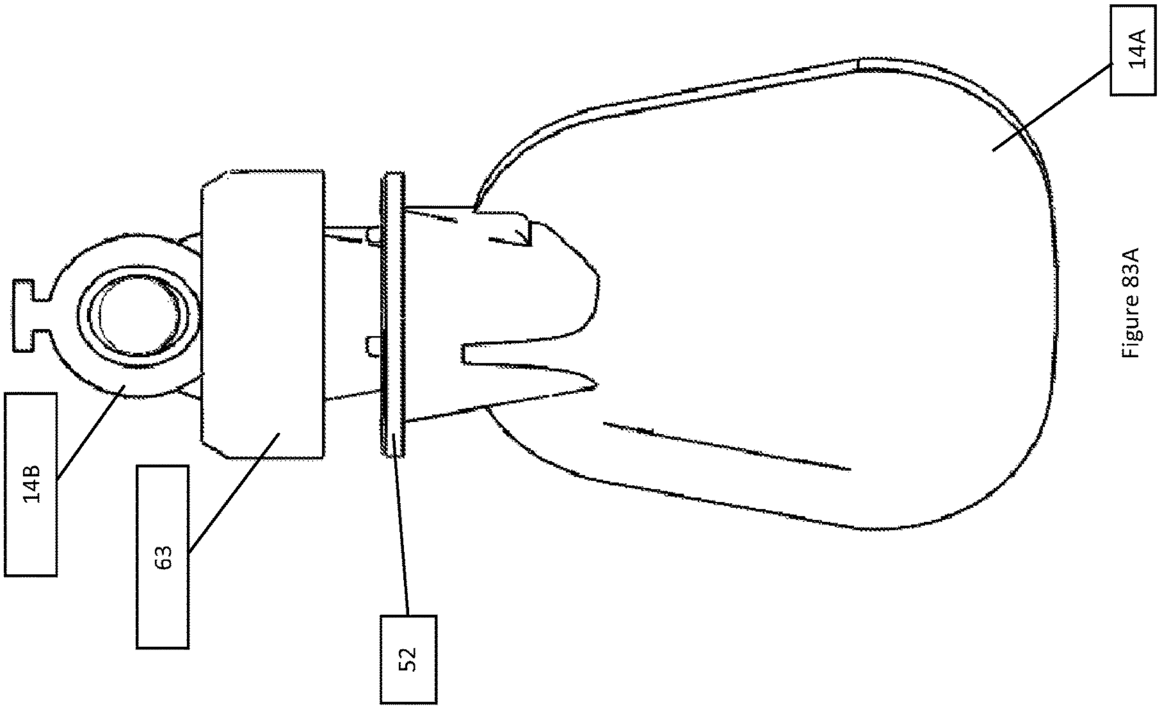

FIG. 83A is a top view of a drug cartridge including the plug adapter of FIG. 82A.

FIG. 83B is a section view of the drug cartridge of FIG. 83A, prior to assembly with a ferrule.

Figure 84B:
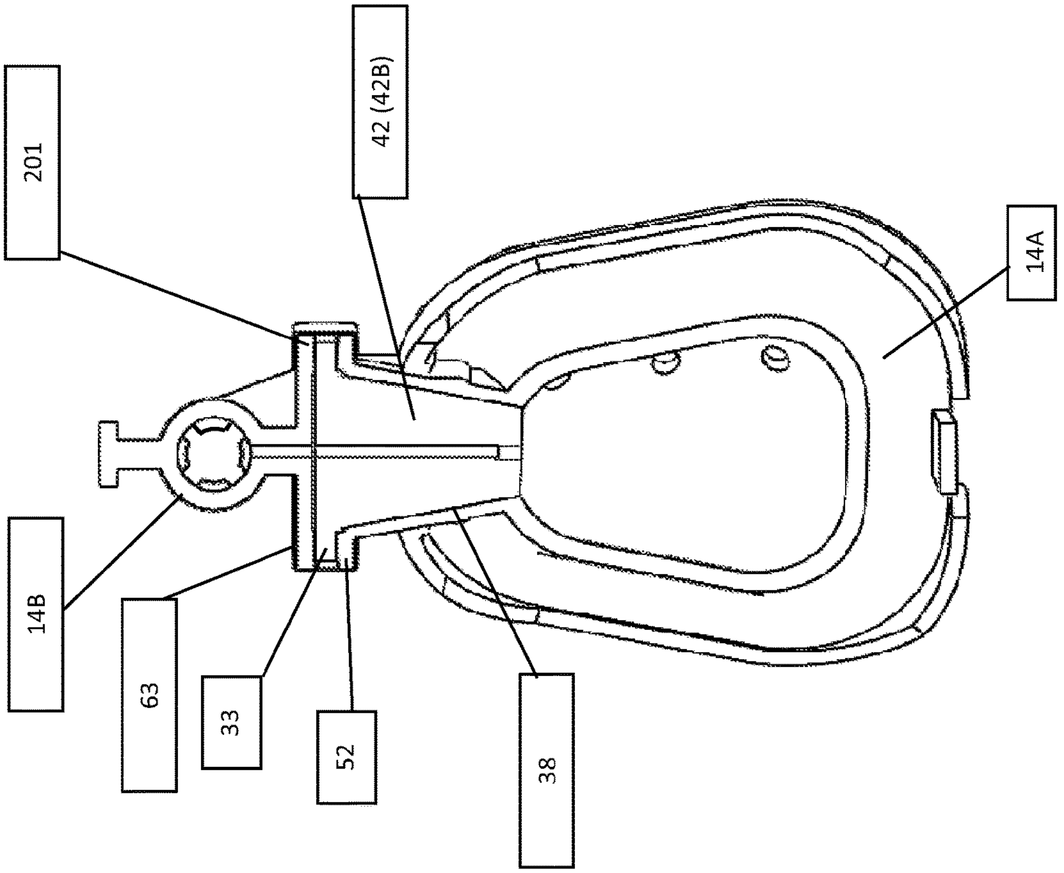
Figure 84A:
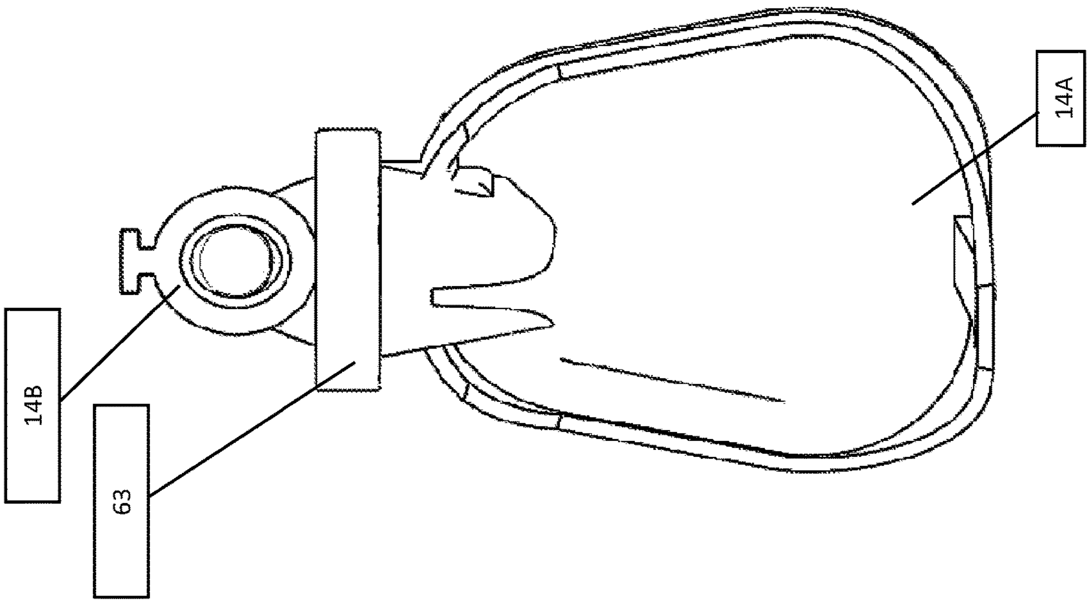

FIG. 84A is a top view of the drug cartridge of FIG. 83A, with the ferrule mounted thereto.

FIG. 84B is a section view of the drug cartridge of FIG. 84A.

Figure 85:
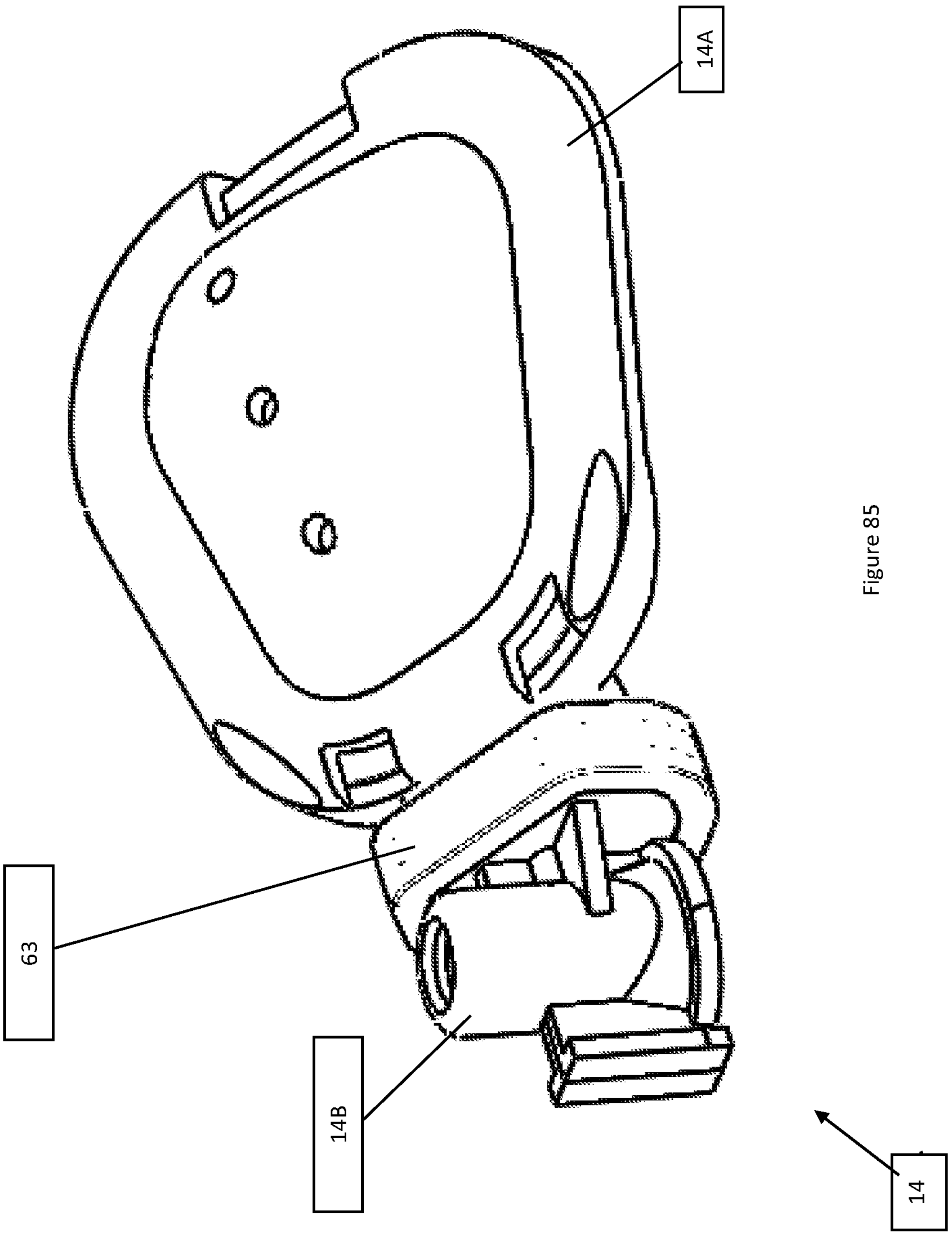

FIG. 85 is an isometric view of a drug cartridge, with a ferrule mounted thereto, in accordance with the subject invention.

Figure 86:
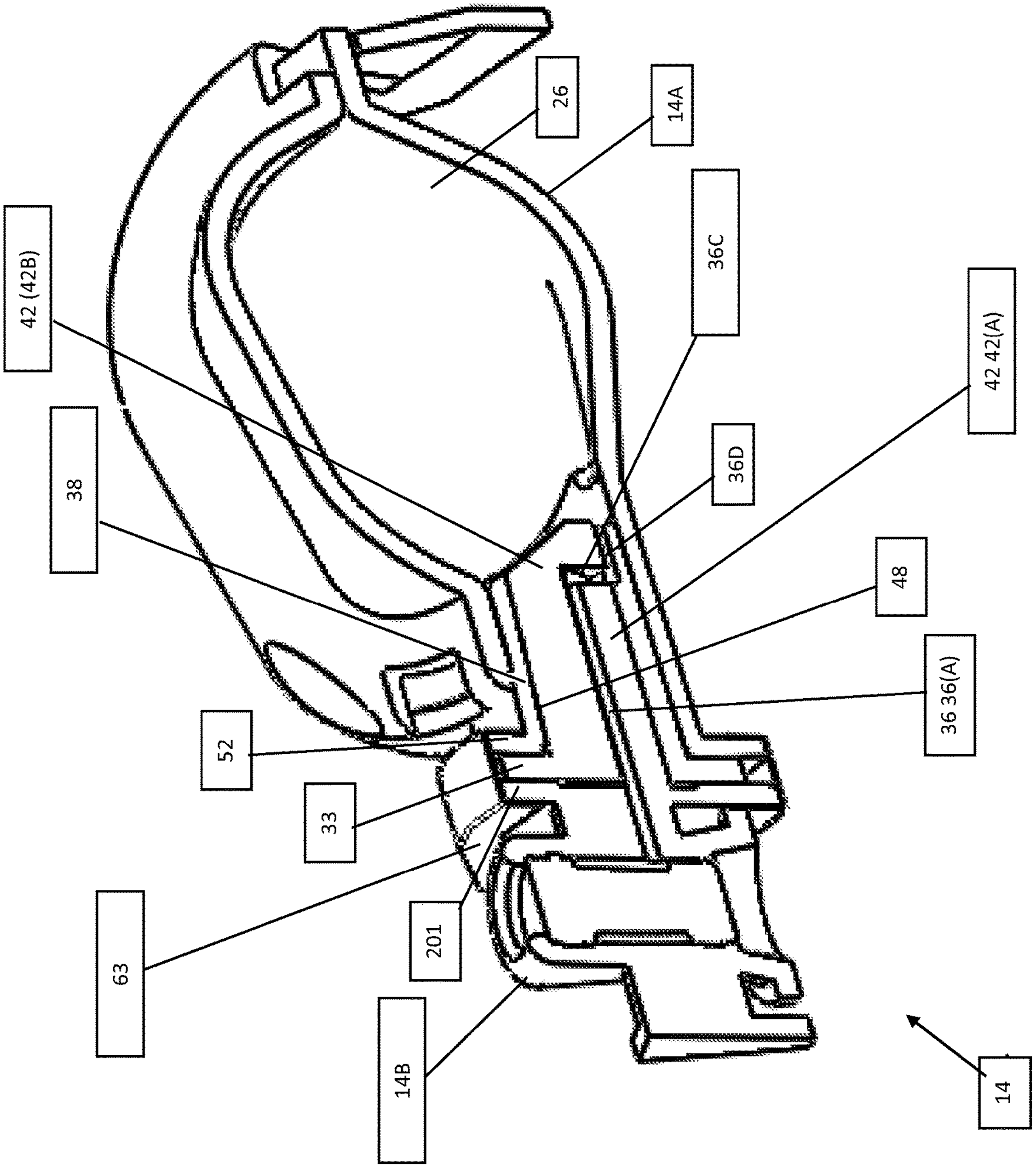

FIG. 86 is a section view of the drug cartridge of FIG. 85.

Figure 87A:
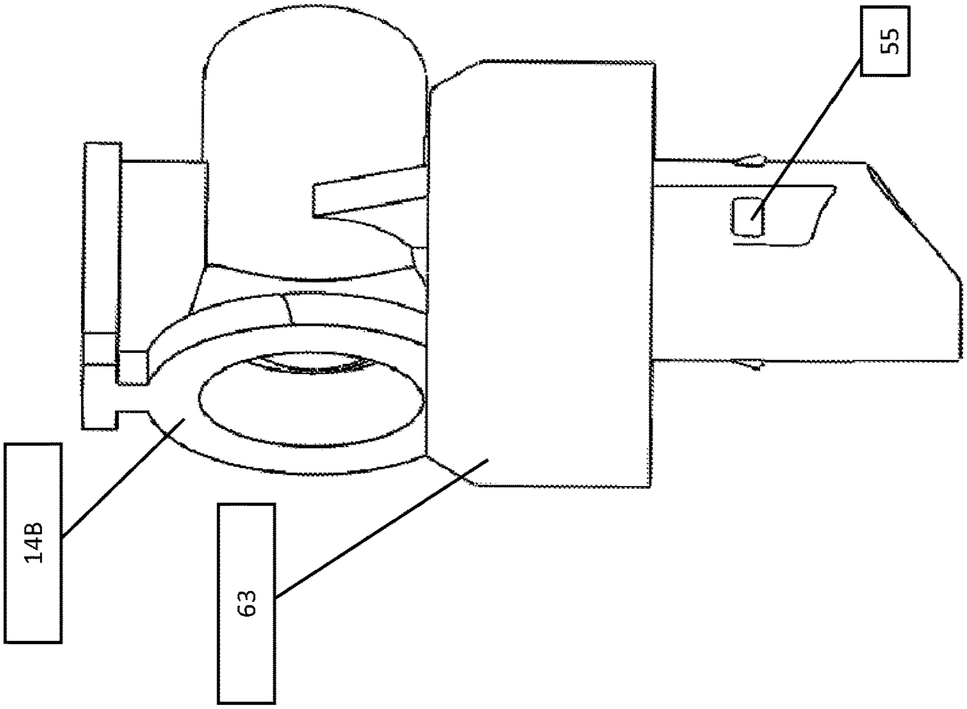

FIG. 87A is a side view of an alternative plug adapter useable with the subject invention.

Figure 87B:
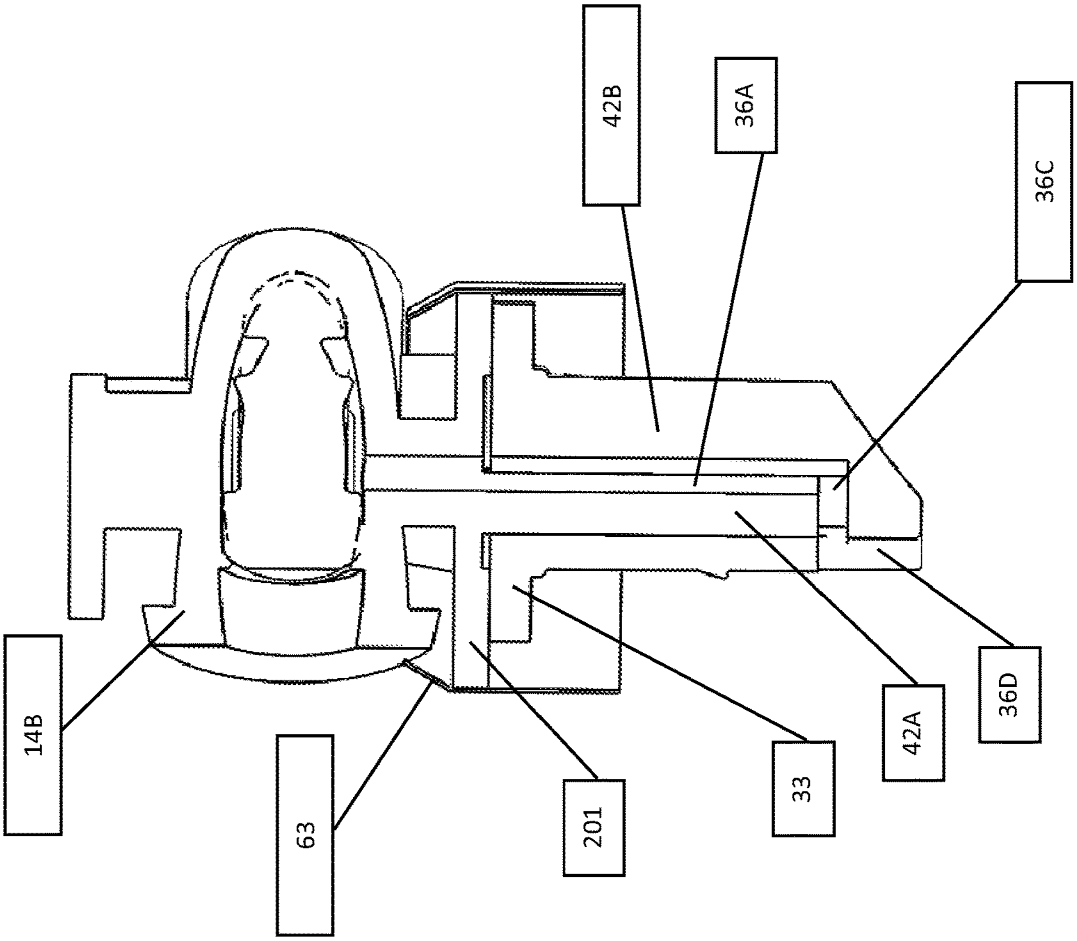

FIG. 87B is a section view of the plug adapter of FIG. 87A.

Figure 88B:
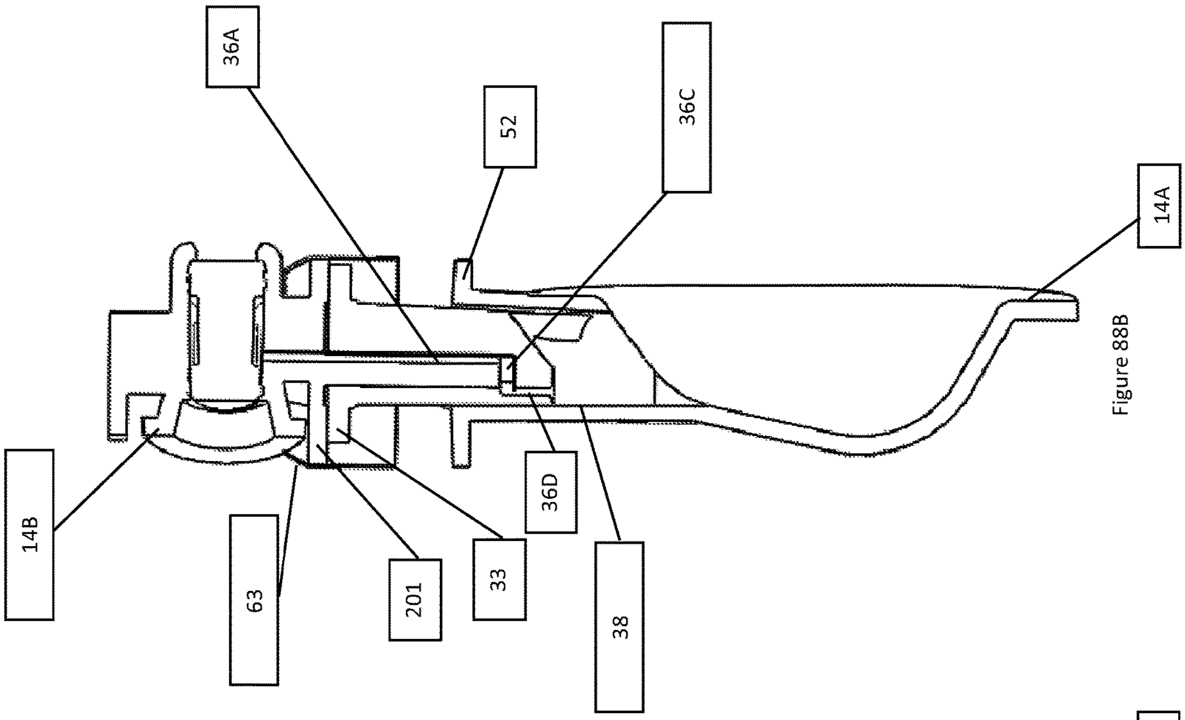
Figure 88A:
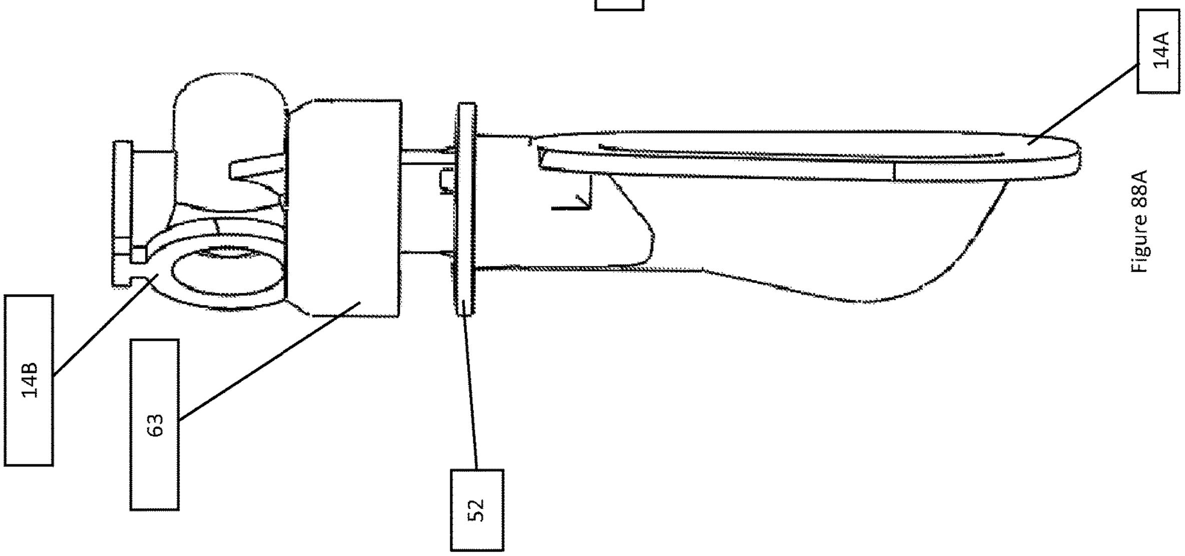

FIG. 88A is a top view of a drug cartridge including the plug adapter of FIG. 87A.

FIG. 88B is a section view of the drug cartridge of FIG. 88A, prior to assembly with a ferrule.

Figure 89B:
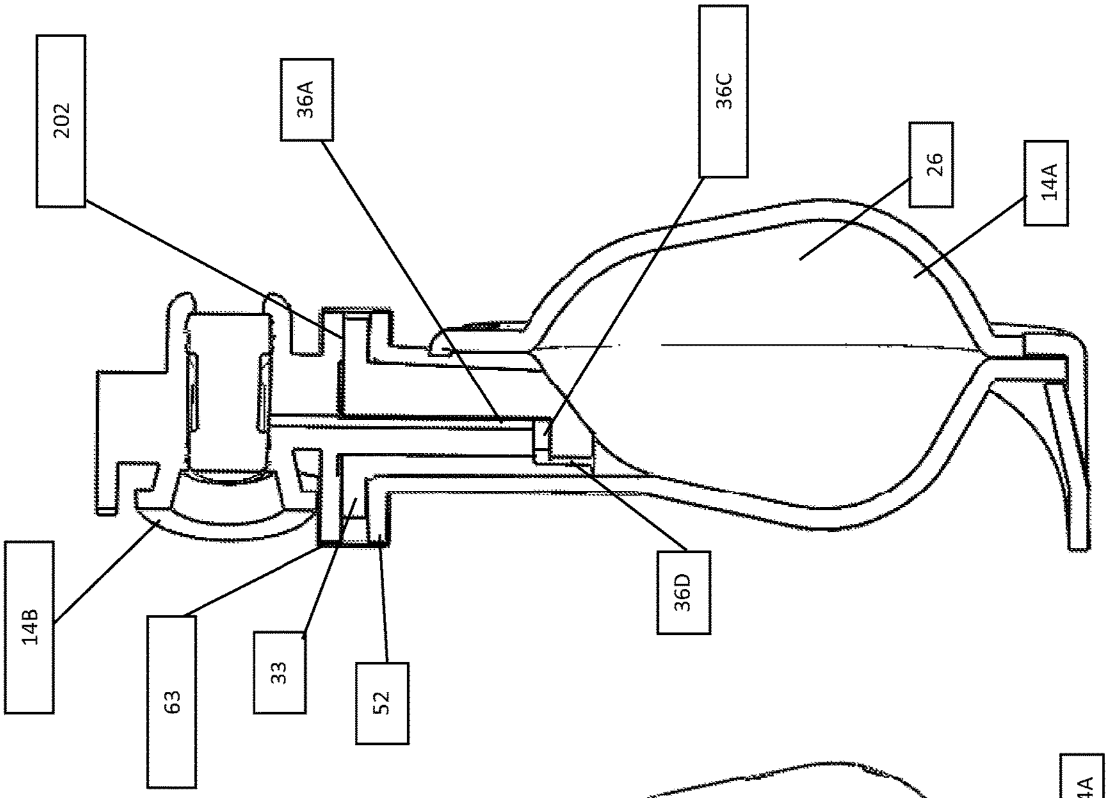
Figure 89A:
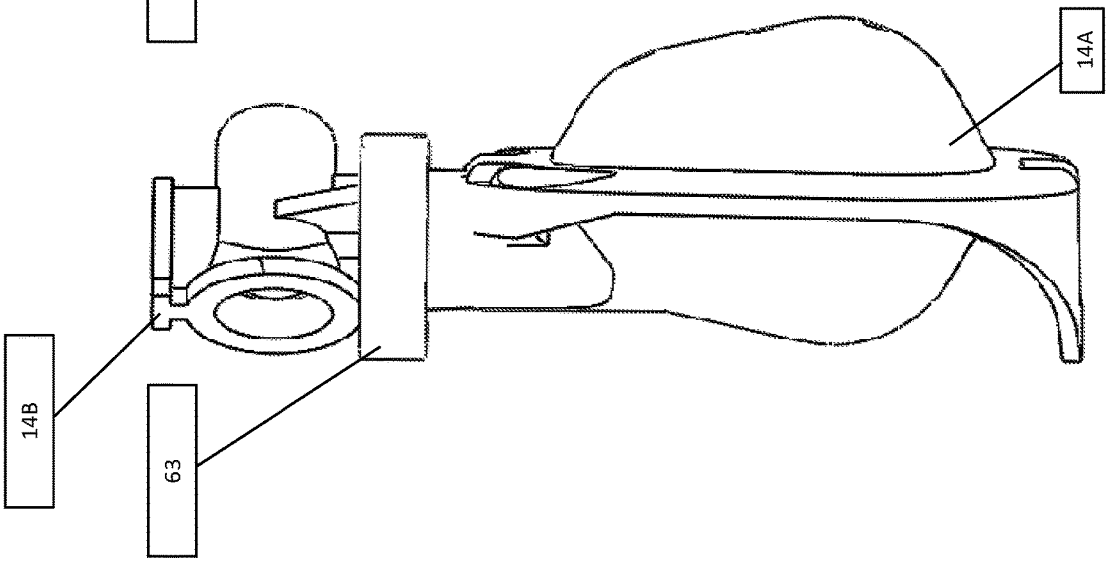

FIG. 89A is a top view of the drug cartridge of FIG. 88A, with the ferrule mounted thereto.

FIG. 89B is a section view of the drug cartridge of FIG. 89A.

FIGS. 90-103 show an alternate embodiment of a drug cartridge useable with a drug delivery device, in accordance with the subject invention.

FIGS. 104-115 show a seal useable with a drug cartridge, in accordance with the subject invention.

FIGS. 116-124 show an actuator for opening the seal shown in FIGS. 104-115, in accordance with the subject invention.

DETAILED DESCRIPTION OF THE INVENTION

In one aspect, the subject invention is directed to methods of preparing a drug cartridge and, separately, a drug delivery device. With reference to the Figures, an exemplary drug delivery device is shown and designated by reference number 10. As will be appreciated by those skilled in the art, various drug delivery devices may be prepared by the method of the subject invention. The configuration and assembly of the components of the drug delivery device may vary and still fall within the scope of the subject invention.

Figure 1:
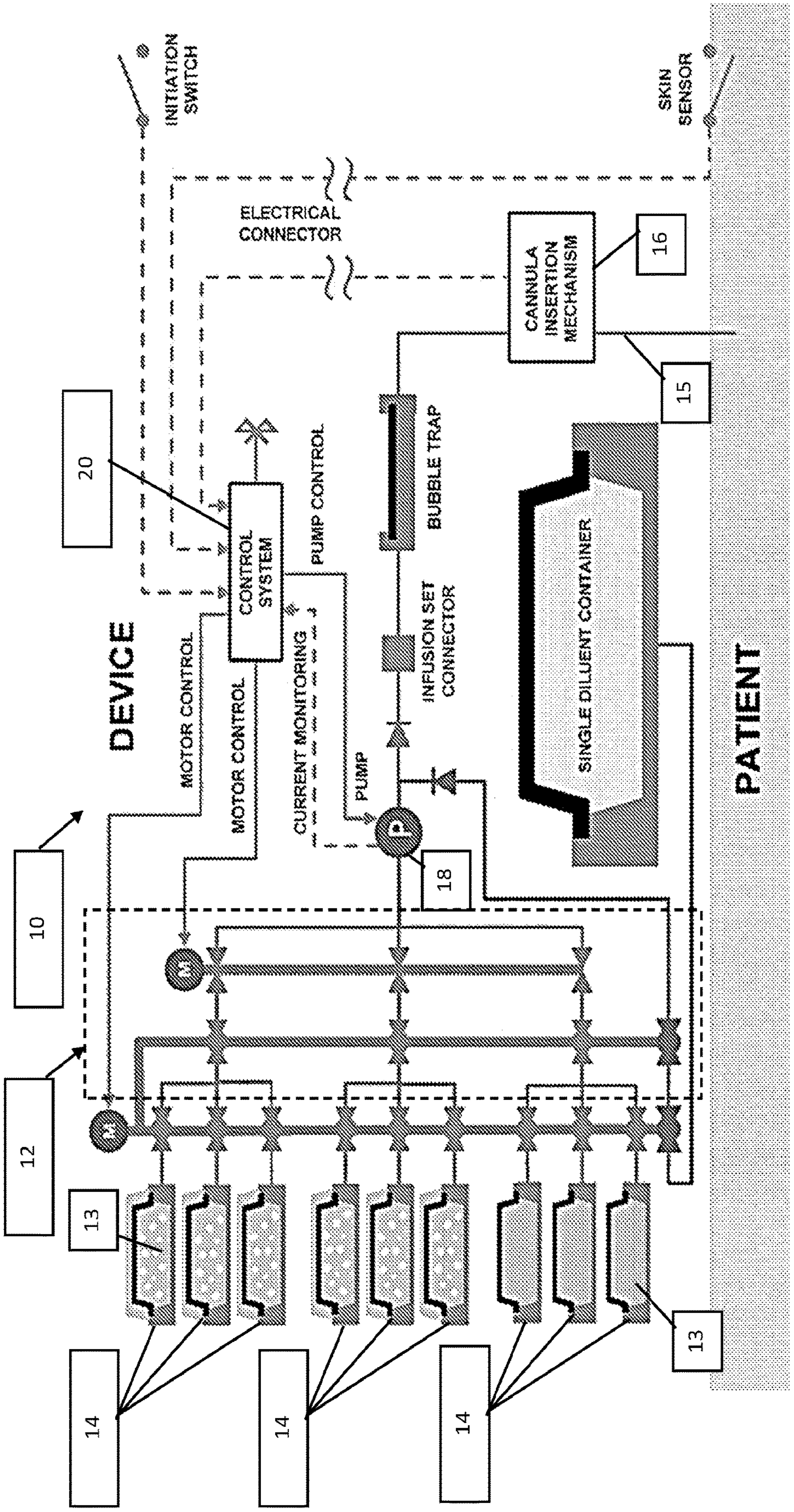
FIG. 1 is a schematic showing architecture, container communication, and functional components of a drug delivery device in accordance with the subject invention.

With reference to FIG. 1, the drug delivery device 10 may include a body 12 to which are attached one or more drug cartridges 14. The drug delivery device 10 is shown as a body-wearable patch-type drug delivery device having a needle support 16, a pump 18, and a control 20. The control 20, which may include a computer processing unit or logic controller, may be configured to control the pump 18 to control flow of drug from, and between, the drug cartridges 14 to a needle 15 for injection into a patient mounted to the needle support 16. The needle 15 may be a standard hypodermic needle or cannula; or may be a soft cannula ensheathed in a rigid sheath. The drug 13 may be caused to flow from one drug cartridge 14 to another, e.g., to deliver a diluent from one drug cartridge 14 to another drug cartridge 14. The pump 18 may be used to extract drug from the drug cartridges 14 and to urge the drug to other drug cartridge(s) 14 and to further urge the drug through defined fluid ducts or pathways to the needle 15 for delivery therefrom into the patient. The pump 18 may be also bi-directionally configured to reverse, causing drug to cycle in and out of the drug cartridge(s) 14, e.g., to facilitate reconstitution. The control 20 may be also configured to cause insertion of the needle 15 into the patient and/or retraction of the needle 15 from the patient in preparing for the drug administration and post drug delivery. Any known configurations for these processes may be utilized. In addition, as shown schematically in FIG. 1, various other components (such as valving, a bubble trap, a motor) may be also provided with the drug delivery device 10. Any source of power, e.g., a stored source of power, such as a battery, may be provided to provide power for operation of the needle 15, the pump 18, the control 20, and valving (as described below). One or motors may be provided to control the pump 18 and the valving. The motor(s) are preferably electrical, such as stepper motors.

Figure 6:
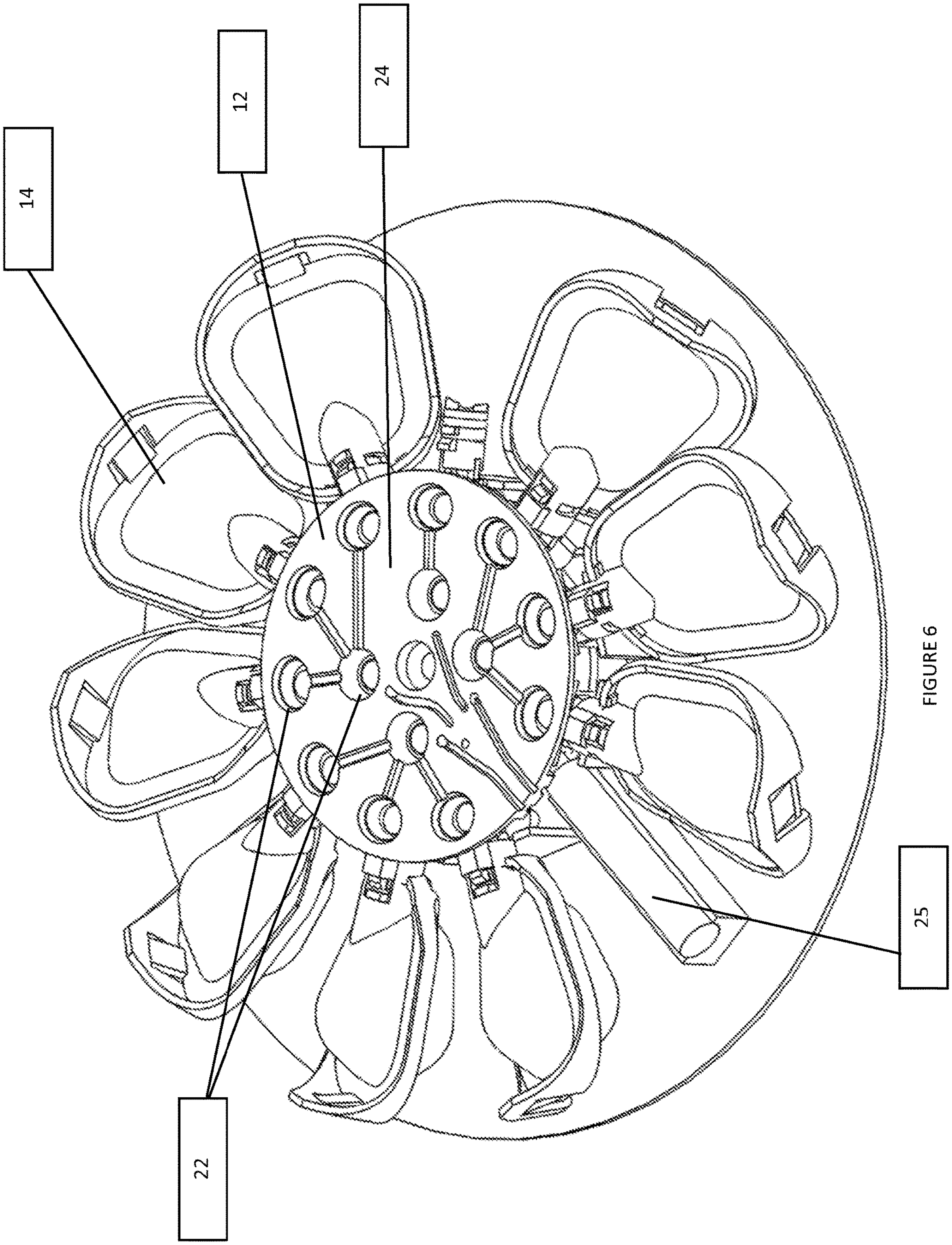
FIG. 6 is an enlarged view of the drug cartridges and body of FIG. 5.
Figure 6B:
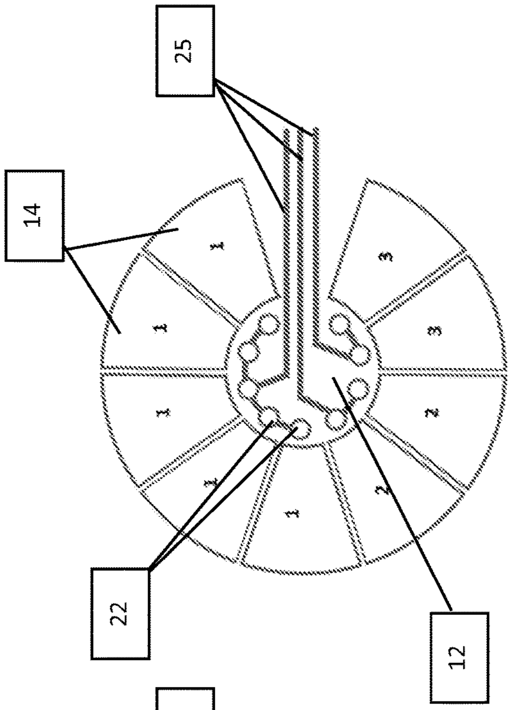
FIG. 6B is a schematic of an assembly configuration, whereby one group of five drug containers and two groups of two drug containers are connected to the body.
Figure 6D:
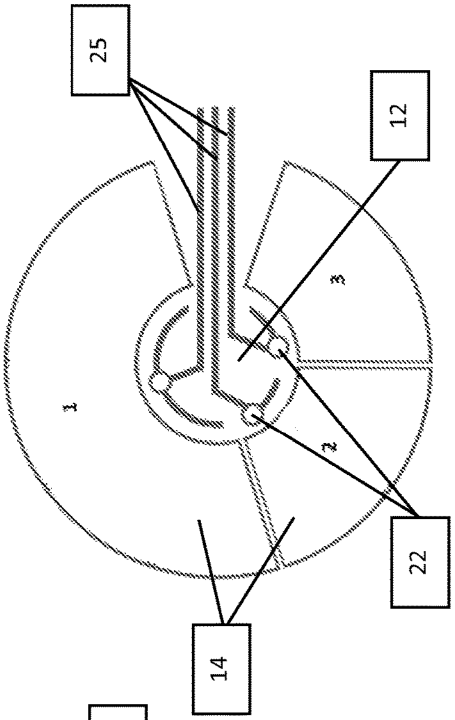
FIG. 6D is a schematic of an assembly configuration, whereby multiple drug containers for each group in 6B are replaced by single larger drug containers.
Figure 6A:
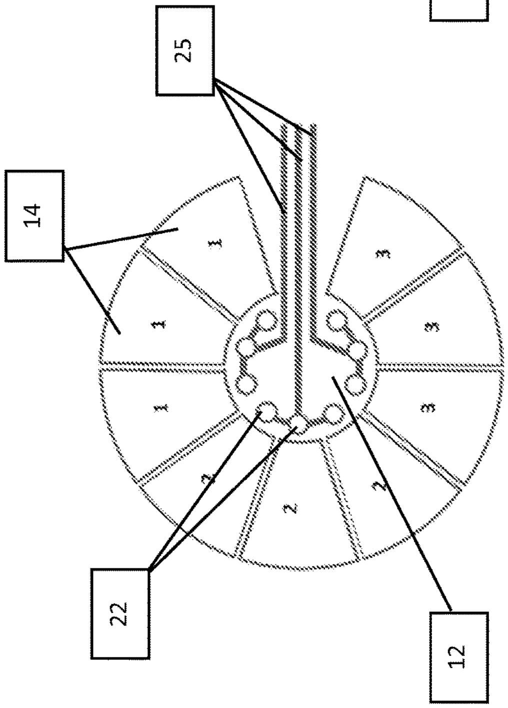
FIG. 6A is a schematic of an assembly configuration, whereby three sets of three drug containers are connected to the body.
Figure 6C:
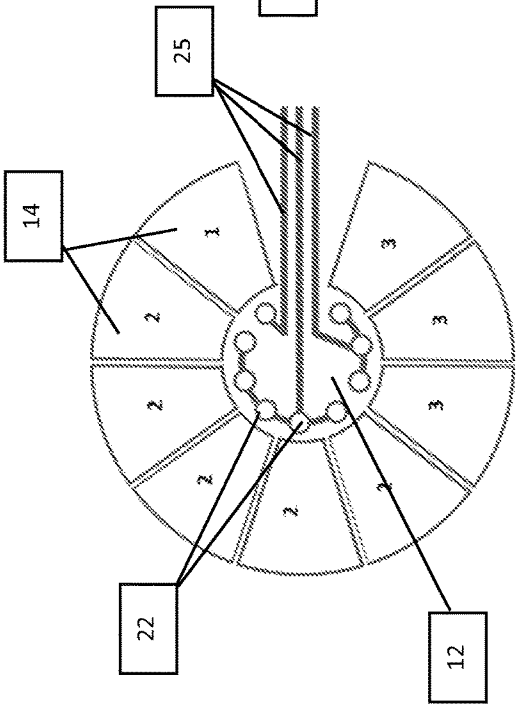
FIG. 6C is a schematic of an assembly configuration, whereby one group of five drug containers, one group of three drug containers, and a separate single drug container are connected to the body.

With reference to FIGS. 2-6, the drug cartridges 14 may be mounted to the body 12 in various configurations, including along a periphery of the body 12. The body 12 may be disc shaped, allowing for the drug cartridges 14 to be mounted about the circumference of the body 12. To facilitate flow of the drug, the body 12 may be formed with a plurality of fluid ducts 22 arranged to extend from the drug cartridges 14 to one or more outlet ducts 25. The fluid ducts 22 may be arranged in any manner, including being single passageways from the drug cartridges 14 to the one or more outlet ducts 25. Alternatively, the fluid ducts 22 may be manifolded to combine several of the fluid ducts 22 in various combinations, possibly with all of the fluid ducts 22 ultimately combining as one fluid flow directed to one or more outlet ducts 25. As shown in FIGS. 6A-6D, the drug cartridges 14 may be combined in various combinations. FIG. 6A shows three groupings of the drug cartridges 14 (designated as numbers 1, 2, and 3), each containing three of the drug cartridges 14, and each grouping feeding into one of the outlet ducts 25. This allows for the drug cartridges 14 within a grouping to be mixed (e.g., the drug cartridges 14 within grouping 1 may be varied to allow for different combinations) with the resultant combinations being possibly further mixed downstream of the outlet ducts 25. FIG. 6B shows three groupings, but not evenly weighted, with grouping 1 including five of the drug cartridges 14, and groupings 2 and 3, each including two of the drug cartridges 14. Variations in size of the groupings may be used to control the amounts and concentration of the resulting drug combinations. Variations in size in groupings may be seen in FIG. 6C as well. FIG. 6D shows the use of various sized drug cartridges 14 to correspond to the groupings, with different sized cartridges providing for variation in amounts of individual components and/or in concentration. For example, the drug cartridge 14 of grouping 1 may be formed to extend along a longer are about the body 12 than either of the drug cartridges 14 corresponding to groupings 2 and 3. As will be appreciated by those skilled in the art, one or more of the groupings may be manifolded together into a common outlet duct 25 (i.e., the outlet ducts 25 may vary in quantity and are not limited to one-to-one correspondence with the groupings of the drug cartridges 14).

Figure 65:
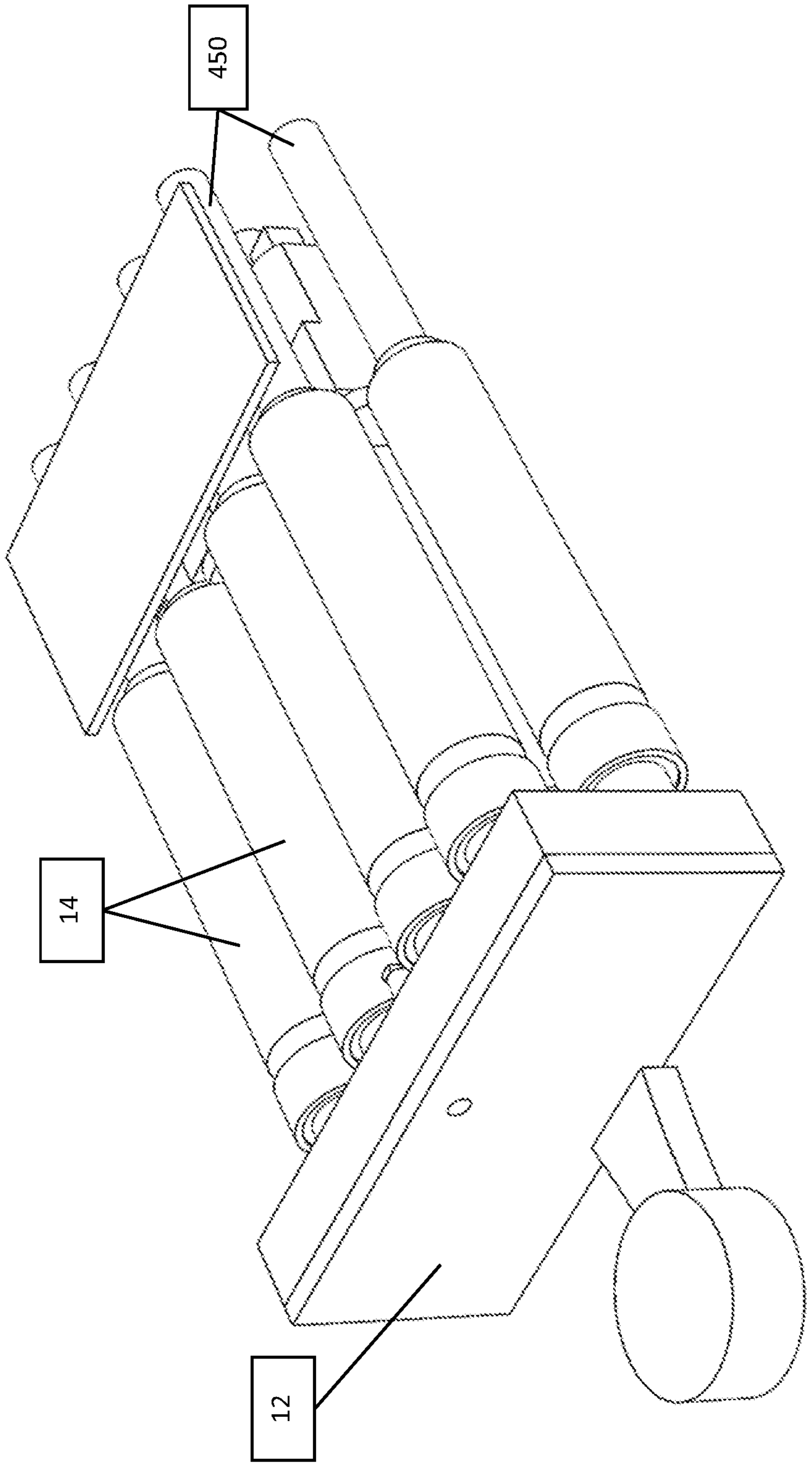
FIG. 65 shows a drug delivery device with barrel-configured drug cartridges, in accordance with the subject invention.
Figure 90:
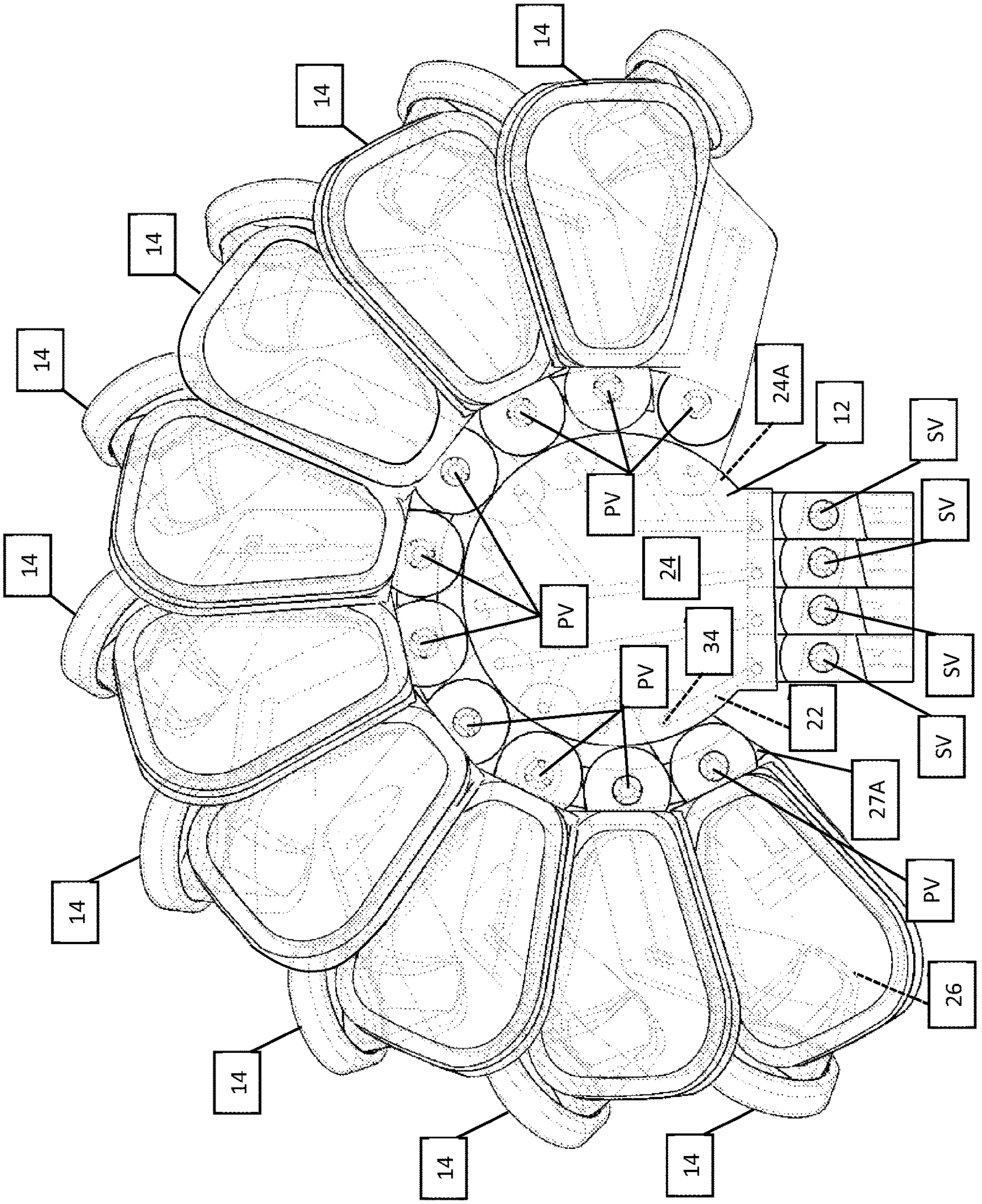
Figure 91:
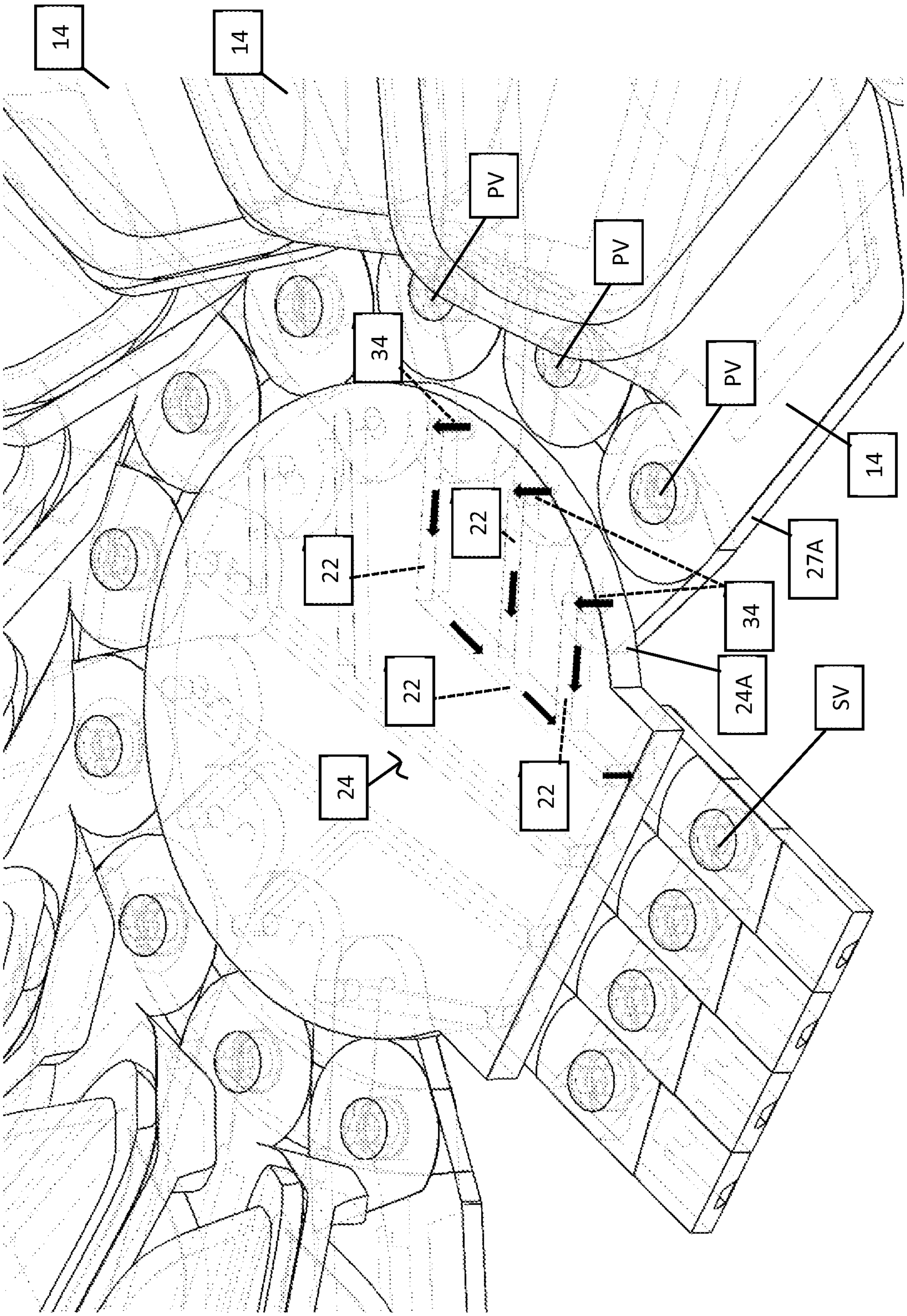
Figure 92:
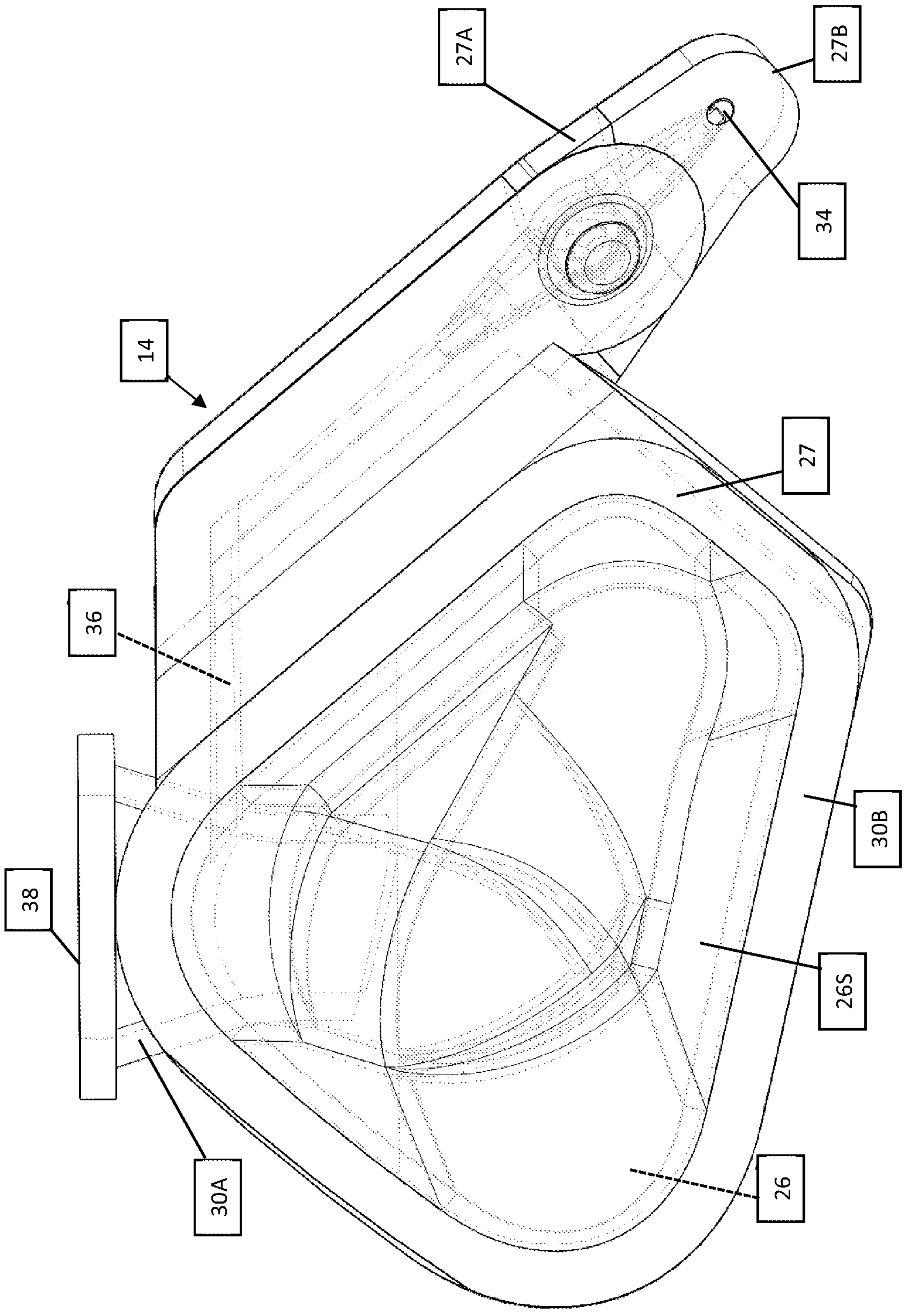
Figure 93:
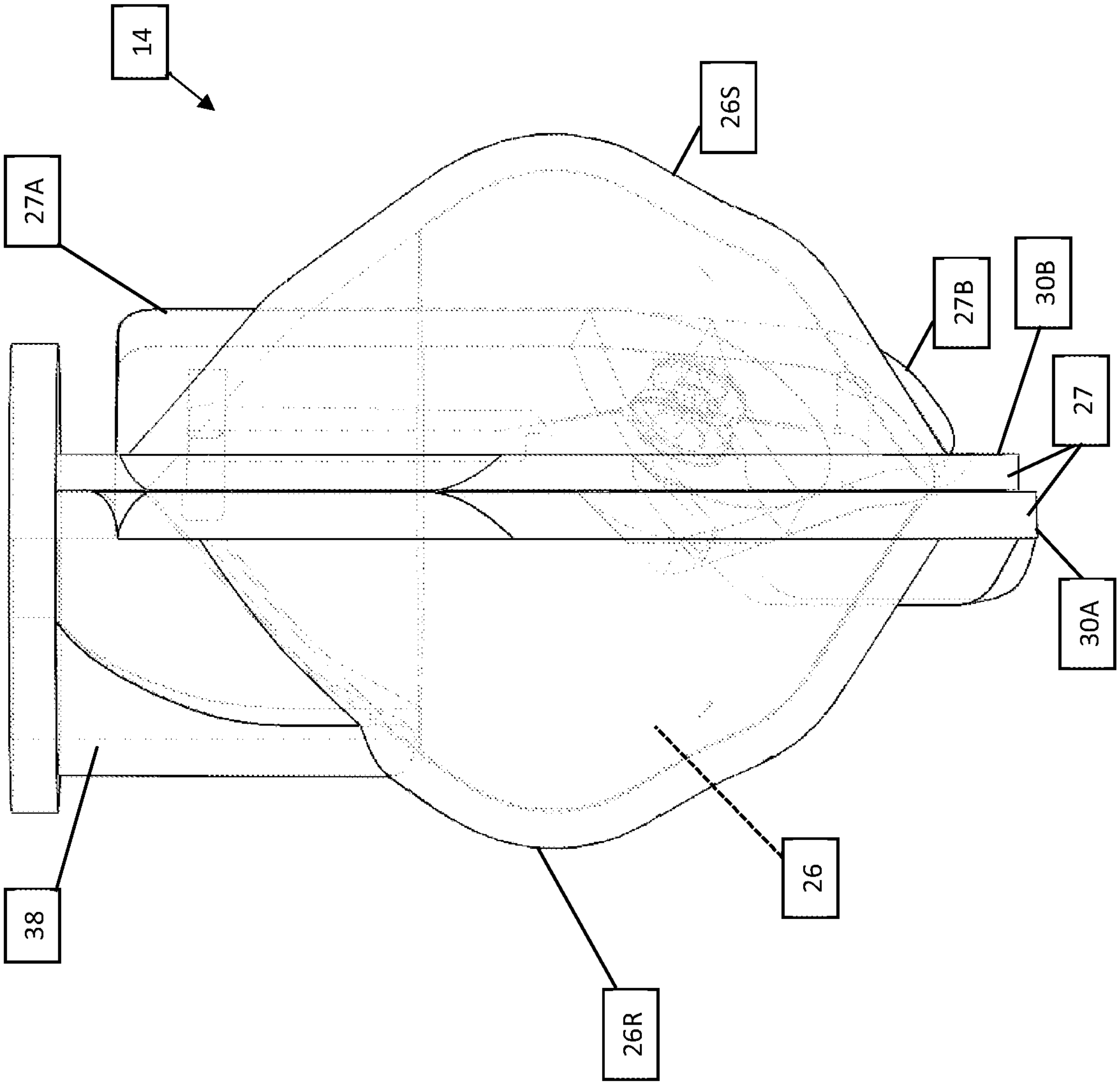
Figure 94:
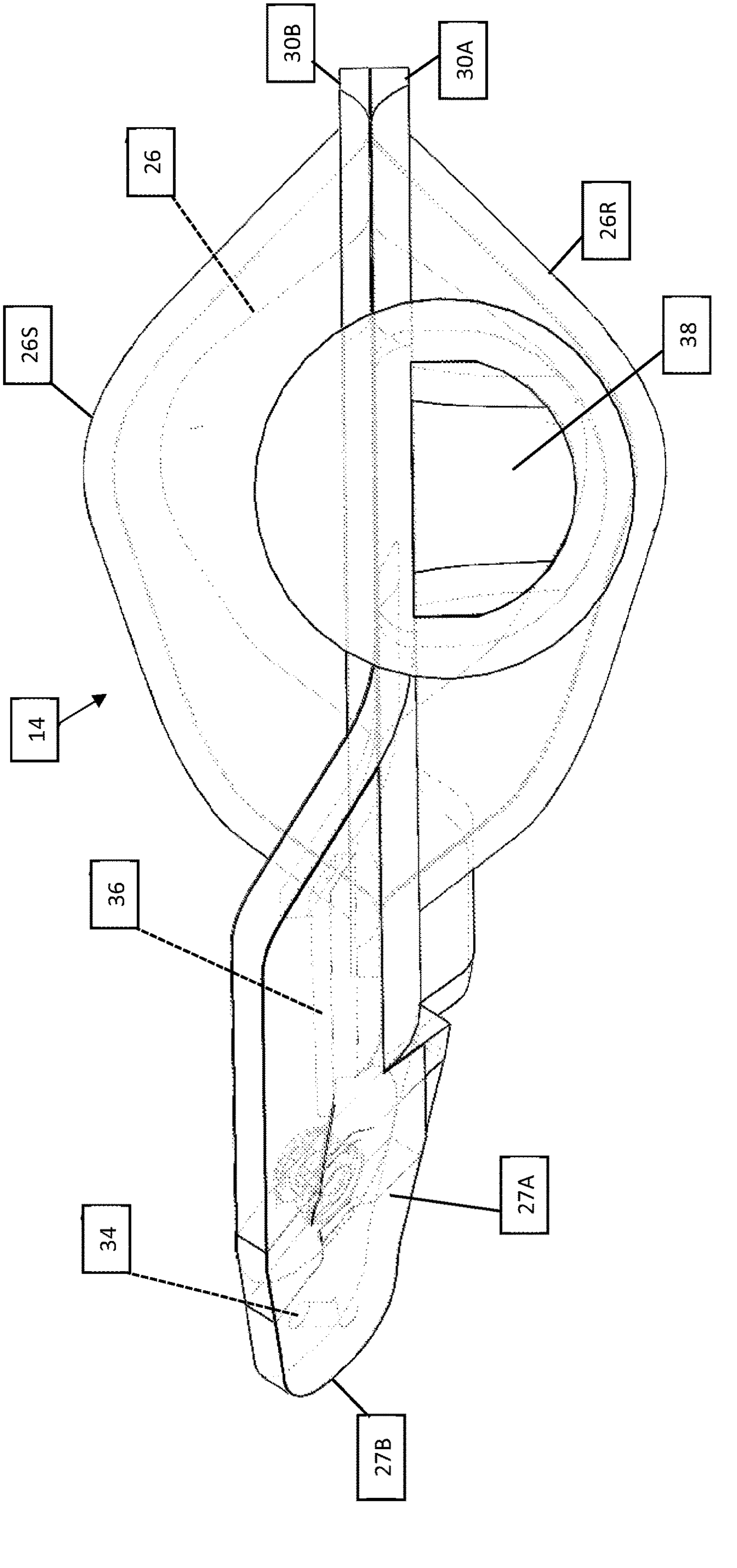

With reference to FIGS. 65-69, the drug cartridges 14 may be mounted to a face of the body 12 so as to extend therefrom in a generally normal direction. In this manner, the drug cartridges 14 may be generally within the footprint of the body 12. With circumference-mounting, as discussed above, the drug cartridges 14 may radiate outwardly from the circumference of the body 12. The drug cartridges 14, arranged about the circumference of the body 12, may be joined to the fluid ducts 22 along the circumferential edge of the body 12 (e.g., as shown in FIG. 6) and/or at points on a face of the body 12 (e.g., as shown in FIGS. 90-91). With face-mounting, as shown in FIG. 65, the drug cartridges 14 may axially extend away from the body 12, e.g., within the footprint thereof. Circumference-mounting may minimize the axial profile of the drug delivery device 10, while, face-mounting may minimize the radial profile of the drug delivery device 10.

The body 12 may be formed in any manner. By way of non-limiting example, the body 12 may be a single monolithic body having the fluid ducts 22 etched, milled, molded, and/or otherwise formed therein. The fluid ducts 22 may be formed along an external surface of the body 12 and/or be recessed within the body 12. The body 12 may be formed of polymeric material.

At least a portion of the fluid ducts 22 may be open to be exposed along a first face 24 of the body 12. This allows for fluid pathways for the drug to be exposed along the first face 24.

Figure 2:
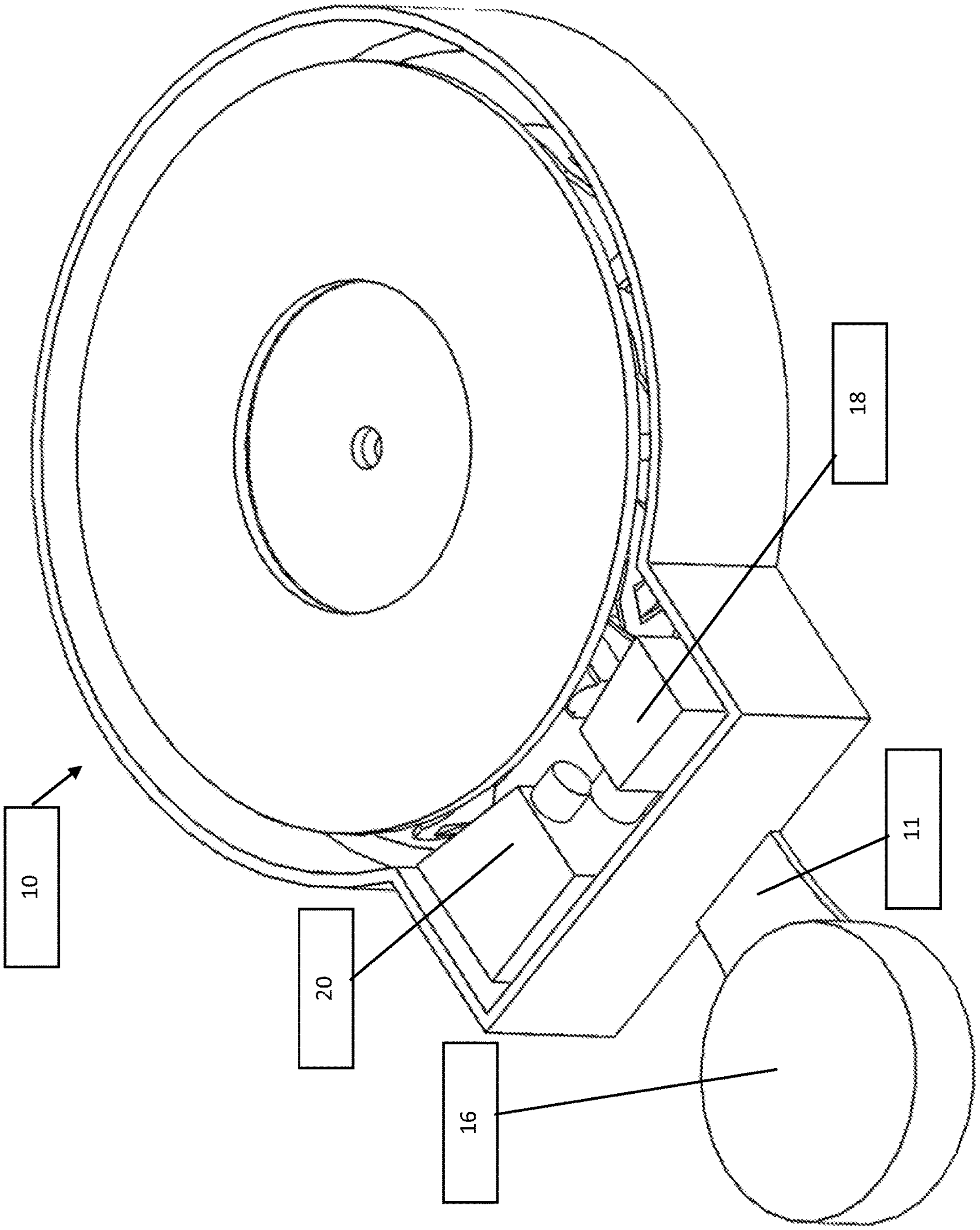
FIG. 2 is an isometric block model of a drug delivery device in accordance, with the subject invention with the top housing removed.
Figure 3:
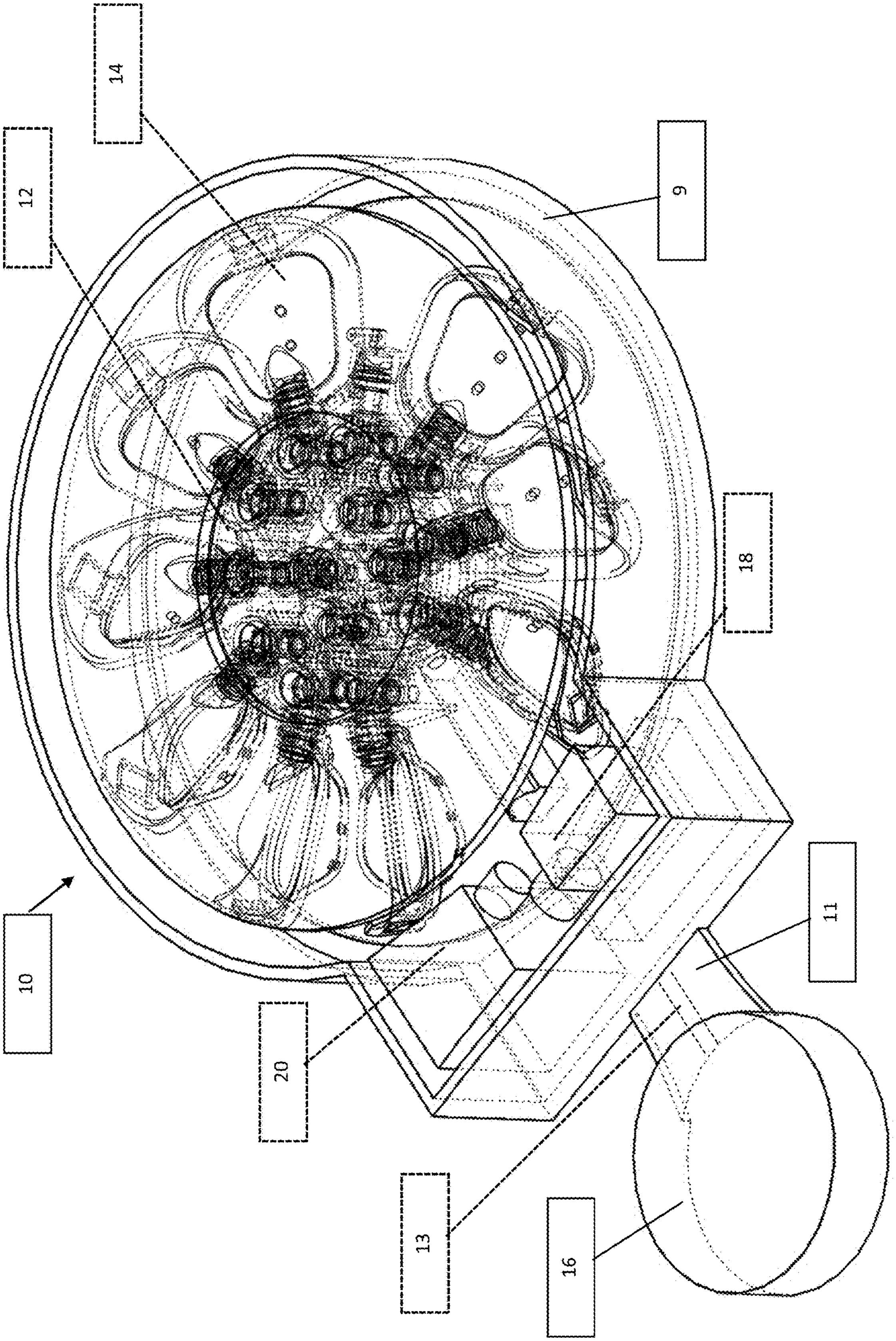
FIG. 3 is an isometric hidden-lines view of the embodiment in FIG. 2, showing the positioning of components within the drug delivery device.
Figure 4:
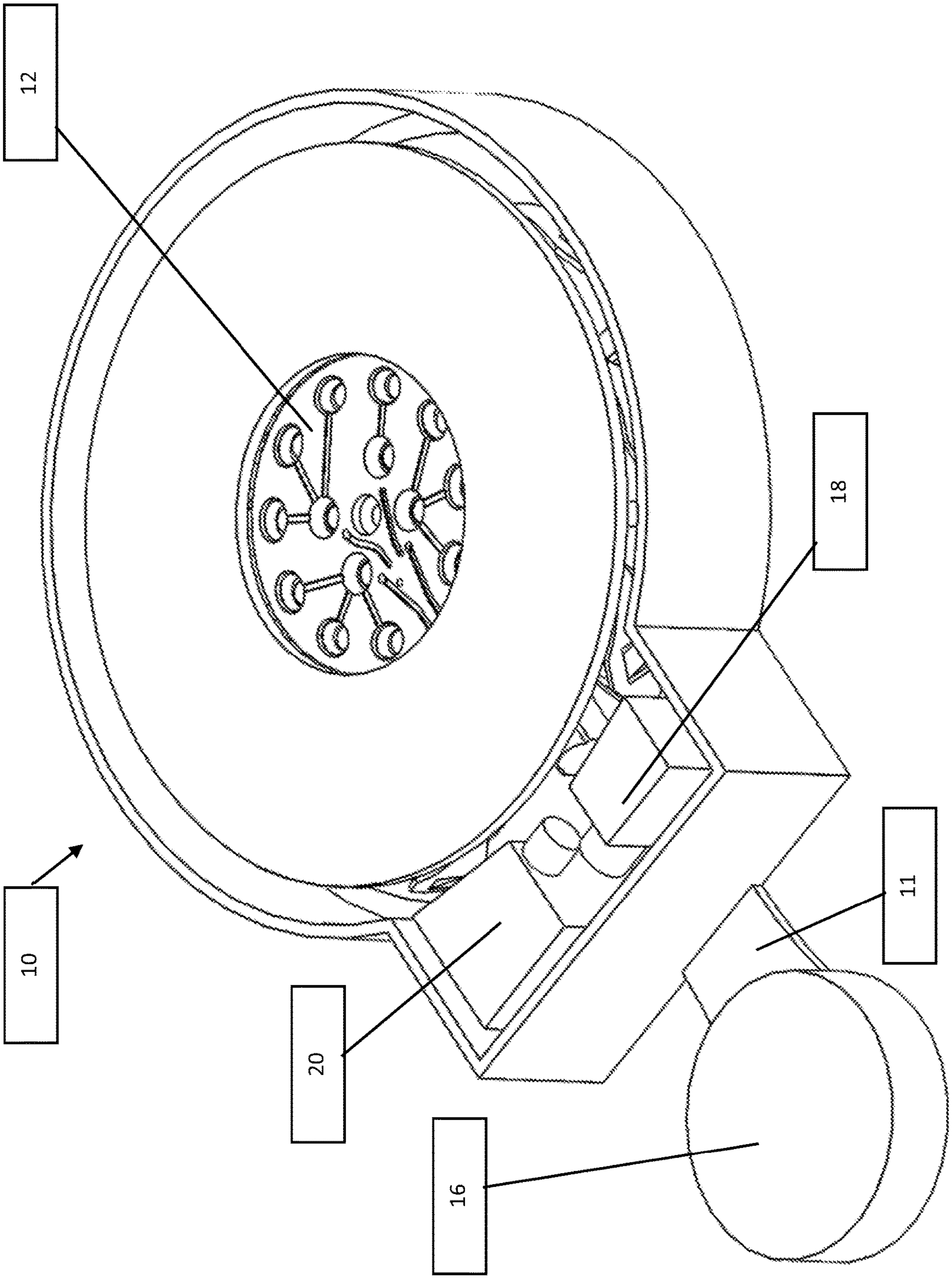
FIG. 4 is an isometric view of the embodiment in FIG. 3 with the barrier removed to show the body.
Figure 5:
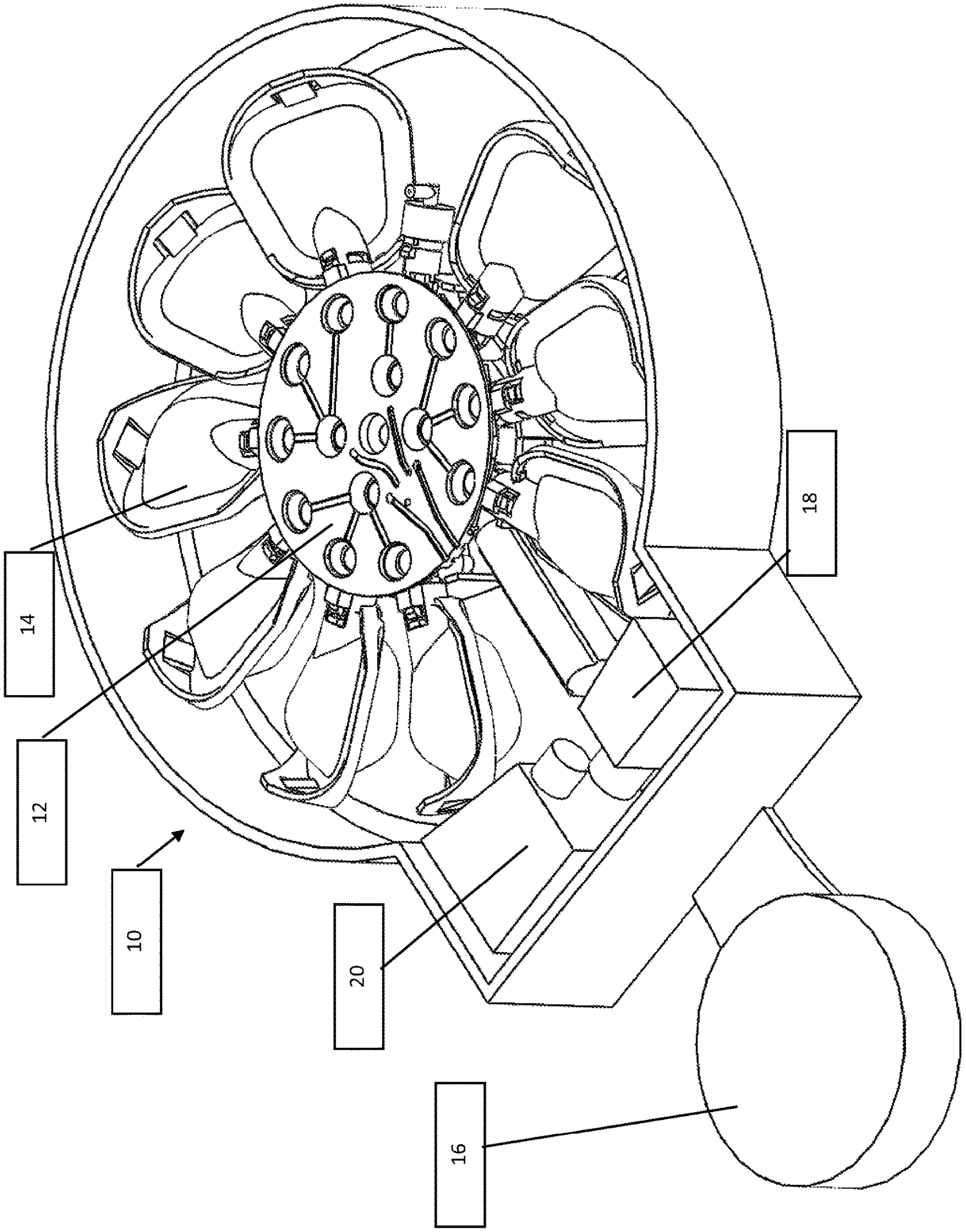
FIG. 5 is an isometric view of the embodiment in FIG. 4 with the diluent pack removed to show the drug cartridges.

As shown in FIGS. 2-4, the body 12 may be connected to the needle support 16 by a flexible tether 11, through which passes at least one fluid passageway 13 formed to convey drug from one or more outlet ducts 25 to the needle 15 for delivery to a patient, the tether 11 may be formed by any flexible materials, such as a polymeric or elastomeric material. In this manner, the body 12 and the needle support 16 may be secured to the body of the patient, with the tether 11 providing a flexible connection therebetween. Preferably, the tether 11 is not directly secured to the patient's body (e.g., the tether 11 is not adhered to the patient's body).

One or more electrical conductors may also pass through the tether 11 to electrically connect the body 12 and the needle support 16. This allows for signal and power transmission between the body 12 and the needle support 16. Alternatively, wireless receivers and/or transmitters may be provided on the body 12 and the needle support 16 to allow for wireless signal transmission therebetween.

Figure 79B:
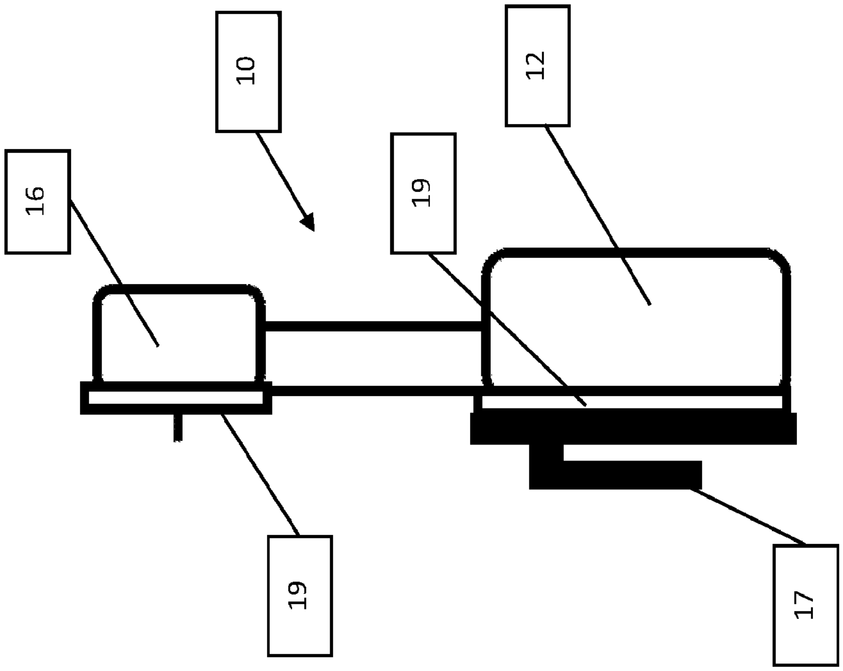
Figure 79A:
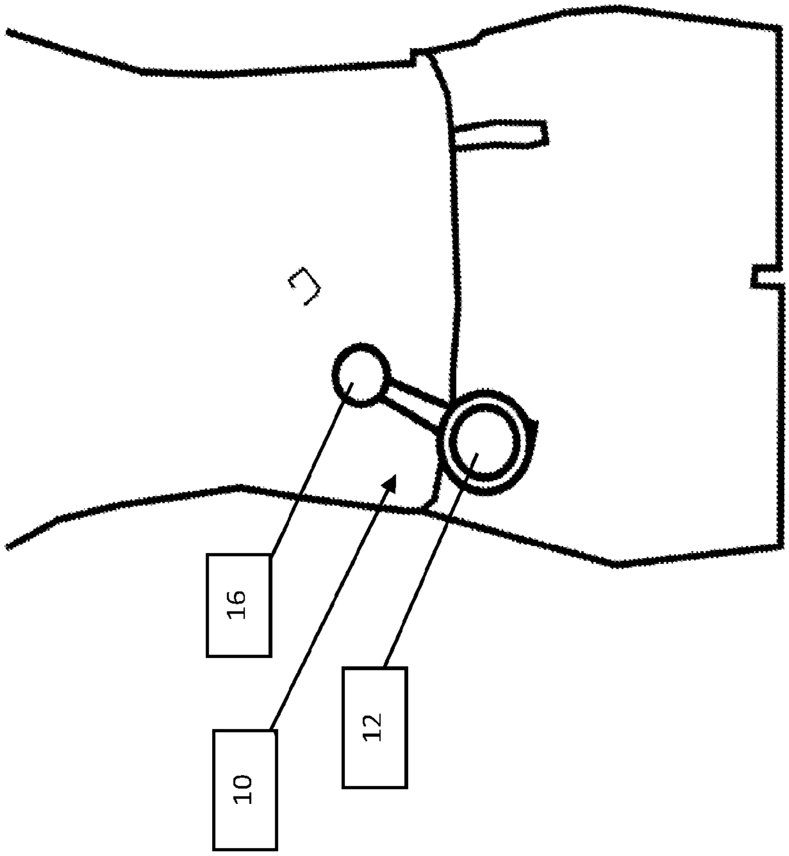
Figure 80B:
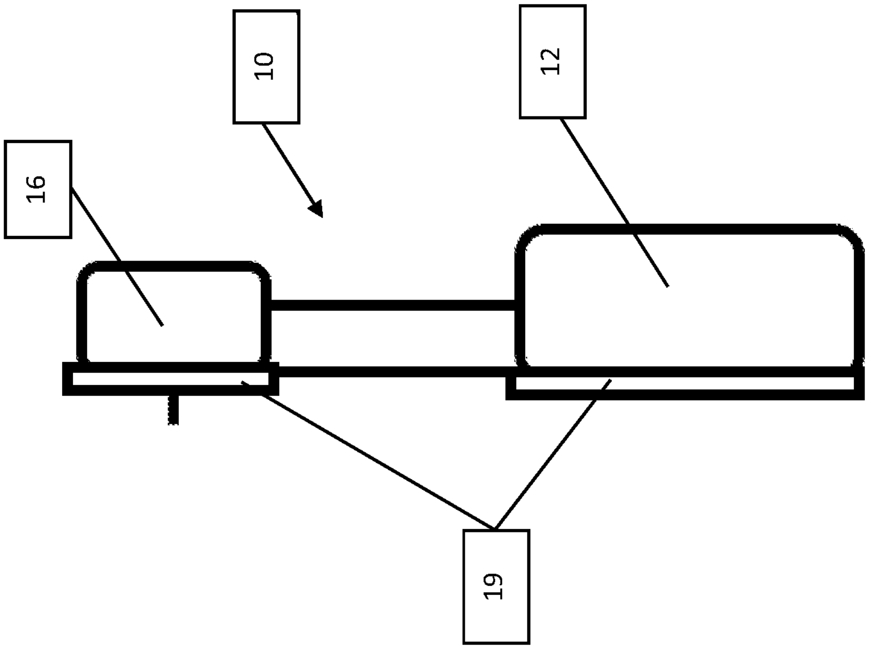
Figure 80A:
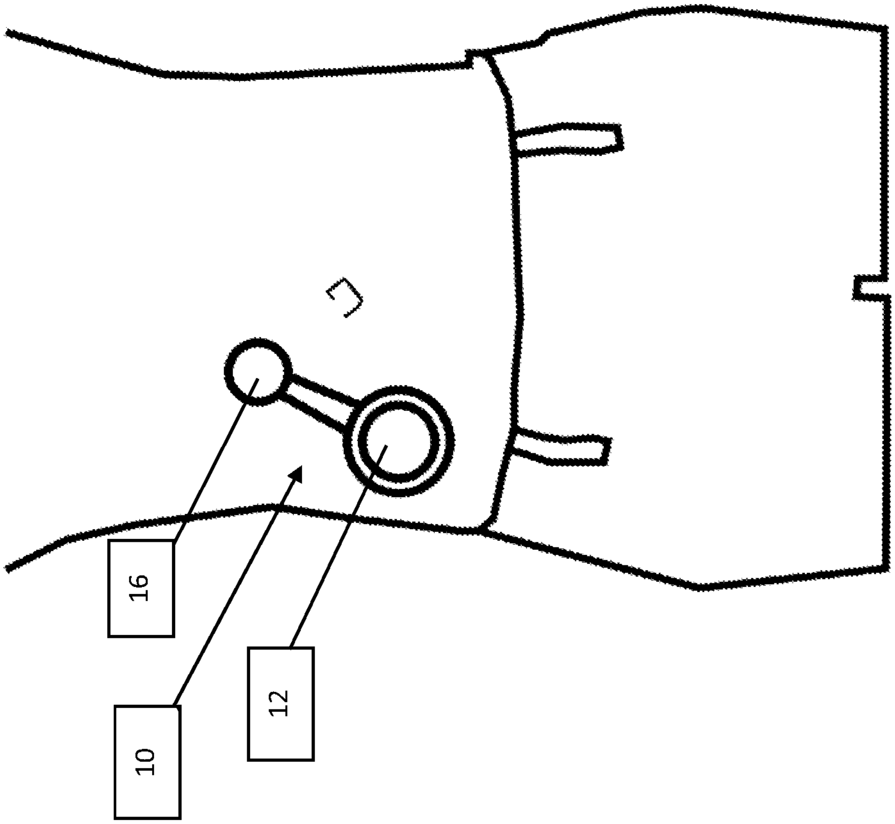
Figure 81B:
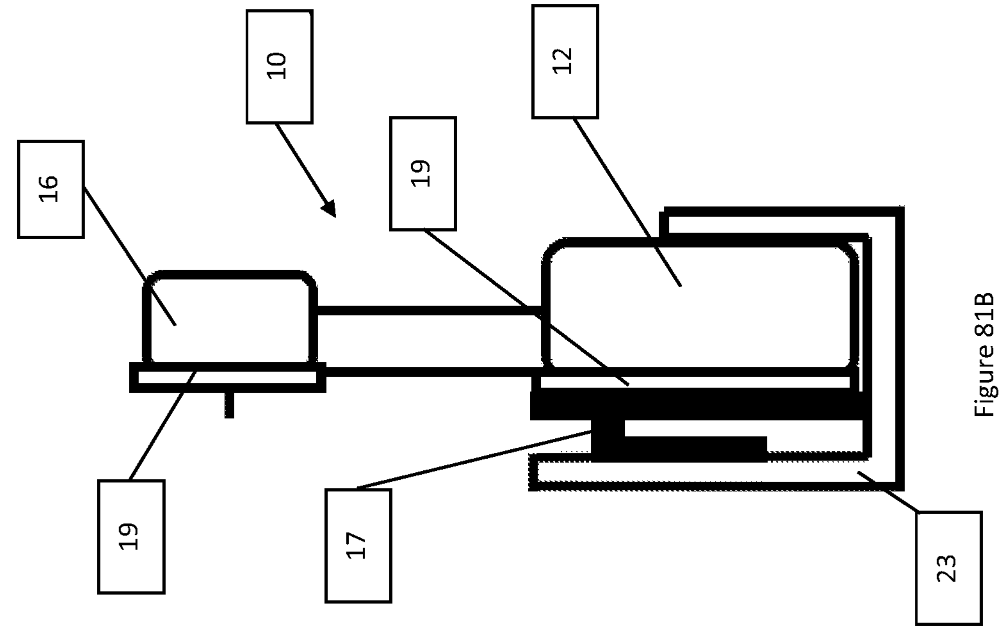
Figure 81A:
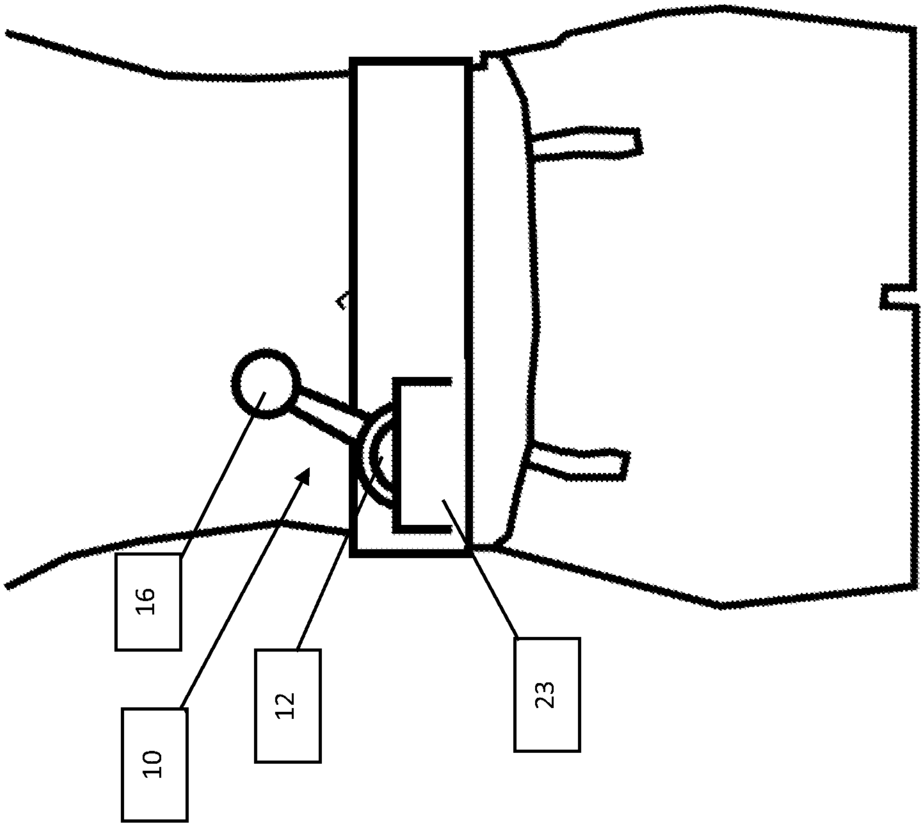

The drug delivery device 10 may be formed multi-bodied, including a body portion corresponding to the body 12 and a separate body portion corresponding to the needle support 16. In addition, the drug delivery device 10 is particularly well-suited for mounting to the physical anatomy of a patient for injection. This allows for on-body injection, particularly allowing for delivery of drug over an extended period-of-time. A patient may conveniently have the drug delivery device 10 mounted on their skin or to a piece of clothing (e.g., clipped to a belt), during injection, allowing for other activities, such as reading, watching entertainment, and so forth. The drug delivery device 10 is preferably for one-time use, being temporarily mounted to the patient's body, as shown in FIGS. 79A-81B. As shown in FIGS. 80A-80B, releasable adhesive 19 may be provided on portions of the drug delivery device 10 corresponding to the body 12 and the needle support 16, such as a pressure-sensitive adhesive, to securely mount the drug delivery device 10 to the patient's body. In addition, or as an alternative, as shown in FIGS. 81A-81B, the drug delivery device 10 may be provided with a belt or strap 21 for securing about a portion of the patient's body, such as the waist, in mounting the drug delivery device 10 to the patient's body. It is preferred that the drug delivery device 10 be securely mounted to minimize inadvertent removal of the needle 15 from the patient during drug delivery. The belt or strap 21 may be provided with a pocket 23 for receiving all or a portion of the drug delivery device 10, such as the portion of the drug delivery device 10 corresponding to the body 12. The needle support 16 may be mounted to the patient with the adhesive 19 with the body 12 portion of the drug delivery device 10 being in the pocket 23 to be supported by the belt or strap 21. Further, as shown in FIGS. 79A-79B, the drug delivery device 10 may be provided with a clip 17 for mounting onto a waistband, or other portion, of a patient's clothing. The needle support 16 may be mounted to the patient with the adhesive 19 with the body 12 being supported by the clip 17. The clip 17 may be secured to the body 12 using any known mode of connection, including fusion, adhesion, and so forth. The clip 17 may be used also in connection with the belt or strap 21, to act as a spacer in the product 23 to better ensure that the body 12 is supported in a stable manner. The clip 17 may be also removable to provide a patient with the option of using it as a clip, or, with removal of the clip 17, using an underlying adhesive 19 in mounting to the body.

As shown in FIG. 3, the drug delivery device 10 may include a housing 9 which encases the body 12. The housing 9 may also contain the pump 18 and the control 20. The one or more outlet ducts 25 may extend through a portion of the housing 9, for example, into communication with the at least one fluid passageway 13 located in the tether 11. A channel may be defined in the housing 9, or tubing or the like may be provided, to define the portions of the one or more outlet ducts 25 extending through the housing 9.

Figure 11:
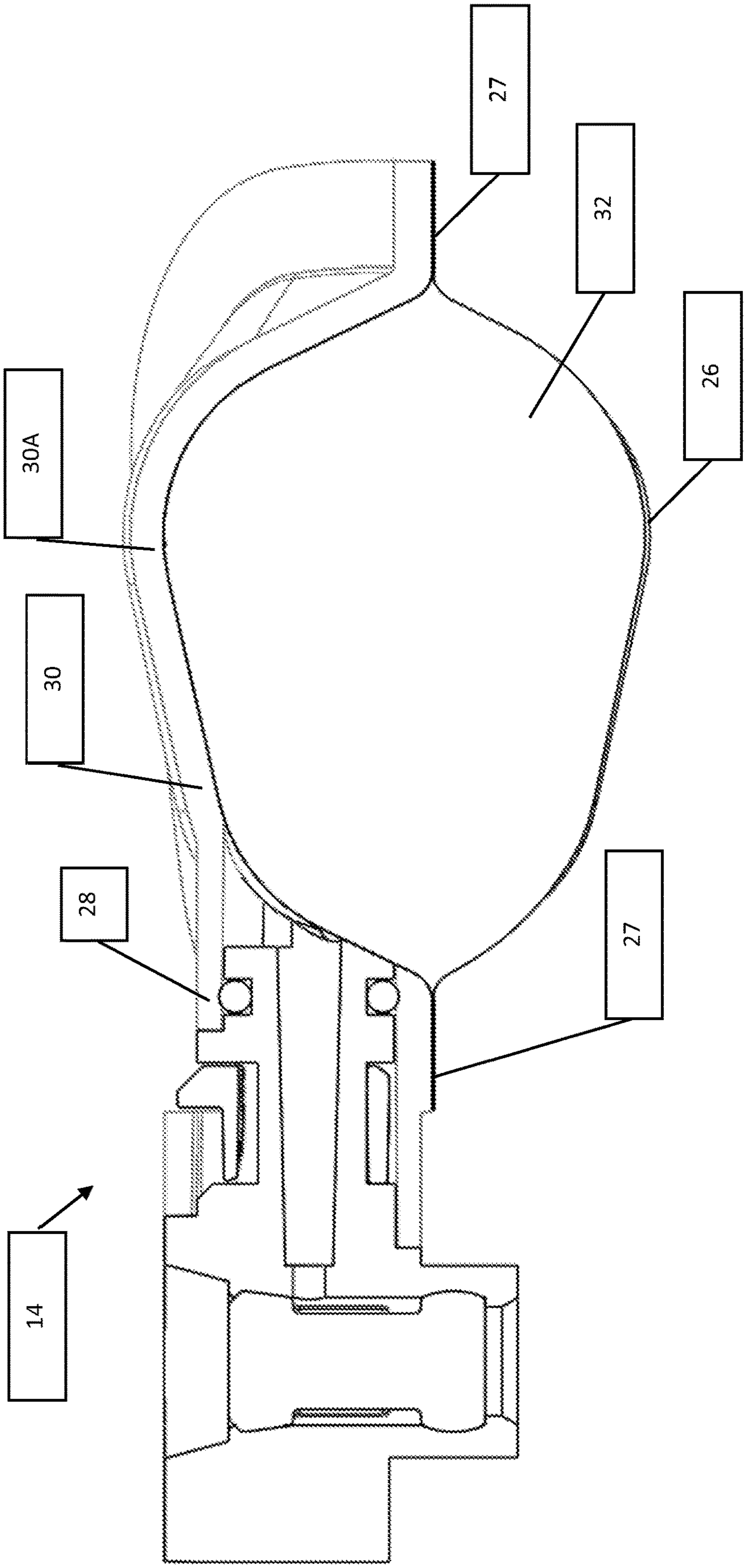
FIG. 11 is a section view of the drug cartridge of FIG. 10, without the lower portion of the rigid shell.
Figure 12:
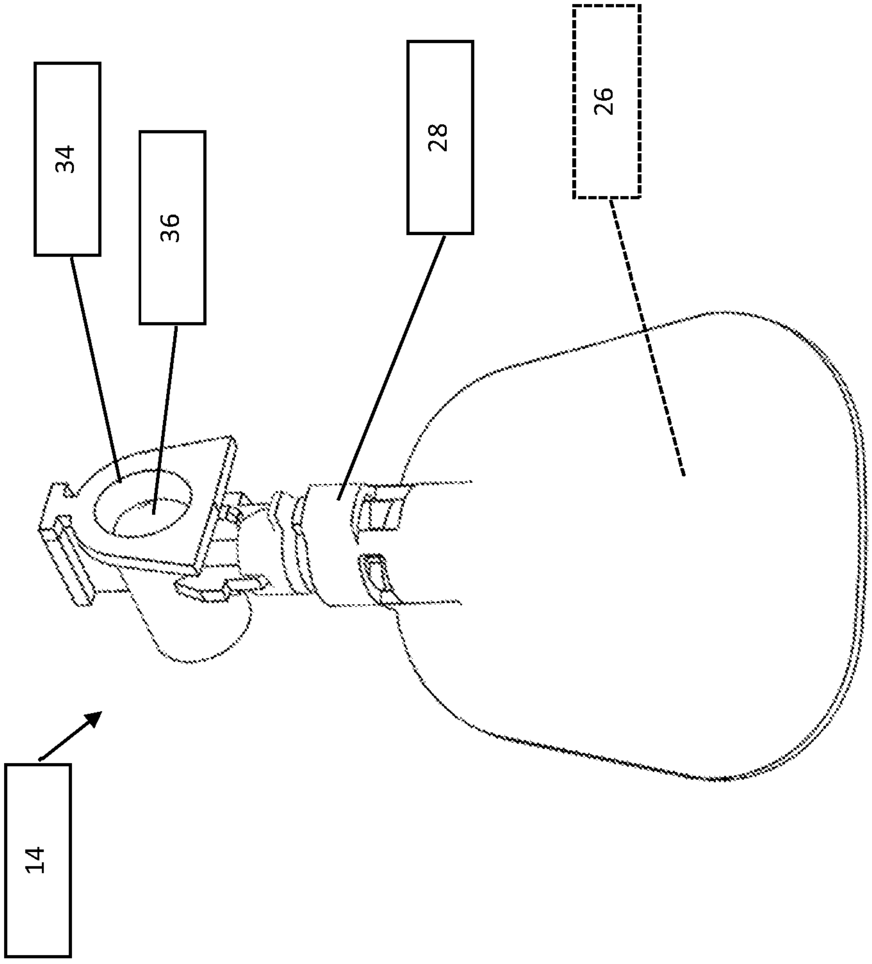
FIG. 12 shows a drug cartridge in a vented state in accordance with the subject invention.

In a further aspect of the subject invention, methods of preparing the drug cartridges 14 are provided. With reference to FIGS. 7-36 and 92-103, the drug cartridges 14 may be provided to be initially separate from the body 12, particularly to allow for pre-filling thereof with drug. As will be appreciated by those skilled in the art, the drug cartridges 14 may be formed in various manners consistent with the disclosure herein. As shown in FIG. 12, the drug cartridges 14 may be each formed to include a reservoir 26 and a cartridge support body 28. The cartridge support body 28 includes a fluid outlet 34 and an internal lumen 36 for conveying drug from the reservoir 26 to the fluid outlet 34.

Figure 8:
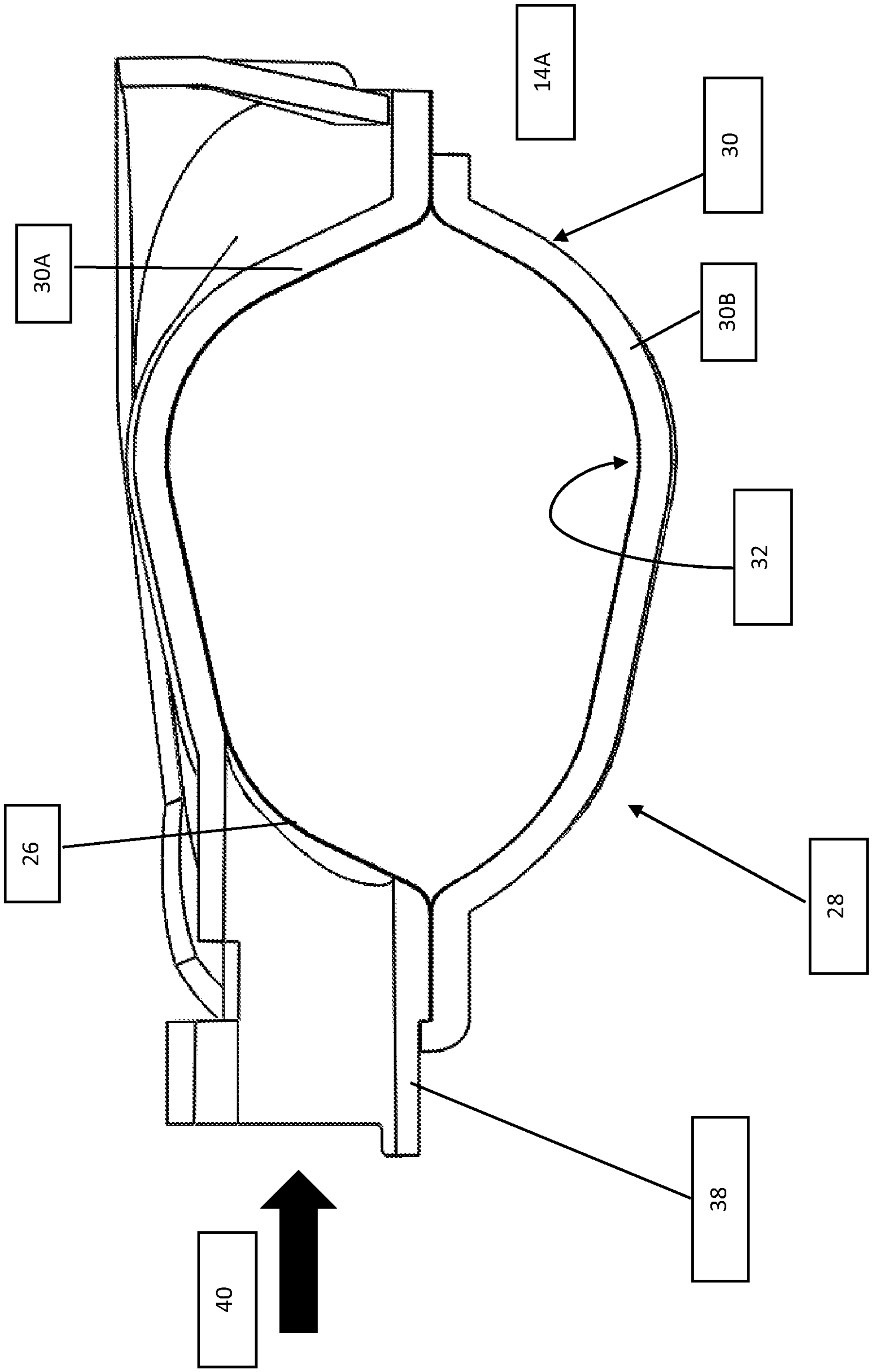
FIG. 8 is a section view of a reservoir section of a drug cartridge in accordance with the subject invention.
Figure 8A:
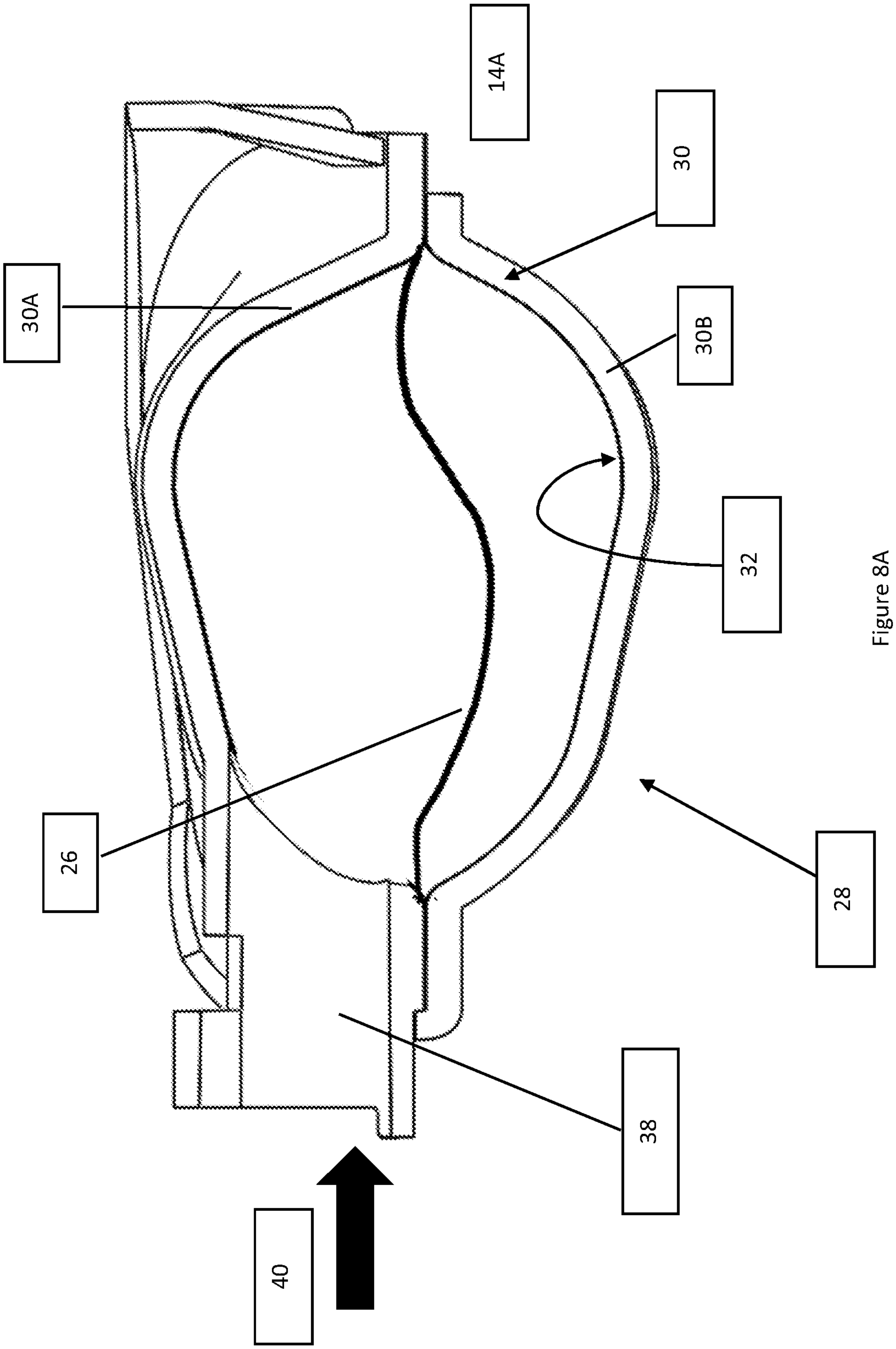
FIG. 8A shows the reservoir component of FIG. 8 with a partially collapsed reservoir.
Figure 10:
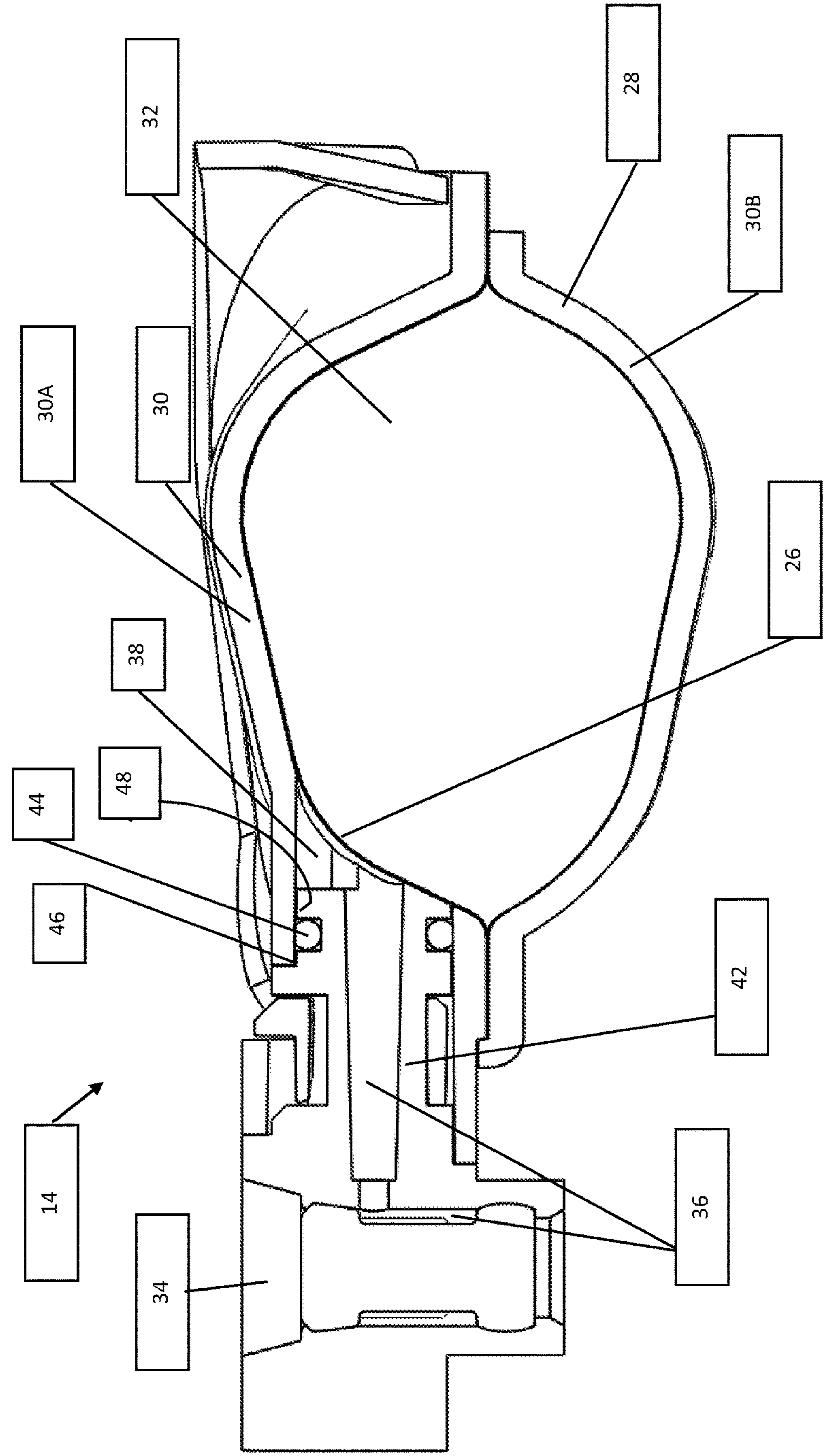
FIG. 10 is a section view of a drug cartridge, illustrating a radially sealed closure, in accordance with the subject invention.
Figure 19:
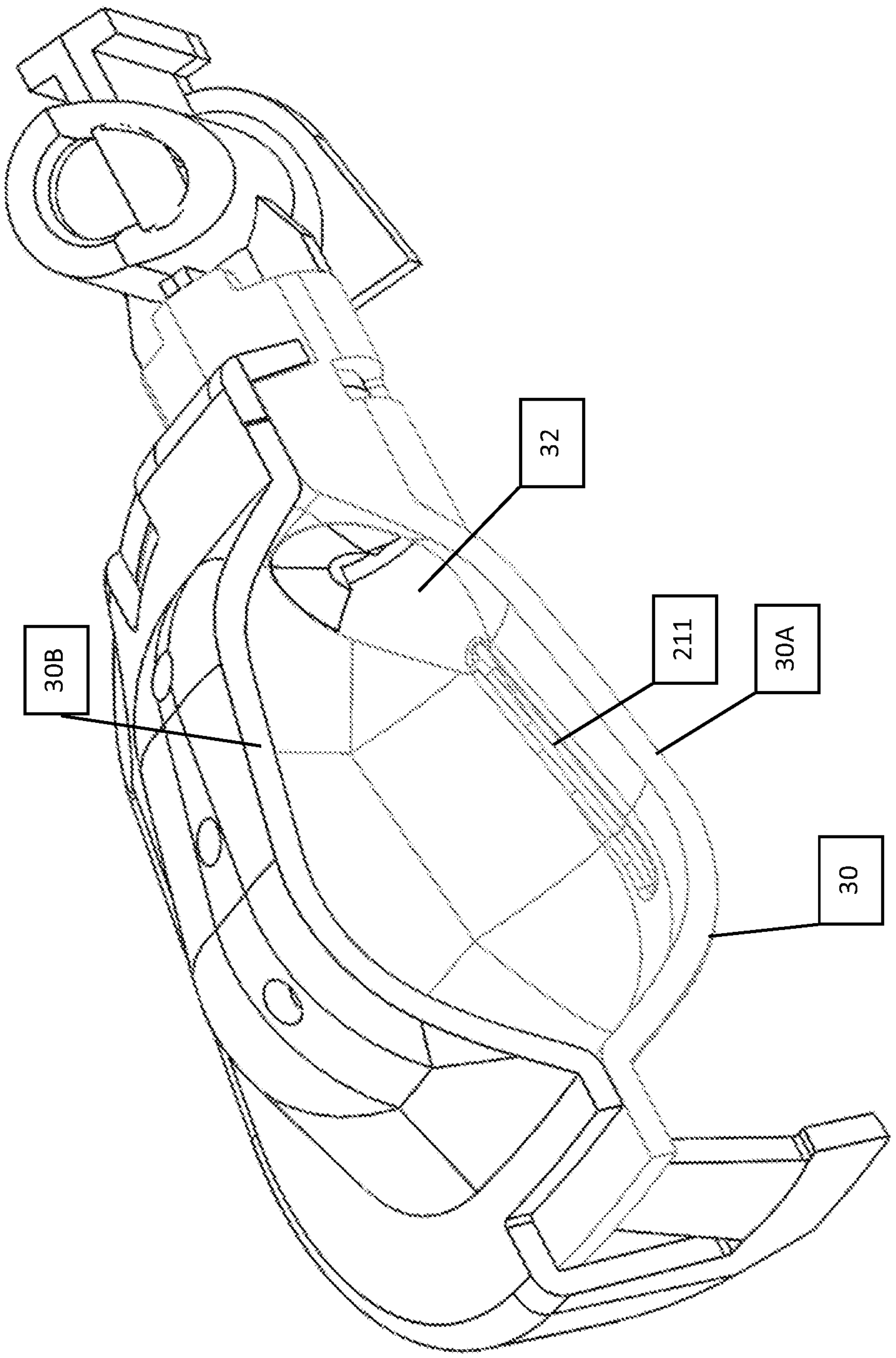
FIG. 19 is a section view of a drug cartridge, illustrating an internal flow channel, in accordance with the subject invention.
Figure 21:
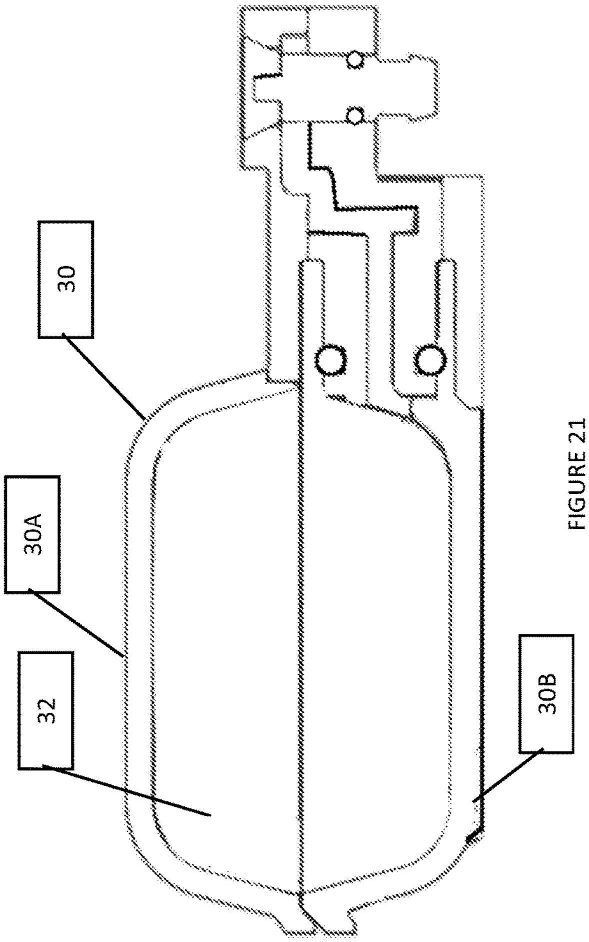
FIG. 21 shows a drug cartridge with a rigid shell that allows for full expansion of the reservoir, in accordance with the subject invention.
Figure 22:
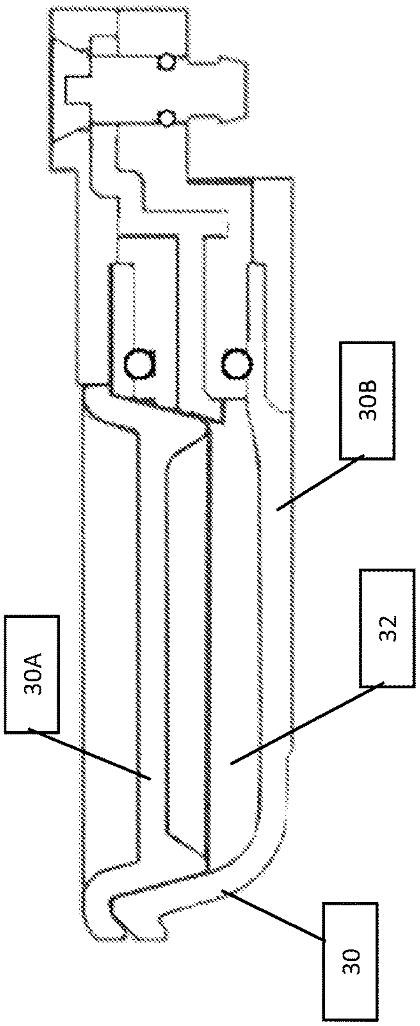
FIG. 22 shows a drug cartridge with a rigid shell that constrains the expansion of the reservoir, in accordance with the subject invention.

To avoid the need for venting of the reservoir during drug delivery, the reservoir 26 may be formed deformable to allow for collapsing during removal of drug. As shown in FIG. 10, the cartridge support body 28 may include a rigid shell 30, which ensconces the reservoir 26. The rigid shell 30 defines an internal volume 32. The rigid shell 30 maintains its shape with the collapsing of the reservoir 26 during use, as shown in FIG. 8A. The rigid shell 30 may be formed from an upper portion 30A joined to a lower portion 30B, e.g., by adhesion, fusion, welding, snap-engaging, heat sealing, and so forth. This two-part arrangement allows for the upper and lower portions 30A, 30B to be placed about the reservoir 26 during assembly. As shown in FIG. 19, one or more channels 211 may be formed on interior portions of the shell 30, e.g., in the upper portion 30A, to provide one or more surface disruptions about the reservoir 26. As shown, for example, in FIG. 29, the channels 211 may be located about the shell 30 and formed as through-holes in the shell 30 to provide venting for the internal volume 32, particularly during expansion and collapse of the reservoir 26 therewithin. The surface disruptions may minimize adhesion of the reservoir 26 to the shell 30 during use, thus, allowing for improved filling and voiding of the reservoir 26. In addition, as shown in FIGS. 21-22, the upper and lower portions 30A, 30B may be formed with concavity or convexity to delimit different size reservoirs.

The reservoir 26 may be elastomeric or a thermoformed membrane, formed as a pouch or joined components (e.g., heat-sealed, laser welded, fused, adhered, and so forth). Compatibility with accommodated drug components and resistance to through-transmission of contaminants are critical for the reservoir 26. As shown in FIG. 11, the reservoir 26 may include a flange 27 which is located between the upper and lower portions 30A, 30B of the rigid shell 30. The lower portion 30B is shown removed in FIG. 11 to best show the flange 27.

In an embodiment, the drug cartridge 14 may be modular to facilitate pre-filling with drug, with the cartridge support body 28 being divided over multiple parts. As shown in FIG. 8, a reservoir section 14A of the drug cartridge 14 may include the reservoir 26, the rigid shell 30, and a filling port 38 defining an open passageway into the reservoir 26. As shown in FIG. 8 by arrow 40, after sterilization of the reservoir section 14A, drug may be introduced through the filling port 38 into the reservoir 26. The drug may be one or more drug components, e.g., a combination of two different drugs, in various physical states. As discussed below, the drug may include solid components which may be reconstituted by the drug delivery device 10 to be ready for use.

Figure 9:
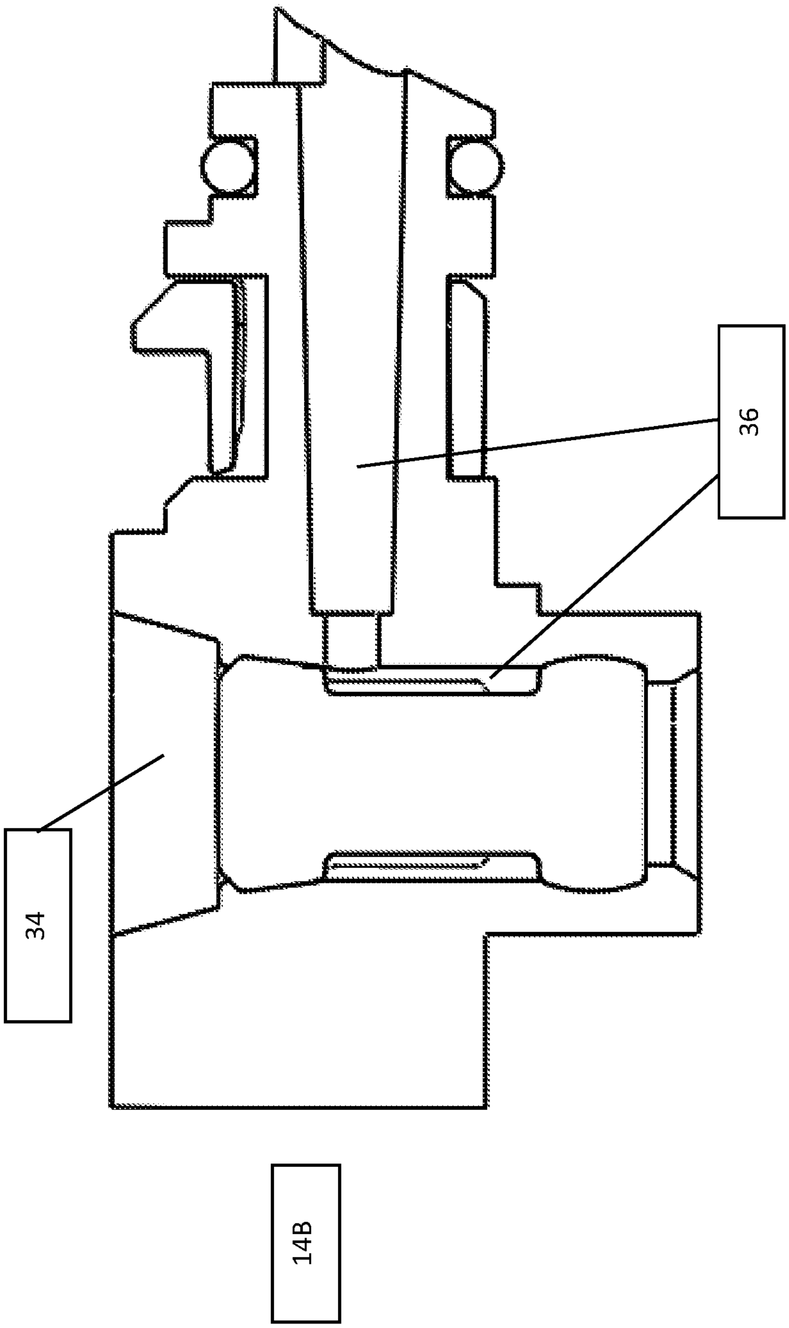
FIG. 9 is a section view of a plug adapter component of a drug cartridge in accordance with the subject invention.

As shown in FIG. 9, a plug adapter 14B of the drug cartridge 14 may be separately provided which is configured to mount to the reservoir component 14A. The plug adapter 14B may include the fluid outlet 34 and the internal lumen 36.

Separate from the filling of the reservoir 26, the internal lumen 36 of the plug adapter 14B may be sterilized with at least one lumen seal being formed on the plug adapter 14B across the sterilized internal lumen 36 to limit ingress of contaminants. The at least one seal may separate the fluid outlet 34 from the sterilized internal lumen 36 or may be located externally of the fluid outlet 34. Details of seal formation are discussed below. As will be recognized by those skilled in the art, the entire internal lumen 36 may not be sealed. For example, a portion of the internal lumen 36 adjacent to the fluid outlet 34, along with the fluid outlet 34, may be outside the seal.

Figure 7:
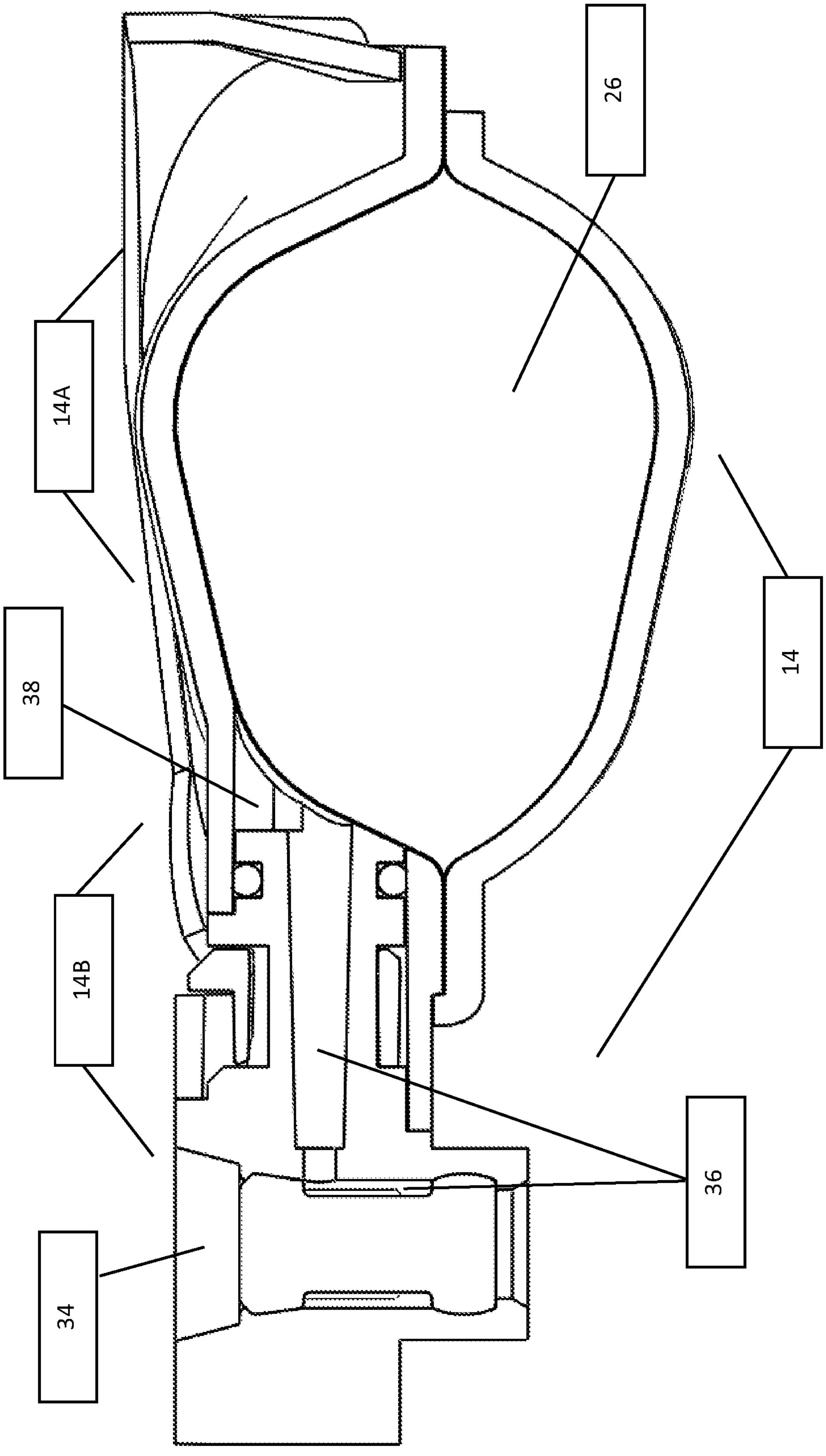
FIG. 7 is a section view of a drug cartridge, including the reservoir section and plug adapter in an assembled state, in accordance with the subject invention.

With the reservoir 26 having been filled, and the internal lumen 36 having been sterilized, the plug adapter 14B may be assembled with the reservoir section 14A to form the drug cartridge 14, as shown in FIGS. 7 and 10. The plug adapter 14B may act to plug the filling port 38. As assembled, a portion of the internal lumen 36 extends through the filling port 38 into communication with the reservoir 26. With this arrangement, a fluid pathway is defined from the reservoir 26 to the fluid outlet 34.

The reservoir section 14A and the plug adapter 14B may be manufactured, placed in sealed packaging, sterilized, and assembled in separate processes. This allows for bulk processing. Once sterilized, the packaged components may be maintained in a clean environment awaiting use, as described herein. The sterilized components, may be handled and assembled in a clean, controlled environment, such as under a clean controlled-environment hood and/or in a clean controlled-environment enclosure or room.

Alternatively, the drug cartridge 14 may be formed as a single component, not requiring the separate reservoir component 14A and plug adapter 14B. As shown in FIGS. 92-95, the upper portion 30A (being shown in a lower position in FIG. 94—it is taken that the upper and lower portions 30A, 30B are first and second portions independent of their gravitational orientation) may be provided with the filling port 38. The flange 27 on the upper portion 30A may be extended to include wing portion 27A. The wing portion 27A is disposed at an angle relative to a plane defined at an interface of the upper and lower portions 30A, 30B. The wing portion 27A also extends outwardly, away from the reservoir 26 to define a free end 27B. The fluid outlet 34 may be defined in the wing portion 27A in proximity to the free end 27B. The internal lumen 36 is provided to extend from the reservoir 26 to the fluid outlet 34 to define a flow path to the fluid outlet 34 from the reservoir 26. As shown in FIG. 90, the wing portion 27A, with the fluid outlet 34 being defined thereon, allows for the drug cartridge 14 to be mounted to a face of the body 12 with the reservoir 26 radiating outwardly from the circumference of the body 12. This allows for a smaller footprint for the drug delivery device 10. The wing portions 27A for the reservoirs 14 may be formed to be tessellated when mounted to the body 12, generally with no gaps therebetween.

With the arrangement of FIGS. 92-103, the filling port 38 and the internal lumen 36 are separately provided. In this manner, the reservoir 26 may be filled through the filling port 38 with the filling port 38 being subsequently sealed, e.g., with an elastomeric plug and/or a crimped cap. To minimize hindrance of the internal lumen 36 during filling, it is preferred that the internal lumen 36 be located in proximity to the filling port 38. This allows for the internal lumen 36 to be located above the majority of the reservoir 26 with the drug cartridge 14 in an upright position for filling, which is preferred for lyophilization.

As described above, the upper portion 30A may be formed to be rigid and to ensconce the reservoir 26. Alternatively, as shown in FIGS. 92-103, the reservoir 26 may be formed integrally with the upper and lower portions 30A, 30B. For example, the flange 27 may be rigid and bound each of the upper and lower portions 30A, 30B. Flexible reservoir walls 26R, 26S may be provided on the upper and lower portions 30A, 30B, respectively, being edge mounted to the flange 27. The flexible reservoir walls 26R, 26S, along with the flange 27, collectively define the reservoir 26. The flexible reservoir walls 26R, 26S may be formed of any elastomeric or thermoformable membrane, such as a film of cyclic olefin copolymer (COC), optionally with a layer of poly-chloro-trifluoro-ethylene (PCTFE). The flexible reservoir walls 26R, 26S are formed to be responsive to the filling of the reservoir 26, as well as, removal of drug therefrom. The flexible reservoir walls 26R, 26S are collapsible with the removal of drug from the reservoir 26 with the reservoir 26 not being vented.

Figure 96:
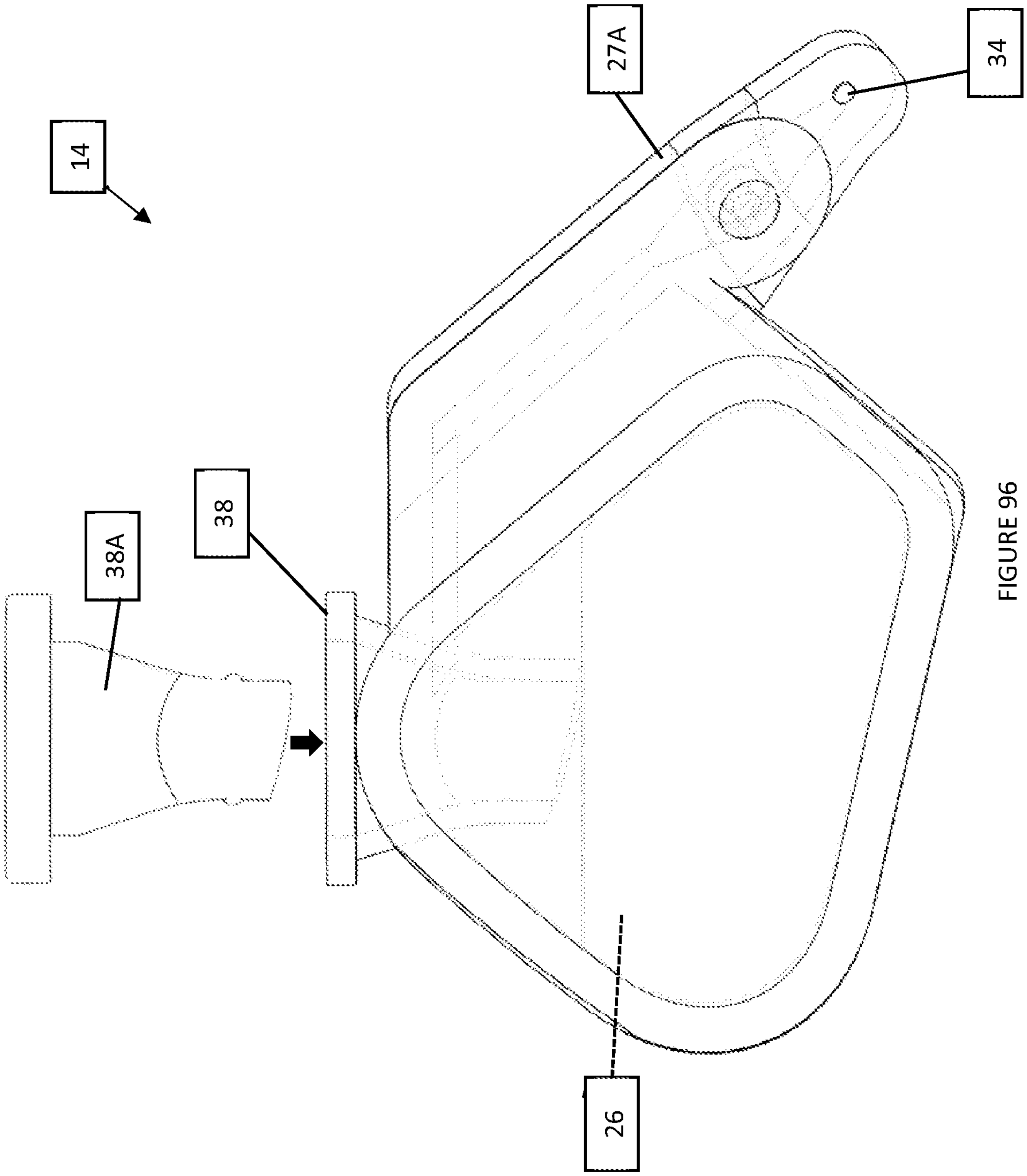

As part of the filling of the reservoir, the drug cartridge 14 may be utilized for lyophilization of drug. Here, drug is initially introduced in a liquid state into the reservoir 26. The plug adapter 14B may include a vent adjustable from an open state to a closed state. Once filled and assembled, the drug cartridge 14, with the vent in an open state, may be subjected to lyophilization conditions (low temperature and vacuum to extract moisture) to cause the drug in the reservoir 26 to lyophilize. Subsequently, the vent on the plug adapter 14B may be adjusted to the closed state. Likewise, as shown in FIG. 96, the filling port 38 may be provided with an adjustable vent plug 38A to facilitate lyophilization of drug in the reservoir 26.

Figure 58:
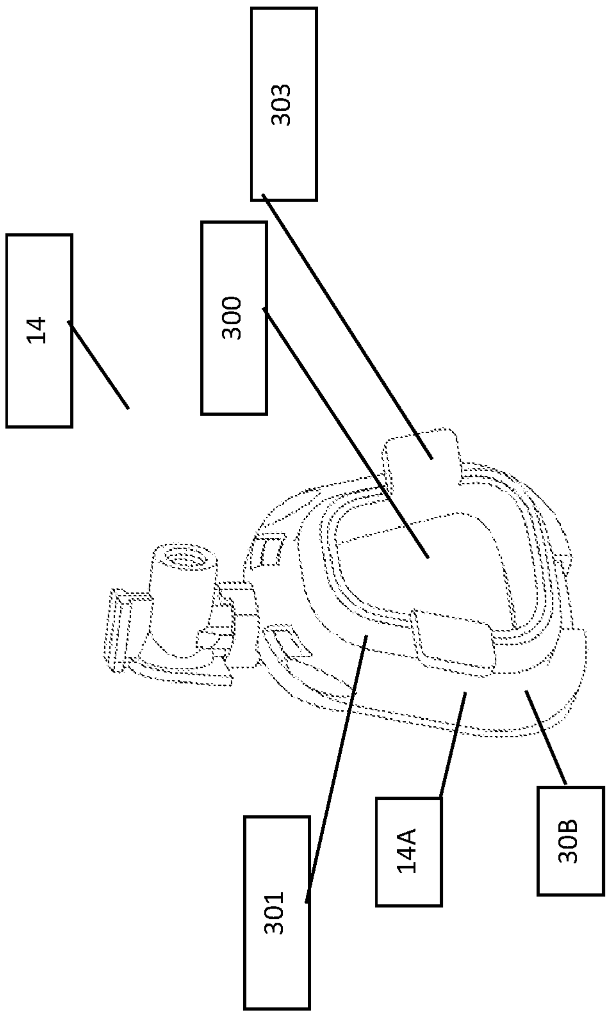
FIG. 58 shows a drug cartridge with a reservoir support useable for dry products, in accordance with the subject invention.
Figure 59:
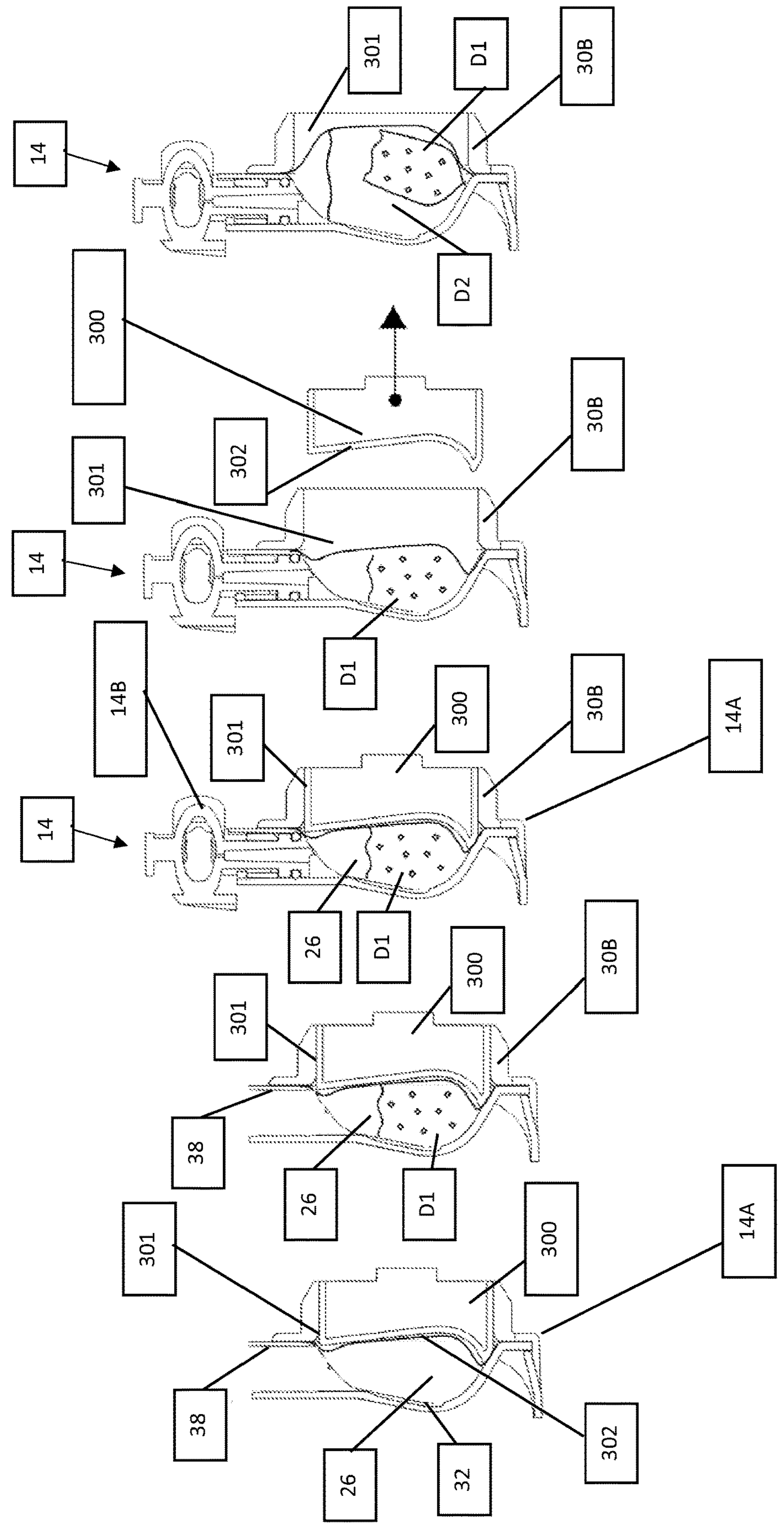
FIG. 59 shows the reservoir support of FIG. 58 in use.

Alternatively, drug in dry form may be initially introduced into the reservoir 26 with subsequent introduction of a diluent to reconstitute the drug into liquid form at the time of use of the drug delivery device. To limit "dead space" in the reservoir 26 during the loading of drug in dry form, a reservoir support 300 may be utilized, as shown in FIGS. 58-64E. By minimizing "dead space," empty volume inside the reservoir 26 is limited. As shown in FIGS. 58-59, the reservoir section 14A, particularly the lower portion 30B of the rigid shell 30, may be formed with an opening 301 formed to receive the reservoir support 300 in the internal volume 32, adjacent to the reservoir 26. The reservoir support 300 includes a front face 302 for limiting the expansion of the reservoir 26. The front face 302 may be contoured to provide the reservoir 26 with a larger volume away from the filling port 38. In this manner, as shown in FIG. 59, with drug in dry form D1 introduced in the reservoir 26, the front face 302 limits the expansion of the reservoir 26. In a filled state, the reservoir 26 may be bulb-shaped. Once the reservoir 26 has been filled with the drug in dry form D1, the plug adapter 14B or the vent plug 38A may be mounted to the reservoir section 14A (upper portion 30A) and then the reservoir support 300 may be removed. Drug in the form of diluent D2 may be then added during reconstitution, with the reservoir 26 expanding. Back pressure may be monitored in loading the drug in the form of diluent D2 to determine the fill level. With minimization of "dead space," pockets of compressible gases are minimized, thus, allowing for pressure readings which are more accurate of actual fill levels. In addition, better control over concentration of the resulting liquid drug may be achieved.

Figure 60:
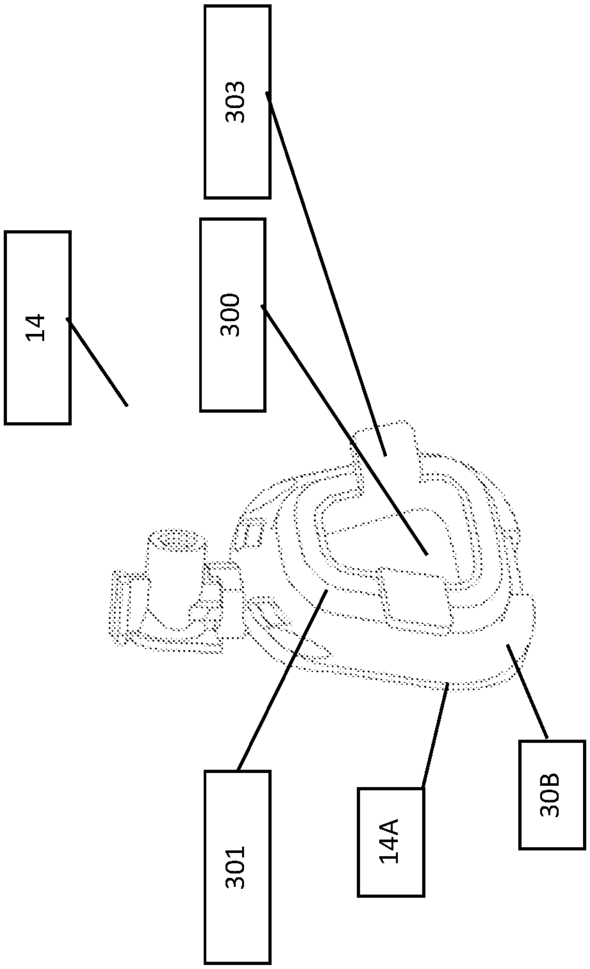
FIG. 60 shows a drug cartridge with an alternate reservoir support useable for dry products, in accordance with the subject invention.
Figure 61:
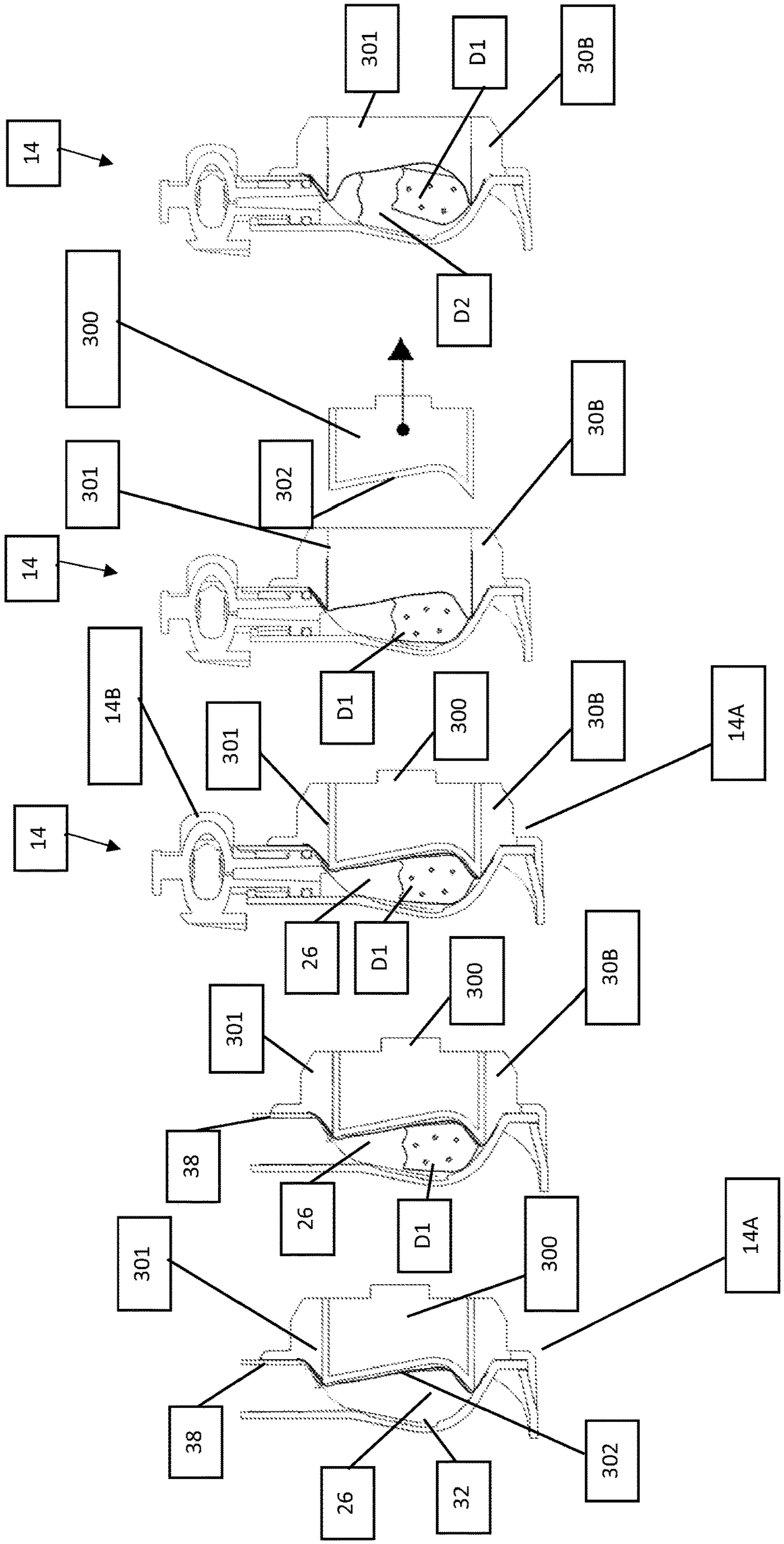
FIG. 61 shows the reservoir support of FIG. 60 in use.

As shown in comparing FIGS. 60 and 61, the reservoir support 300, including the front face 302, may be provided with different configurations corresponding to different volumes of drug. FIG. 61 is directed to a smaller drug volume, requiring less volume in the reservoir 26, than that shown in FIG. 59. As such, the reservoir support 300 is provided with added length to extend deeper into the internal volume 32, positioning the front face 302 to provide greater restriction to the expansion of the reservoir 26 than as shown in FIG. 59.

Figure 62:
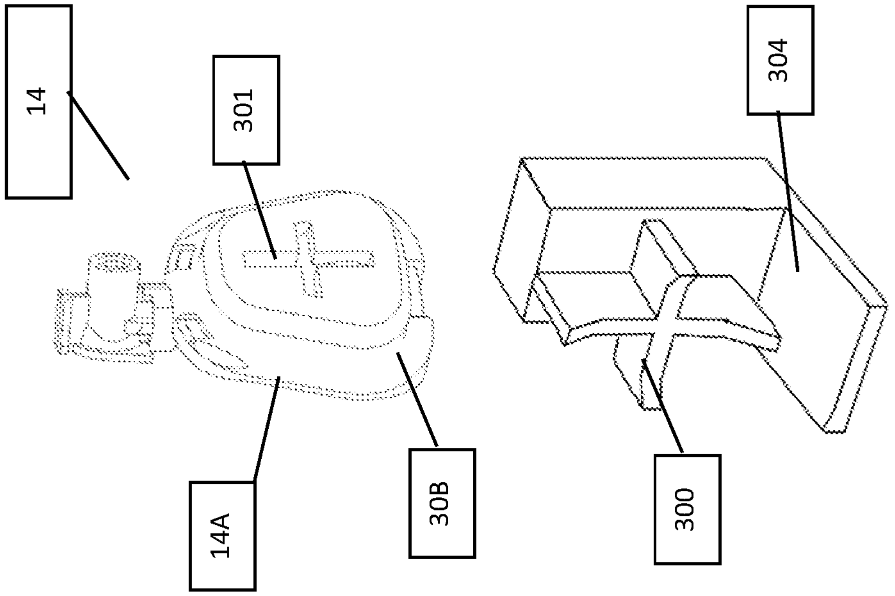
FIG. 62 shows a drug cartridge with a reservoir support fixture, in accordance with the subject invention.
Figure 63:
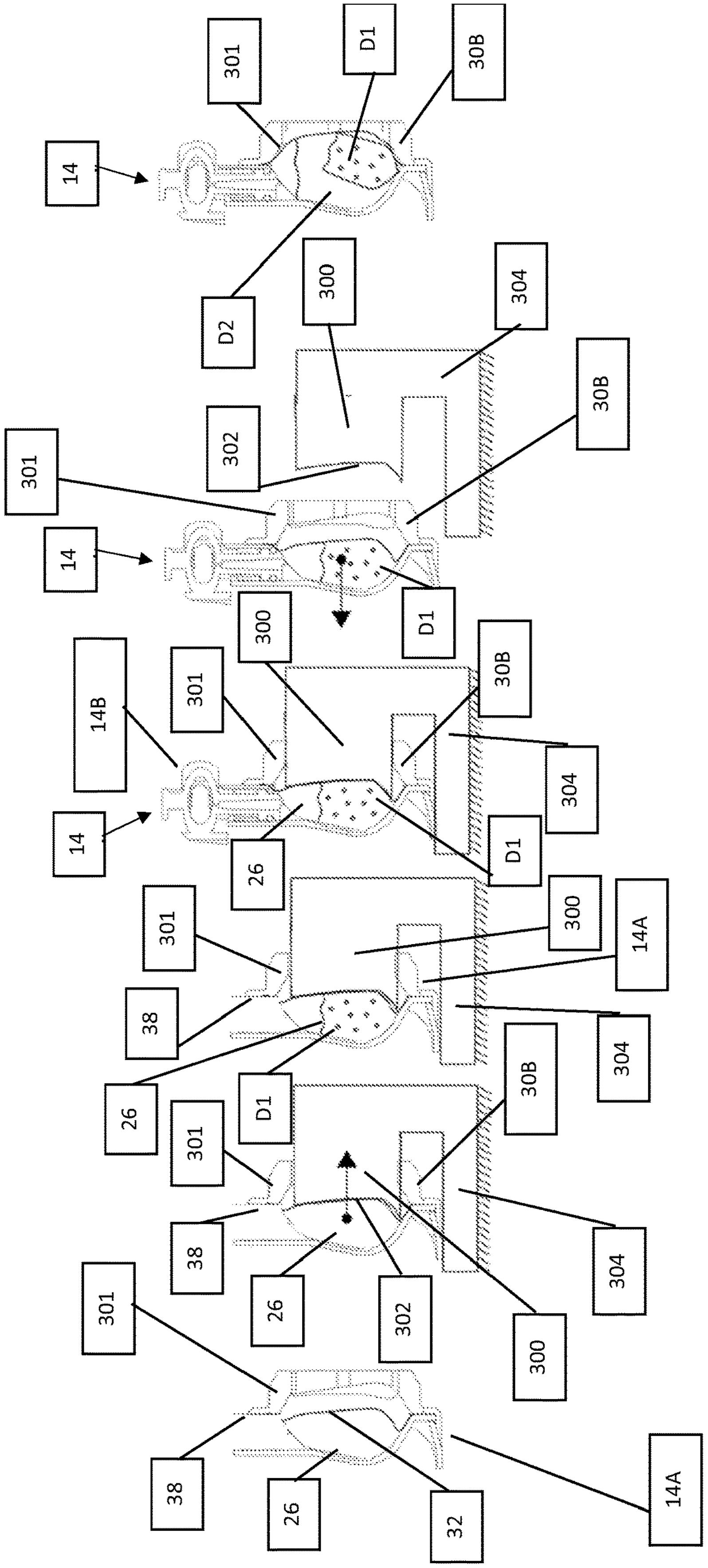
FIG. 63 shows the reservoir support fixture of FIG. 62 in use.

The opening 301 may be formed to closely receive the reservoir support 300 to allow for removable mounting of the reservoir support 300 in the opening (e.g, by friction or interference fit). To facilitate handling of the reservoir support 300, particularly for removal from the opening 301, outwardly extending tabs 303 may be provided, as shown in FIGS. 58 and 60. Alternatively, as shown in FIGS. 62 and 63, the reservoir support 300 may be provided as a separate tool or fixture which is insertable into the opening 301 formed on the rigid shell 30. This allows for the front face 302 to be positioned at various locations within the reservoir 26, depending on the extent of insertion of the reservoir support 300 into the rigid shell 30. The opening 301 may be provided with a cruciform shape, with the profile of the reservoir support 300 matching, to act as a guide therefor. In this configuration, as shown in FIGS. 62-63, the reservoir support 300 may be provided with a support 304.

Figure 64A:
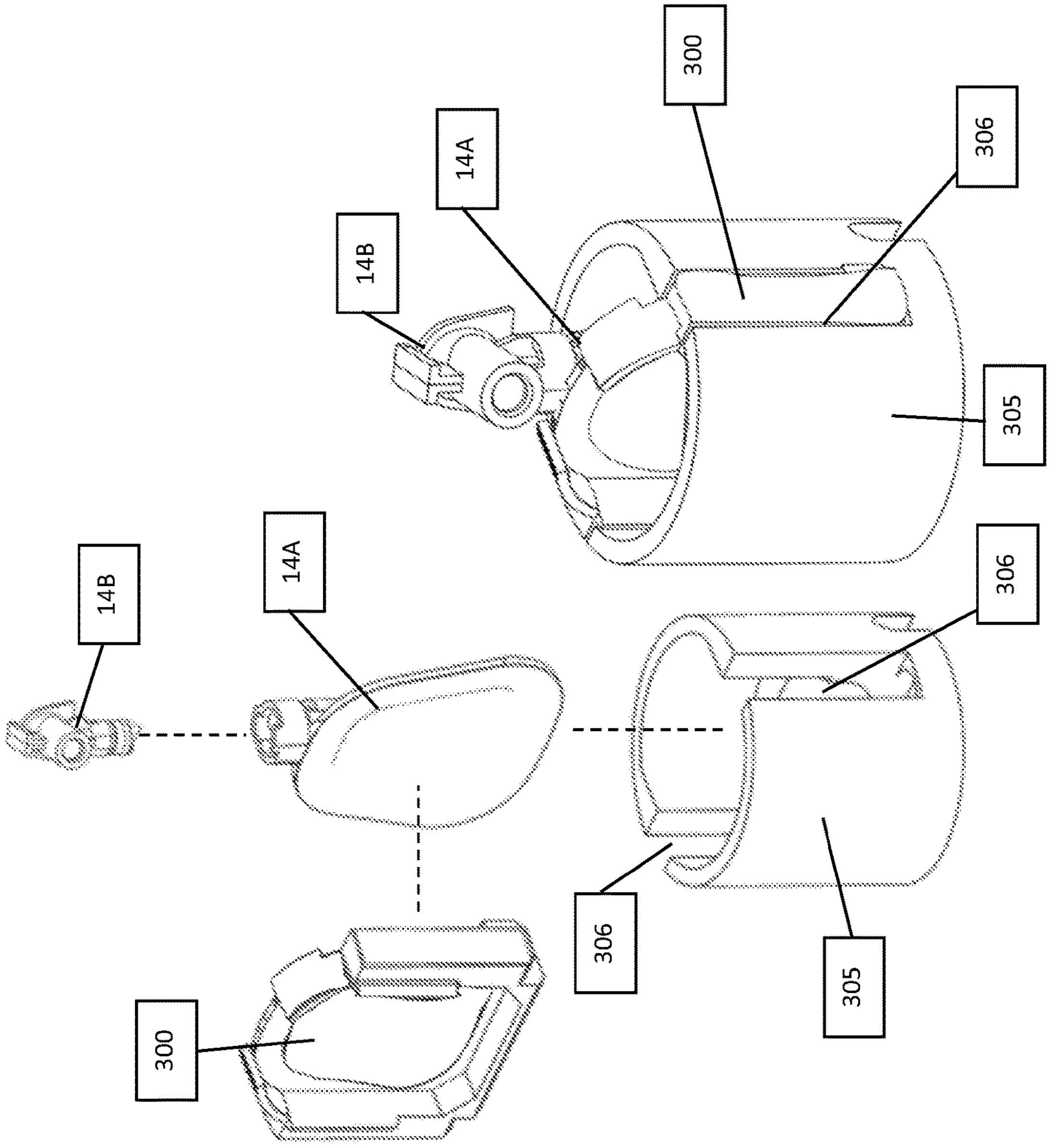
FIG. 64A shows a jig useable with the subject invention.

FIG. 64A shows a cup-shaped jig 305 having slots 306 formed therein for receiving the reservoir section 14A mounted to the reservoir support 300. The slots 306 may be formed to be slightly greater than the edge thickness of the reservoir support 300 for close fit therewithin. The jig 305 may be used to hold the reservoir section 14A/reservoir support 300 combination during any of the filling processes described above in connection with FIG. 59, 61, or 63. In addition, the jig 305 may be internally contoured to match the external surface contours of the reservoir section 14A and the reservoir support 300, in order to maximize contact area. Advantageously, the jig 305 may hold the reservoir section 14A and the reservoir support 300 during lyophilization. By matching the internal contour of the jig 305 with external surface contours of the reservoir section 14A and the reservoir support 300, heat transfer between the components may be maximized. Material for the jig 305 may be selected to have high thermal conductivity to promote heat transfer during lyophilization (e.g., anodized aluminum).

Figure 64B:
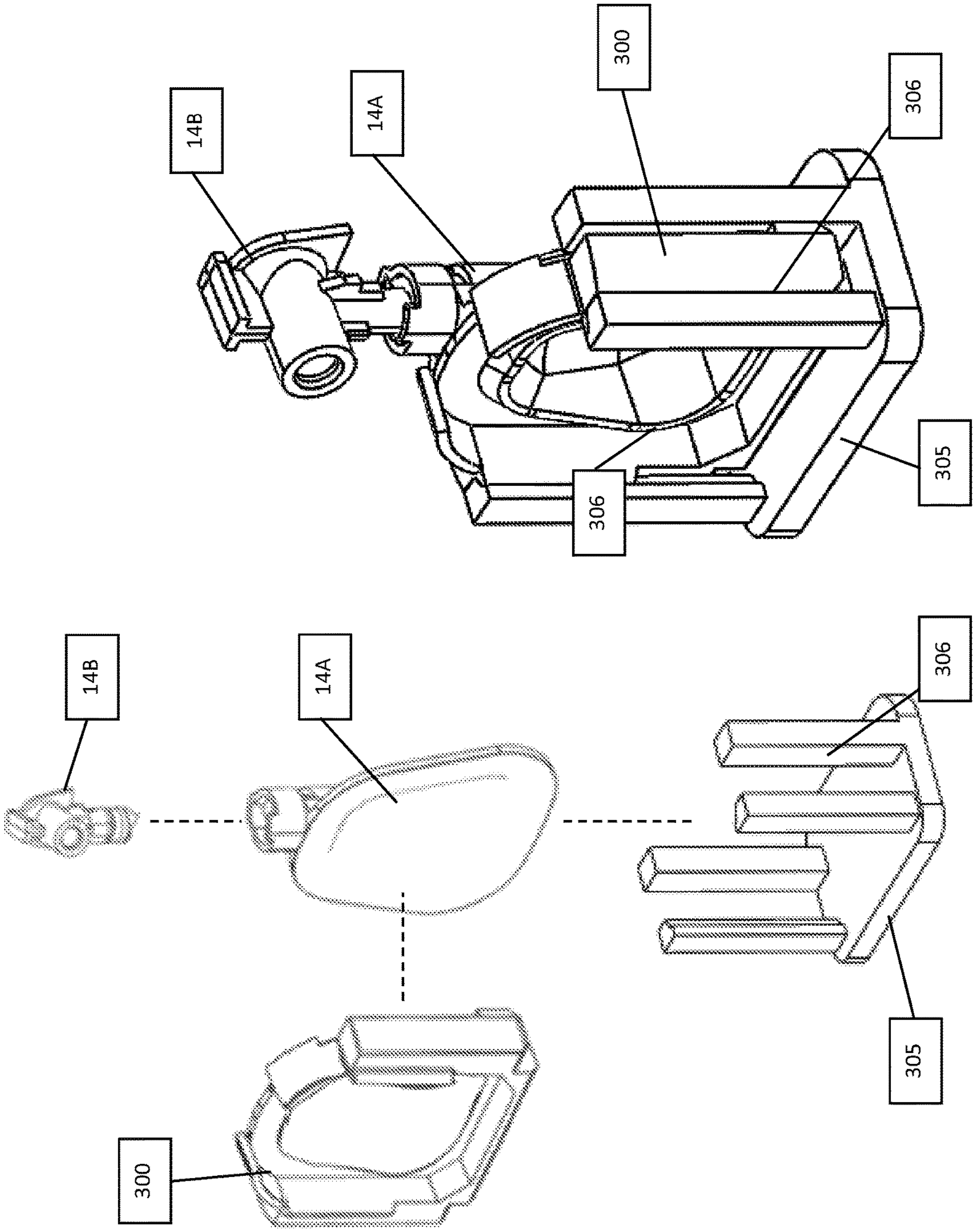
FIG. 64B shows an open jig useable with the subject invention.

An alternative open jig 307 is shown in FIG. 64B, having slots 306 formed therein for receiving the reservoir section 14A mounted to the reservoir support 300. The open jig 307 leaves exposed major portions of the reservoir section 14A to promote heat transfer via radiation and convection during lyophilization. This allows for more uniform heat transfer across the surface of the reservoir section 14A, as compared to the cup-shaped jig 305, which relies on conduction through the matching internal contours of the jig 305, as well as radiation and convection for the upper portion of the reservoir section 14A.

Figure 64C:
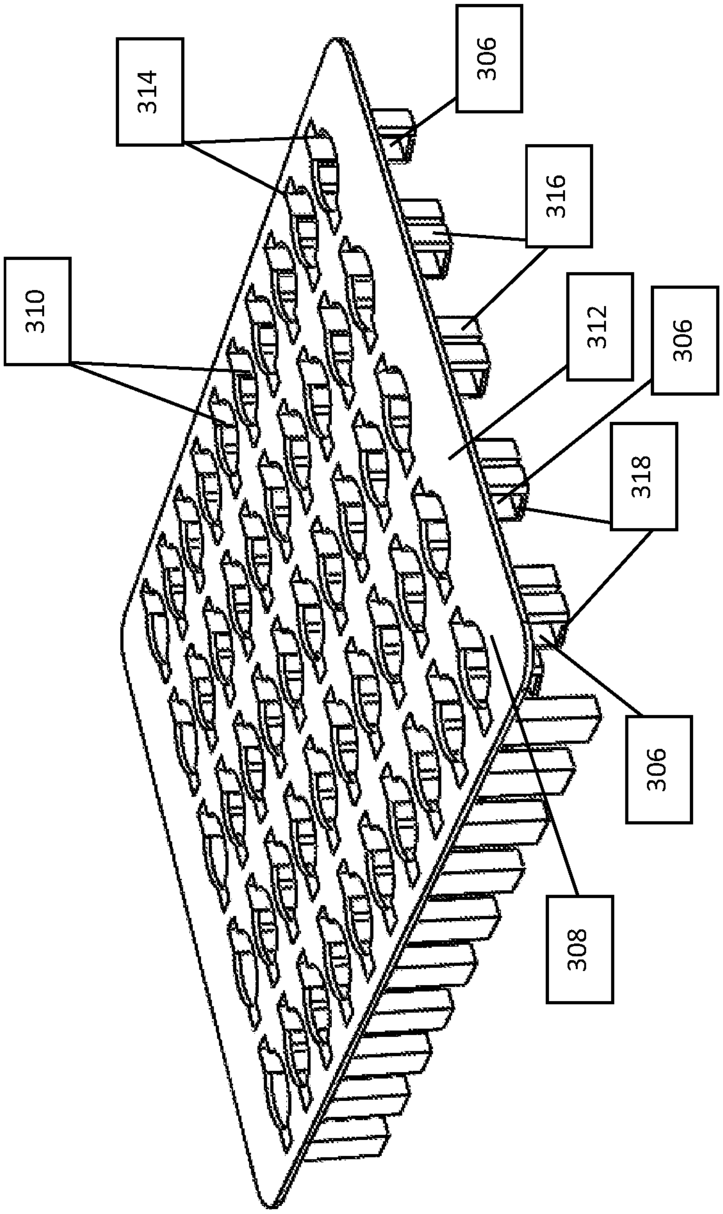
FIG. 64C shows a tray useable with the subject invention.
Figure 64D:
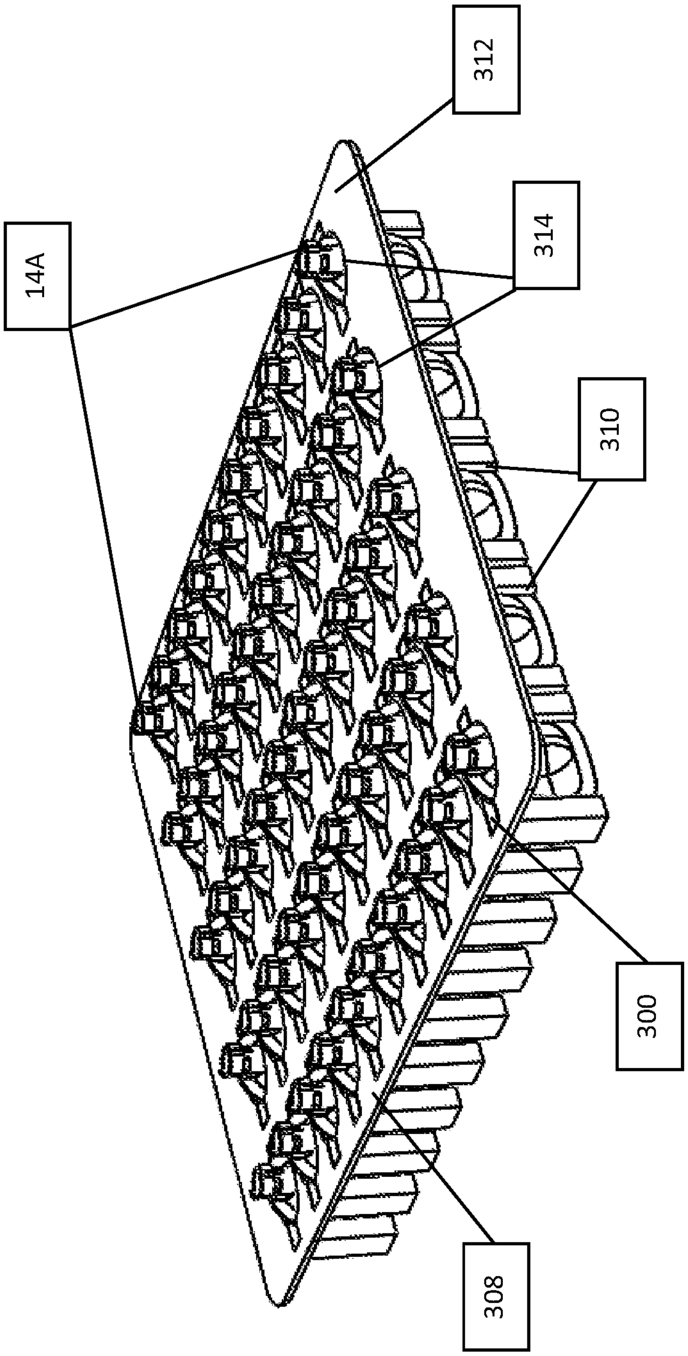
FIG. 64D shows the tray of FIG. 64C loaded with drug cartridges.
Figure 64E:
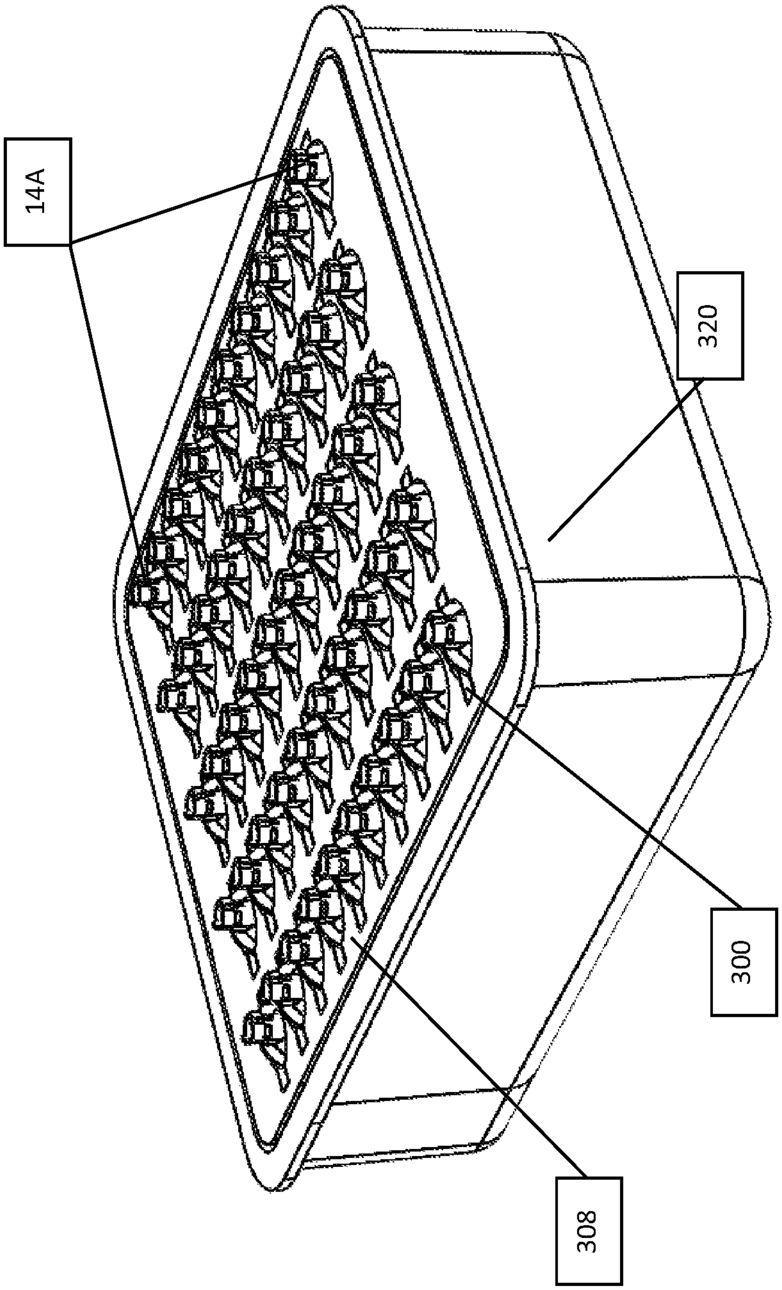
FIG. 64E shows the loaded of FIG. 64D placed in a tub.

Both the jig 305 and the open jig 307 may be placed in a support structure, such as a tray or tub, in various quantities to allow for batch lyophilization and transportation. Alternatively, as shown in FIGS. 64C-64E, a tray 308 may be provided formed with wells 310 each configured to receive the reservoir sections 14A having the reservoir support 300 mounted thereto. The tray 308 includes a support panel 312 with openings 314 for the wells 310. Each of the openings 314 includes a profile to allow the reservoir section 14A, with the reservoir support 300 mounted thereto, to pass through. For example, as shown in FIG. 64C, the openings 314 may each include a profile having an enlarged central area, e.g., generally elliptical area, with laterally extending wings, e.g., rectangular wings. Each of the wells 310 includes a pair of legs 316 depending downwardly from the support panel 312. The legs 316 are each internally open to define the slots 306 for receiving the reservoir sections 14A. A bottom 318 is provided for each of the legs 316 to restrict downward movement of the reservoir sections 14A within the slots 306.

As shown in FIG. 64D, the tray 308 permits a plurality of the assembled reservoir sections 14A/reservoir supports 300 to be accommodated in the wells 310. The wells 310 may be arranged in various arrays to permit efficient packing. As shown in FIG. 64E, the tray 308, once loaded, may be placed in a tub 320 for subsequent processing and transportation. The support panel 312 preferably has portions extending beyond the wells 310 which allow for the support panel 312 to be edge supported by the tub 320. Preferably, the legs 316 are out of contact with the tub 320 with the tray 308 placed in the tub 320 (i.e., spacing is present between the legs 316 and sidewalls of the tub 320). In addition, preferably, the tub 320 is provided with sufficient depth to avoid contact between the tub 320 and the reservoir sections 14A with the tray 308 placed in the tub 320 (i.e., spacing is present between the bottoms 318 and a base of the tub 320). The tray 308 may be formed from a polymeric material and formed by molding.

As will be understood by those skilled in the art, the plug adapter 14B may be replaced with the vent plug 38A in each of the embodiments of FIGS. 58-64E.

The drug cartridge 14, as being pre-filled, acts as a drug container during transportation and storage, prior to use. The materials of the drug cartridge 14 must be compatible with the corresponding drug. In addition, the drug cartridge 14 must be provided with sufficiently robust scaling to withstand ingress of contaminants over the duration of the expected time to use.

Figure 13:
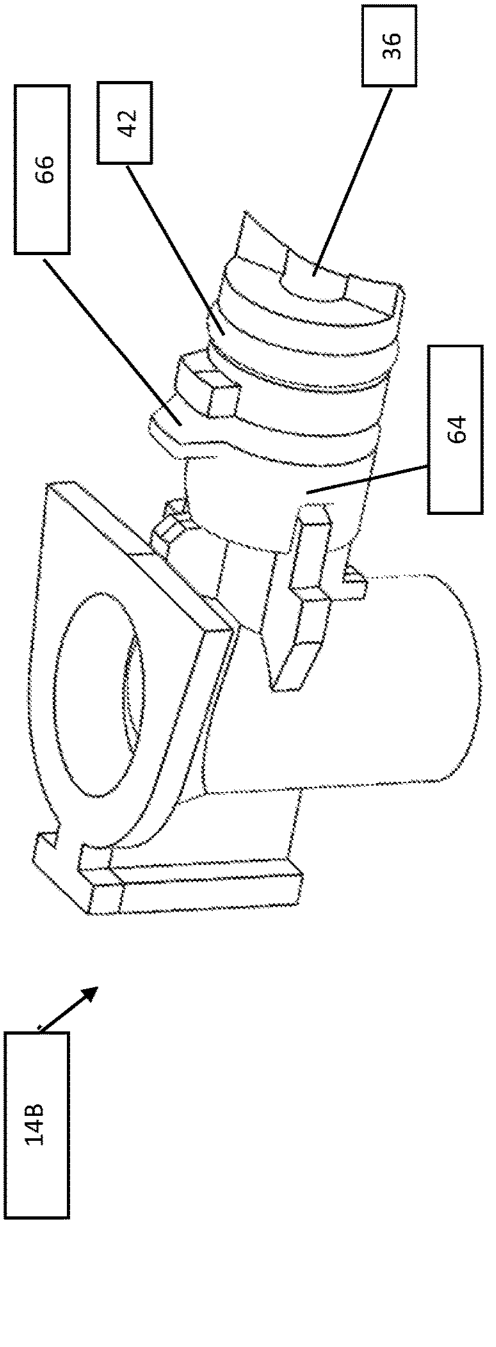
FIG. 13 is a detailed view of a plug adapter useable for radial sealing in accordance with the subject invention.
Figure 14:
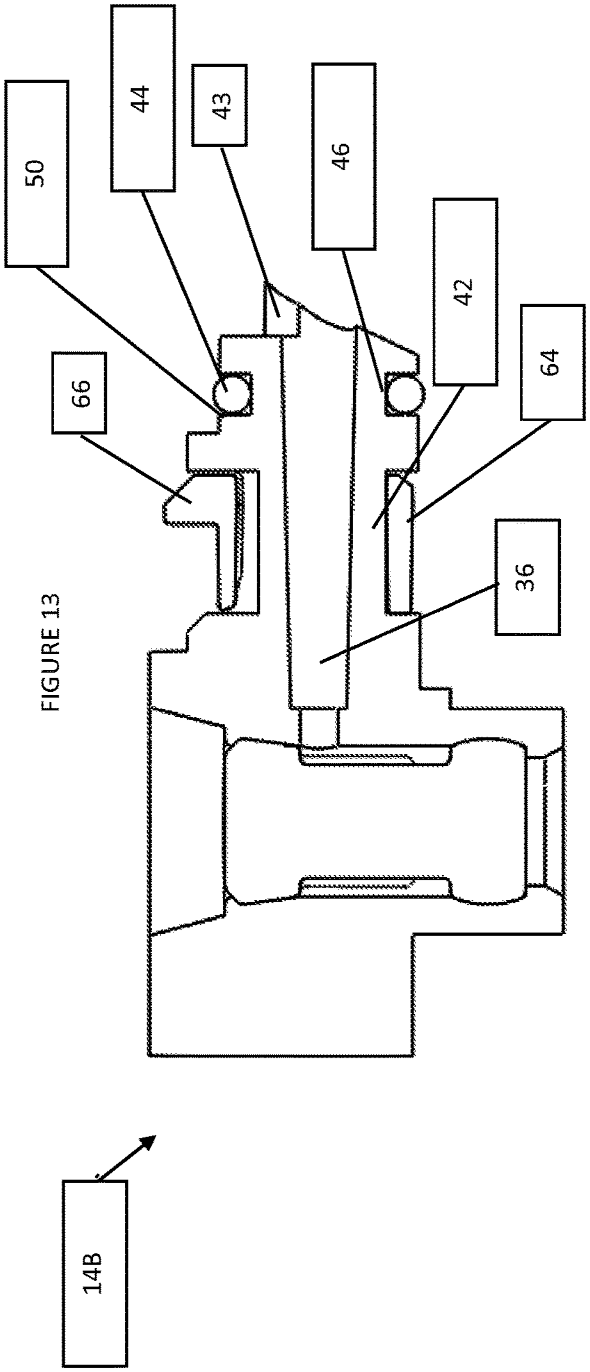
FIG. 14 is a section view of the plug adapter of FIG. 13.
Figure 15:
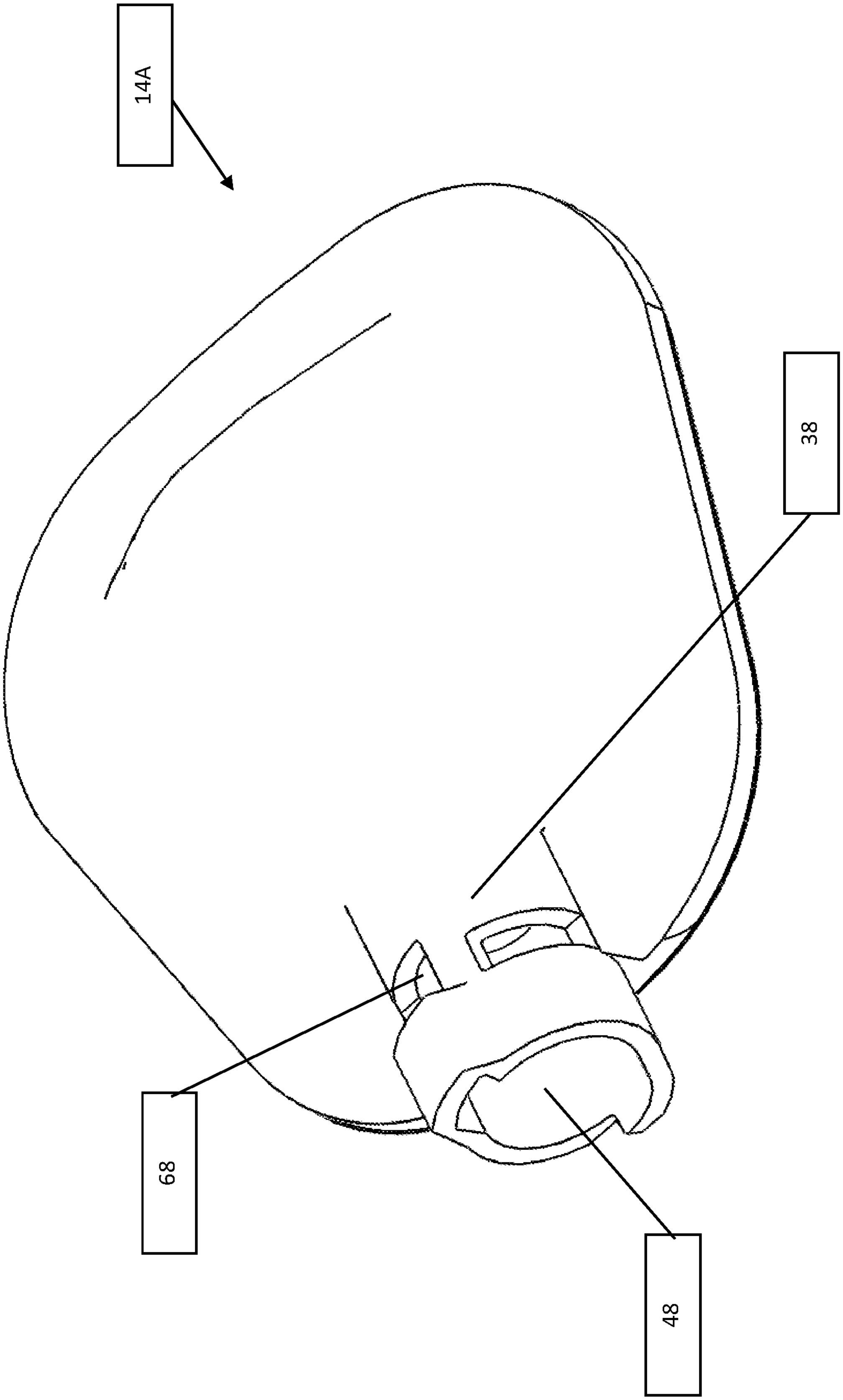
FIG. 15 is an isometric view of a reservoir section useable for radial sealing in accordance with the subject invention.
Figure 24:
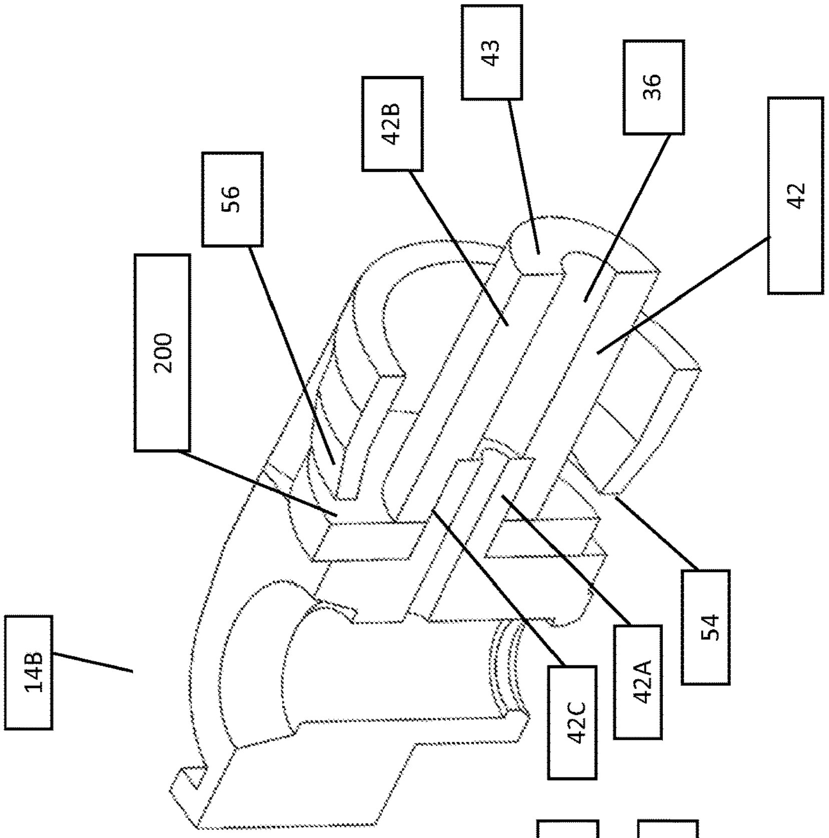
FIG. 24 shows a section view of the plug adapter of FIG. 23, with a seal in place.
Figure 23:
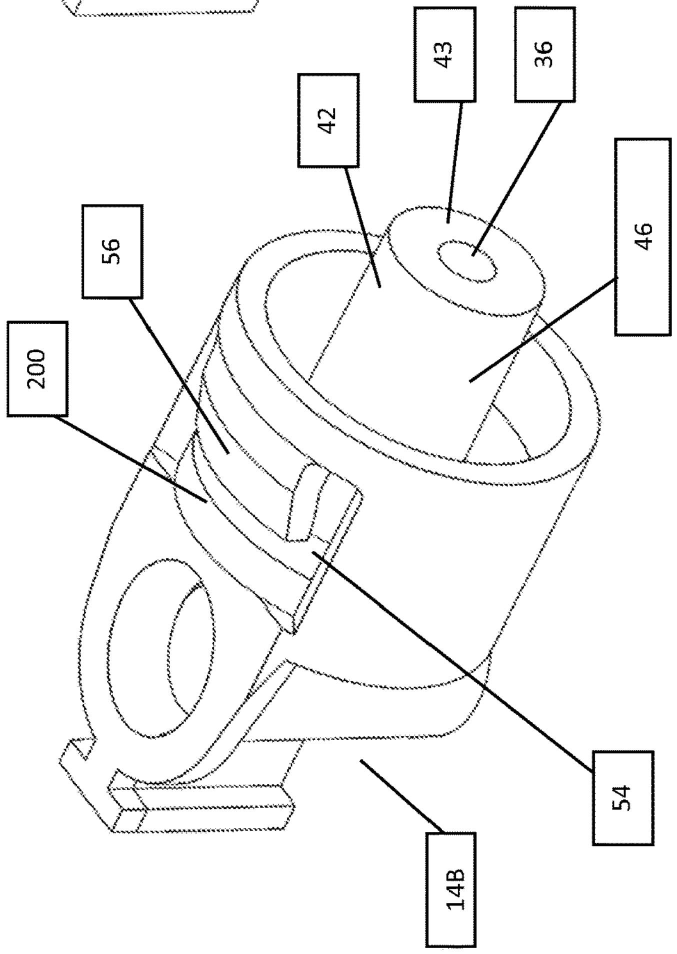
FIG. 23 shows a plug adapter useable with the subject invention which utilizes a face seal and inwardly directed detents.
Figure 25:
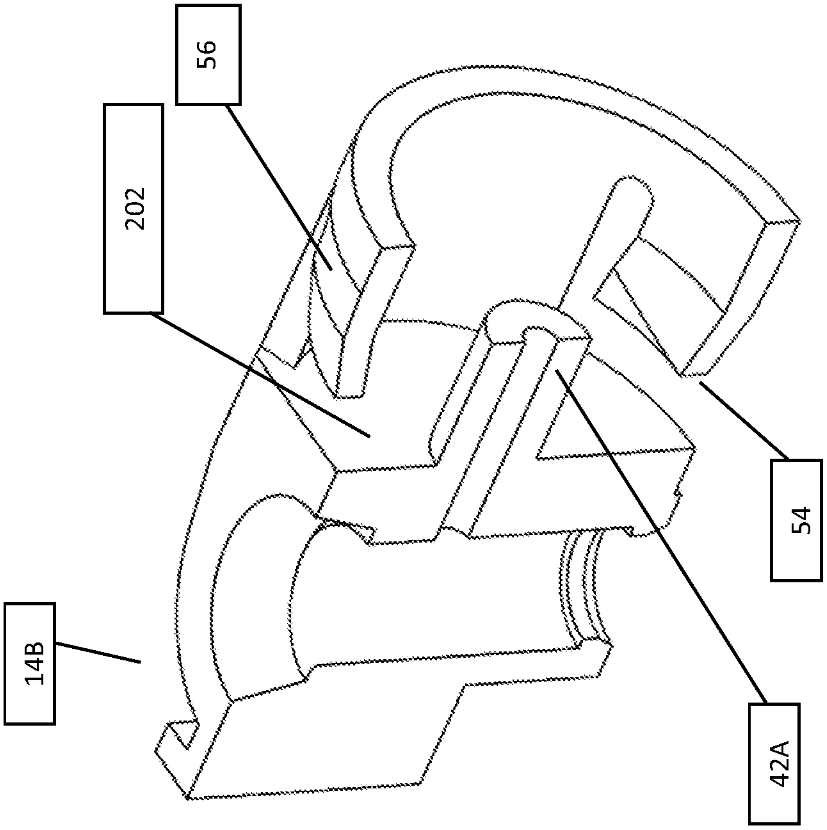
FIG. 25 shows a section view of the plug adapter of FIG. 23, without a seal in place.
Figure 27:
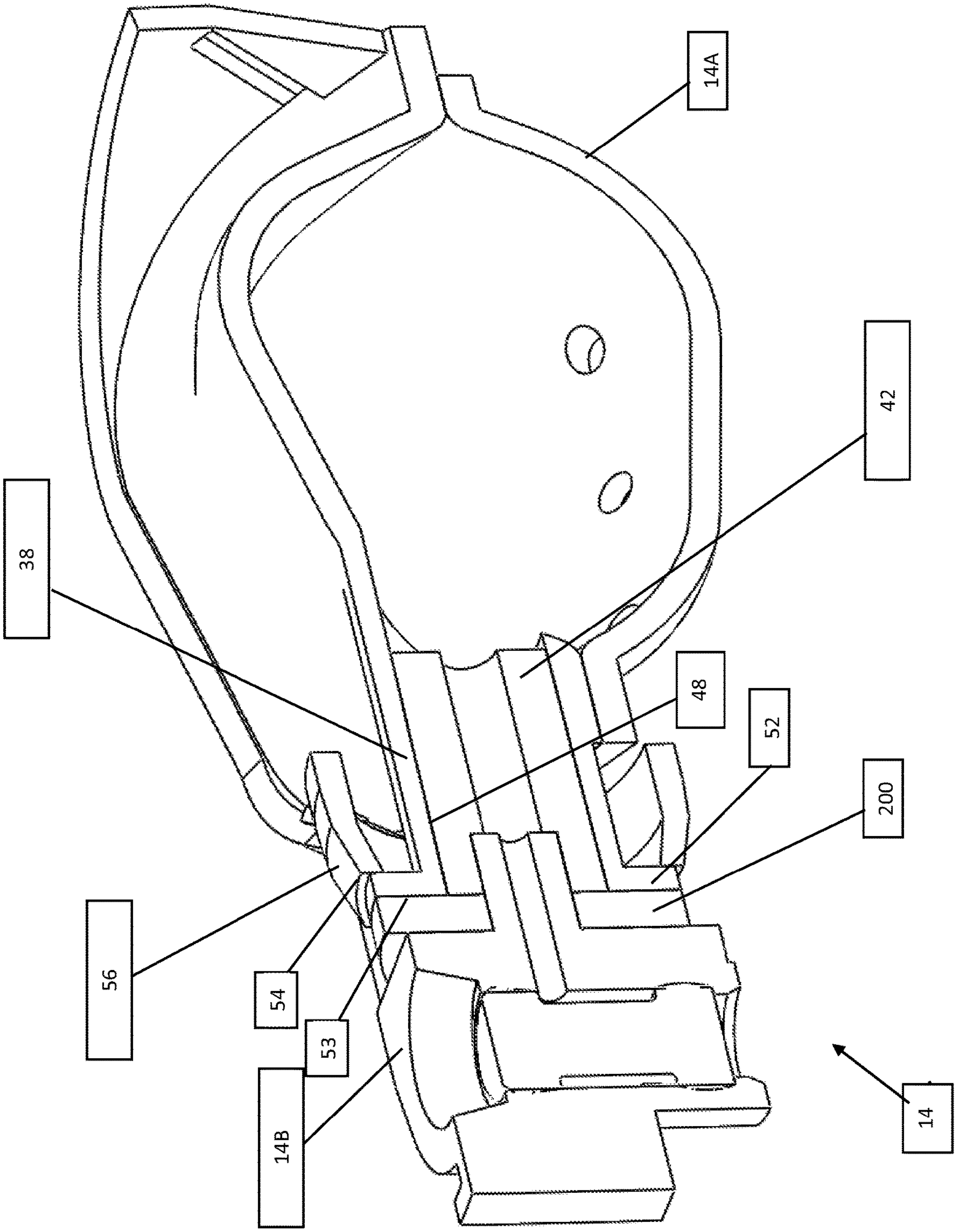
FIG. 27 is a section view of a drug cartridge that utilizes the face seal reservoir of FIG. 26 and the plug adapter of FIG. 23.
Figure 28:
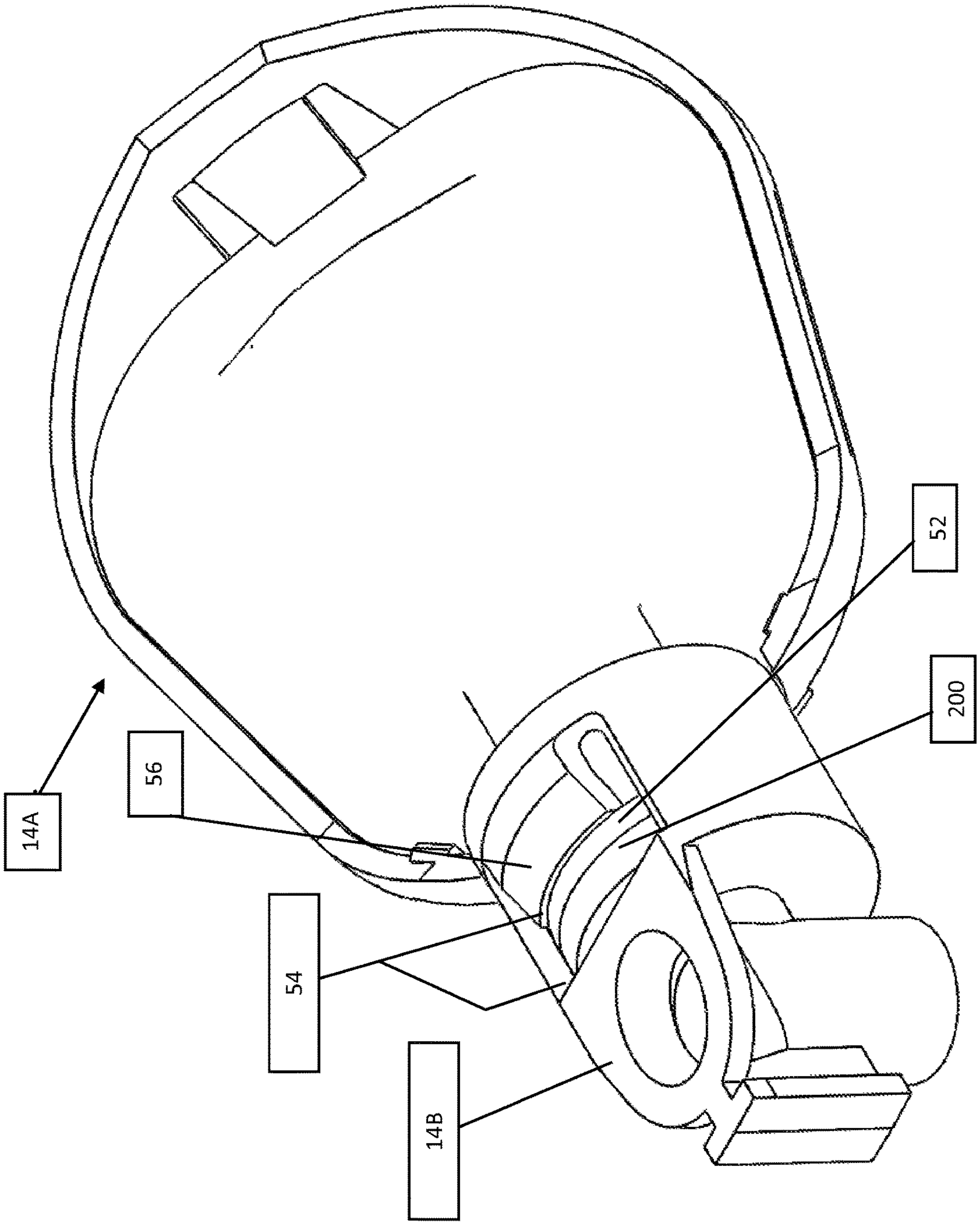
FIG. 28 is an isometric view of the drug cartridge of FIG. 27.

The plug adapter 14B may be formed to assemble with the reservoir section 14A in forming the drug cartridge 14 in various manners. As shown in FIGS. 13 and 14, a portion of the internal lumen 36 may be defined in an elongated neck 42, defined in the plug adapter 14B, which terminates at neck end 43. The neck 42 is formed to be telescopingly received in the filling port 38. One or more seals 44 may be provided between an external surface 46 of the neck 42 and an internal surface 48 of the fluid port 38. The seals 44 (e.g., O-rings) are preferably secured to the external surface 46, e.g., by being seated in sealing channels 50. Alternatively, as shown in FIGS. 23-25, the external surface 46 of the neck 42 may be formed smooth, optionally tapered, e.g., convergently towards neck end 43. As shown in FIG. 27, this allows the neck 42 to create a face seal with the internal surface 48 of the fluid port 38 through tight face-to-face interengagement therebetween.

Figure 26:
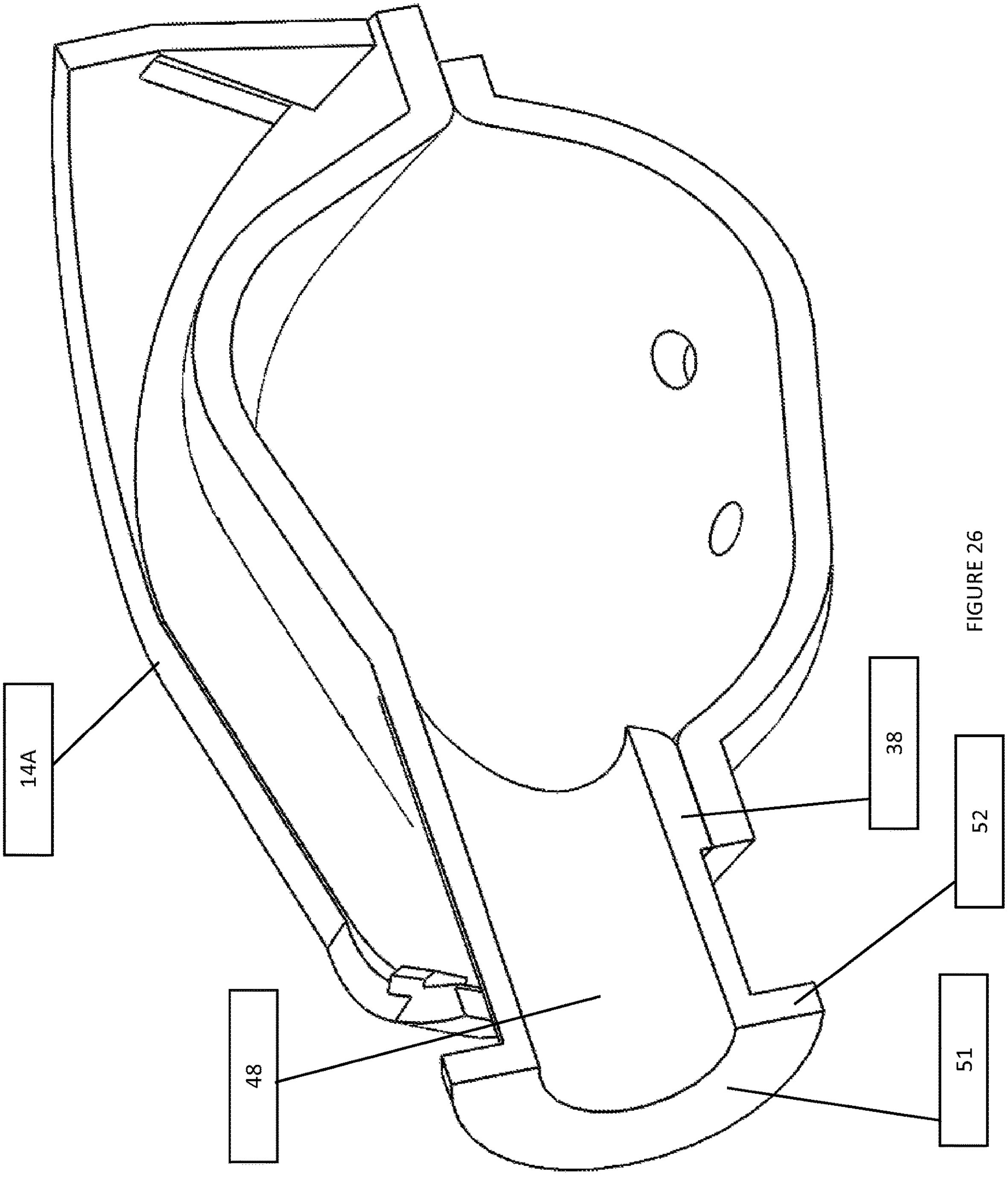
FIG. 26 shows a reservoir that may be assembled to the face seal plug adapter of FIG. 23.
Figure 29:
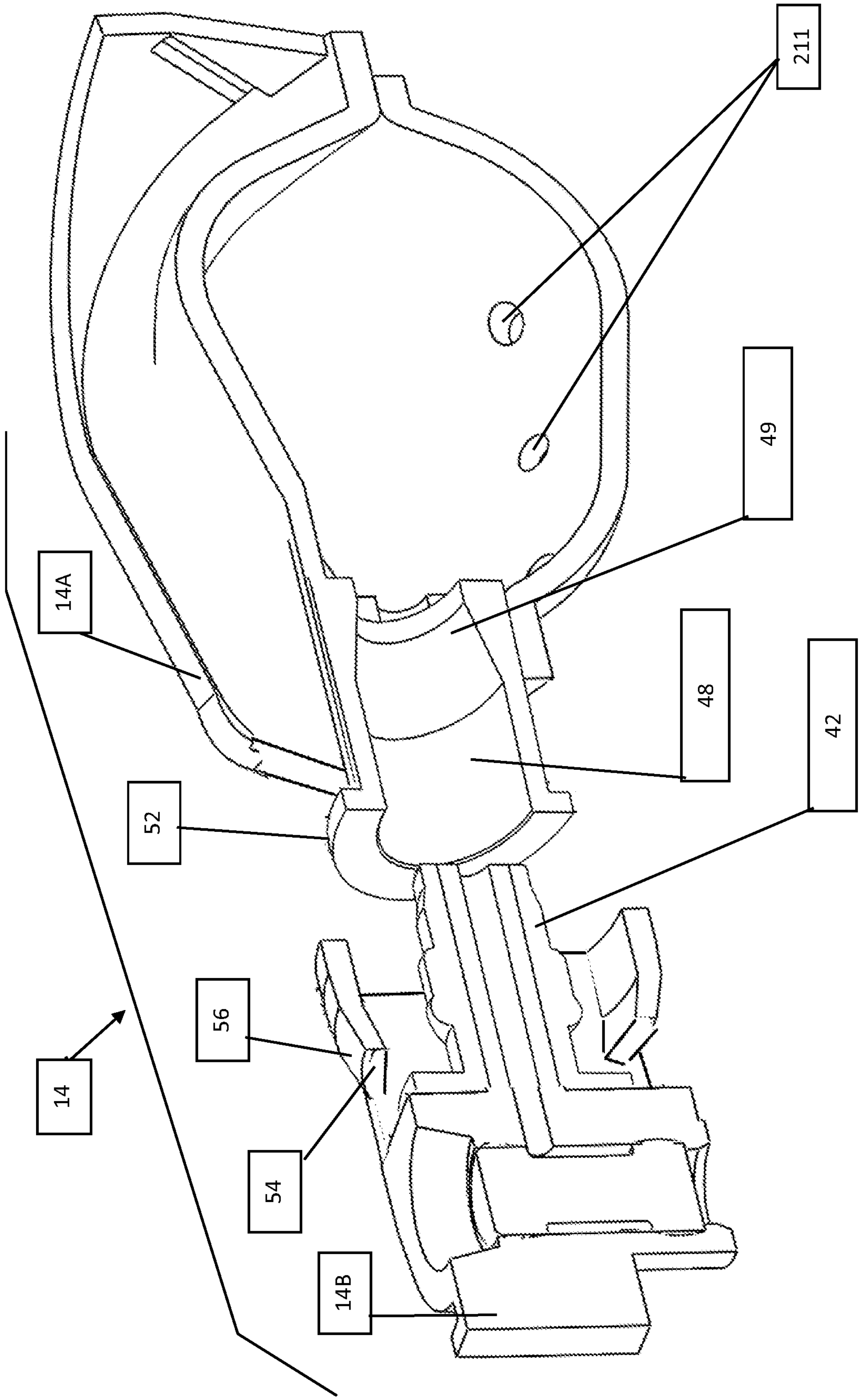
FIG. 29 is a section view of a drug cartridge that utilizes the face seal reservoir and plug adapter, with the plug adapter having venting passageways along the neck, and the reservoir having a tapered neck.
Figure 30:
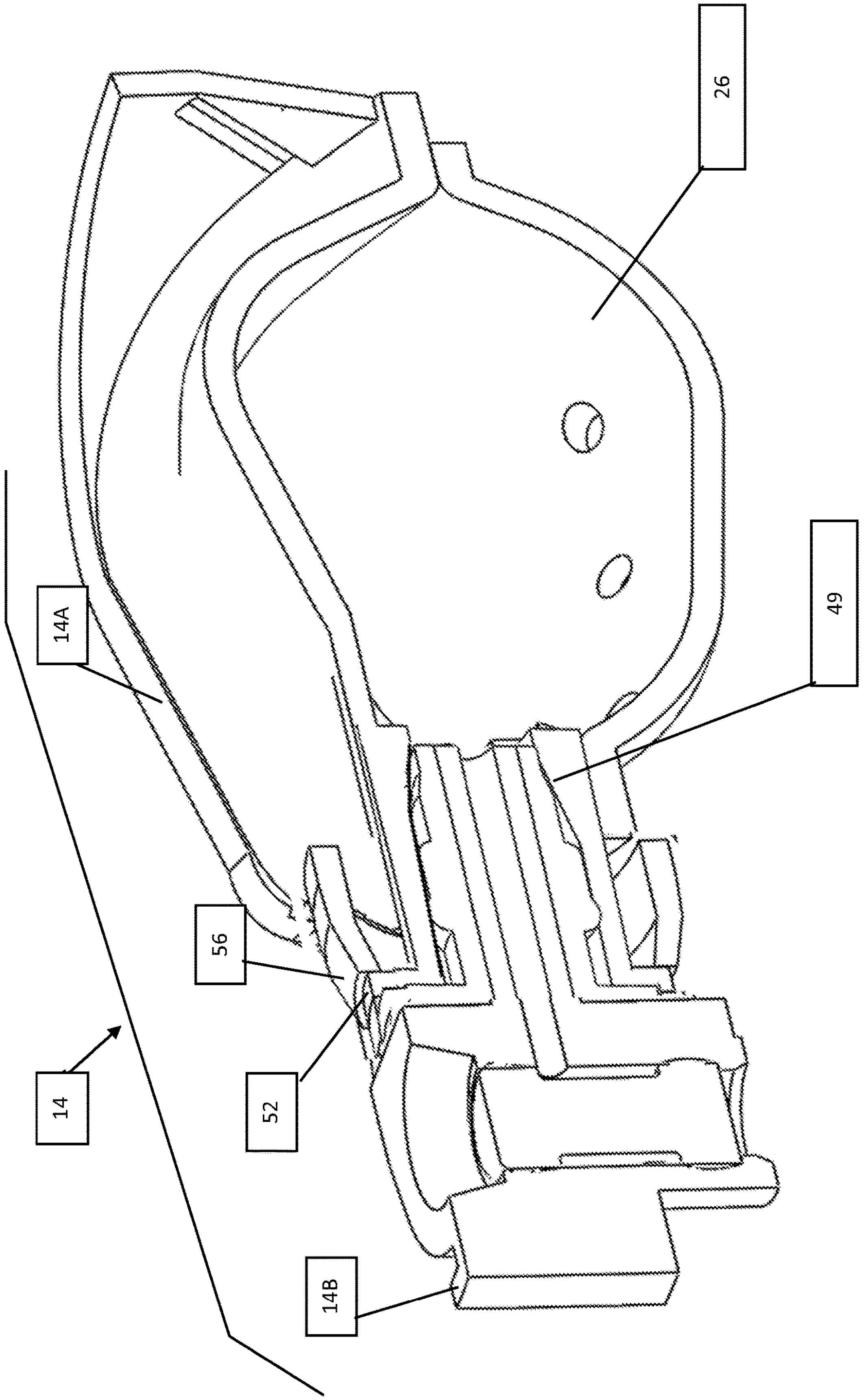
FIG. 30 is a section view of the drug cartridge of FIG. 29 in the sealed position.

Cooperating locking members may be provided between the reservoir section 14A and the plug adapter 14B to allow for locking therebetween upon assembly. As shown in FIG. 26, the filling port 38 may terminate at a locking rib 52 formed to snap engage a locking channel 54 formed in the plug adapter 14B, as shown in FIGS. 29 and 30. An inwardly directed detent 56 may be provided along the locking channel 54 to limit reverse movement of the filling port 38 away from the plug adapter 14B.

To enhance the integrity of the connection, as shown in FIGS. 23-28, a flexible seal 200 may be disposed in the locking channel 54 to pressingly engage the locking rib 52 with the plug adapter 14B being mounted to the reservoir section 14A. The locking rib 52 may be flange-shaped. Preferably, there is face-to-face engagement between an outer surface 51 of the locking rib 52 and the flexible seal 200.

It is preferred that the flexible seal 200 be formed of a resilient material suitable for scaling, such as an elastomeric material, a foam, a thermoplastic, a metal, and so forth. With the plug adapter 14B being formed from a thermoplastic material, the flexible seal 200 must be assembled to achieve two-material construction. To facilitate assembly, the neck 42 may be formed as a two-piece component with a base stem 42A to which is mounted sleeve 42B. Portions of the internal lumen 36 passes through both the base stem 42A and the sleeve 42B. The seal 200 may be annular shaped to be inserted into the locking channel 54, circumscribing the base stem 42A, and placed against external face 202. The sleeve 42B may then be mounted to the base stem 42A so as to overlap an inner portion of the seal 200. The sleeve 42B may be provided with a mounting channel 42C formed to telescopingly receive the base stem 42A. The sleeve 42B may be fixed to the base stem 42A using any known technique, including, but not limited to, adhesion, fusion, friction fit, interference fit, shrink fit, and so forth.

As shown in FIGS. 82A-84B, the sleeve 42B may be tapered along with the filling port 38 to provide a shape-mating fit therebetween. In addition, or alternatively, the base stem 42A and the sleeve 42B may be varied to define a portion of the internal lumen 36, particularly the first lumen portion 36A. As shown in FIGS. 86-89, the sleeve 42B may be formed to overlap an end of the base stem 42A, with the base stem 42A partially encircling the first lumen portion 36A. This allows for at least one change in direction to be defined in the internal lumen 36, particularly adjacent to the reservoir 26. Advantageously, one or more changes leading into the reservoir 26 limits the momentum of any liquid being introduced into the reservoir for reconstitution, as discussed below, thereby minimizing foaming and splashing. In particular, a third lumen portion 36C may be defined transverse to the first lumen portion 36A, defining a change in direction in the internal lumen 36. In addition, a fourth lumen portion 36D may be defined communicating the third lumen portion 36C and the reservoir 26, transversely disposed to the third lumen portion 36C, to provide a secondary change in direction in the internal lumen 36.

Figure 18:
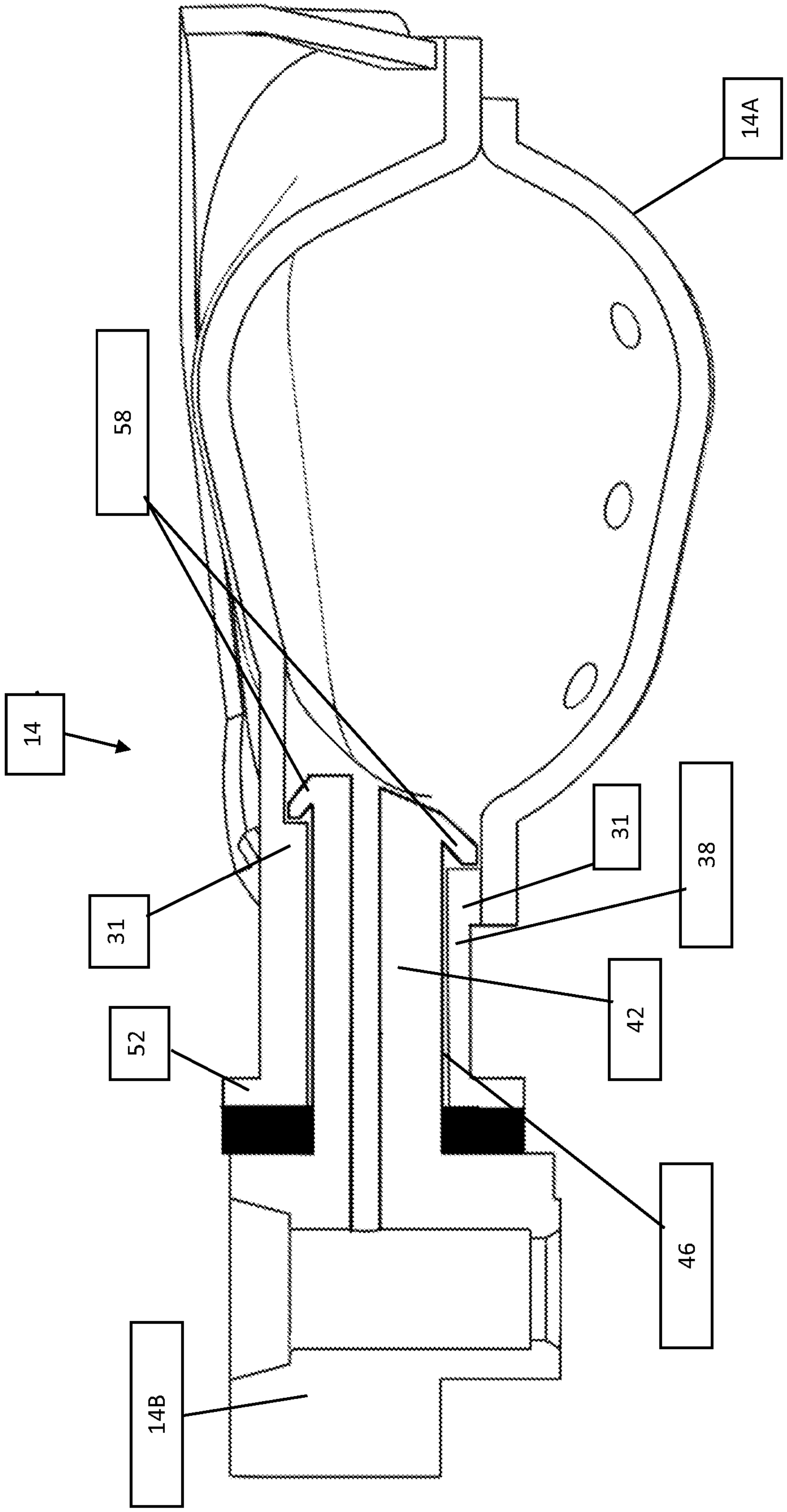
FIG. 18 is a section view of a drug cartridge, illustrating a face seal with internal retention features, in accordance with the subject invention.

Alternatively, as shown in FIG. 18, the locking rib 52 may be formed to extend radially inwardly of the filling port 38 with a locking collar 58 extending outwardly from the external surface 46 of the neck 42 formed to snap engage against inward shoulders defined by inward portions 31 of the locking rib 52. This arrangement likewise resists separation of the filling port 38 from the plug adapter 14B.

Further, as shown in FIGS. 13-16, a locking ring 64 may be provided about the neck 42 having locking tab 66 formed to snap engage a locking opening 68 formed in the reservoir section 14A. Seals may be provided as needed. Also, the external face 202 of the plug adapter 14B may act as a stop to define proper positioning between the reservoir component 14A and the plug adapter 14B. As will be appreciated by those skilled in the art, other locking arrangements may be utilized.

In addition, or alternatively, a ferrule 63 may be used to maintain the plug adapter 14B mounted to the reservoir section 14A, as shown in FIGS. 82-89B. The sleeve 42B may be provided with a locking flange 33, and the plug adapter 14B may include a stop flange 201, on which the external face 202 is located. The ferrule 63 may be formed of material capable of being crimped, including a metal or polymer sufficient malleable to be crimped (with or without heat or other external factors). As shown in FIGS. 82A-83B and 87A-88B, the ferrule 63 may initially be provided as a blank having a tubular body with sufficient diameter, and length, to encompass, the stop flange 201, the locking flange 33, and the locking rib 52. As shown in FIGS. 84A-86 and 89A-89B, with crimping, the ferrule 63 is conformed to tightly engage the stop flange 201, the locking flange 33, and the locking rib 52, with the stop flange 201 and the locking rib 52 pressing inwardly against the locking flange 33, to create a mechanical lock therebetween. Preferably, the ferrule 63 is formed with sufficient length to be bent to cover face portions of the stop flange 201 and the locking rib 52. As will be appreciated by those skilled in the art, the ferrule 63 may be formed as a sleeve, which is heat-shrinkable or weldable or adherable, to tightly conform to the stop flange 201, the locking flange 33, and the locking rib 52. The ferrule 63 should have sufficient stability, once affixed, to avoid creep, to avoid unwanted loosening.

As shown in FIGS. 32A-32E, as a further alternative, the plug adapter 14B may be latched to the reservoir section 14A to form a connection therebetween. Here, the locking rib 52 may be configured as a flange about the internal surface 48 of the filling port 38. Upstanding walls 57 may be provided on opposing sides of the outer surface 51 of the locking rib 52 to provide a yoke shape. Locking recesses 54A may be formed in the upstanding walls 57 formed to snap fittingly receive locking detents 52A defined on opposing surfaces of the plug adapter 14B. The upstanding walls 57 should be provided with some flexibility to allow outward deflection in permitting the locking detents 52A to be inserted into the locking recesses 54A. To enhance the integrity of the seal between the plug adapter 14B and the reservoir section 14A, the flexible seal 200 may be provided in the form of a gasket configured to rest on the outer surface 51 with a central opening providing access therethrough to the interior of the filling port 38.

It is noted that the interengagement between the locking detents 52A and the locking recesses 54A may be used to assemble the plug adapter 14B and the reservoir section 14A together with subsequent joining of elements, for example, having portions of the upstanding walls 57 joined to the plug adapter 14B using one or more of adhesion, fusion, and welding. In addition, or alternatively, the locking detents 52A may be joined to the locking recesses 54A using one or more of the aforementioned techniques.

Figure 32A:
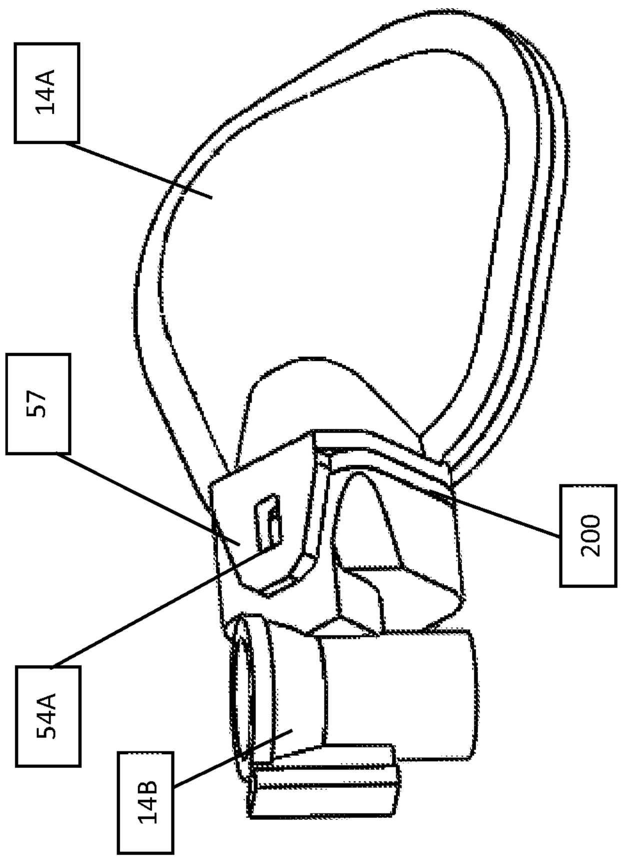
FIG. 32A is an isometric view of a drug cartridge that utilizes a latching arrangement between the plug adapter and the reservoir section.
Figure 32B:
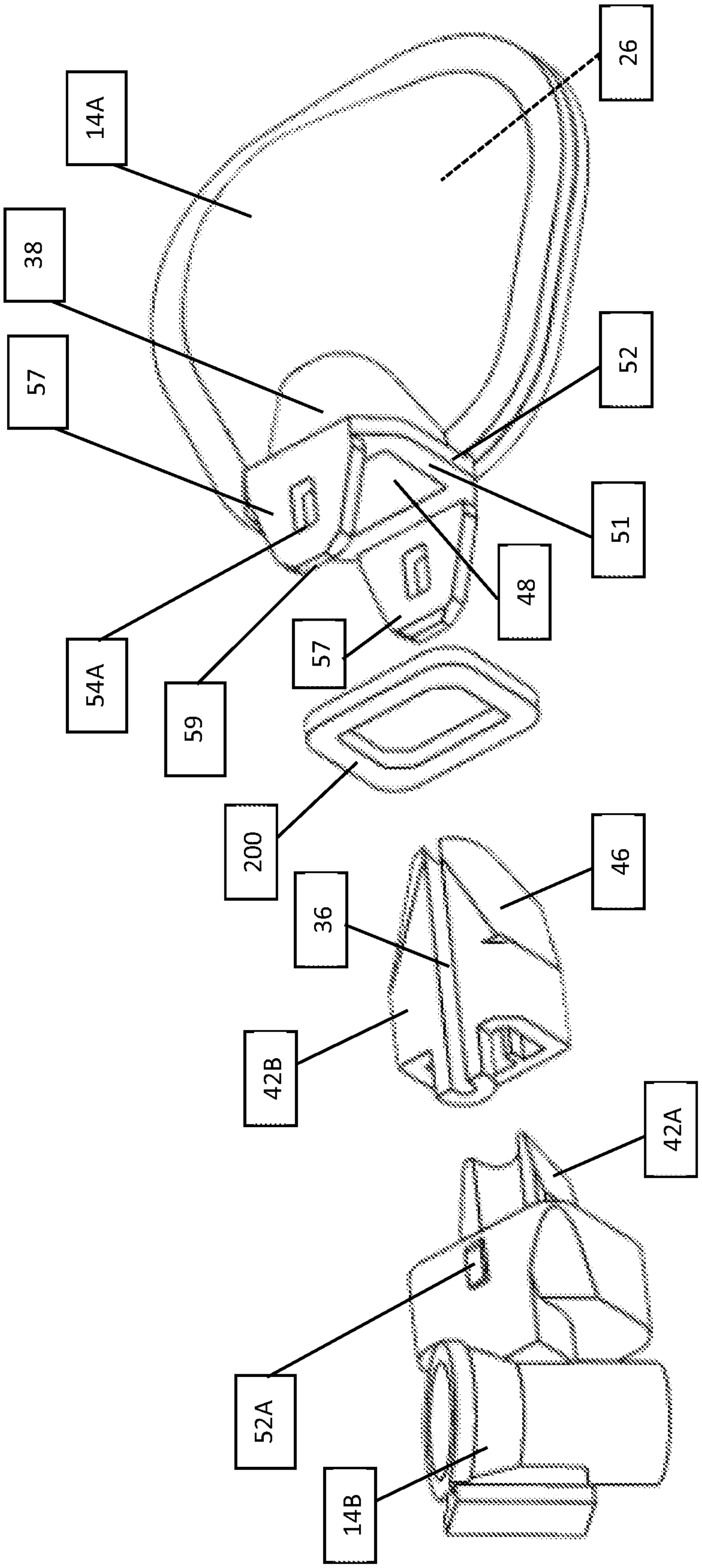
FIG. 32B is an exploded isometric view of the drug cartridge of FIG. 32A.
Figure 32C:
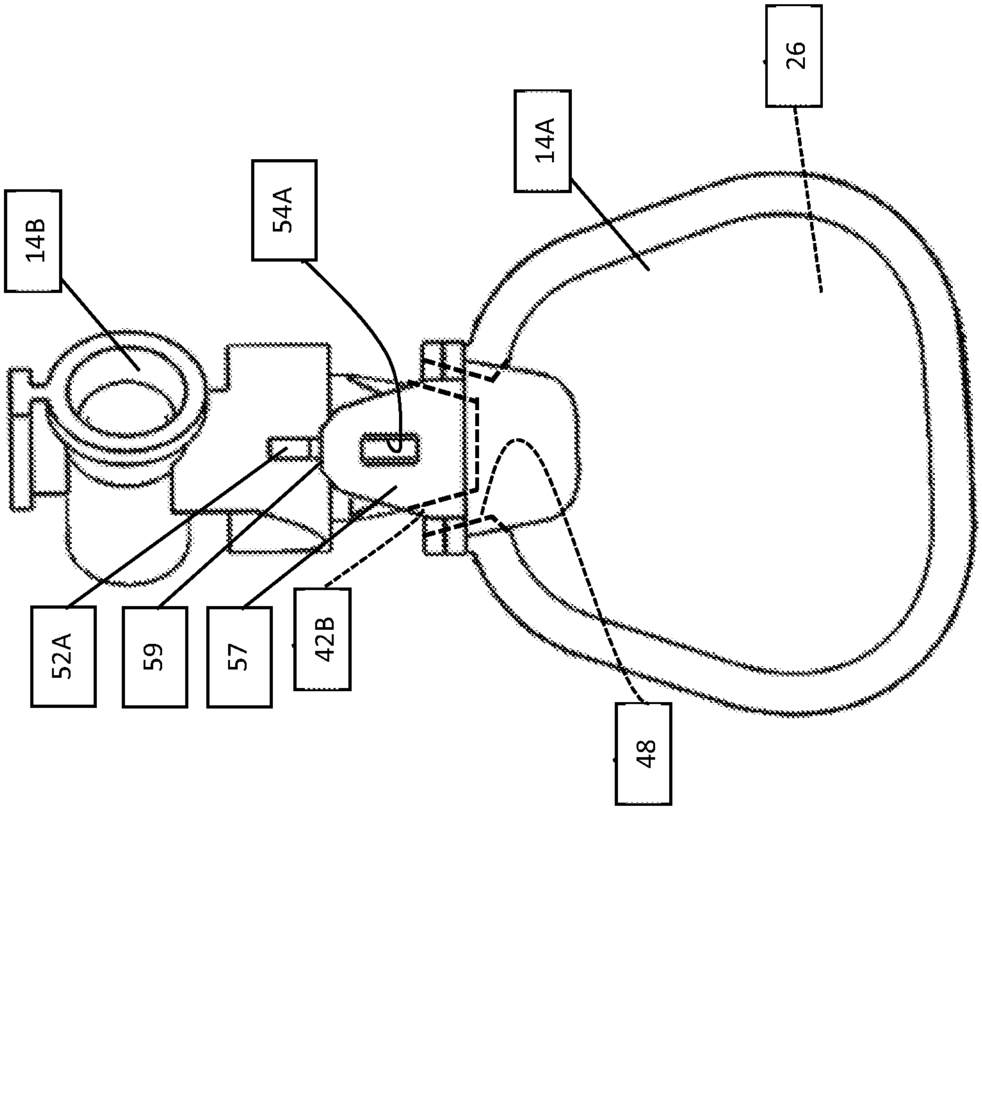
FIG. 32C shows the plug adapter of FIG. 32A in the vented position.
Figure 32D:
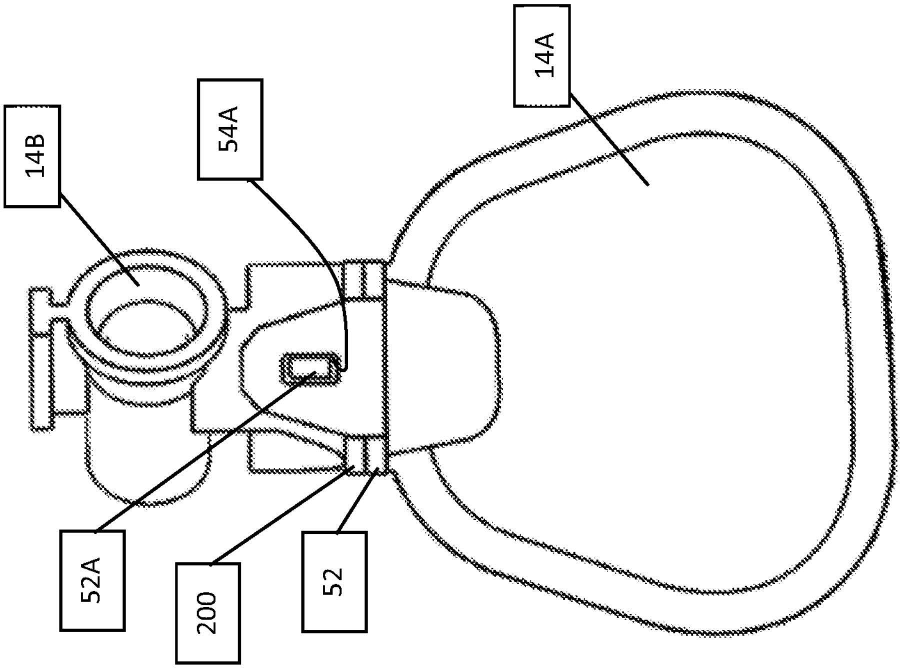
FIG. 32D is shows the plug adapter of FIG. 32A in the sealed position.
Figure 32E:
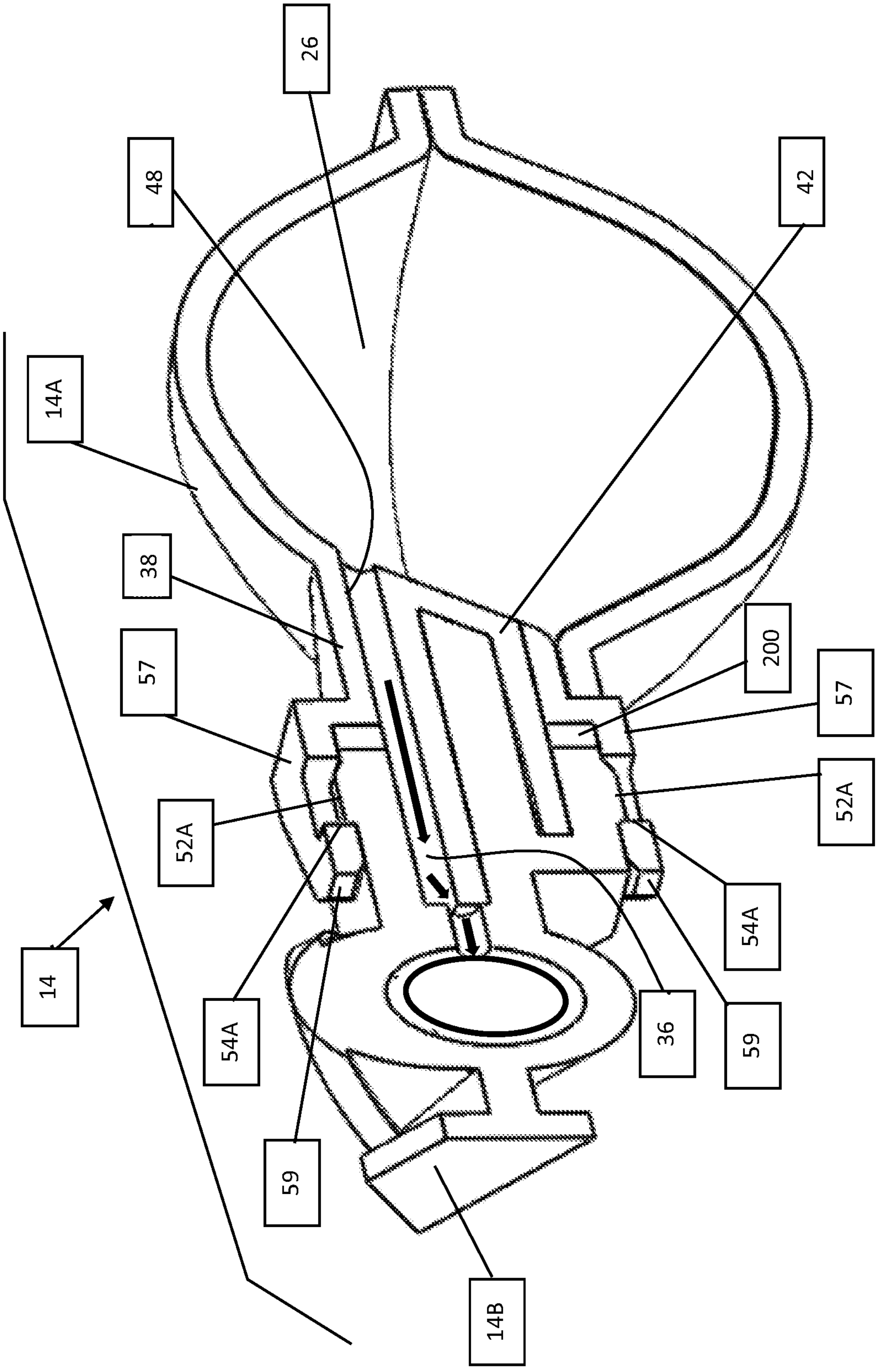
FIG. 32E is a section view of the drug cartridge of FIG. 32D with the plug adapter in the sealed position.

As shown in FIG. 32B, the plug adapter 14B may be provided with a two-piece construction, as discussed above, with the sleeve 42B being mounted to the base stem 42A to form the neck. In addition, the sleeve 42B may have a polygonal profile with one or more faces being tapered. The filling port 38 may have a similarly formed cross-section, converging in a direction towards the reservoir 26 to provide a shape-mating fit with the sleeve 42B. With this configuration, as shown in FIG. 32C, the plug adapter 14B may be partially inserted into the filling port 38 to allow venting of the reservoir 26. To maintain plug adapter 14B in the venting state, leading edges 59 of the upstanding walls 57 may be located to act as a stop against the locking detents 52A. The leading edges 59 are located to space the sleeve 42B from the internal surface 48 of the filling port 38. As shown in FIG. 32D, with the locking detents 52A being urged past the leading edges 59 and into snap fitting engagement with the locking recesses 54A, the sleeve 42B is urged into scaling contact with the internal surface 48. FIG. 32E shows in cross-section the plug adapter 14 in the sealed state.

Figures 20A, 20B, 20C:
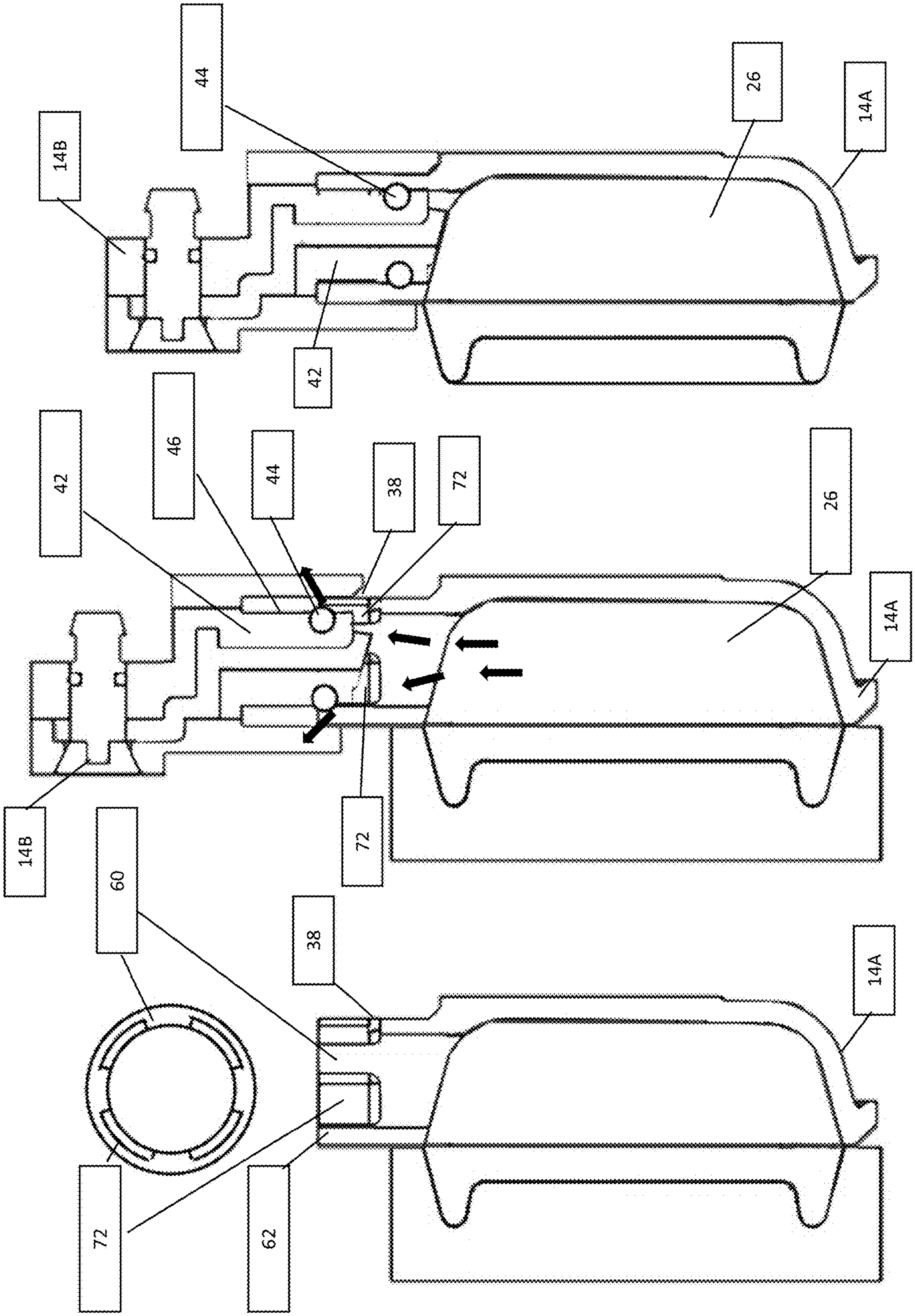
FIG. 20A shows an open reservoir section, oriented for filling, in accordance with the subject invention.
FIG. 20B shows the reservoir section of FIG. 20A with a plug adapter in a vented position.
FIG. 20C shows the plug adapter fully seated with the reservoir section of FIG. 20A.

To configure the drug cartridge 14 with an adjustable vent, for example, for lyophilization as described above, as shown in FIGS. 20A-20C, at least one venting passageway 72 may be defined at the mouth 62 of the filling port 38. The venting passageways 72 may be defined as recessed channels in the internal surface 48 of the filling port 38 with one or more venting protrusions 60 separating the venting passageways 72. The venting protrusions 60 are preferably discontinuous about the inner periphery of the mouth 62. As shown in FIG. 20B, to allow for venting, the neck 42 is inserted into the filling port 38 to no further than the length of the venting protrusions 60 to maintain the one or more seals 44 above the ends of the venting passageways 72. This allows for an open vent state with the venting passageways 72 being in open communication with the reservoir 26. The vent may be adjusted to a closed state, as shown in FIG. 20C, with further insertion of the neck 42 into the filling port 38 so that the one or more seals 44 are located between the venting passageways 72 and the reservoir 26 to close off communication therebetween.

Figure 16:
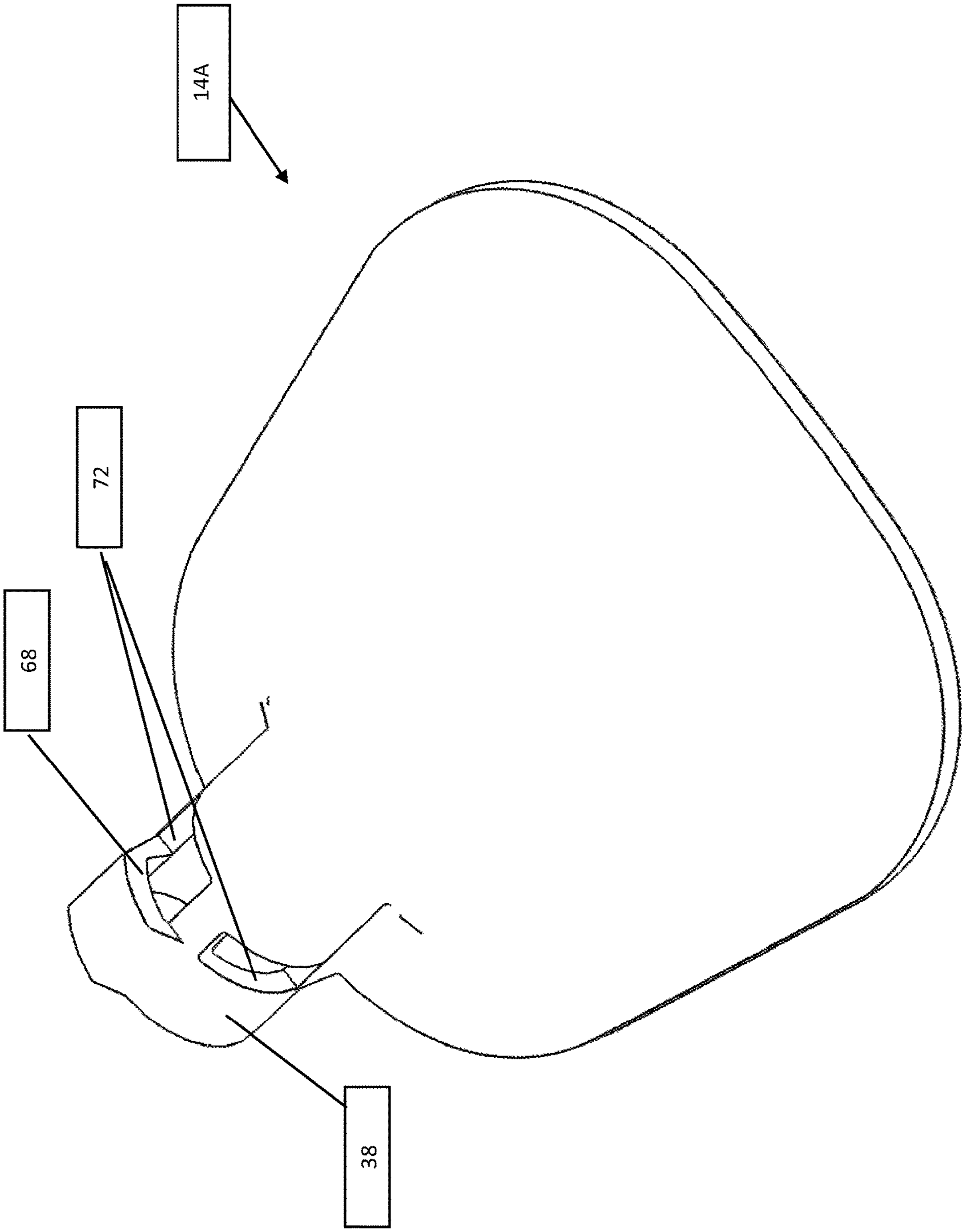
FIG. 16 is an alternate view of the reservoir section of FIG. 15 to illustrate retaining features for a radially sealed closure.
Figures 17A, 17B, 17C:
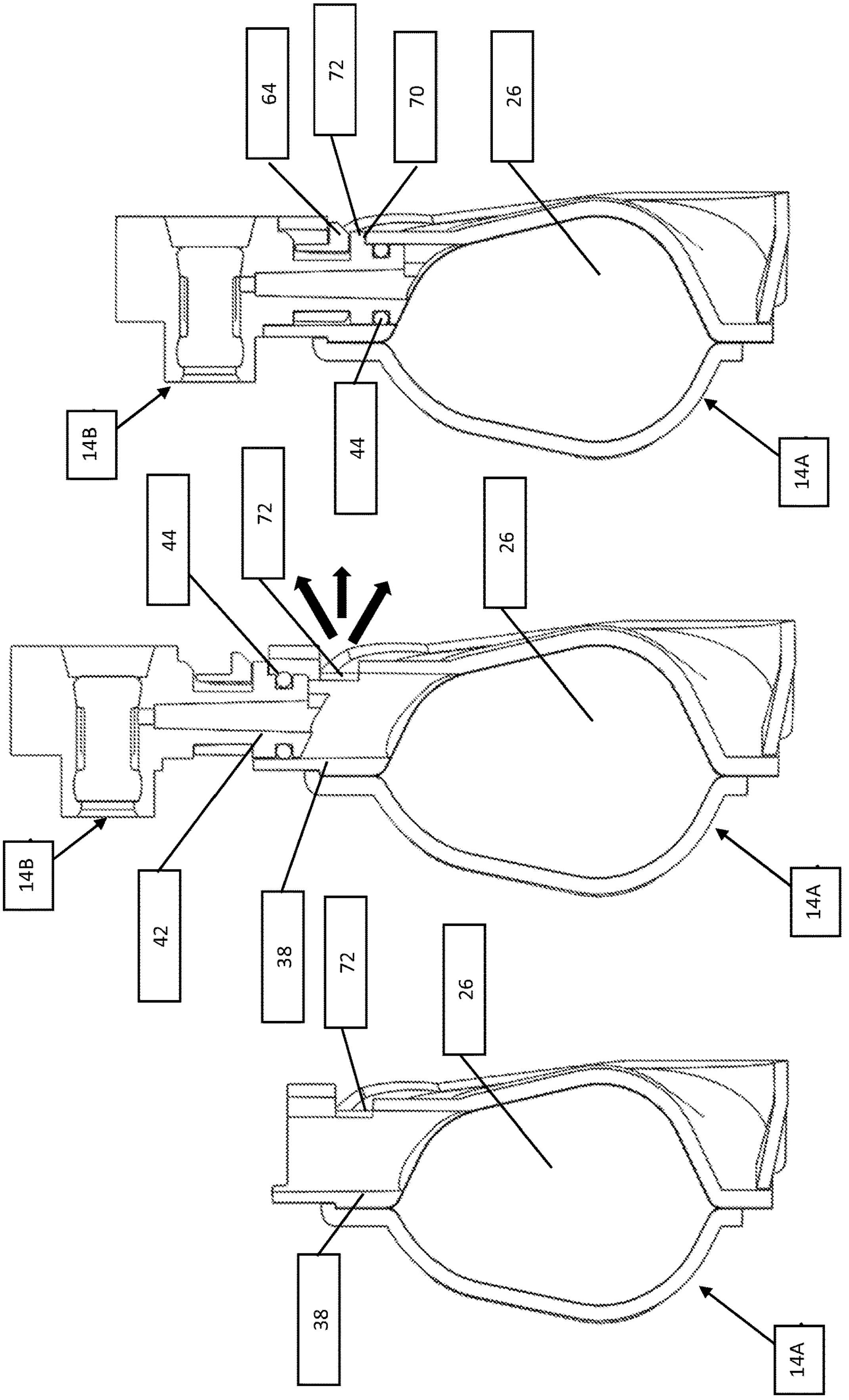
FIG. 17A shows a reservoir section, oriented for filling, in accordance with the subject invention.
FIG. 17B shows the reservoir section of FIG. 17A with a plug adapter in a vented position.
FIG. 17C shows the plug adapter fully seated with the reservoir section of FIG. 17A.

With the embodiment of FIGS. 20A-20C, vented gases by-pass portions of the plug adapter 14 to escape. Alternatively, as shown in FIG. 16, the venting passageways 72 may be formed as through-holes through the filling port 38. This provides unrestricted venting directly to external atmosphere. As shown in FIGS. 17A-17C, venting is achieved in the same manner as described above with the open vent state shown in FIG. 17B and the closed vent state shown in FIG. 17C, with the one or more seals 44 being adjusted in the same fashion.

Figure 31A:
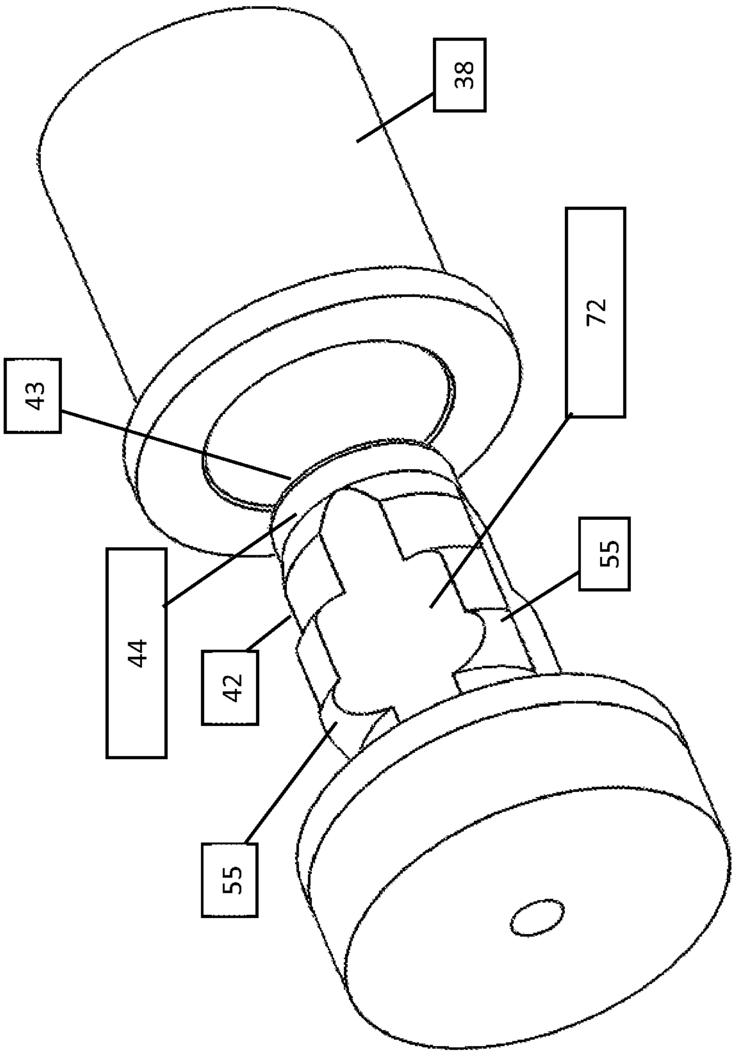
FIG. 31A is an isometric view of the sealing elements of the drug cartridge of FIG. 29.
Figure 31B:
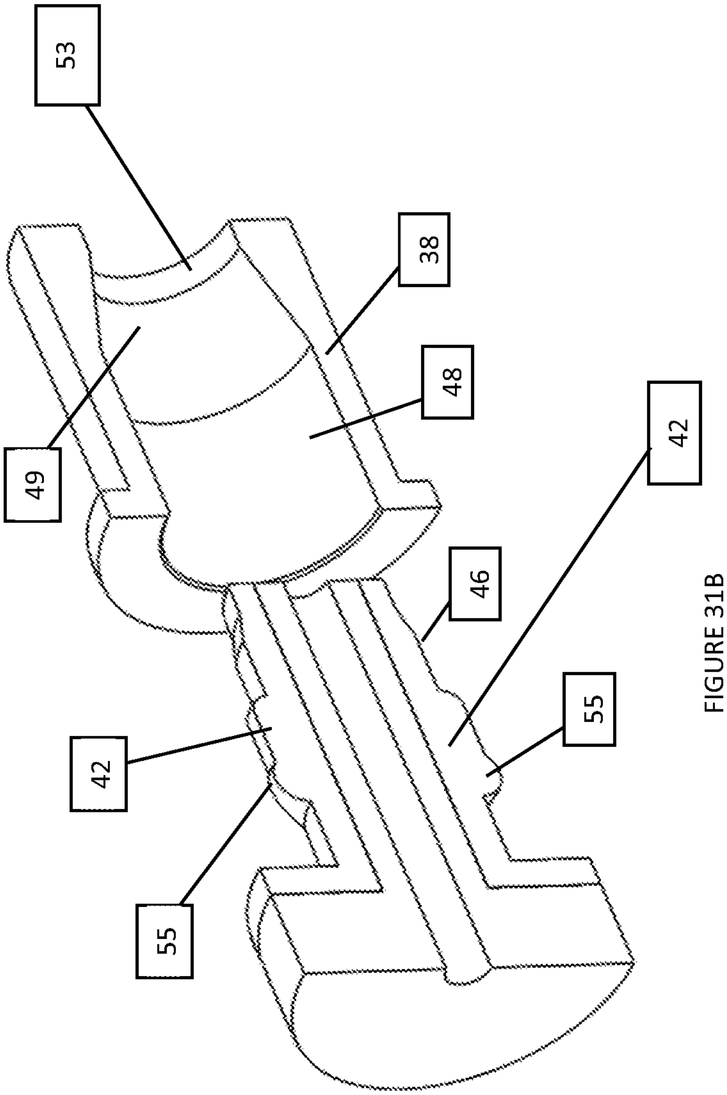
FIG. 31B is a section view of the sealing elements of FIG. 31A.
Figures 33A, 33B, 33C, 33D:
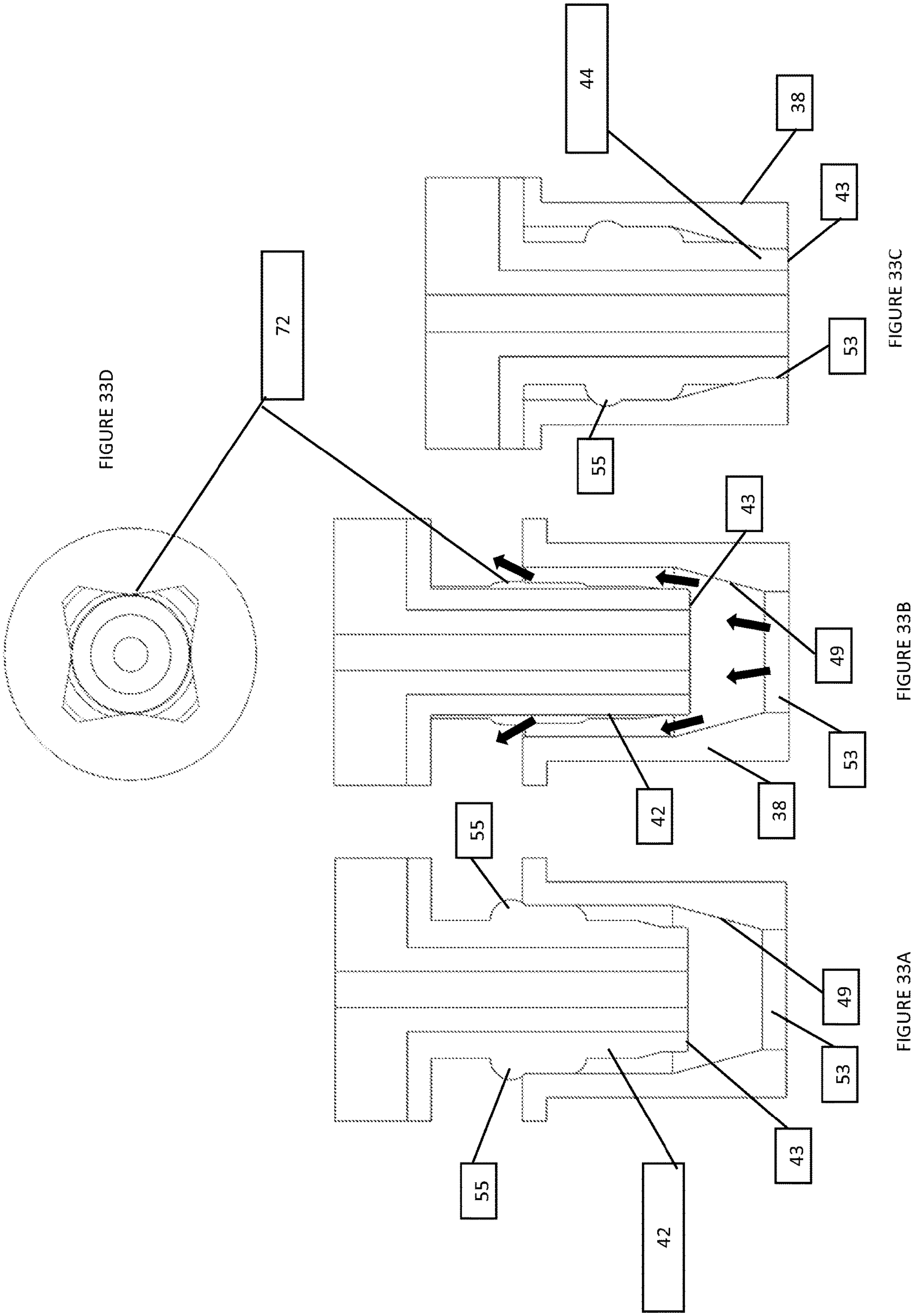
FIG. 33A shows the sealing elements of FIG. 31A in the vented position. The cut plane is positioned such that the protruding beads are visible.
FIG. 33B shows the sealing elements of FIG. 31A in the vented position for lyophilization.
FIG. 33C shows the sealing elements of FIG. 31A in the sealed position.

In addition, as shown in FIGS. 31A-31B, the internal surface 48 of the filling port 38 may include a tapered section 49, adjacent the reservoir 26, which is convergently tapered in a direction towards the reservoir 26 to define a reduced-diameter opening 53. A plurality of protruding beads 55 may be formed on the external surface 46 of the neck 42 with the venting passageways 72 being defined therebetween. The protruding beads 55 are configured to pressingly engage the filling port 38. The at least one seal 44 is located on the external surface 46 of the neck 42 between the protruding beads 55 and the neck end 43. As shown in FIGS. 33A-33B, to achieve the open vent state, the neck 42 is inserted into the filling port 38 with the neck end 43 being out of contact with the tapered section 49. As shown in FIG. 33C, further insertion of the neck 42 into the filling port 38 causes the vent to close with the neck end 43 being received in the opening 53 and with the at least one of the seals 44 coming into sealing engagement with the tapered section 49 of the internal surface 48 to close off communication between the venting passageways 72 and the reservoir 26.

Figure 97:
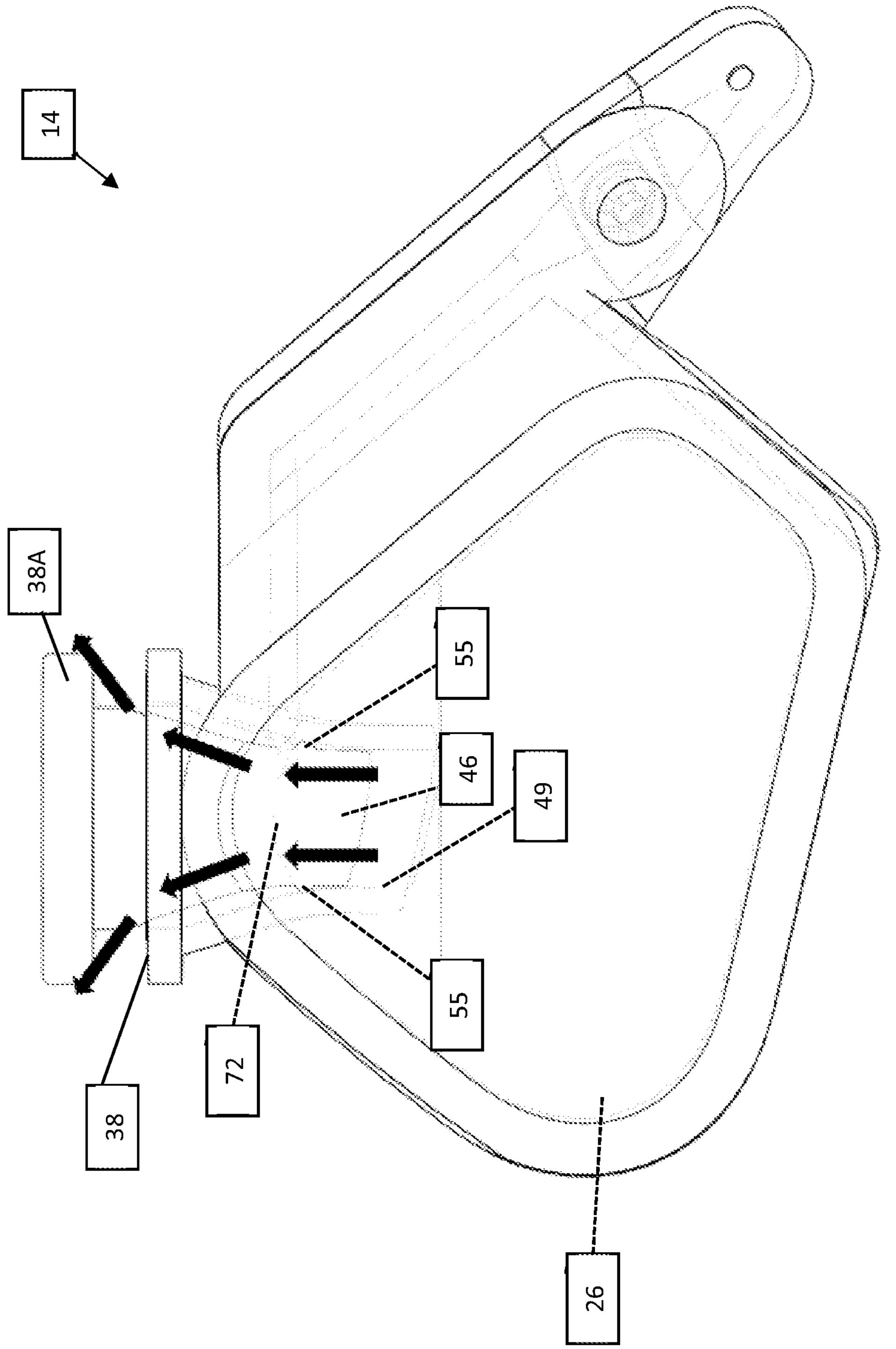
Figure 98:
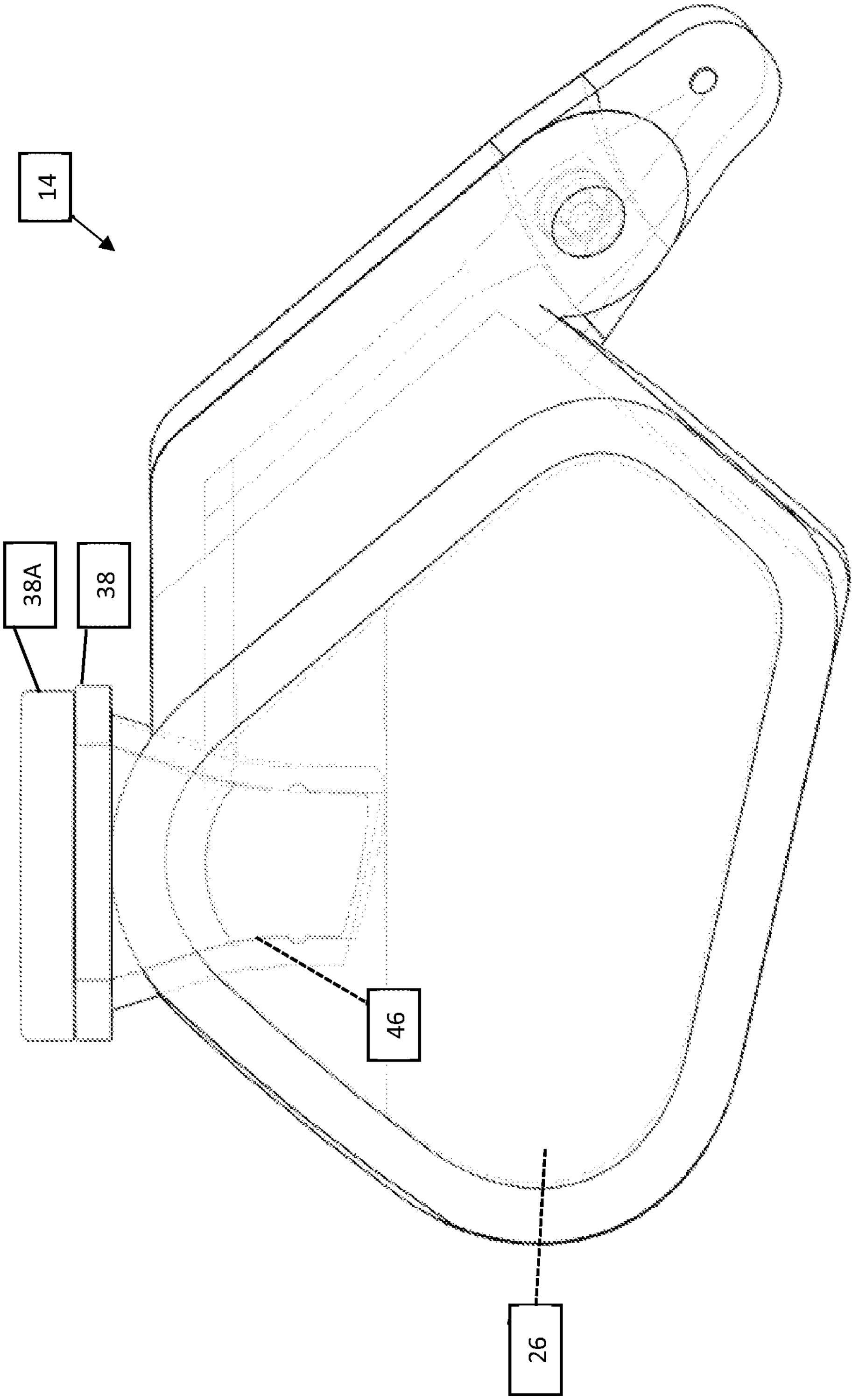
Figure 99:
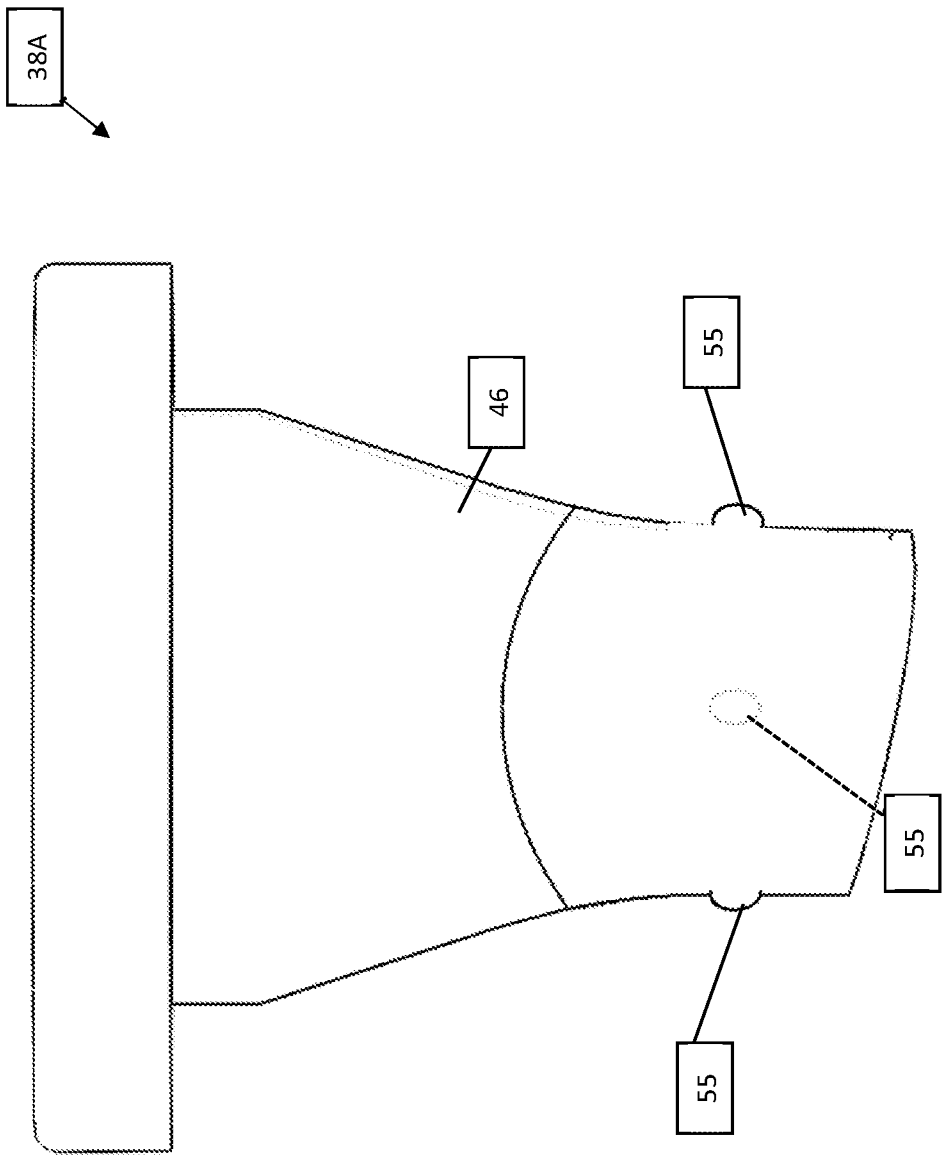
Figure 100:
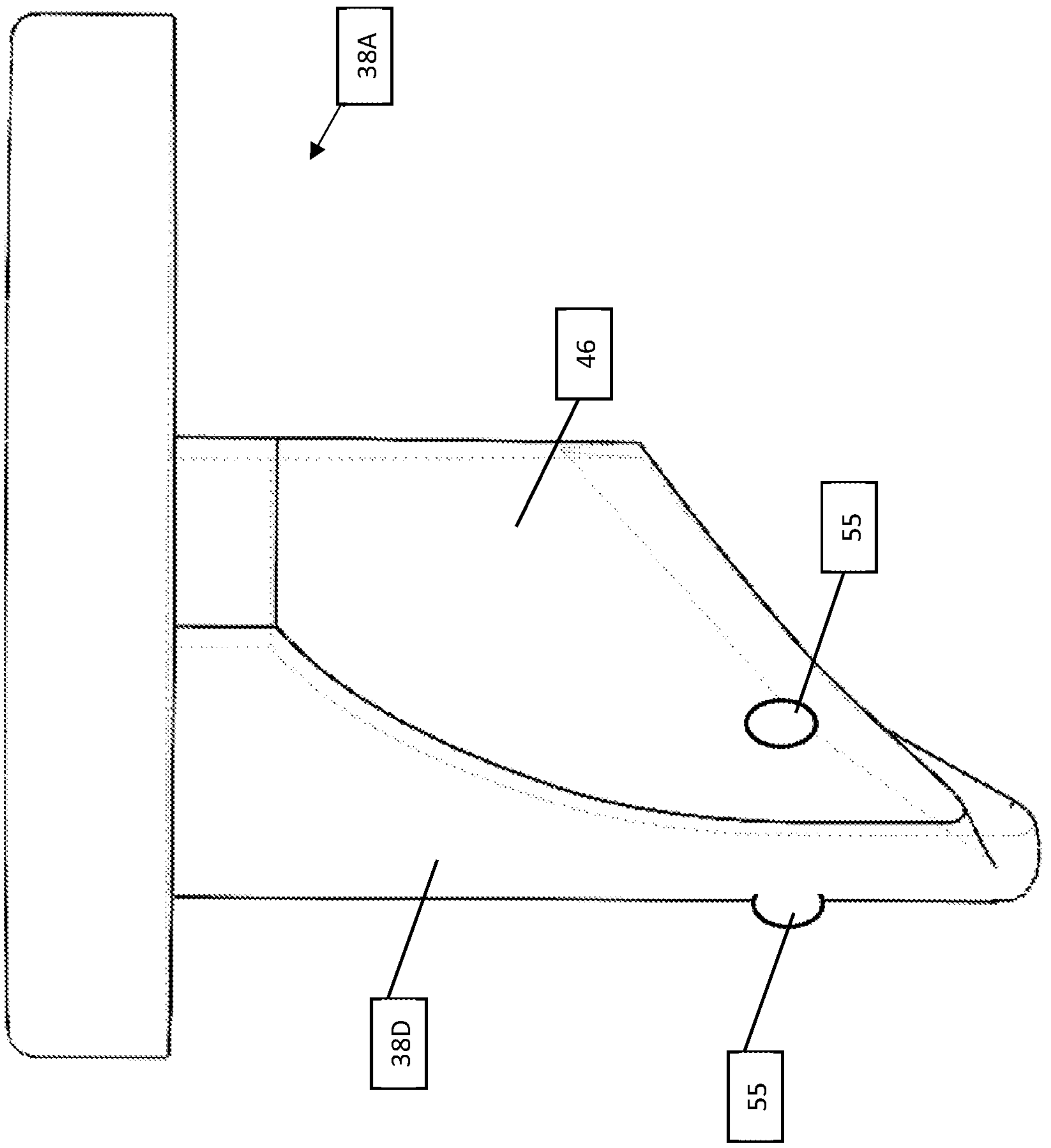
Figure 101:
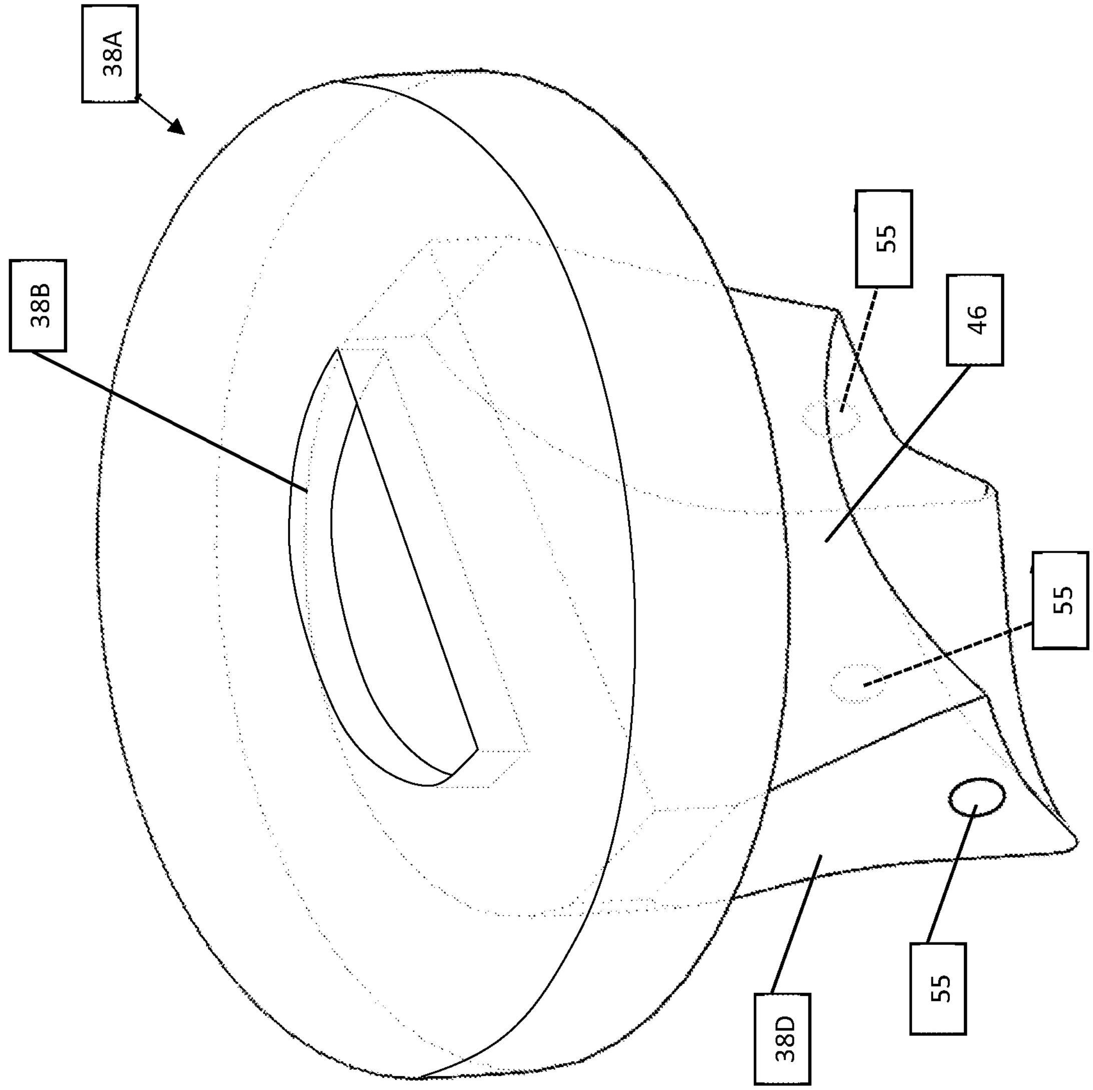
Figure 102:
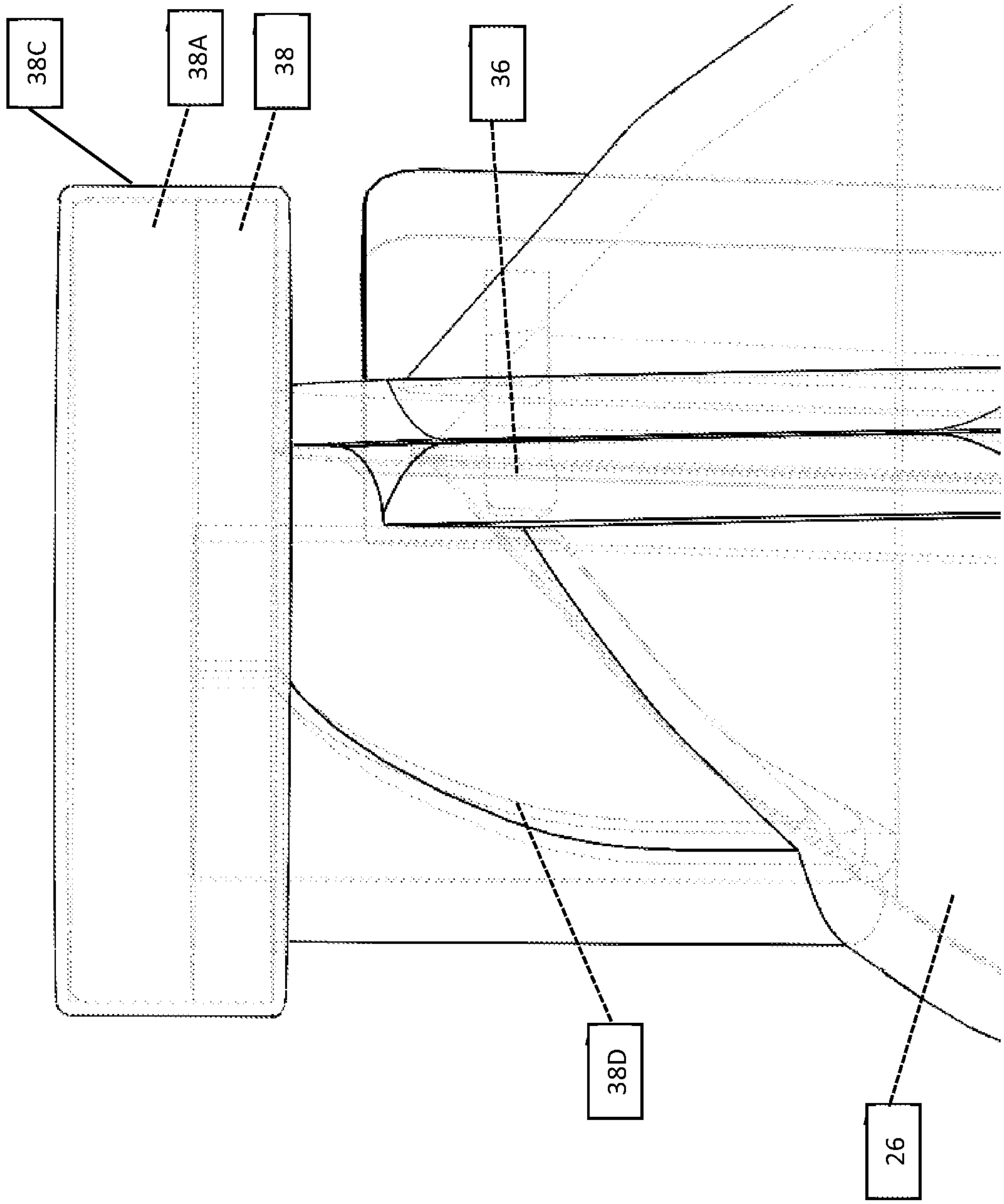
Figure 103:
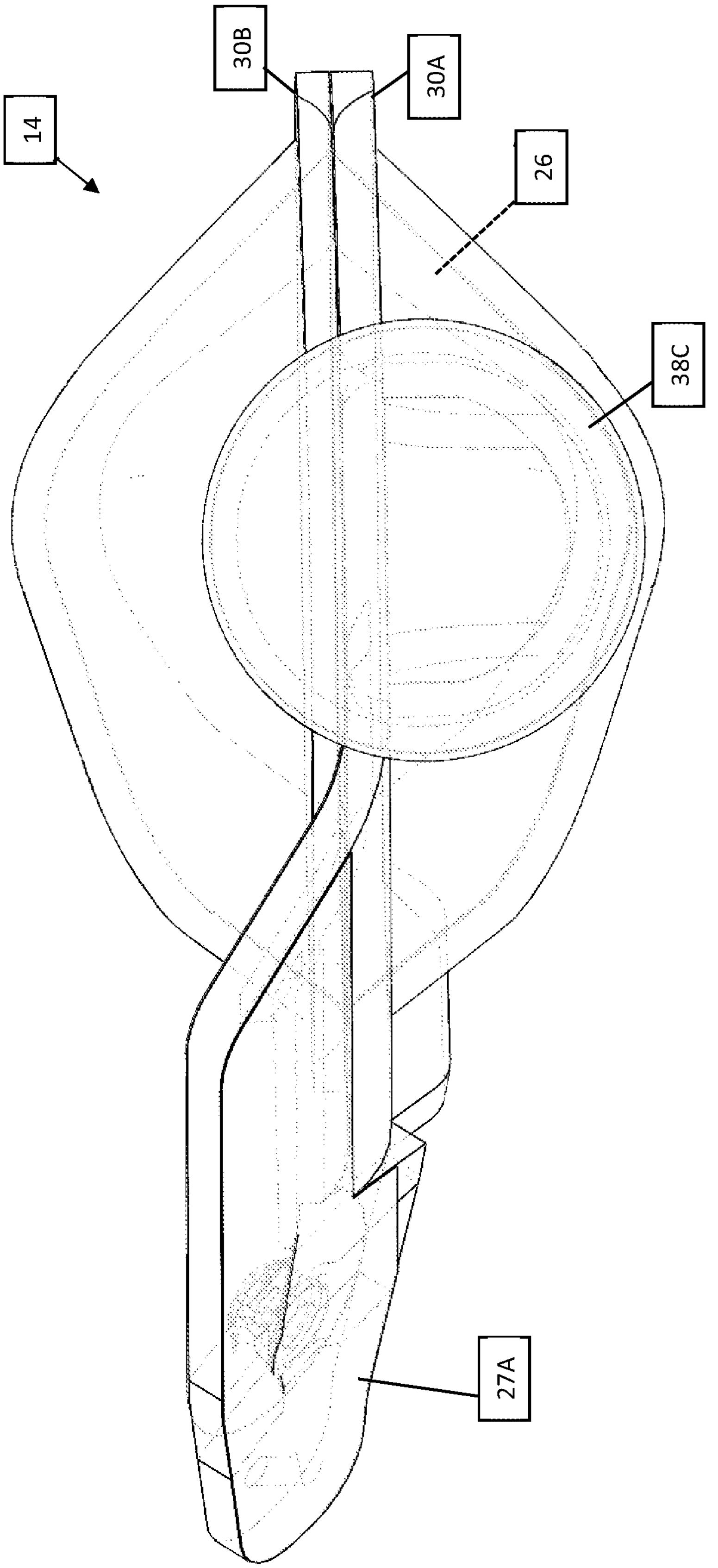
Figure 104:
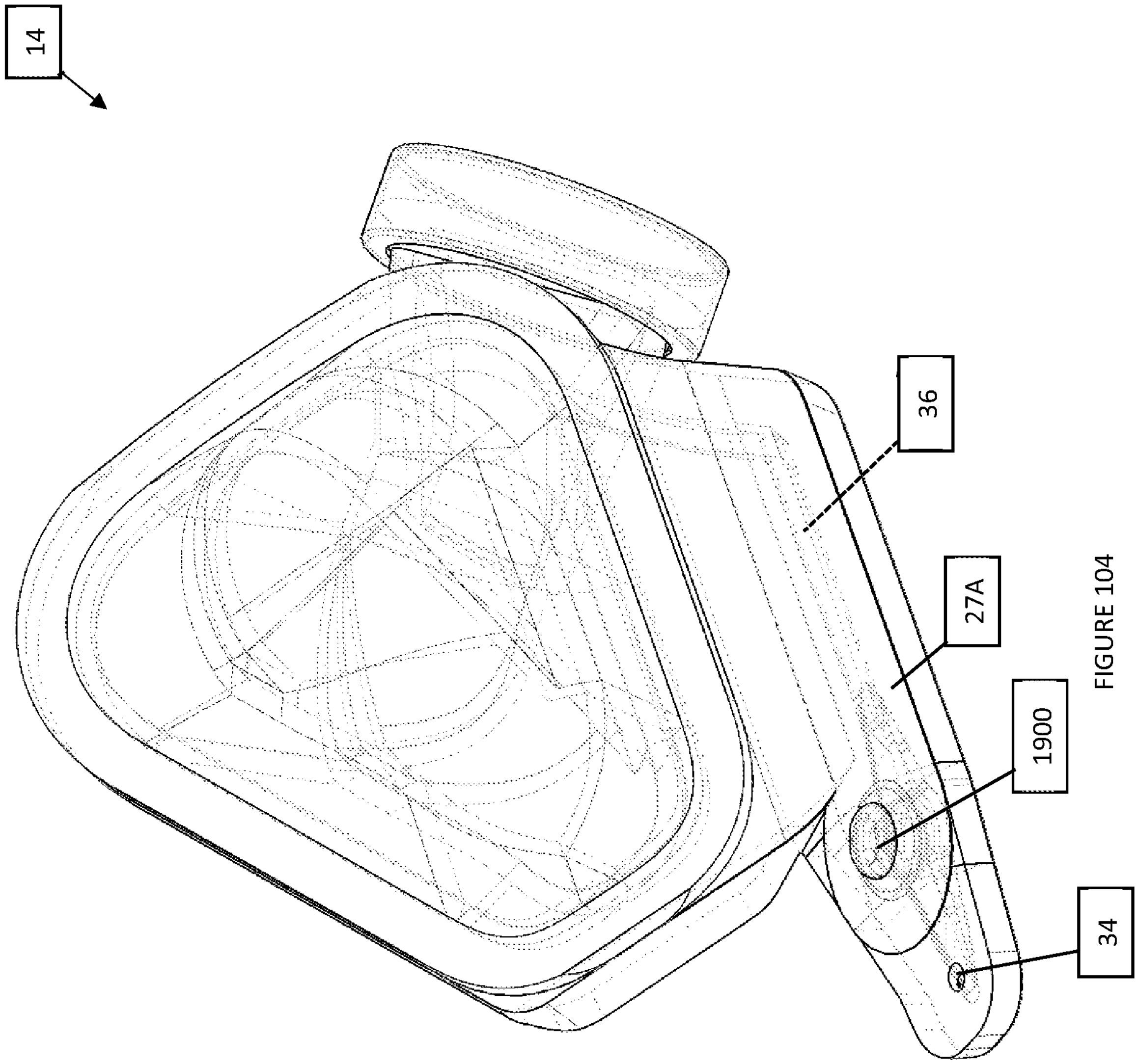
Figure 105:
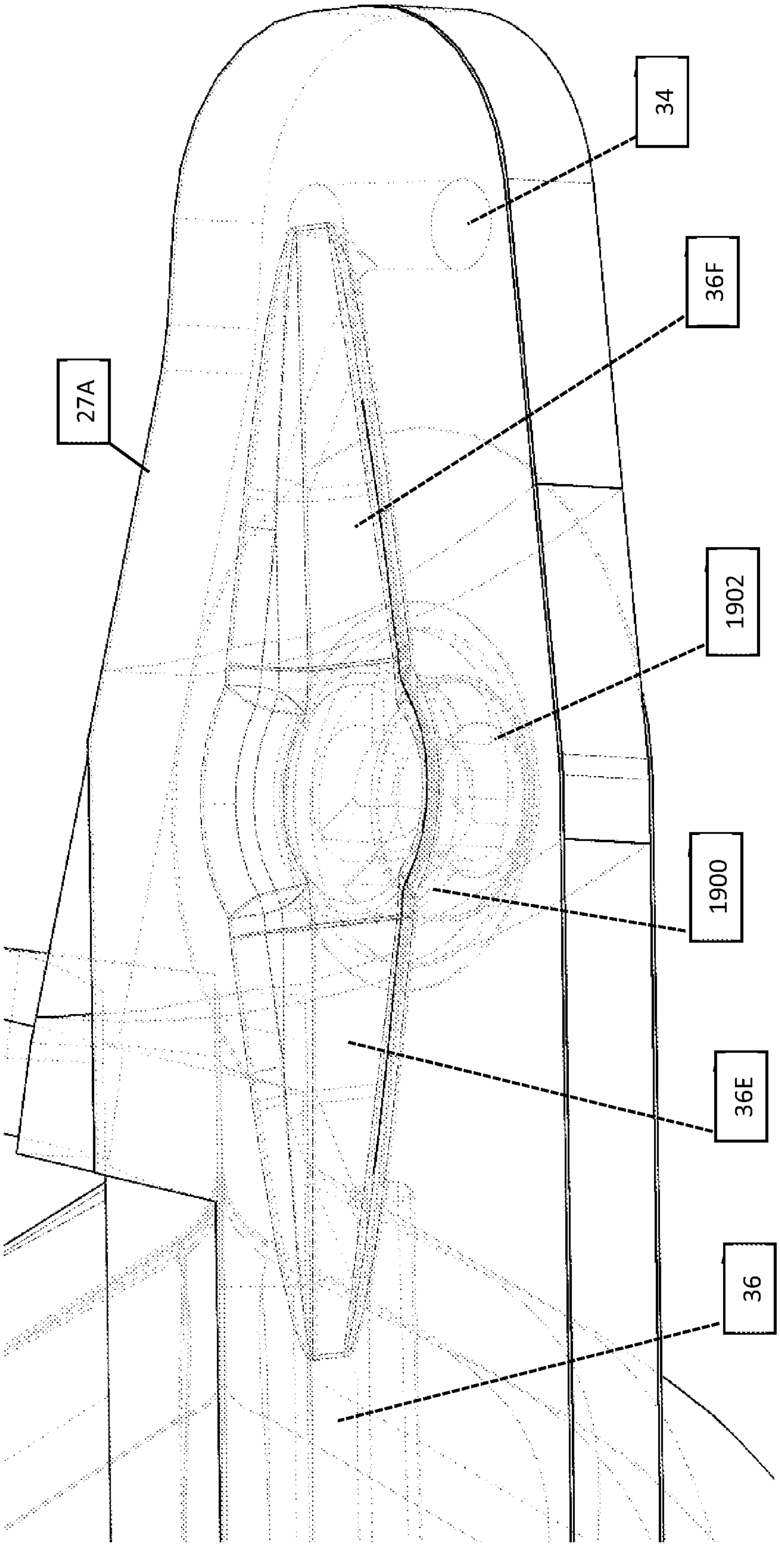
Figure 106:
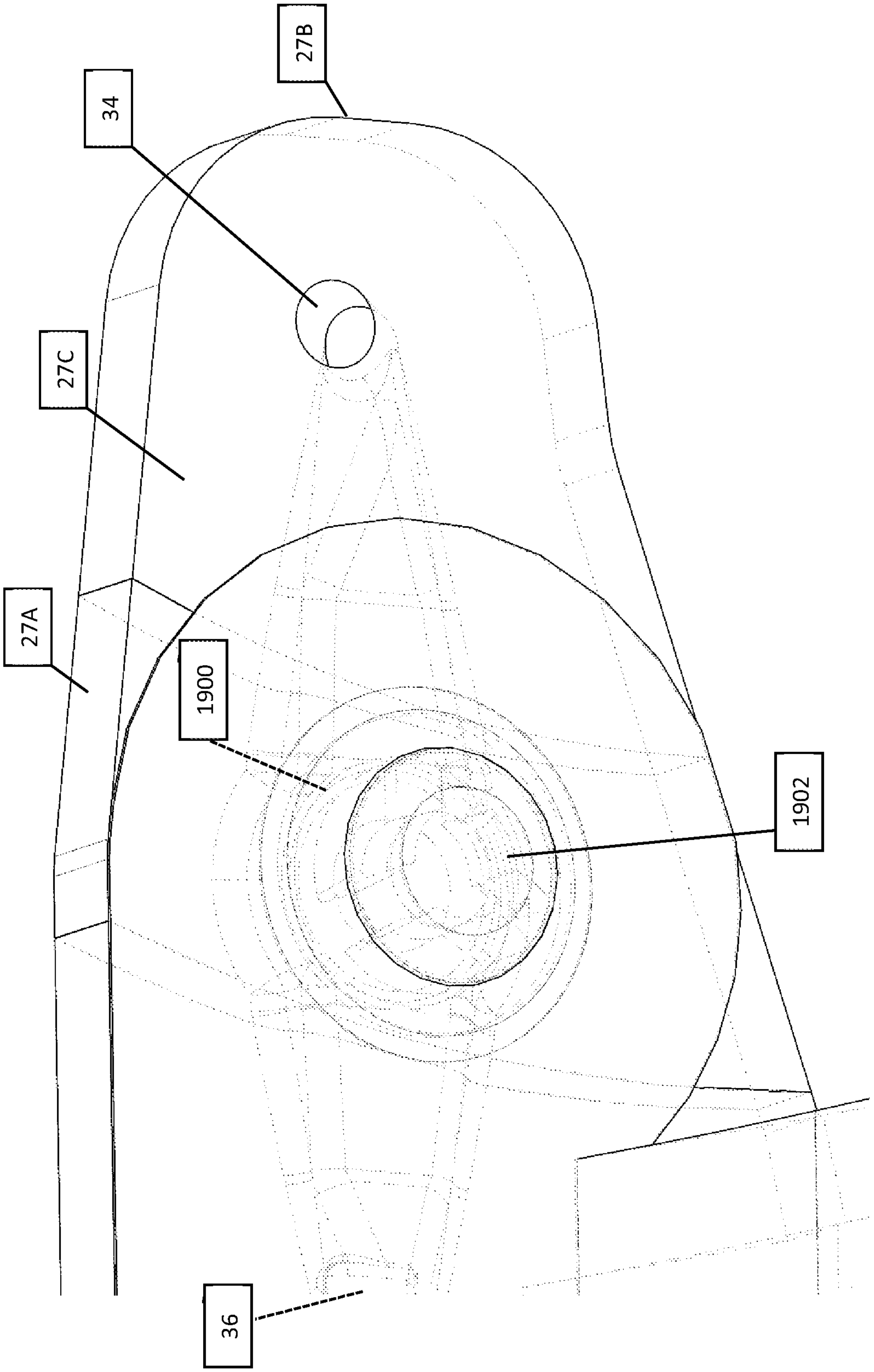

Alternatively, as shown in FIGS. 99-101, the vent plug 38A may be provided with the protruding beads 55 on the external surface 46 thereof. The vent plug 38A may include a hollow 38B on an upper surface thereof, which is engageable by a pick-and-place machine or other tool for insertion into the filling port 38. To prepare the drug cartridge 14, drug is introduced into the reservoir 26, after sterilization, through the filling port 38. Thereafter, as shown in FIG. 97, the vent plug 38A (after sterilization) may be partially inserted into the filling port 38 into an open, venting state with the venting passageways 72 being defined between the external surface 46 of the vent plug 38A and the filling port 38. Preferably, to achieve the venting state, the vent plug 38A is inserted into the filling port 38 to have the protruding beads 55 come into contact with the tapered section 49, with portions of the external surface 46 located about the protruding beads 55 being spaced from the filling port 38. The protruding beads 55 resiliently engage the filling port 38 to provide a holding force for the vent plug 38A in the venting state. The drug cartridge 14 may then be subjected to lyophilization conditions (low temperature and vacuum to extract moisture) to cause the drug in the reservoir 26 to lyophilize. During lyophilization, the vent plug 38A acts to retain the drug in the reservoir 26 while allowing venting about the vent plug 38A. Once lyophilization is completed, the vent plug 38A may be further inserted into the filling port 38 into a closed state, as shown in FIG. 98, with the external surface 46 generally coming into face-to-face contact with the filling port 38 to form a tight seal therewith. A crimped cap 38C may be provided to secure the vent plug 38A to the filling port 38, as shown in FIG. 102.

The vent plug 38A may be formed of an elastomeric material which is sterilizable. It is preferred that the vent plug 38A be oversized relative to the filling port 38 and sufficiently resilient to compress when urged to the closed state.

To best ensure stability of the vent plug 38A within the filling port 38, it is preferred that the filling port 38 be provided with a generally D-shaped cross-section (FIG. 94) with vent stem 38D of the vent plug 38D having a matching D-shaped cross-section formed to shape mate with the D-shaped filling port 38. With the vent plug 38A inserted into the filling port 38, the interengagement of the curved portion of the vent stem 38D with the curved portion of the filling port 38 provides multi-axial stability to the vent plug 38A relative to the filling port 38. In addition, the inner surface 38E of the vent stem 38D, as being on the inside of the curved profile of the vent stem 38D, may also define a venting passageway 72 with the vent plug 38A in the open, venting state.

It is noted that the internal lumen 36 may be shown open in certain figures in connection with the venting feature. The internal lumen 36 may be sealed, particularly in a portion of the plug adapter 14B not shown, and, thus, cannot provide venting.

Figure 34A:
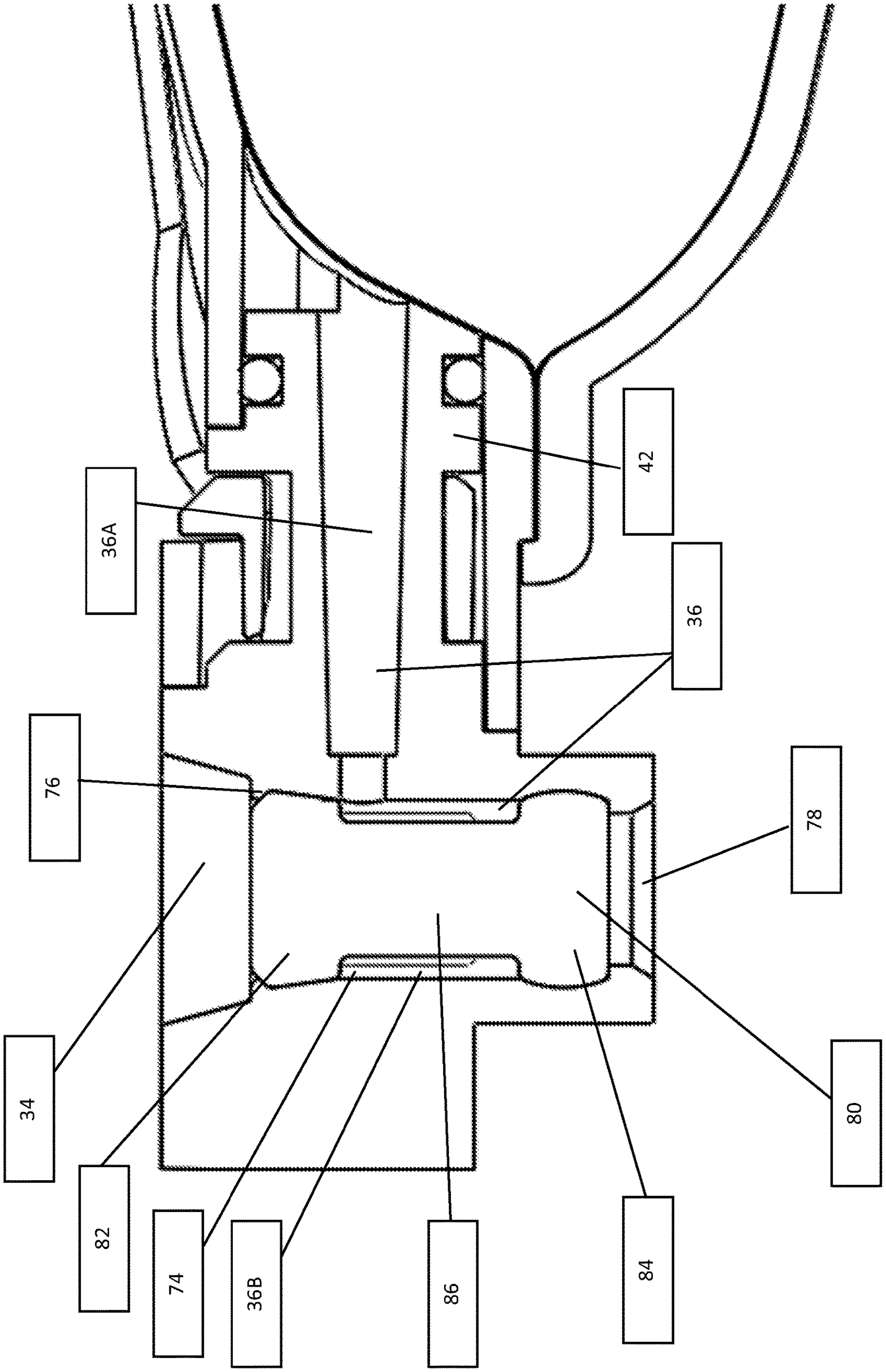
FIG. 34A is a section view of a plug adapter in the sealed position, in accordance with the subject invention.
Figure 35A:
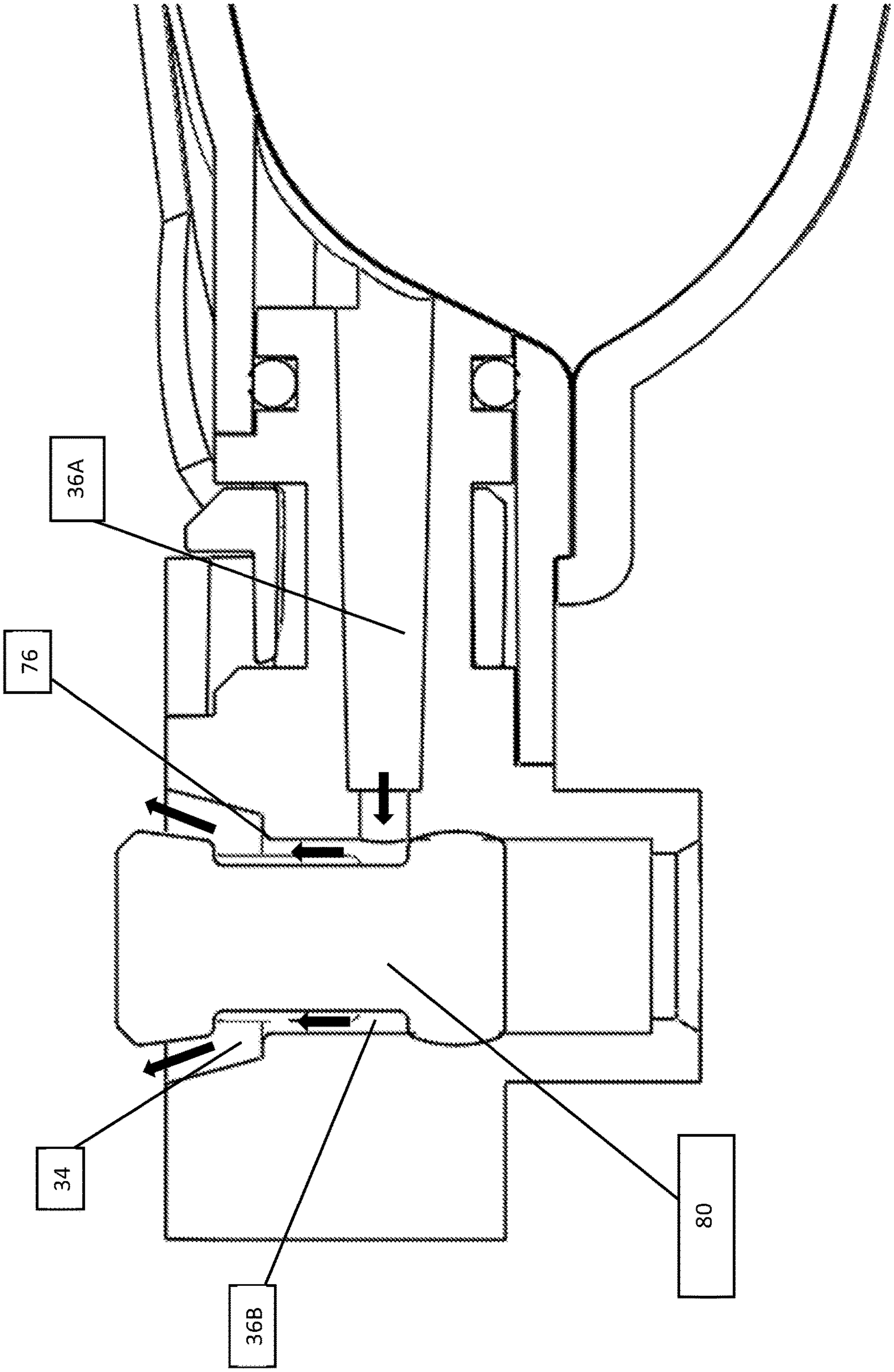
FIG. 35A is a section view of the plug adapter of FIG. 34, in the opened position.

The internal lumen 36 may be sterilized using any technique. The seal may be formed also using any technique. By way of non-limiting example, as shown in FIG. 34A, the internal lumen 36 may be provided with a first lumen portion 36A which extends from the reservoir 26, e.g., through the neck 42. A second lumen portion 36B may be disposed transversely to the first lumen portion 36A. At a first end 74, the second lumen portion 36B terminates at a valve seat 76 located at an interface of the fluid outlet 34 and the inner lumen 36. A second end 78 of the second lumen portion 36B may be open. A valve 80 may be located in the second lumen portion 36B. The valve 80 may be spool shaped having first and second enlarged lands 82, 84 connected by an elongated core 86. To form the seal, the first land 82 is seated in the valve seat 76. Thus, portions of the internal lumen 36 inside of the first land 82 are sealed from contaminants. To cause un-sealing, as shown in FIG. 35A, the valve 80 may be shifted within the second lumen portion 36B to separate from the valve seat 76.

The second end 78 of the second lumen portion 36B may be formed closed, or sealed with a plug or other element. The second end 78 may be provided open to allow for a control element to extend into the second lumen portion 36B to engage the valve 80 in causing shifting thereof. With the second end 78 being open, the second land 84 is positioned between the second end 78 and the first lumen portion 36A to seal the internal lumen 36. In this manner, sterility may be maintained particularly along the first lumen portion 36A and portions of the second lumen portion 36B leading towards the fluid outlet 34. The valve 80 is formed such that the second land 84 remains continuously between the first lumen portion 36A and second end 78 during shifting of the valve 80.

The valve 80 may include elastomeric and/or non-elastomeric materials. The valve 80 requires sufficient internal resilience to maintain the formed seal. In addition, as discussed below, the valve 80 may be exposed to ultraviolet radiation, x-ray radiation, pulsed light or electron-beam treatment. Appropriate material selection is required.

As will be appreciated by those skilled in the art, the valve 80 provides a seal which is inside of the internal lumen 36, thus leaving open the fluid outlet 34 exposed. With this arrangement, sterility of the internal lumen 36 to the reservoir 26, and the reservoir 26, is maintained. Further sterilization, however, will be required, e.g., of the fluid outlet 34, for actual use.

Figure 34B:
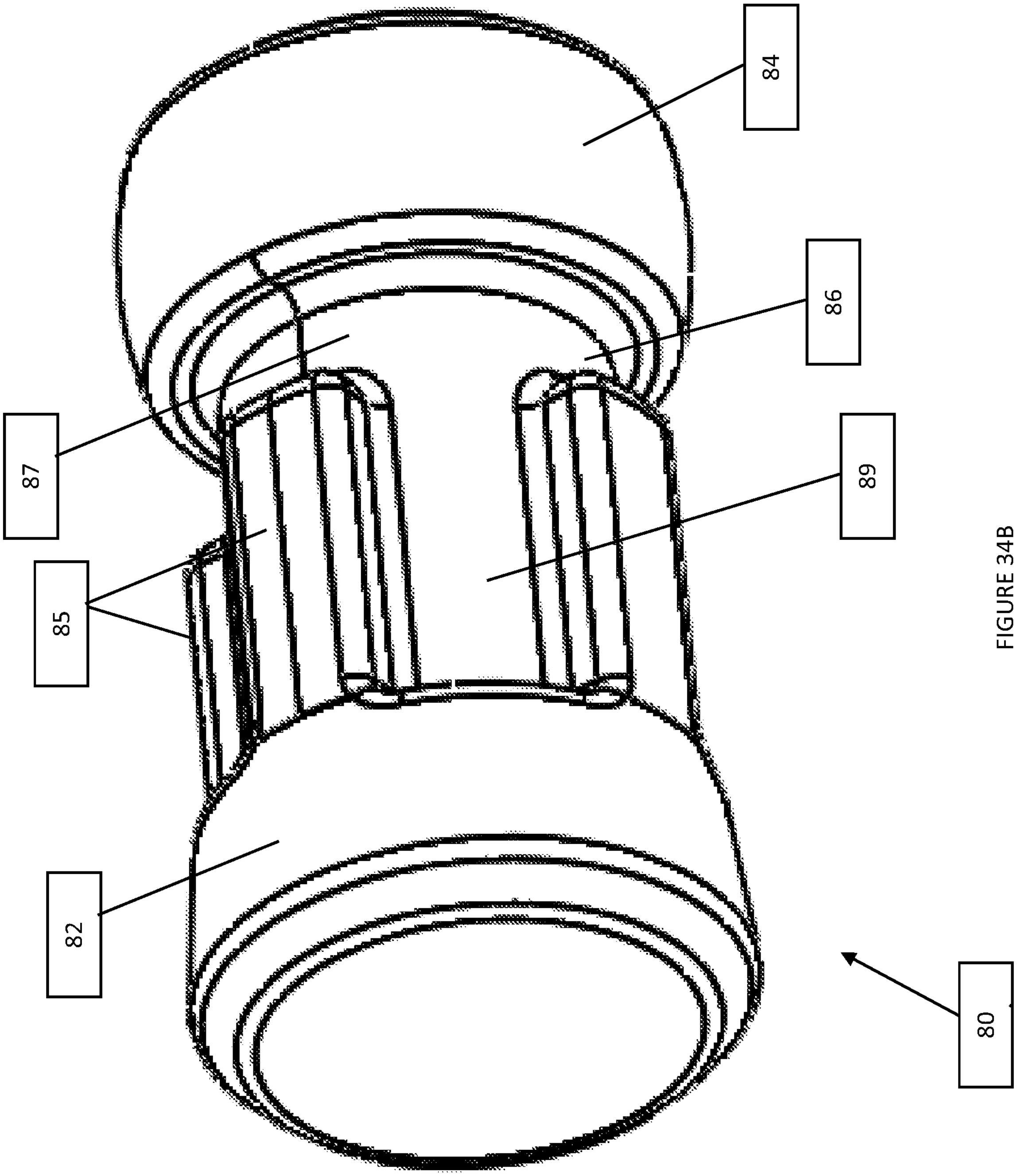
FIG. 34B is a perspective view of a valve useable with the plug adapter, in accordance with the subject invention.
Figure 34C:
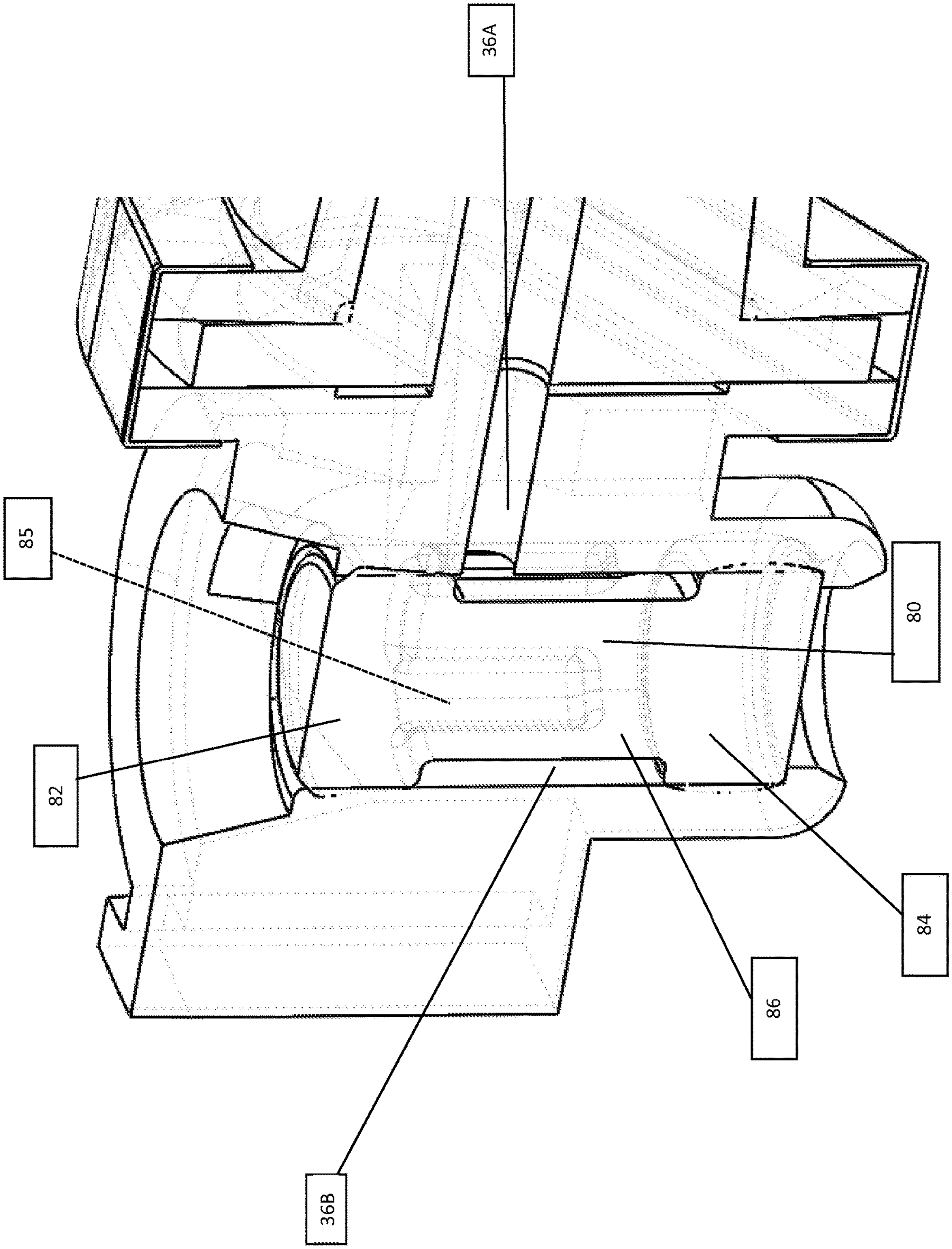
FIG. 34C is a section view of a plug adapter using the valve of FIG. 34A, in the sealed position.
Figure 35B:
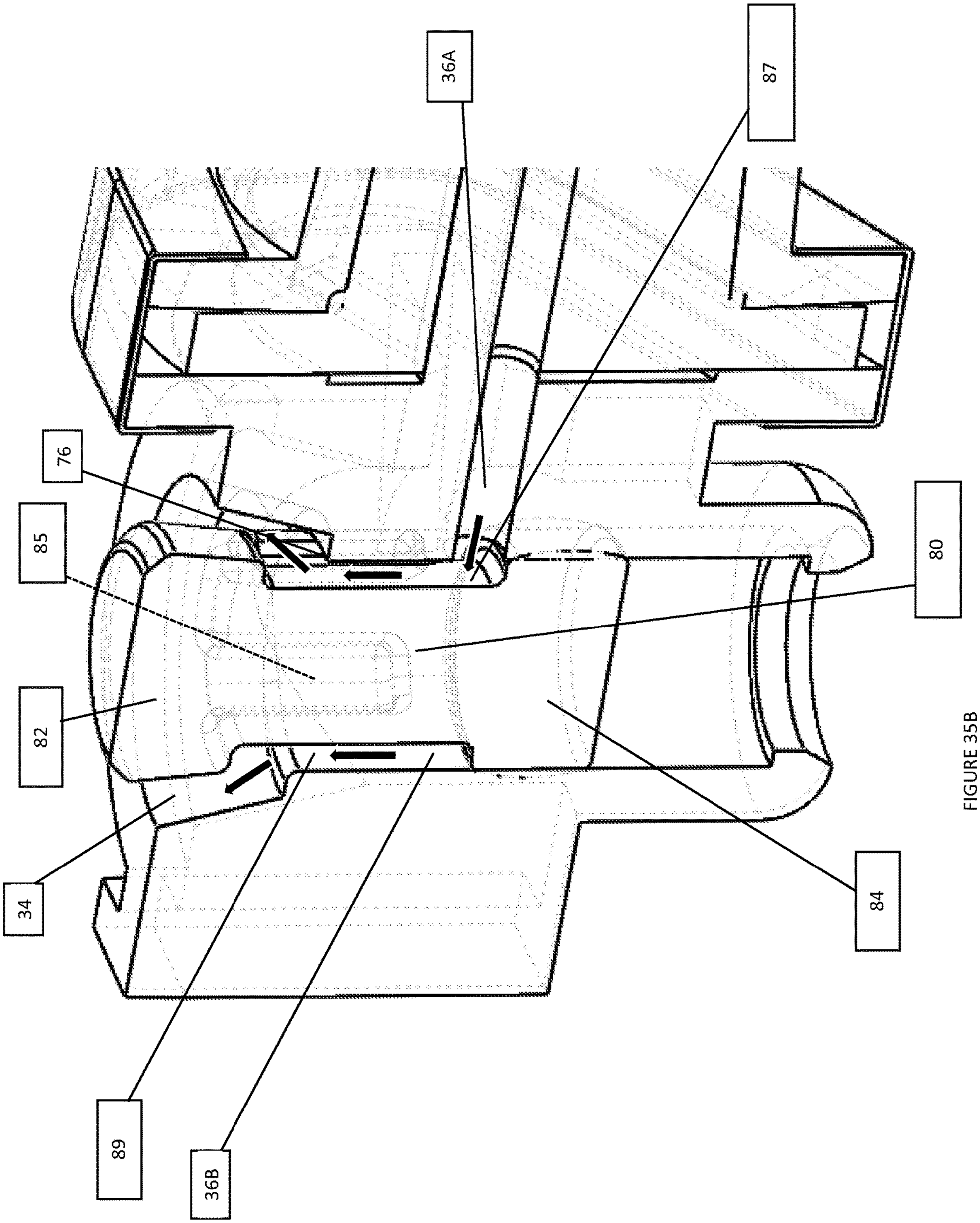
FIG. 35B is a section view of a plug adapter using the valve of FIG. 34A, in the opened position.

As shown in FIGS. 34B and 34C, the valve 80 may include a plurality of spaced-apart positioning ribs 85 extending longitudinally along the elongated core 86 from the first land 82. Preferably, the positioning ribs 85 are spaced from the second land 84 to define an open ring 87 between the positioning ribs 85 and the second land 84, about the elongated core 86. The positioning ribs 85 collectively define an outer diameter which is larger than the diameter of the valve seat 76. Thus, as shown in FIG. 35B, the positioning ribs 85 engage the valve seat 76 to center the valve 80 within the valve seat 76, and provide stability to the valve 80 in the un-scaled position. Channels 89 are defined between the positioning ribs 85 to allow flow therethrough with the valve 90 being un-sealed (with the positioning ribs 85 engaging the valve seat 76). Preferably, the positioning ribs 85 are parallel to define the channels 89 are parallel.

Figure 95:
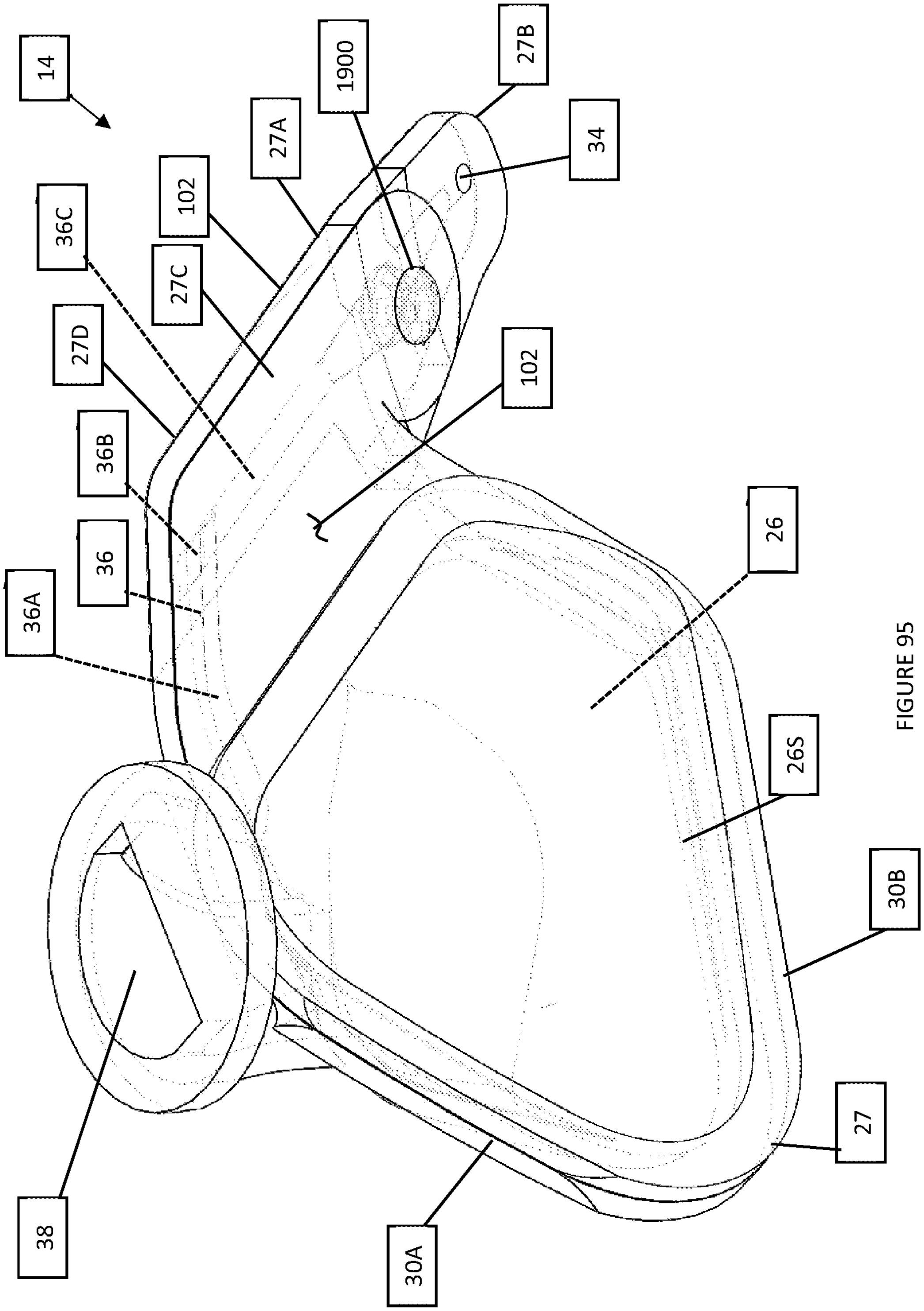

As shown in FIG. 95, the internal lumen 36 may be formed in similar manner described above in connection with the fluid ducts 22. In particular, the first lumen portion 36A may be formed along a first face 27C of the wing portion 27A to be exposed for sterilization. The second lumen portion 36B may provide a change in direction with the third lumen portion 36C formed along a second face 27D of the wing portion 27A. The first and third lumen portions 36A, 36C, as being open trenches, allow for sterilization including the second lumen portion 36B. A barrier 102 (discussed infra) may be provided on each of the first face 27C and the second face 27D to seal the first lumen portion 36A and the third lumen portion 36C. Alternatively, the flexible reservoir walls 26R, 26S may be extended through the flange 27 on opposing sides of the wing portion 27A to provide the barriers 102 seal the first and third lumen portions 36C. As will be understood by those skilled in the art, the internal lumen 36 may be provided in various configurations with different portions being exposed or recessed along the wing portion 27A. Within these configurations, exposed portions of the internal lumen 36 are covered to provide closed flow paths.

Figure 107:
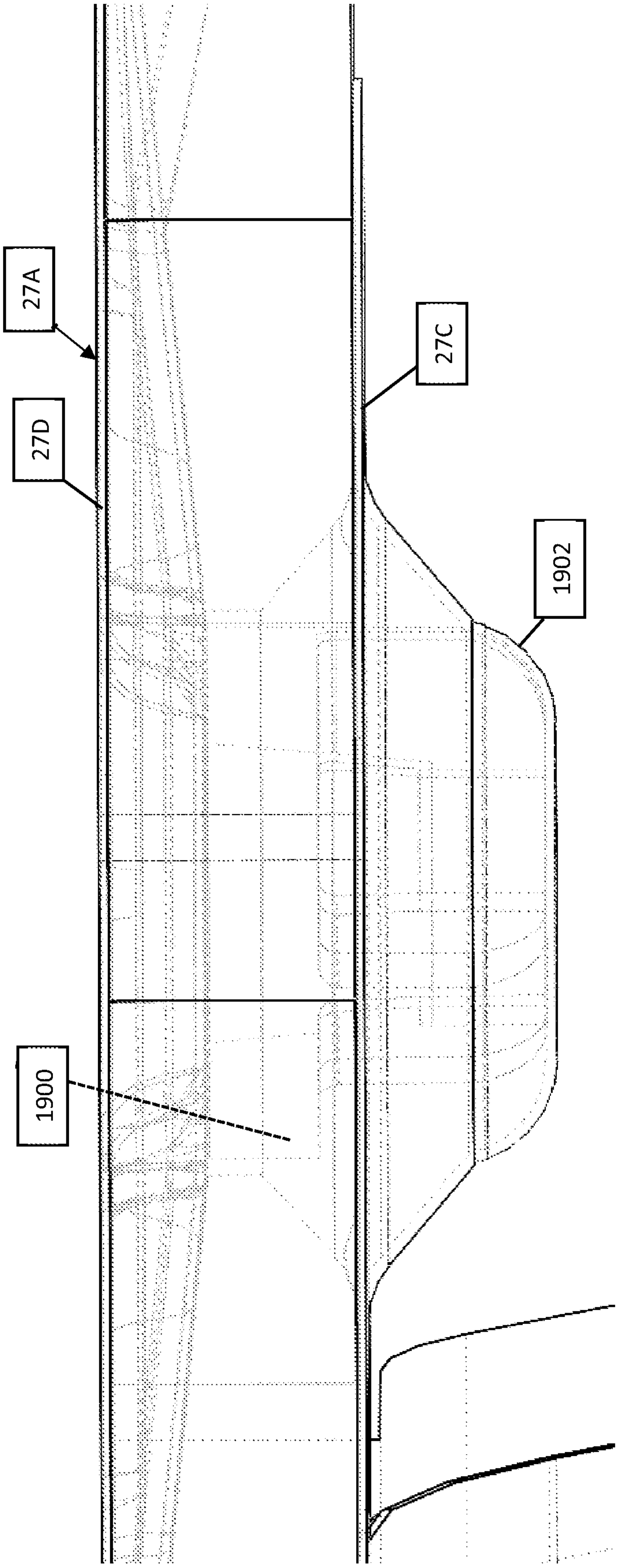
Figure 108:
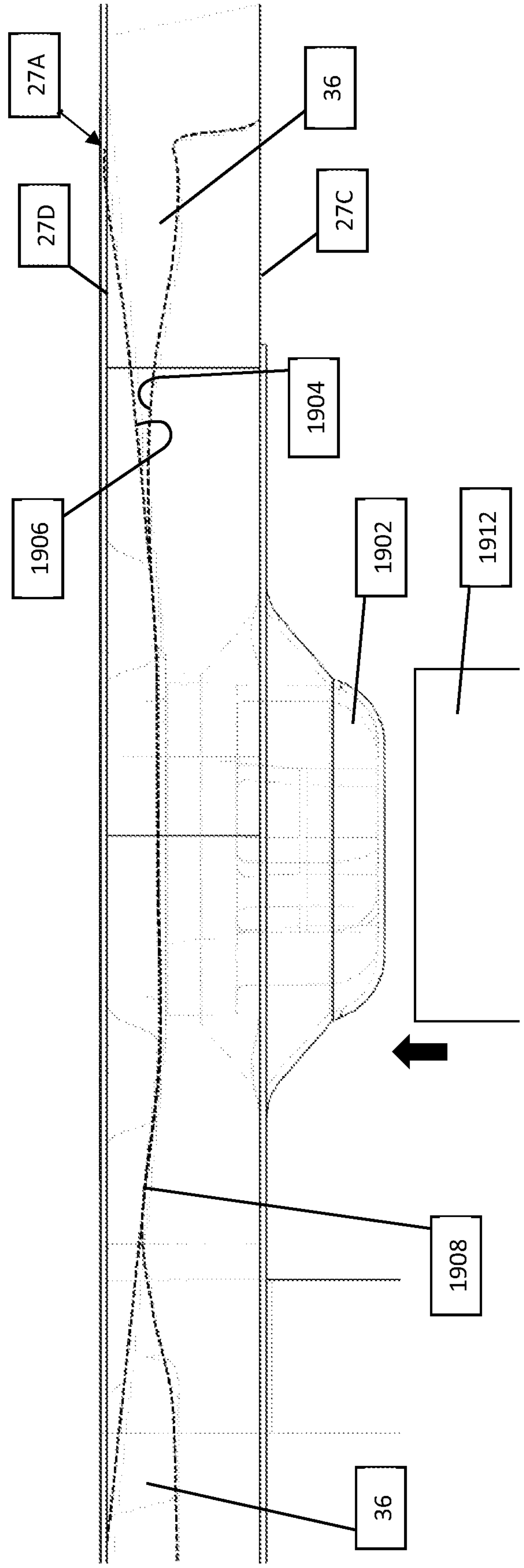
Figure 109:
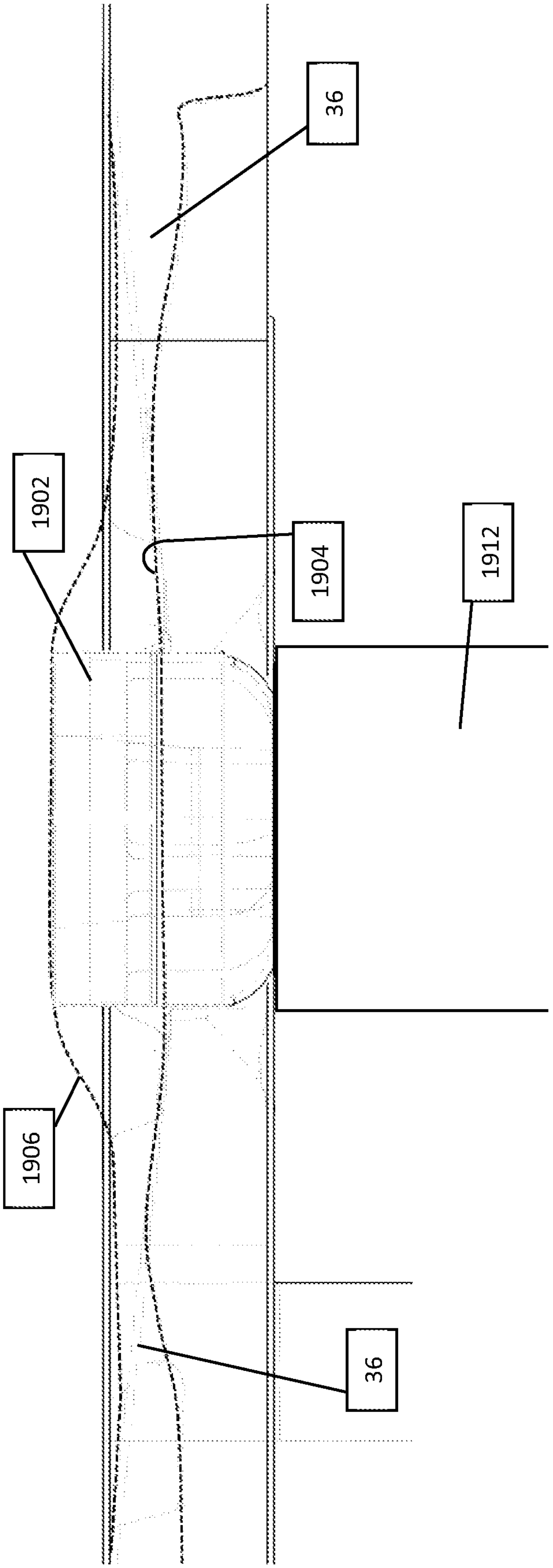
Figure 110:
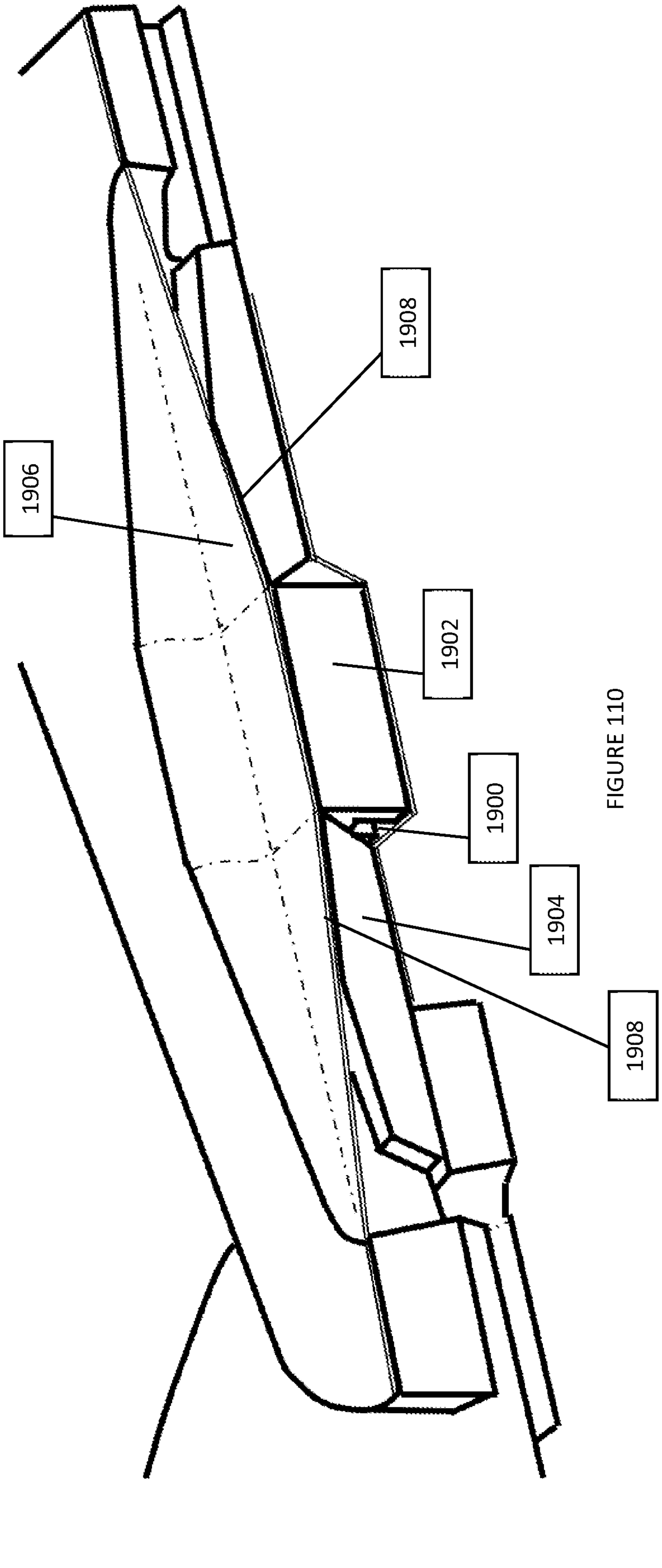
Figure 111:
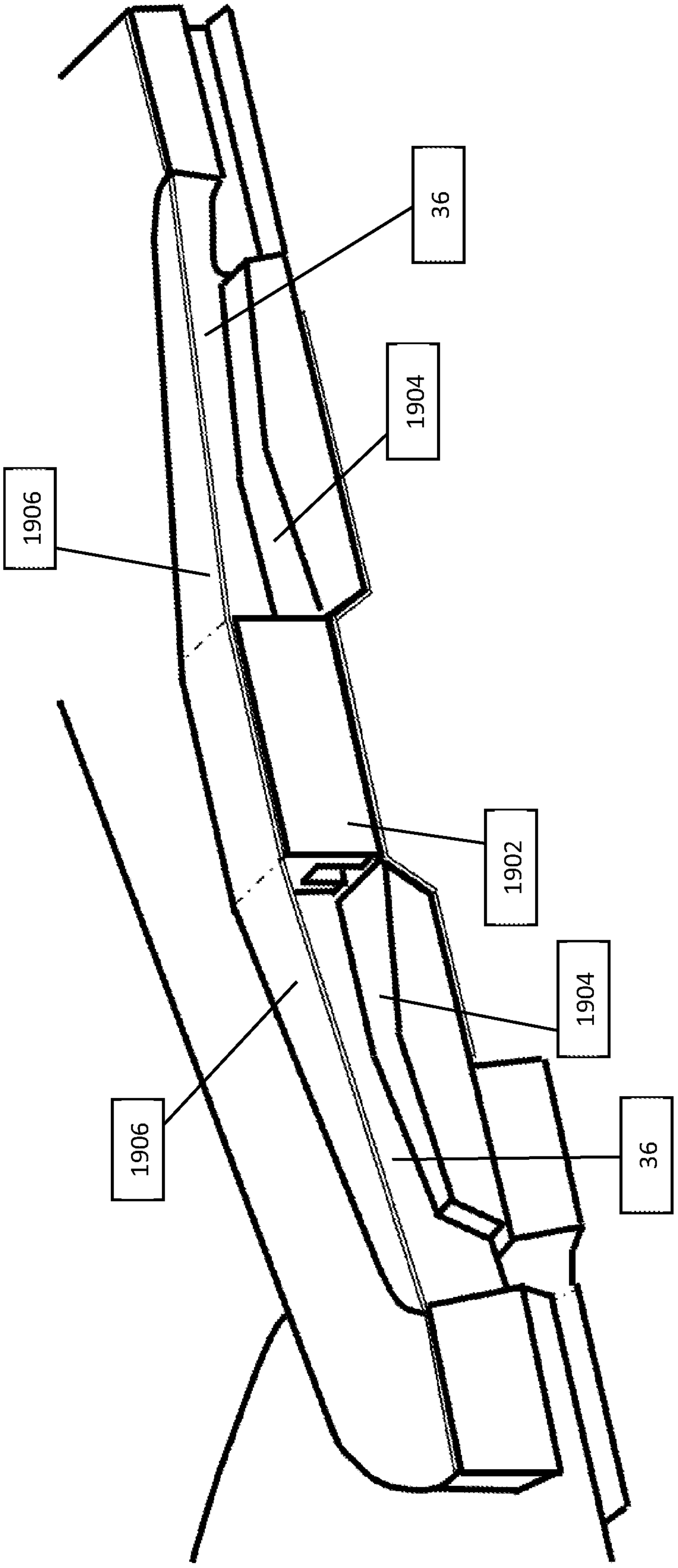
Figure 112:
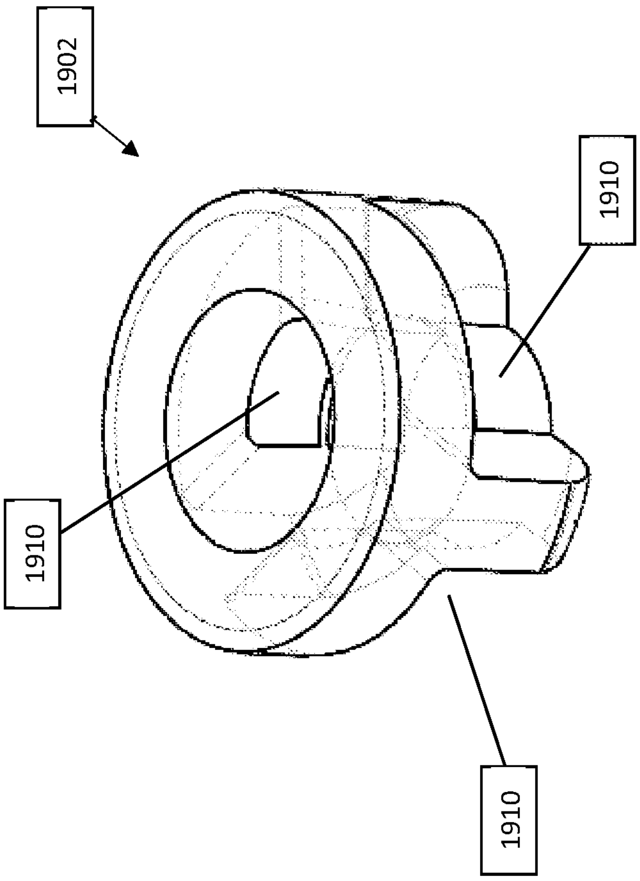
Figure 113:
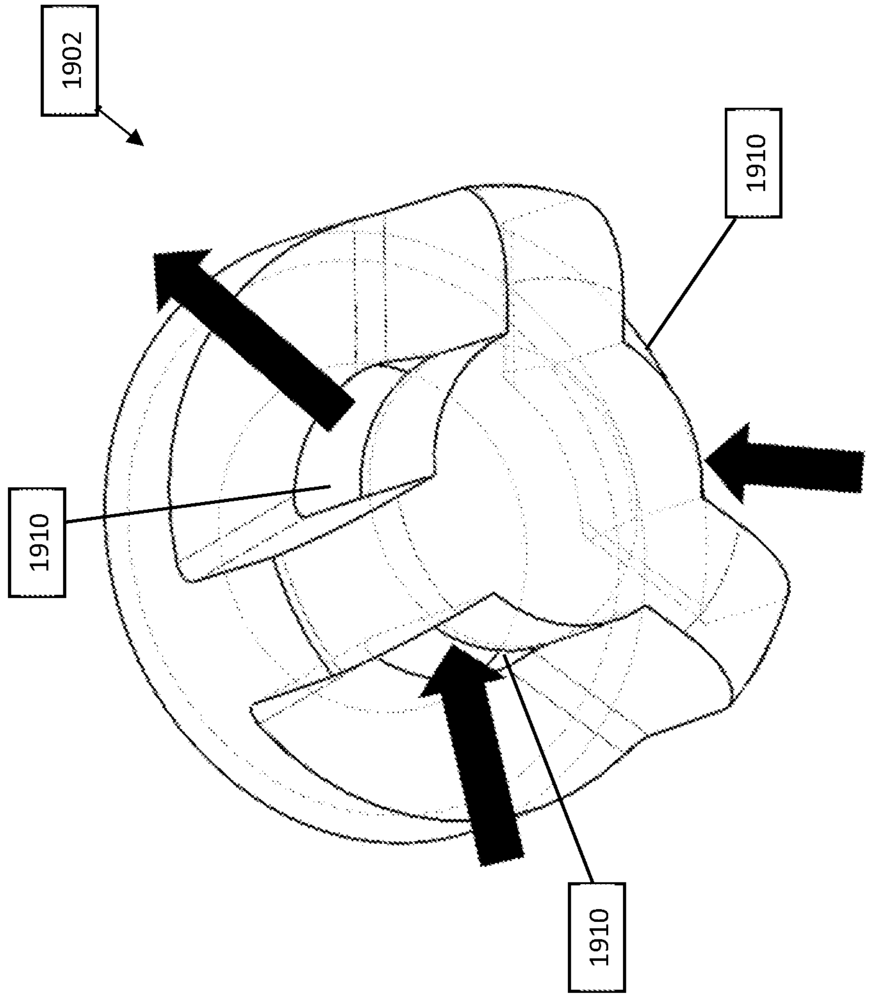
Figure 114:
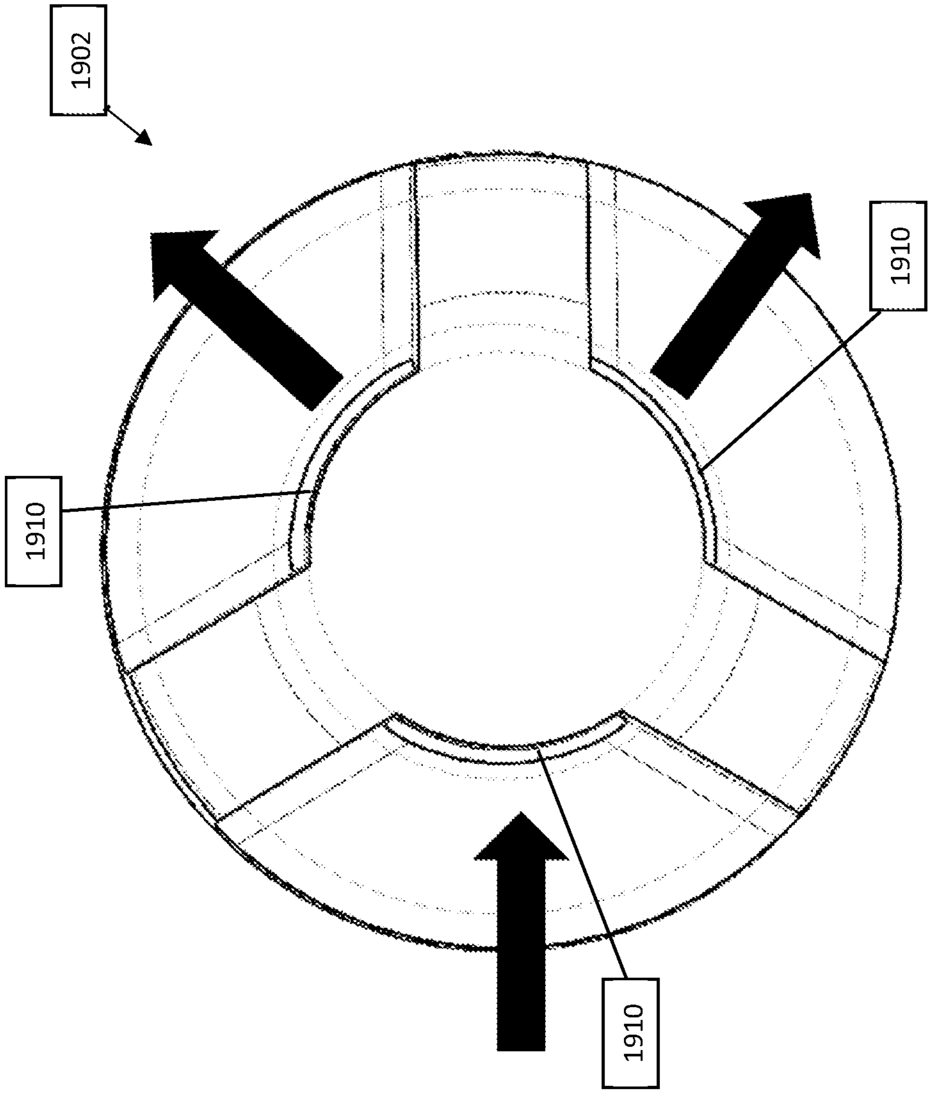
Figure 115:
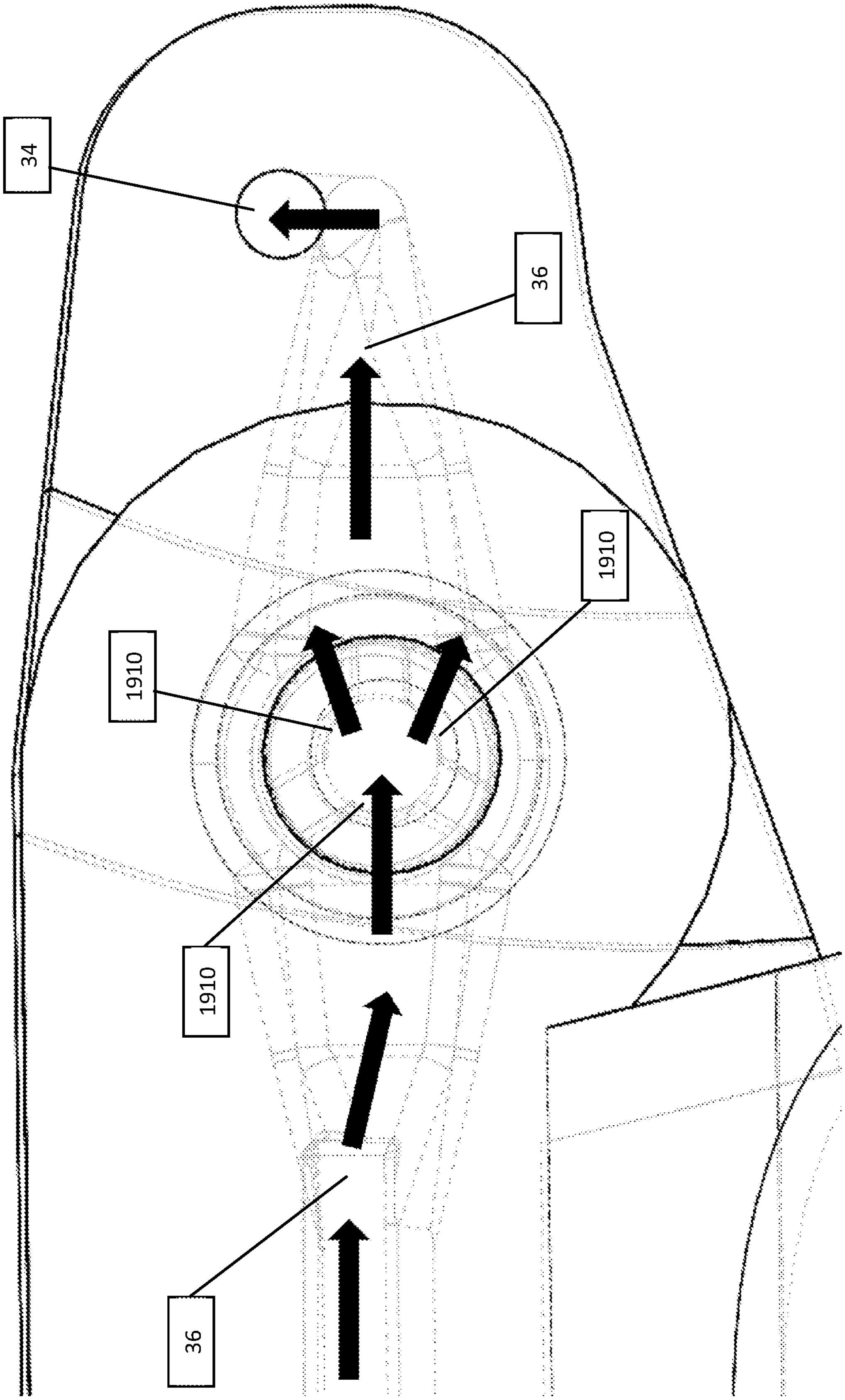
Figure 116:
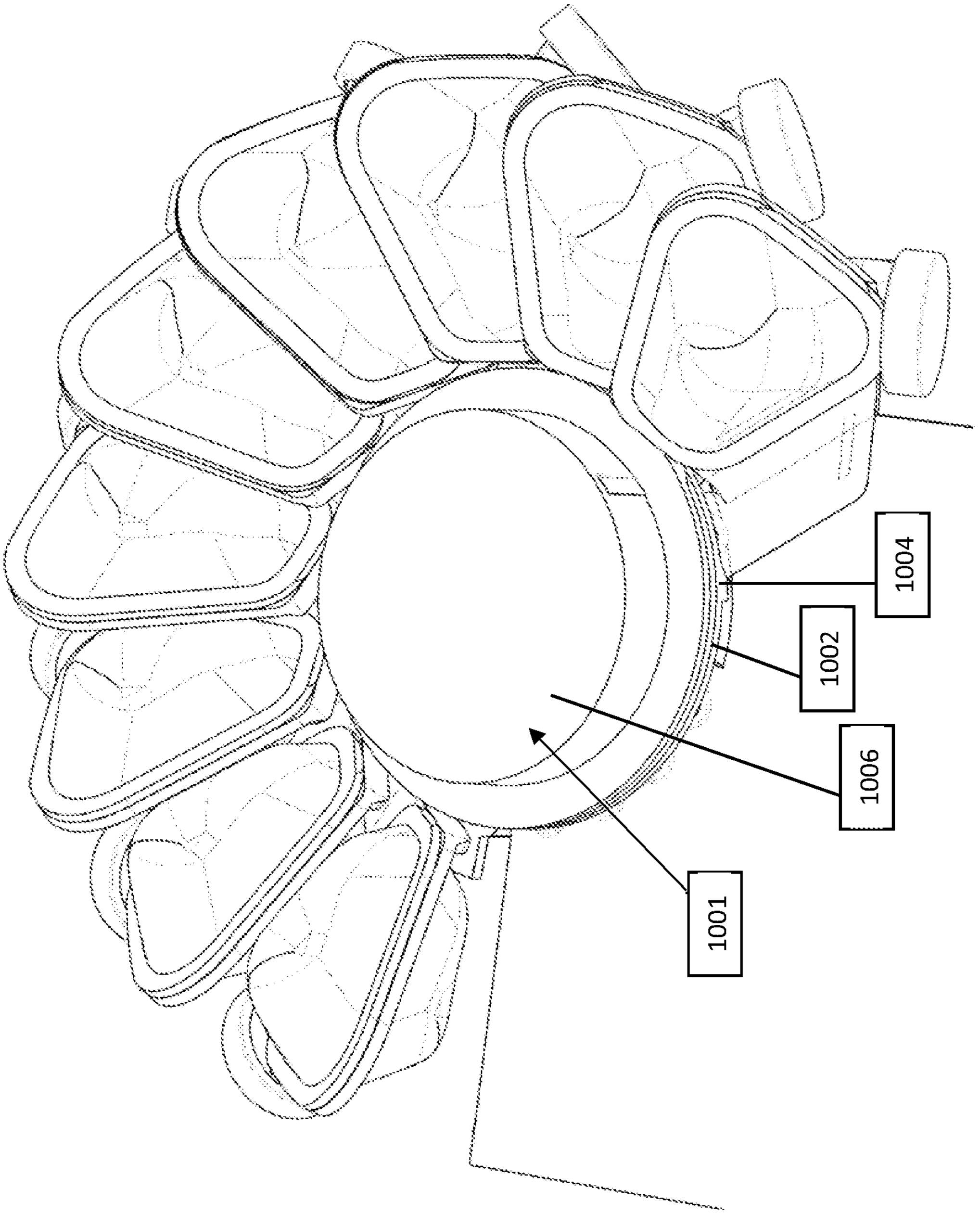
Figure 117:
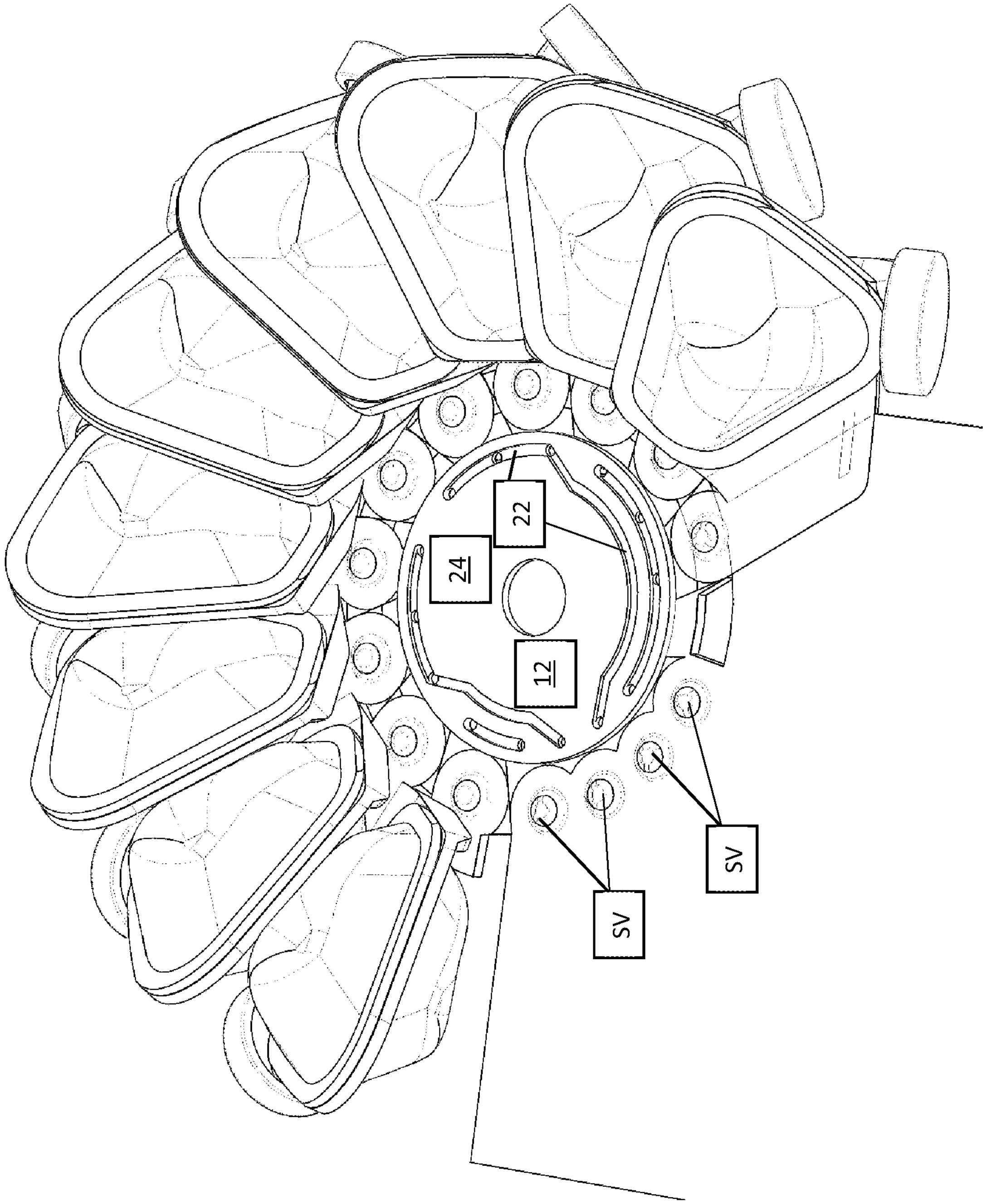
Figure 118:
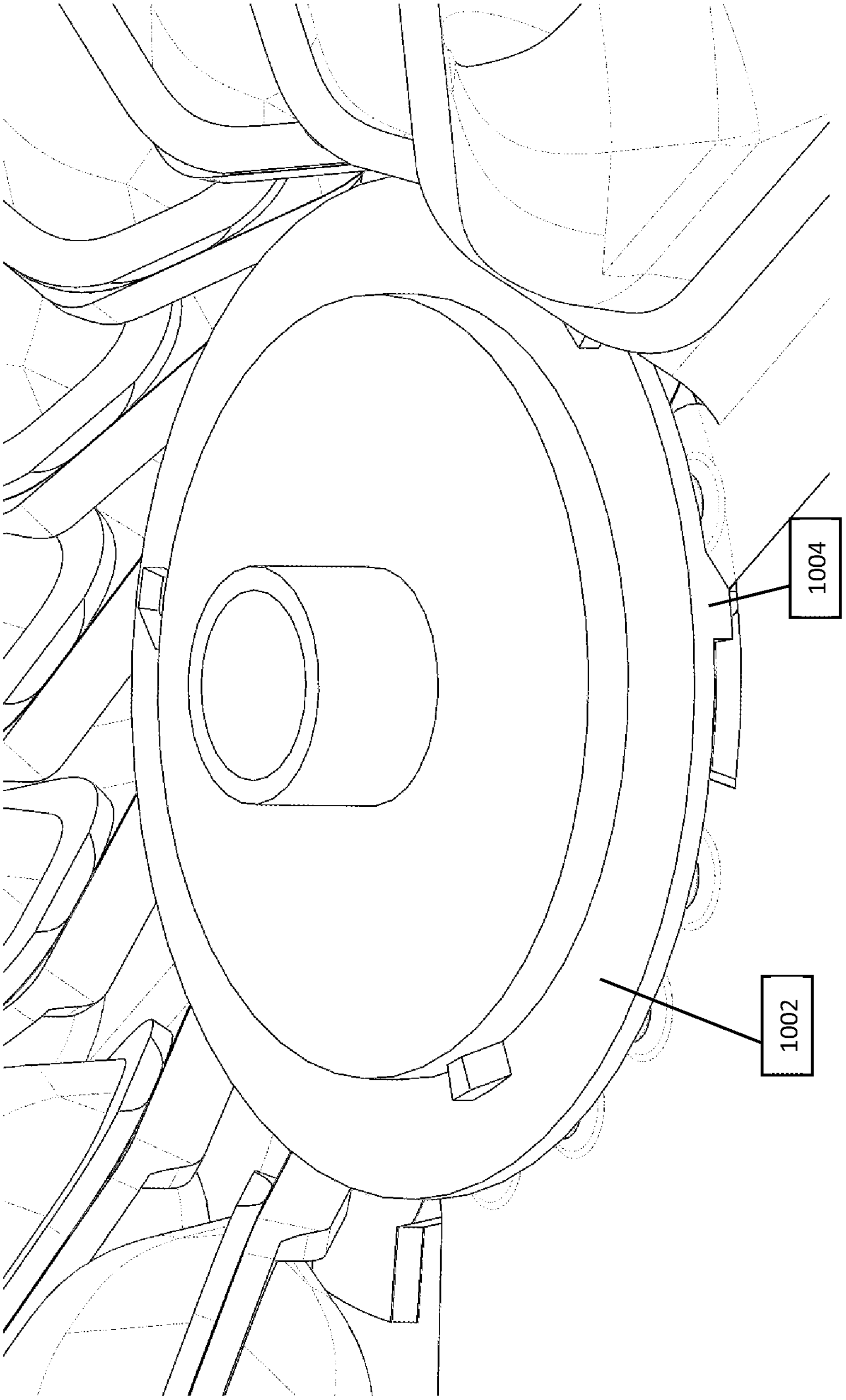
Figure 119:
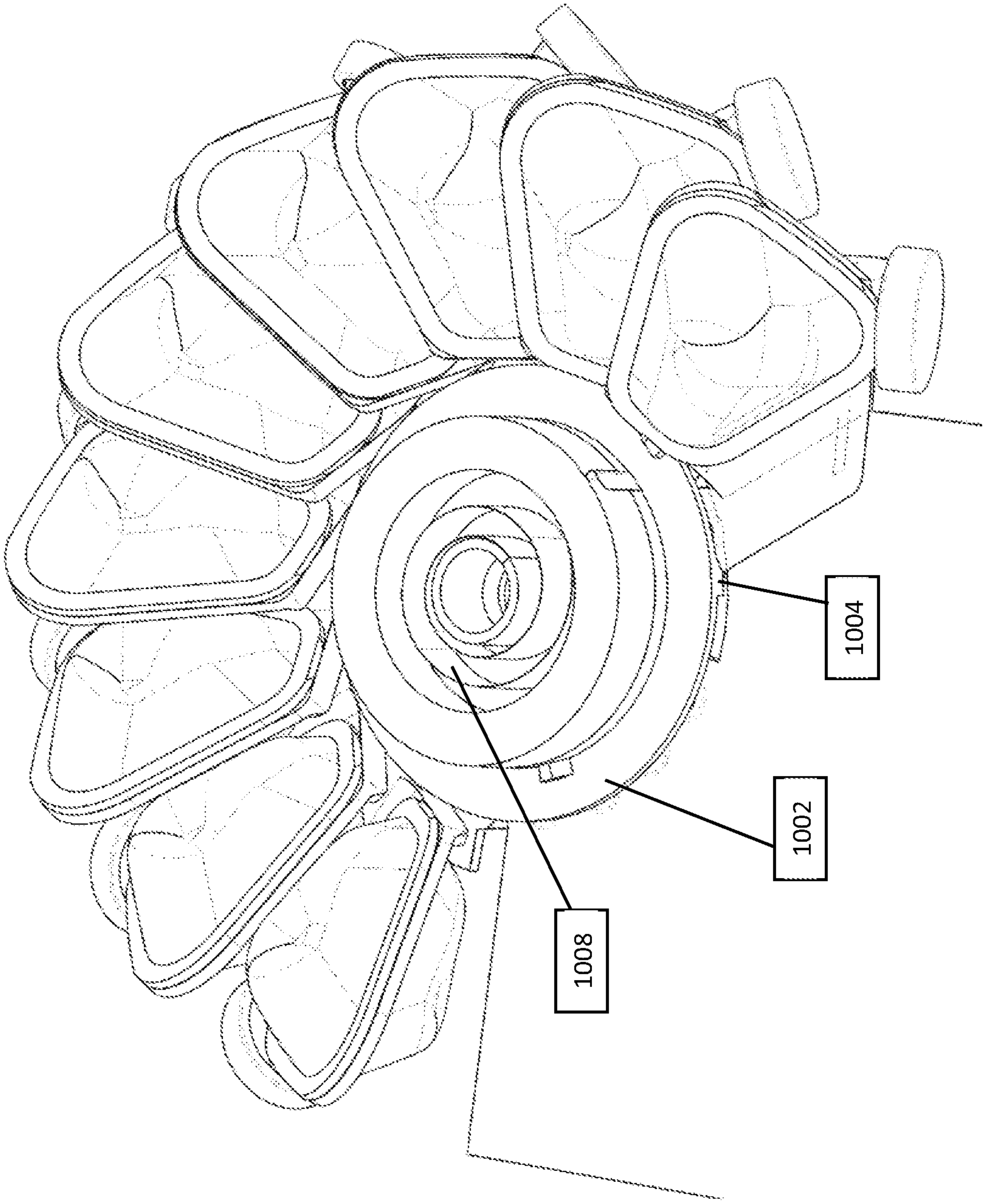
Figure 120:
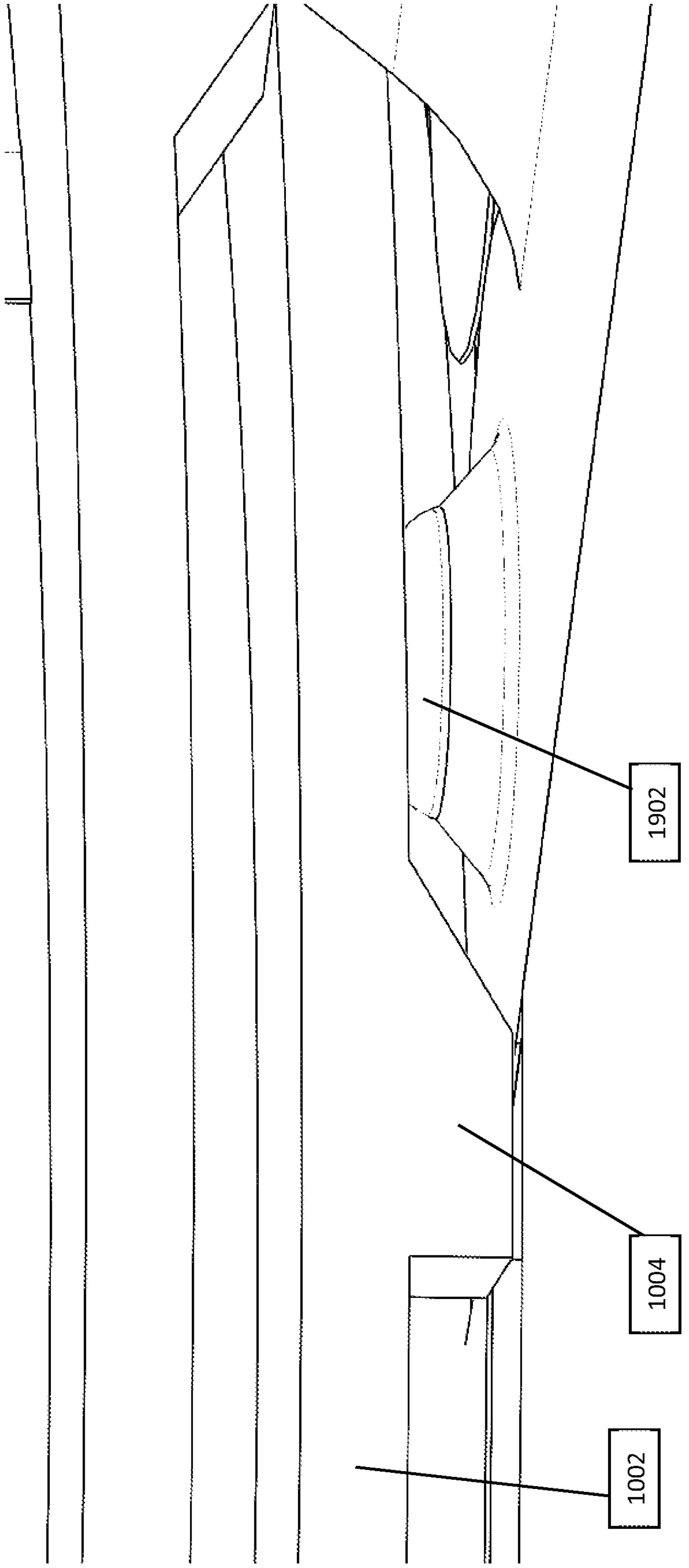
Figure 121:
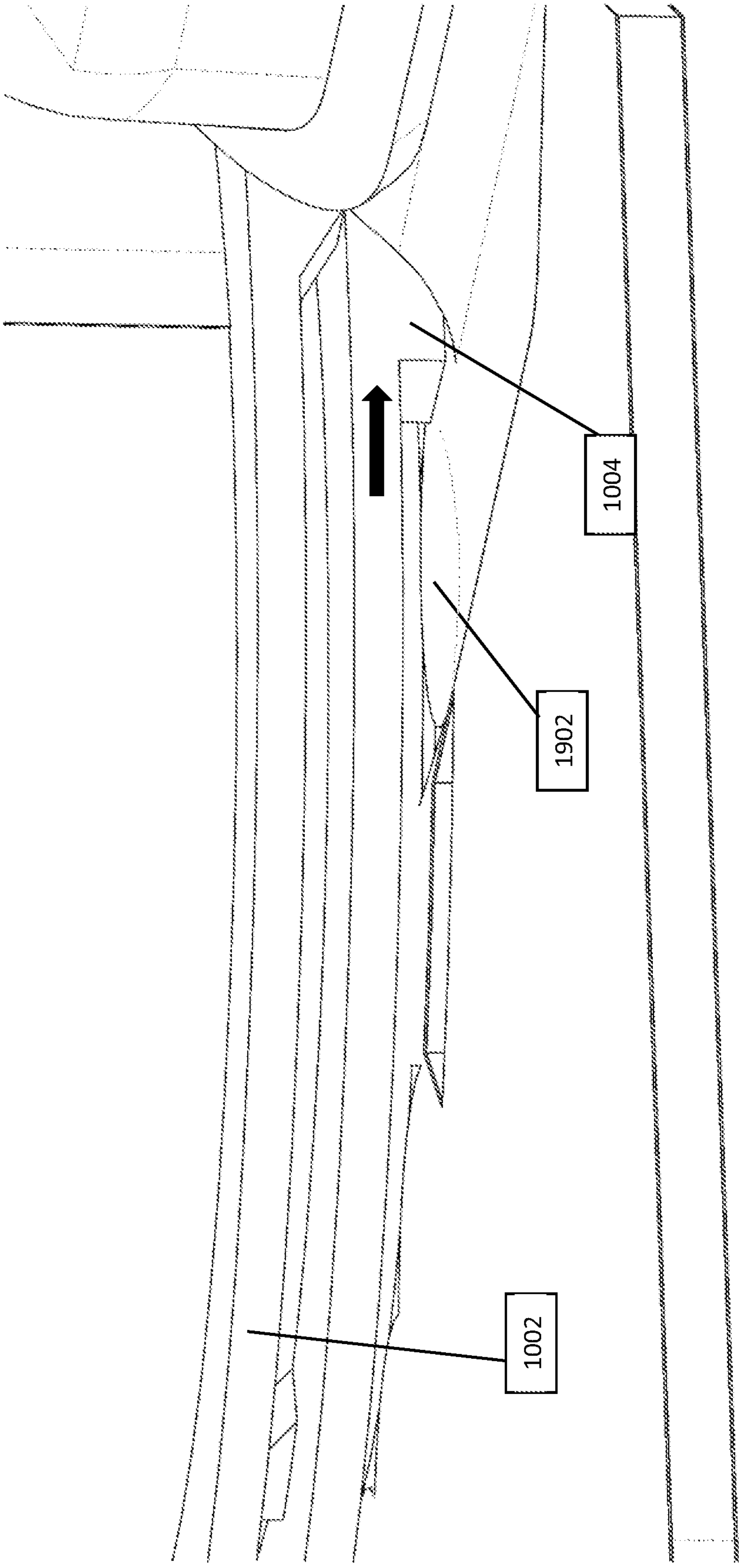
Figure 122:
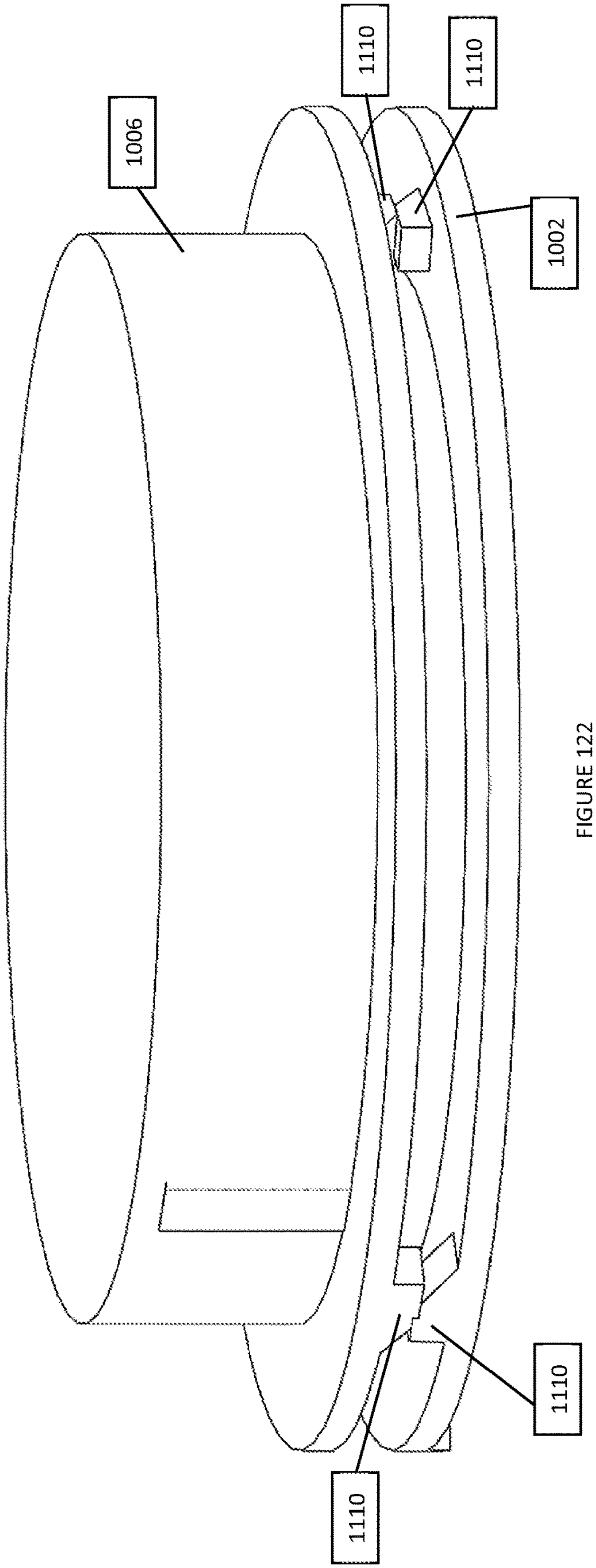
Figure 123:
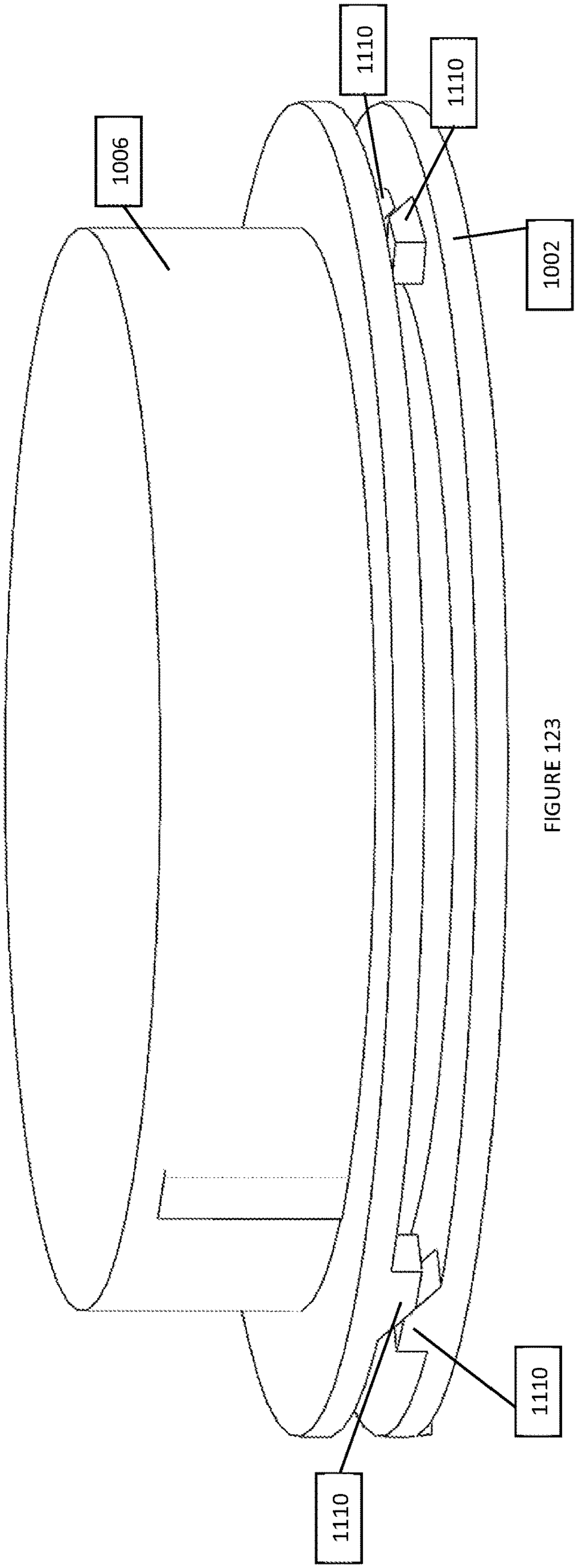
Figure 124:
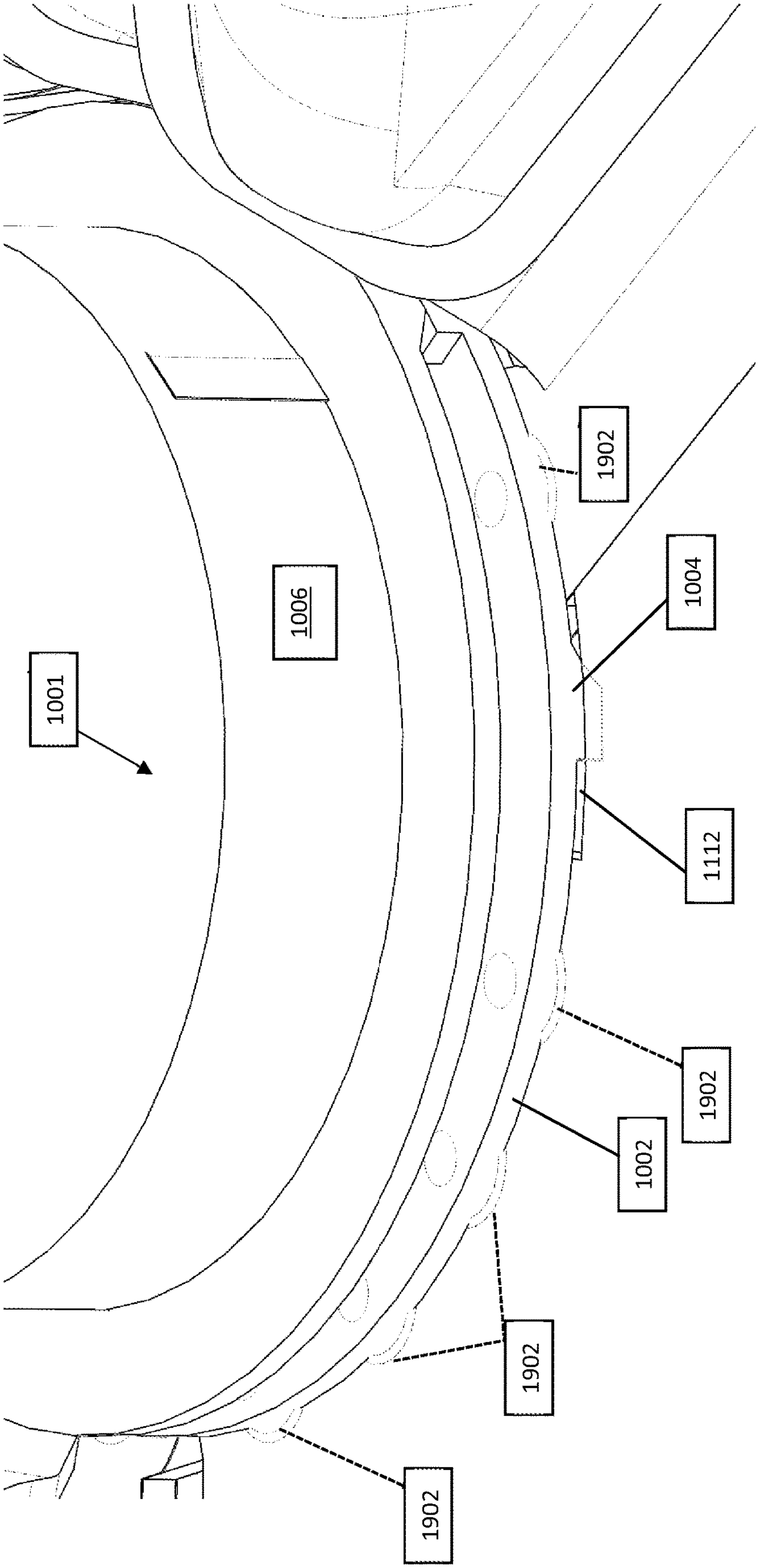

As an alternative to the valve 80, a seal may be provided along the internal lumen 36 upstream from the fluid outlet 34. As shown in FIGS. 104-115, a well 1900 may be formed in the wing portion 27A along the internal lumen 36. A shiftable seal element 1902 is provided seated in the well 1900. The well 1900 is formed along the internal lumen 36 so as to cause an interruption therein in the fluid path to the fluid outlet 34. As shown in FIG. 107, the shiftable seal element 1902 is in a closed state, protruding from the first face 27C of the wing portion 27A. As shown in FIGS. 108 and 110, with the shiftable seal element 1902 in the closed state, a sealing surface 1904, located about the well 1900, is joined with a sealing sheet 1906 spanning across the well 1900 to define at least one seal 1908 along the internal lumen 36 impervious to fluid or liquid flow. The sealing sheet 1906 also is secured to the shiftable seal element 1902 so that the pressing of the shiftable seal element 1902 into the well 1900 to an open state results in delamination of the scaling sheet 1906 from the sealing surface 1904, undoing of the seal 1908, and the opening of the internal lumen 36 across the well 1900. As shown in FIGS. 112-114, the shiftable seal element 1902 includes open passageways 1910 which come into alignment with the internal lumen 36 with the shiftable well 1902 being in the open state. The open passageways 1910 are provided at multiple radial locations to ensure flow through the shiftable seal element 1902, regardless of its radial orientation within the well 1900. As shown in FIG. 115, with the shiftable seal element 1902 in the open state, the internal lumen 36 is open with an unobstructed flow path to the fluid outlet 34.

As will be appreciated by those skilled in the art, any means of pressing may be utilized to press the shiftable seal elements 1902 into the open state, including manual or automated pressing. For example, as shown in FIGS. 108-109, a driven actuator 1912 may be utilized which applies pressure to the shiftable sealing element 1902 to cause displacement thereof.

Portions of the internal lumen 36 adjacent to the well 1900 may be enlarged. In particular, the internal lumen 36 may have a divergent portion 36E leading into the well 1900 and a convergent portion 36F leading out of the well 1900. The sealing surface 1904 may be located within the divergent portion 36E and the convergent portion 36F. In addition, the sealing surface 1904 may be raised about the well 1900 with the shiftable seal element 1902 being seated within the sealing surface 1904 in the closed state.

The sealing sheet 1906 may be any material which may be sufficiently secured to the sealing surface 1904 to form the seal 1908 and then be non-destructively separated from the sealing surface 1904. The scaling sheet 1906 forms a portion of the internal lumen 36 in the open state, requiring structural integrity post-delamination. By way of non-limiting example, the sealing sheet 1906 may be a thermoformable film with the sealing surface being thermoplastic (e.g., cyclic olefin copolymer). The sealing sheet 1906 may be an extension of one of the barriers 102, including being an extension of one of the flexible reservoir walls 26R, 26S. For example, the flexible reservoir wall 26R may be extended through the flange 27 to cover open portions of the internal lumen 36 and to act as the sealing sheet 1906.

Like the valve 80, the sealing sheet 1906 provides a seal which is inside of the internal lumen 36 and spaced from the fluid outlet 34, thus leaving the fluid outlet 34 exposed. With this arrangement, sterility of the internal lumen 36 to the reservoir 26, and the reservoir 26, is maintained. Further sterilization, however, will be required of the fluid outlet 34, for actual use.

The cross-section of the fluid outlet 34 and/or the internal lumen 36 (e.g., the second lumen portion 36B) may be varied to minimize volume loss and to minimize the diameter thereof. For example, as shown in FIG. 82A, the fluid outlet 34 may be formed with a non-circular cross-section, e.g., an oval cross-section. In addition, one or more sides of the cross-section may be truncated. With the second lumen portion 36B having a non-circular cross-section, the valve 80 may be formed to conform to the cross-section of the second lumen portion 36B.

Figure 67A:
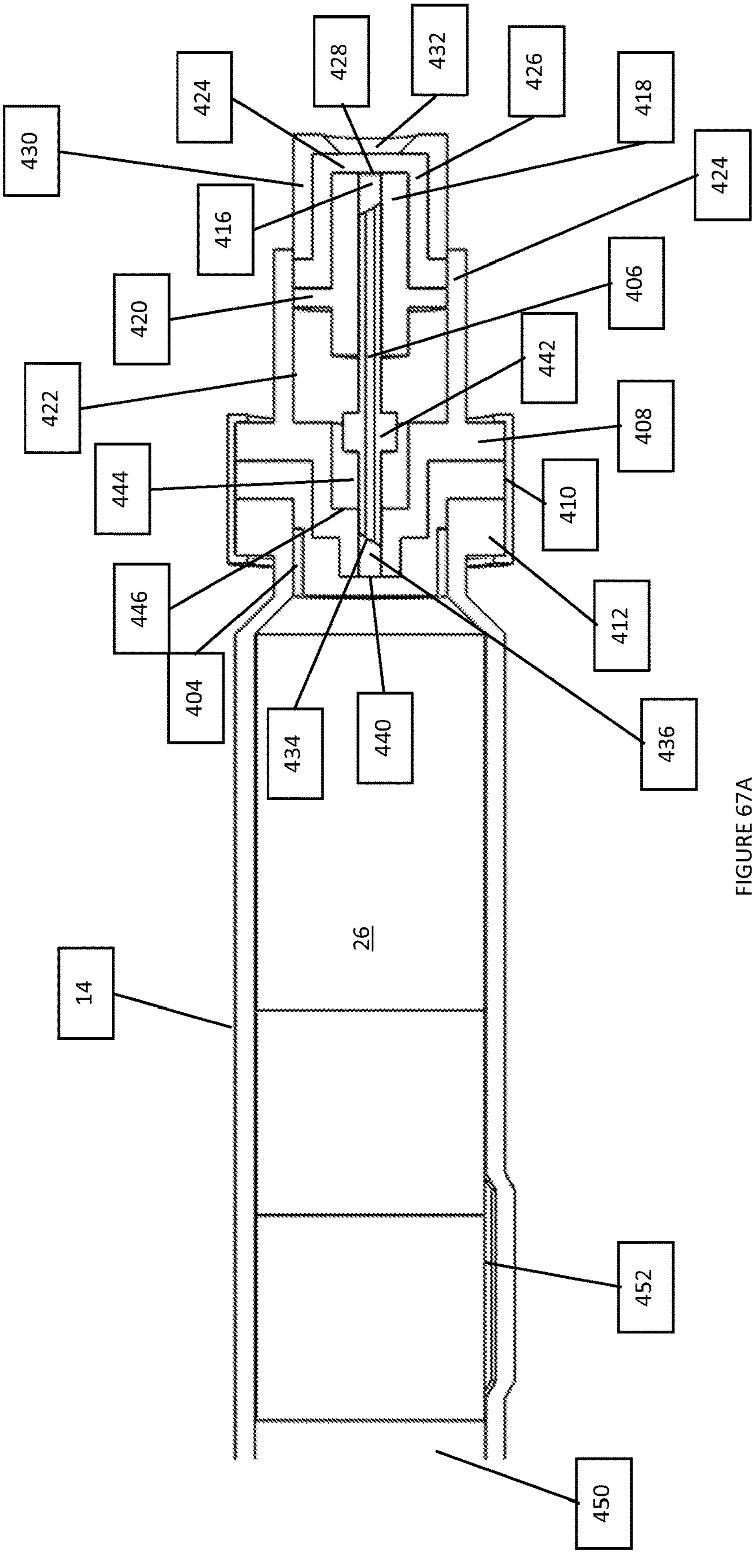
FIG. 67A shows a barrel-configured drug cartridge, in a sealed state, in accordance with the subject invention.
Figure 67B:
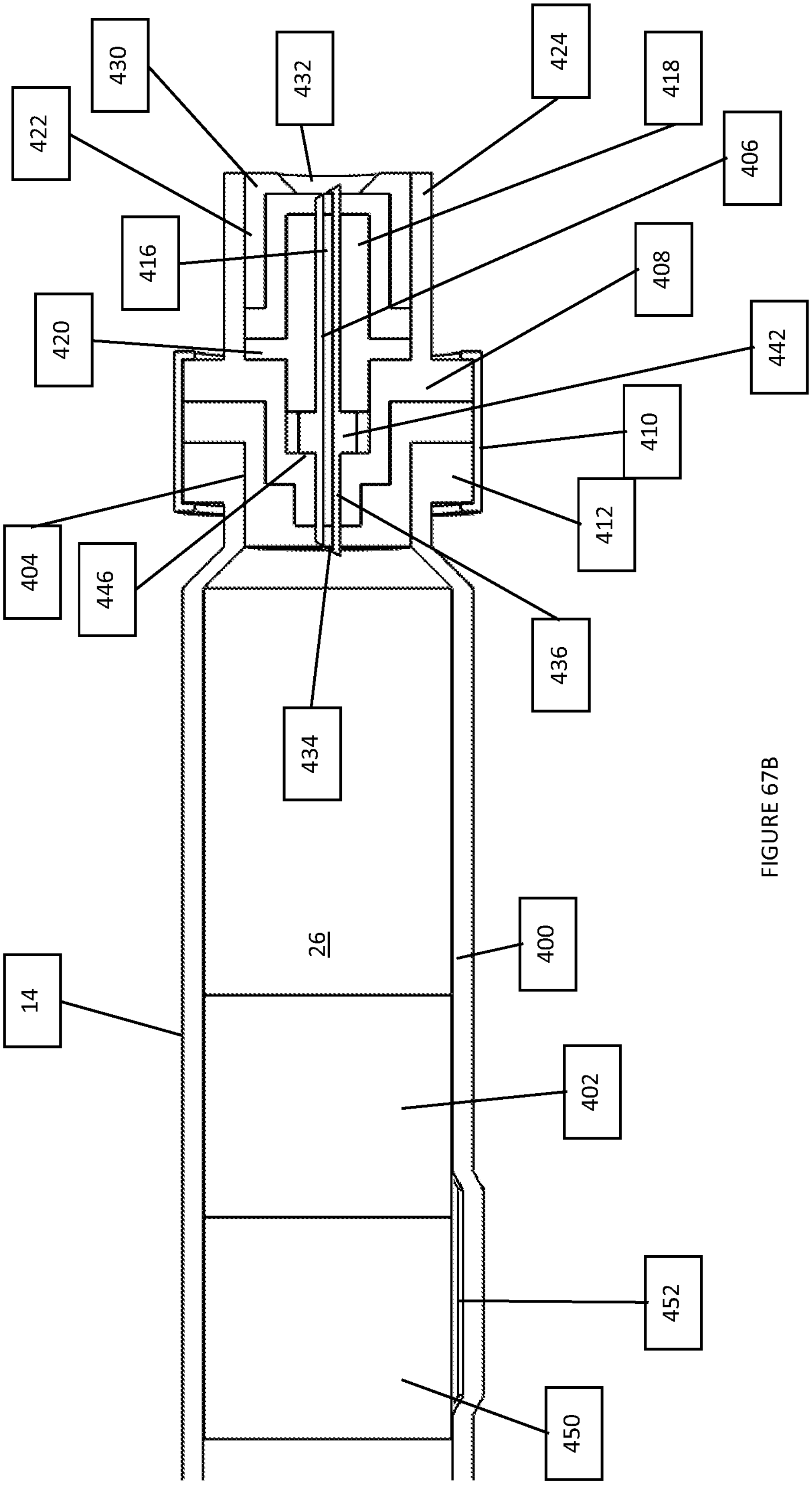
FIG. 67B shows the drug cartridge of FIG. 67A in an actuated state.
Figure 68:
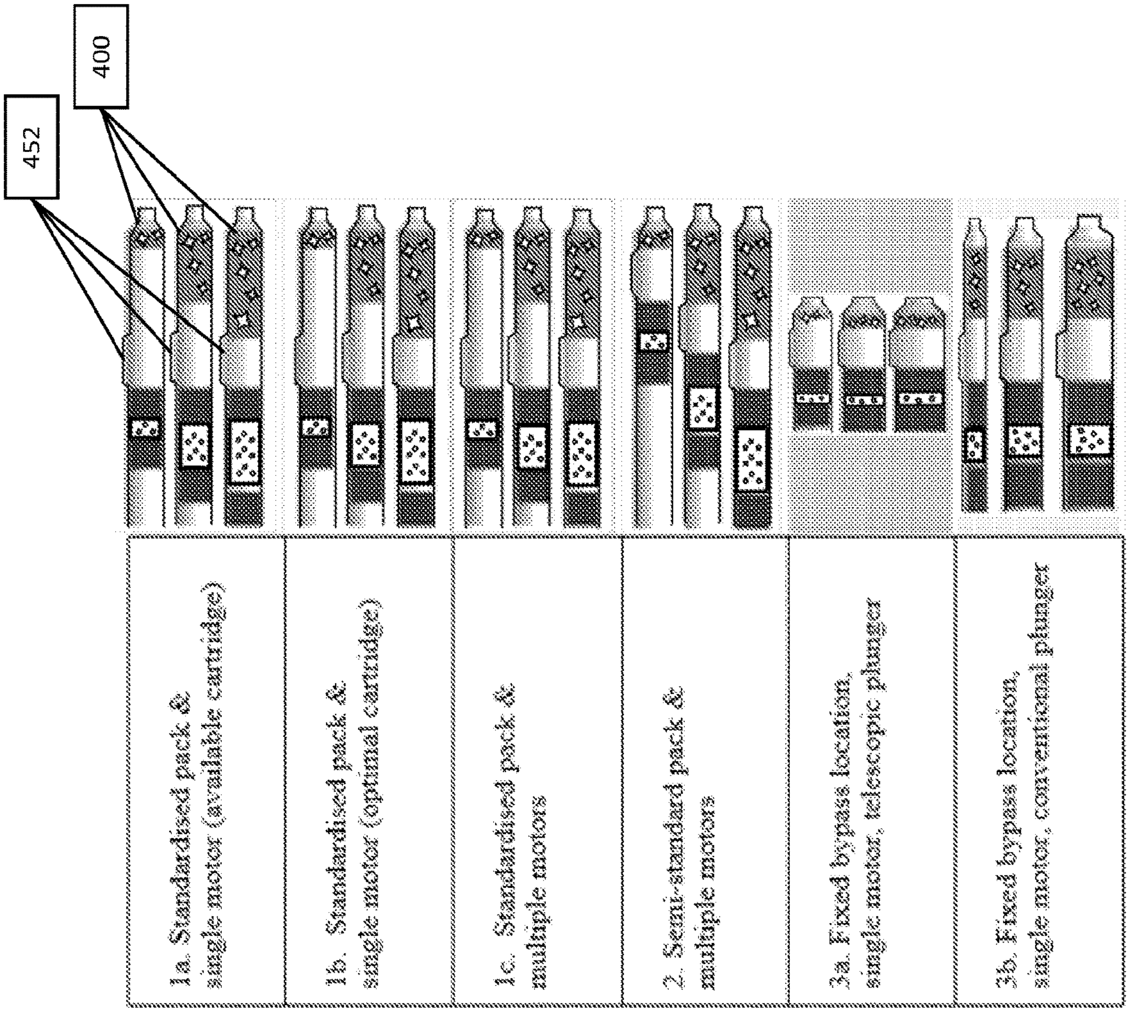
FIG. 68 illustrates various configurations of barrel-configured drug cartridges with by-pass channels.
Figure 69:
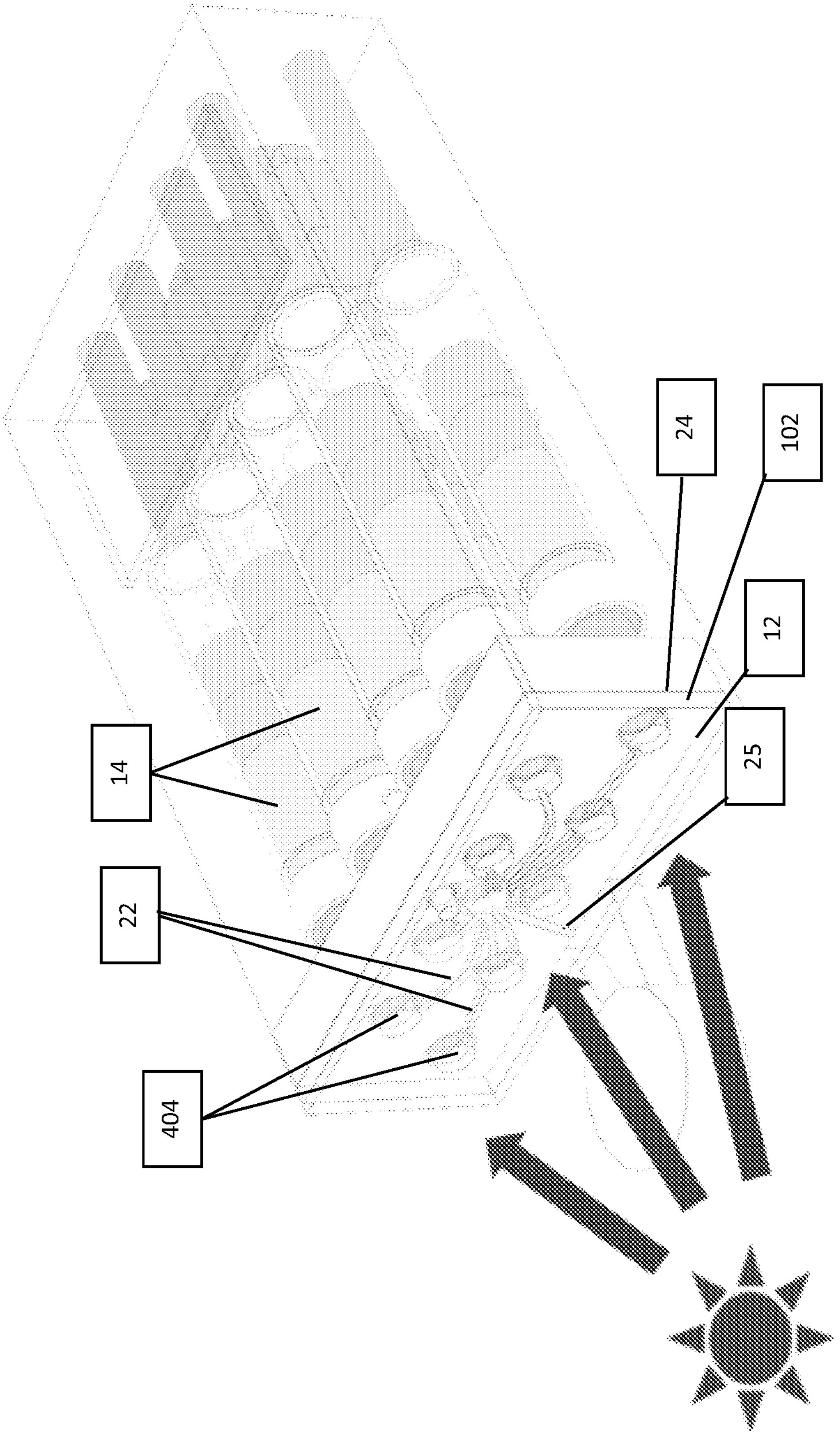
FIG. 69 shows sterilization of a portion of the drug delivery device of FIG. 65.

As shown in FIGS. 65-72, as an alternative to the configuration of drug cartridge 14 described above, the drug cartridges 14 may be configured to include a barrel 400 with a piston 402 configured to slide along therewithin in fluid-tight contact, in some manner as a syringe. Here, the reservoir 26 is defined by the barrel 400 distally of the piston 402 so that distal advancement of the piston 402 causes the reservoir 26 to contract and drug to be expelled therefrom via an outlet 404. As shown in FIG. 69, the outlets 404 may be in communication with the fluid ducts 22, formed in the body 12, leading to one or more of the outlet ducts 25. The fluid ducts 22 may be arranged in parallel between the outlets 404 and/or in series, so that flow passes through one or more of the outlets 404 in being conveyed to the one or more of the outlet ducts 25.

Figure 66:
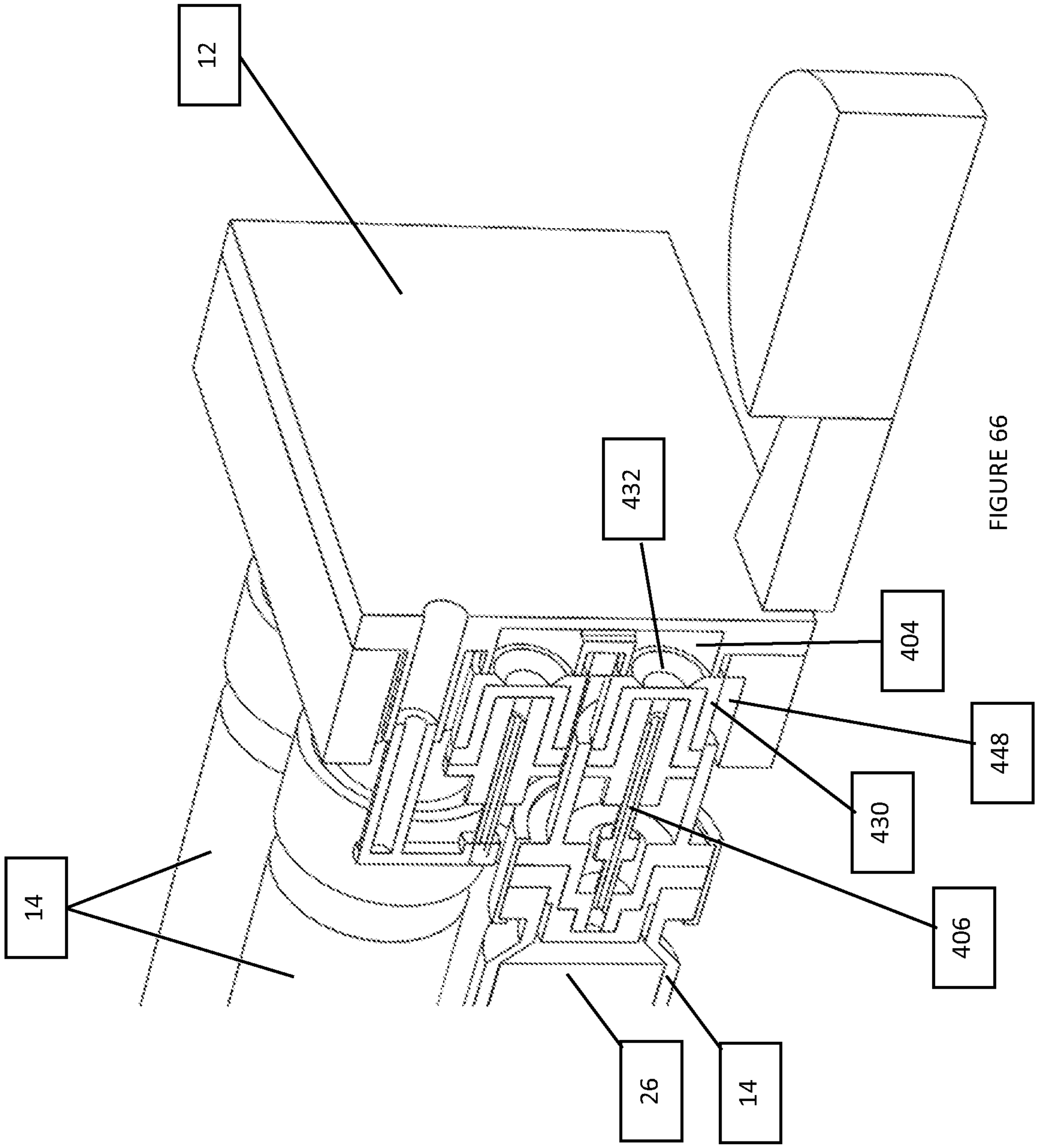
FIG. 66 is a section view of the drug delivery device of FIG. 65.

The outlets 404 may be each sealed to maintain sterility of the reservoir 26 prior to use. With reference to FIGS. 66, 67A, and 67B, for each of the barrels 400, a delivery cannula 406 may be provided, movably disposed within a hub 408 retained by collar 410 to neck 412 of the barrel 400. As shown in FIG. 67A, in a pre-use state, a distal end 414 of the delivery cannula 406 may be seated within open channel 416 of fixing member 418. The fixing member 418 acts to retain the distal end 414 of the delivery cannula 406 in a fixed location. The fixing member 418 may include a radially protruding guide collar 420 formed to slide along an internal surface 422 of guide ring 424, formed on the hub 408 to distally protrude from the collar 410. The guide collar 420 may also act to hold the fixing member 418 in fixed location relative to the guide ring 424.

A distal seal 426 may be provided to span across, and thereby seal, a distal end 428 of the open channel 416. The distal seal 426 may be formed to be cup-shaped with a portion of the fixing member 418 being telescoped therein. The distal seal 426 may include an outer flange 428 in sliding contact with the internal surface 422 of the guide ring 424. A cup-shaped pressing member 430 may be mounted over the distal seal 426 with a needle opening 432 axially aligned with the distal end 414 of the delivery cannula 406. The pressing member 430 is formed to slide within the guide ring 424.

In addition, as shown in FIG. 67A, in the pre-use state, a proximal end 434 of the delivery cannula 406 may be seated with hub channel 436. A proximal seal 438 may be provided to span across, and thereby seal, a proximal end 440 of the hub channel 436.

The fixing member 418 may be formed of an elastomeric material and the open channel 416 may be formed to snugly receive the distal end 414 of the delivery cannula 406. This arrangement will provide for holding force for maintaining the delivery cannula 406 in the position shown in FIG. 67A. It is particularly desired to maintain spacing between the distal end 414 of the delivery cannula 406 and the distal seal 426, and to maintain spacing between the proximal end 434 of the delivery cannula 406 and the proximal seal 438, prior to use. A positioning ring 442 may be provided about the delivery cannula 406, which is spaced from the hub 408 in the pre-use state. The hub 408 may be formed with a hollow 444 distally of the hub channel 436, to accommodate the positioning ring 442. A stop shoulder 446 may be formed about the hub channel 436 at a proximal end of the hollow 444.

The distal seal 426 and the proximal seal 438 may be each formed of an elastomeric material which is pierceable and provides for anti-microbial scaling.

To prepare for use, force is applied to cause the pressing member 430 to move proximally relative to the barrel 400. This results in proximal displacement of the fixing member 418 relative to the hub 408, with proximal movement of the delivery cannula 406 relative to the hub 408, as shown in FIG. 67B. With sufficient proximal displacement, the proximal end 434 of the delivery cannula 406 breaches the proximal seal and comes into communication with the reservoir 26. In addition, the positioning ring 442 comes into contact with the stop shoulder 446 to restrict further proximal movement of the delivery cannula 406. With the delivery cannula 406 being held by the stop shoulder 446, and with further proximal displacement of the fixing member 418 relative to the barrel 400 under force of movement by the pressing member 430, the distal end 414 of the delivery cannula 406 is caused to breach the distal seal 426 to extend through the needle opening 432. This allows for communication with one or more of the fluid ducts 22 via the outlet 404.

With reference to FIG. 66, the pressing members 430 may be seated in recesses 448 formed in the body 12 so as to be non-movably fixed relative to the body 12. The barrels 400 may be caused to be displaced distally relative to the body 12, thus, causing the pressing members 430 to move proximally relative to the barrels 400, as discussed above. This allows for flow paths to be created between the reservoirs 26 of the barrels and the fluid ducts 22.

As shown in FIG. 65, the drug delivery device 10 may also include plungers 450, each aligned with one of the barrels 400, to extend thereinto and cause distal displacement of the respective piston 402. The barrels 400 are open-ended (at the proximal ends) to allow the plungers 450 to enter into the barrels 400 in engaging the pistons 402. It is noted that, with the barrels 400 be sealed as described above, and with the reservoirs 26 containing drug in incompressible form (solid or liquid), the distally-directed pressing of the pistons 402, by the plungers 450, shall result in distal displacement of the barrels 400. With sufficient distal displacement, the proximal movement of the pressing members 430 relative to the barrels 400, as described above, may be achieved.

With the drug cartridges 14 being configured to include the barrels 400, any barrel configuration may be utilized. For example, as shown in FIGS. 67A, 67B, and 68, one or more of the barrels 400 may be provided with by-pass channels 452. As will be recognized by those skilled in the art, the by-pass channels 452 allow for two- or more part mixing within the barrels 400. The piston 402 of a barrel 400 may be initially located to separate the reservoir 26 into two parts, each containing a separate component (liquid-liquid or liquid-dry combinations). With distal advancement of the piston 402, the components may be brought together with mixing and/or reconstitution transpiring. FIG. 68 shows schematically different possible arrangements for multi-component mixing or reconstitution.

In addition, as shown in FIGS. 70-72 and 74-78, the barrels 400 may be disposed about the circumference of the body 12. With reference to FIGS. 74-78, one of the plungers 450 may be utilized which is rotatable relative to the body 12 to come into selective alignment with the barrels 400. The plunger 450 may be bi-directionally rotatable, allowing for rapid alignment with the barrels 400 in sequence, as needed. In addition, the barrels 400 may contain two or more drug components, separated by moveable pistons 402, each formed to sealingly slide along the inside of one of the barrels 400. For example, within one or more of the barrels 400, a first drug component 456 may be provided, separated by the piston 402, from a second drug component 457. Configurations for barrels/movable pistons to allow for reconstitution and/or mixing are known in the art. For example, as is known in the art, the by-pass channel 452 may be provided in each of the barrels 400 which allows first and second drug components 456, 457 to mix upon sufficient displacement of the piston 402. The second drug component 457 may be in liquid form, and incompressible, thus transmitting force of movement from the plunger 450 to the piston 402, through the second drug component 457. The barrels 400 may be open-ended to accept the plunger 450 with the outlets 404 of the barrels 400 being directed radially outwardly from the body 12. Secondary pistons 461 may be provided to seal the second drug components 457 within the barrels 400. For each of the barrels 400, the plunger 450 may be caused to pressingly engage the secondary piston 461 in causing displacement thereof, resulting in displacement of the piston 402, with force of movement being transmitted through the second drug component. With sufficient displacement of the piston 402, the piston 402 overlaps with the by-pass channel 452, thereby creating a fluid pathway across the piston 402 between the first and second drug components 456, 457. With further displacement of the secondary piston 461, the second drug component 457 is urged through the by-pass channel 452 to mix with the first drug component 456. Further displacement causes the secondary piston 461 to come into engagement with the piston 402. With even further displacement, the secondary piston 461 and the piston 402 are collectively displaced causing the mixed first and second drug components 456, 457 to be expelled from the outlet 404, as shown in FIGS. 75-78.

Figure 70:
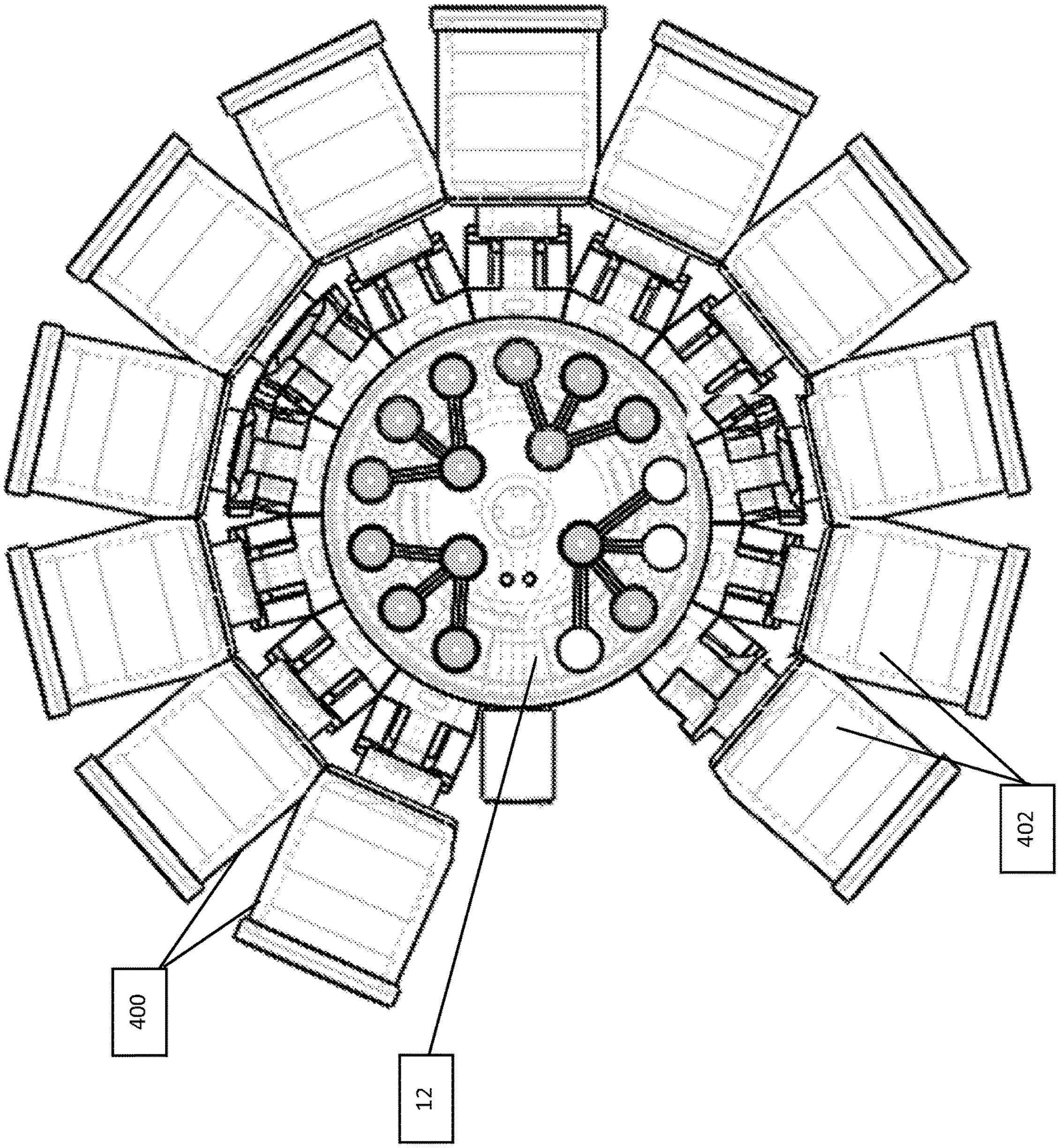
FIG. 70 shows a drug delivery device with an alternate barrel-configured drug cartridge, in accordance with the subject invention.
Figure 71:
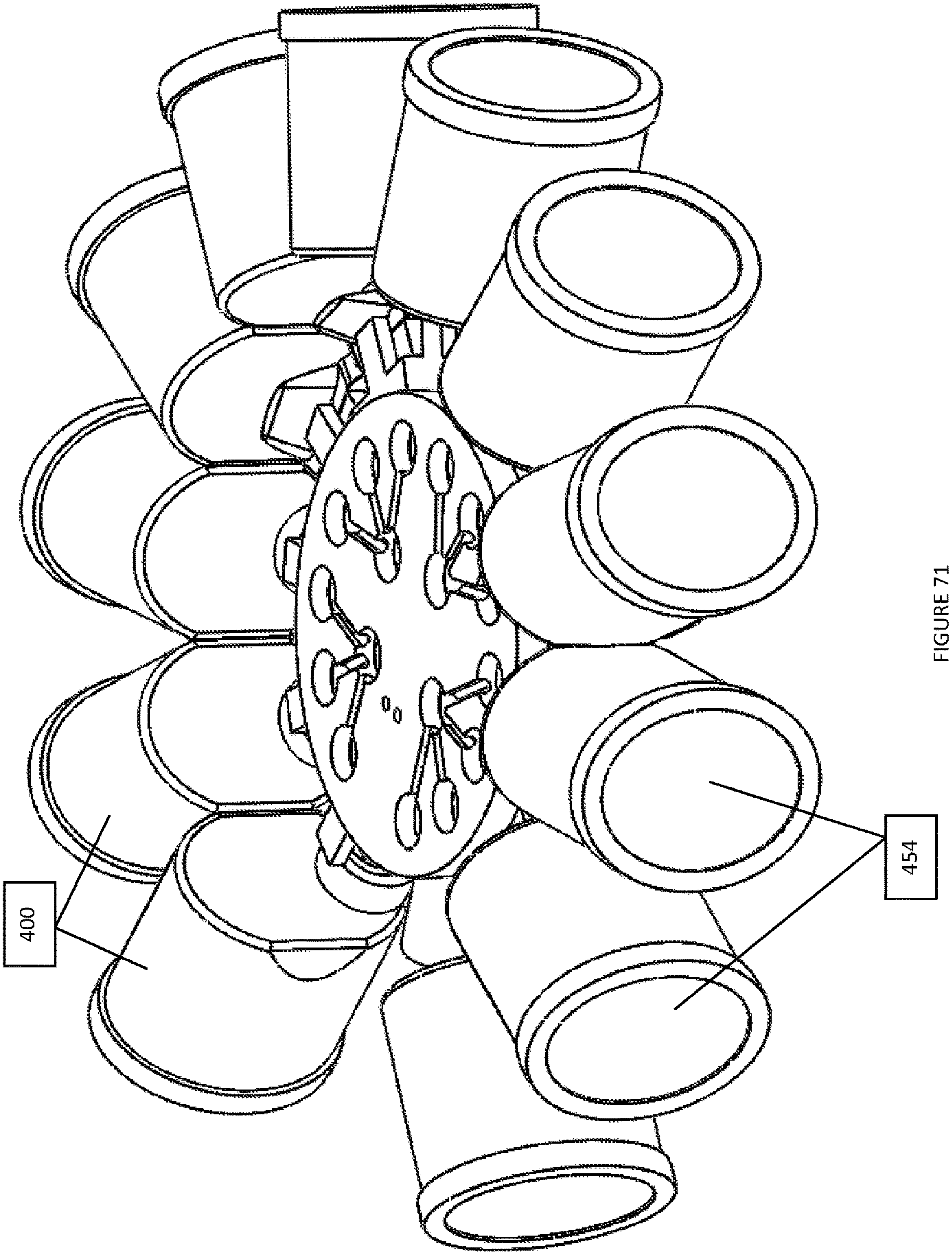
FIG. 71 is an isometric view of the drug delivery device of FIG. 70.
Figure 72:
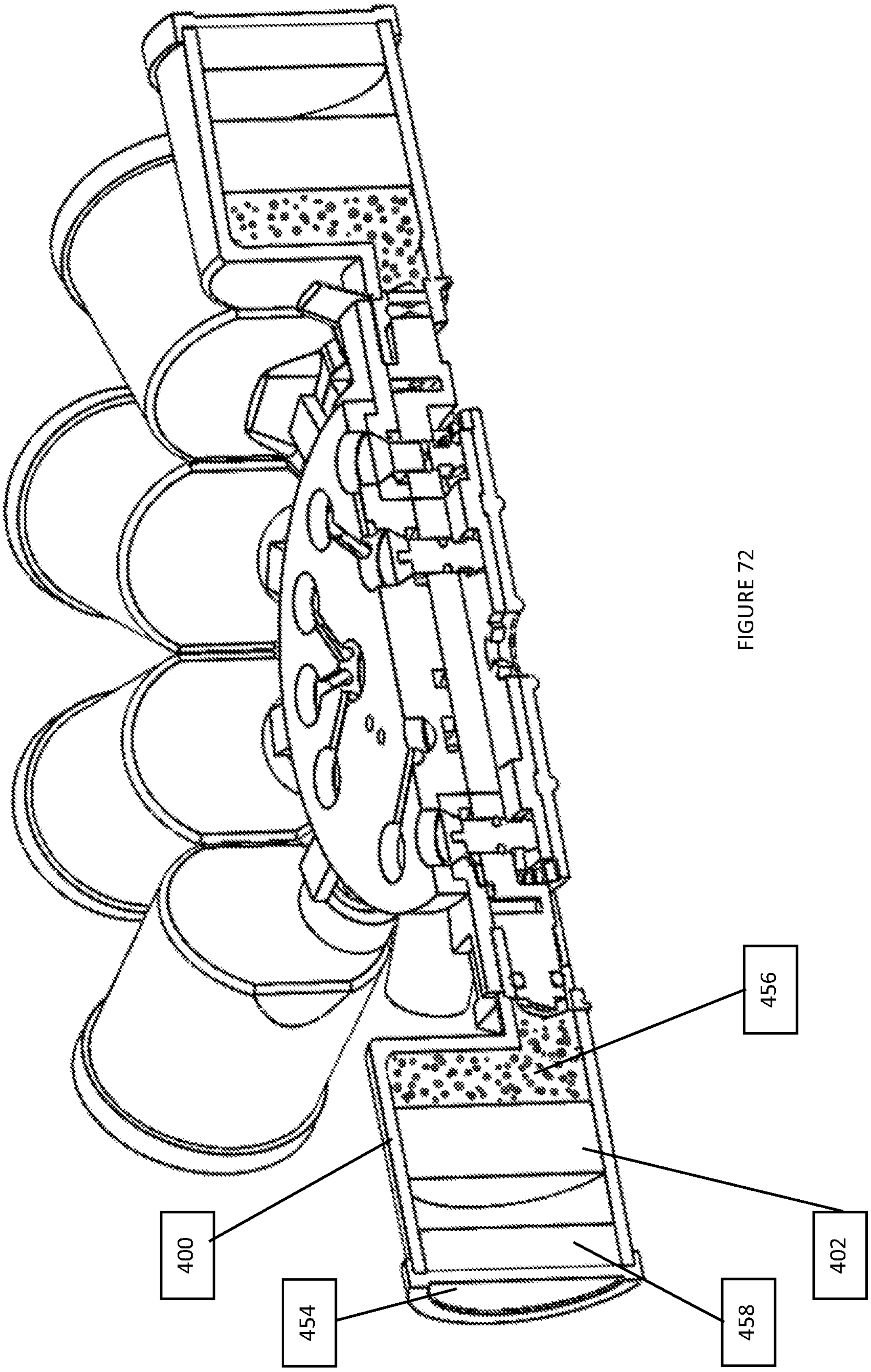
FIG. 72 is a section view of the drug delivery device of FIG. 70.

In addition, as shown in FIGS. 70-72, the barrels 400 may be configured to accommodate the first drug component 456, which may be in a dry state or a liquid state, and mixed with at least one further liquid component, introduced into the barrels 400 via the body 12. In this manner, the drug component 456 may be reconstituted and/or mixed with one or more other drug components provided from outside the respective barrels 400. Pistons 402 may be used to delineate a reduced volume within each of the barrels 400, for the first drug component 456, prior to use. This allows for a limited-volume pocket to be defined to house the first drug components 456 in a compacted state. With diluent or other liquid being pumped into the barrels 400, the pistons 402 may be displaced (e.g., radially outwardly), thus increasing the volume inside the barrels 400 about the first drug components 456, in reconstituting the first drug components 456 and/or forming a mixture therewith. Once prepared, the resulting reconstituted drug or drug mixture may be withdrawn from the barrels 400 via the body 12, e.g., by negative pressure generated by the pump 18. The barrels 400 in this configuration may be closed-ended, e.g., with rear seals 454 sealing the proximal ends thereof to define a sterile envelope for the interior of each of the barrels 400. The rear seals 454 may be vented to allow for pressure equilibration with displacement of the pistons 402. For example, the rear seals 454 may each include a micro-filtration element (e.g., 0.2 micron filtration element) to provide sterile venting, whereby air may be expelled from the barrels 400 with ingress of microbes thereinto being inhibited. In addition, one or more spacers 458 may be provided rearwardly of the pistons 402 to limit travel thereof. The spacers 458 may be used to control the permissible displacement of the pistons 402, thereby controlling the permissible resulting volumes for drug component 456 and any introduced other component(s). This allows for control over the volume and concentration of any resulting reconstituted drug or mixture. The spacers 458 may be porous or have openings to allow for free movement of air therethrough with displacement of the pistons 402.

Various arrangements, in addition to the valve 80 and the sealing sheet 1906, may be utilized to form the seal on the drug cartridge 14, e.g., forming a seal on the plug adapter 14B across the sterilized internal lumen 36. These arrangements provide for a seal which will require further sterilization, like the arrangement utilizing the valve 80 or the sealing sheet 1906. This category of seals shall be referenced as the "non-sterile connection seal arrangements." In addition, seal arrangements may be provided which provide for sterile connection to the body 12 of the drug delivery device 10, thus eliminating the need for later sterilization of the drug cartridge 14, including the fluid outlet 34. This category of seals shall be referenced as the "sterile connection seal arrangements." It is noted that certain arrangements may provide for the seal to be located within the internal lumen 36 and certain arrangements provide for the seal to be located external of the fluid outlet 34.

Figure 36A:
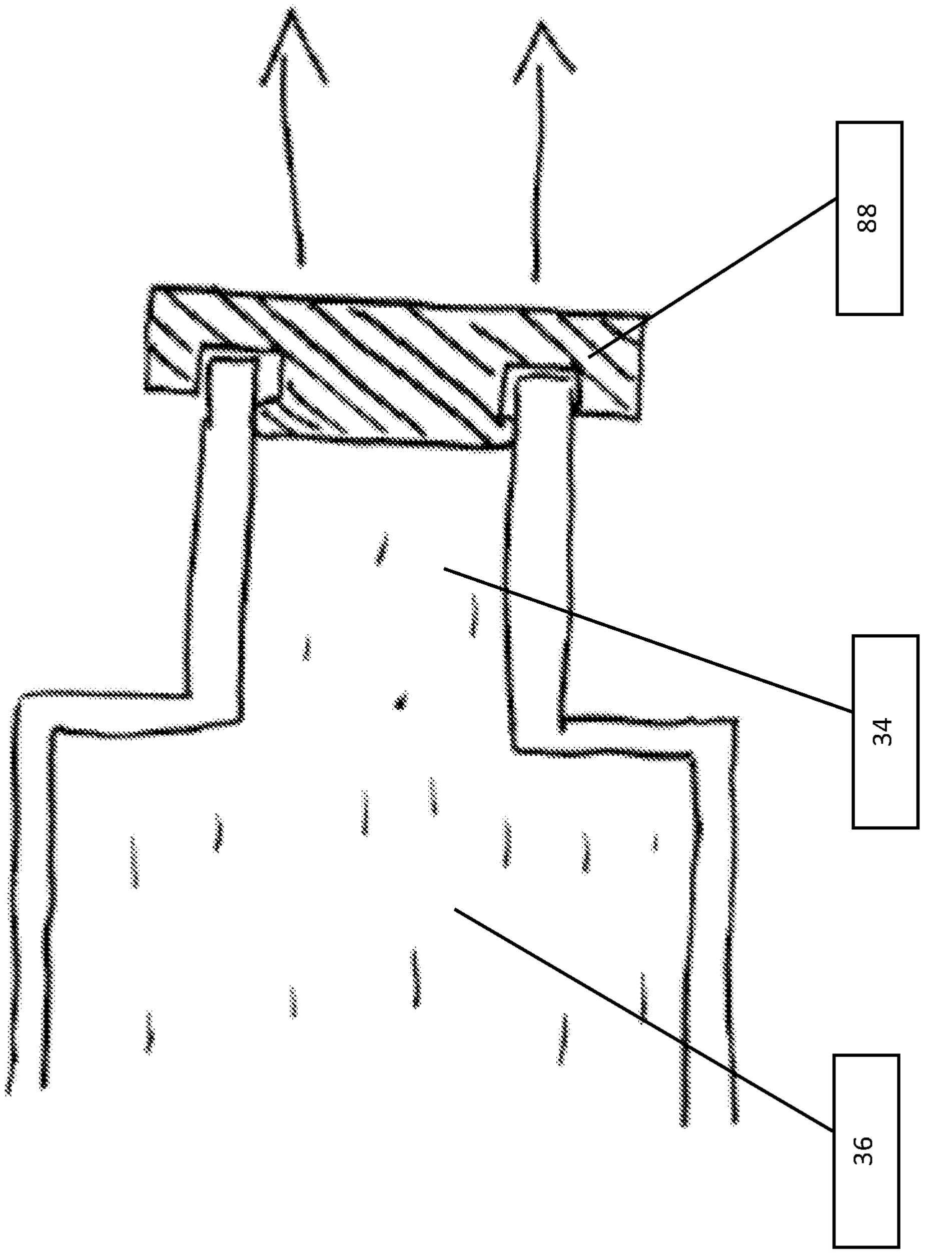
FIG. 36A shows a method of accessing a drug cartridge by translating a plug, in accordance with the subject invention.
Figure 36B:
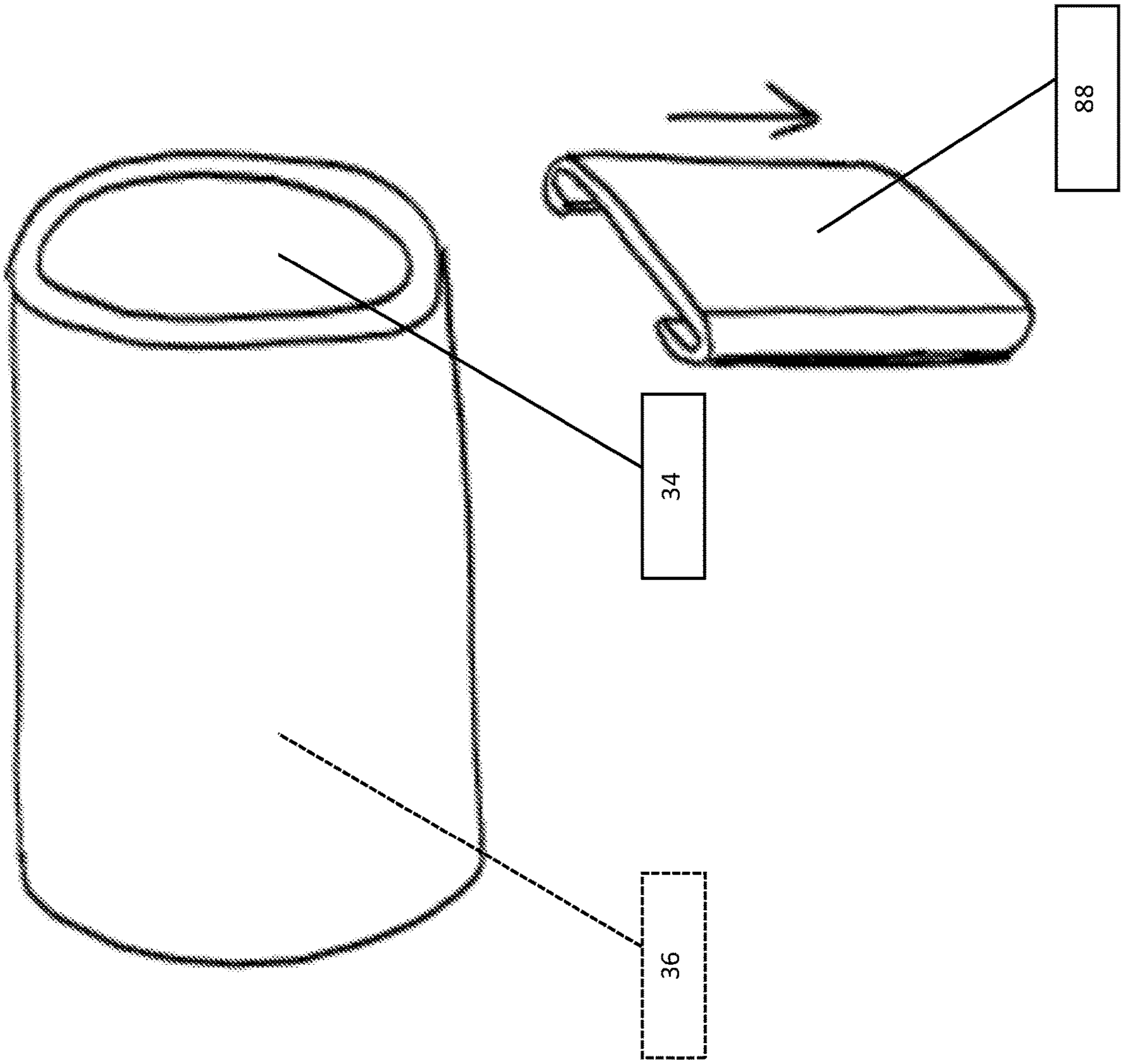
FIG. 36B shows a method of accessing a drug cartridge by sliding a seal away from an outlet, in accordance with the subject invention.
Figure 36C:
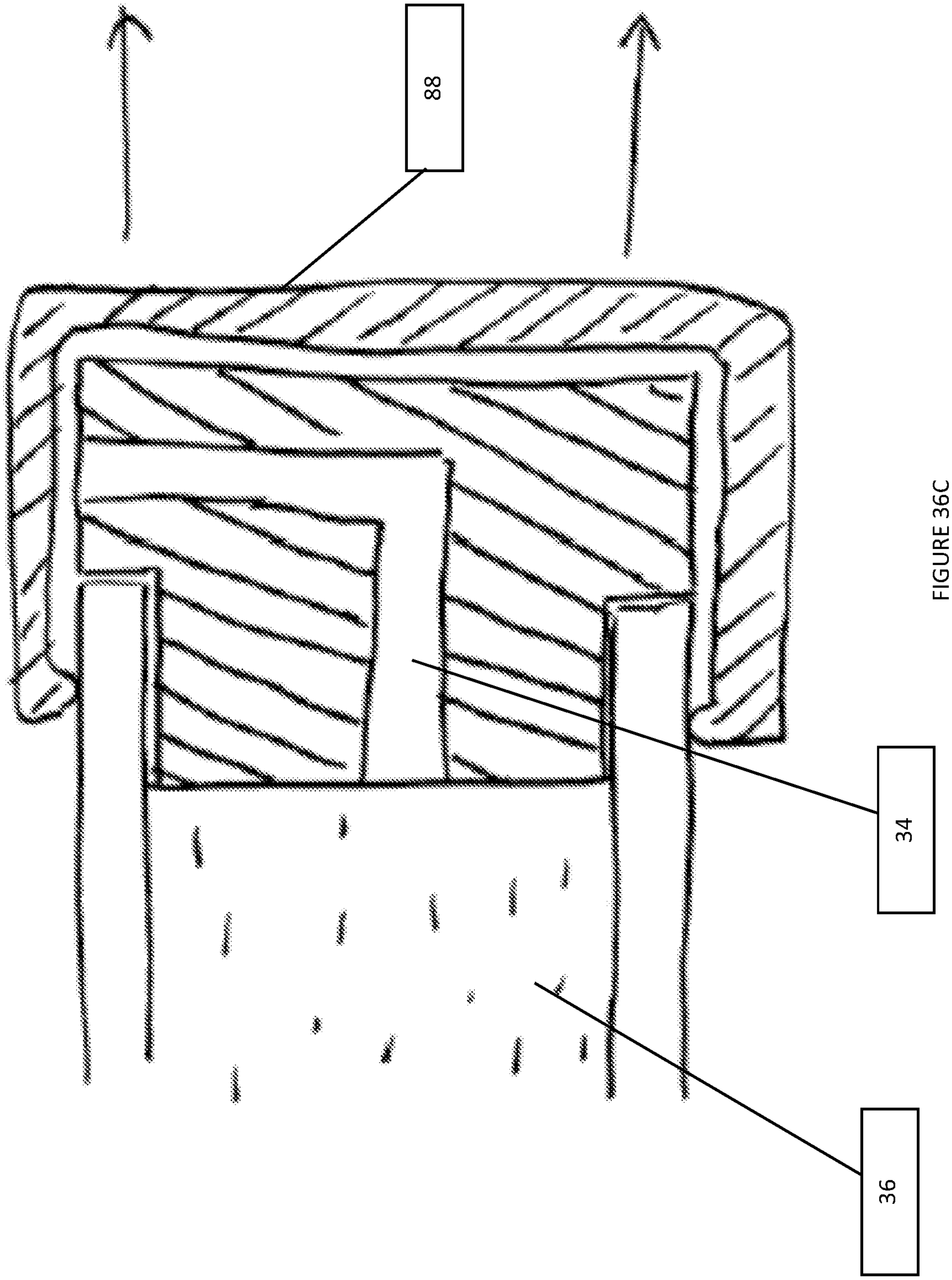
FIG. 36C shows a method of accessing a drug cartridge by translating a lid, in accordance with the subject invention.
Figure 36D:
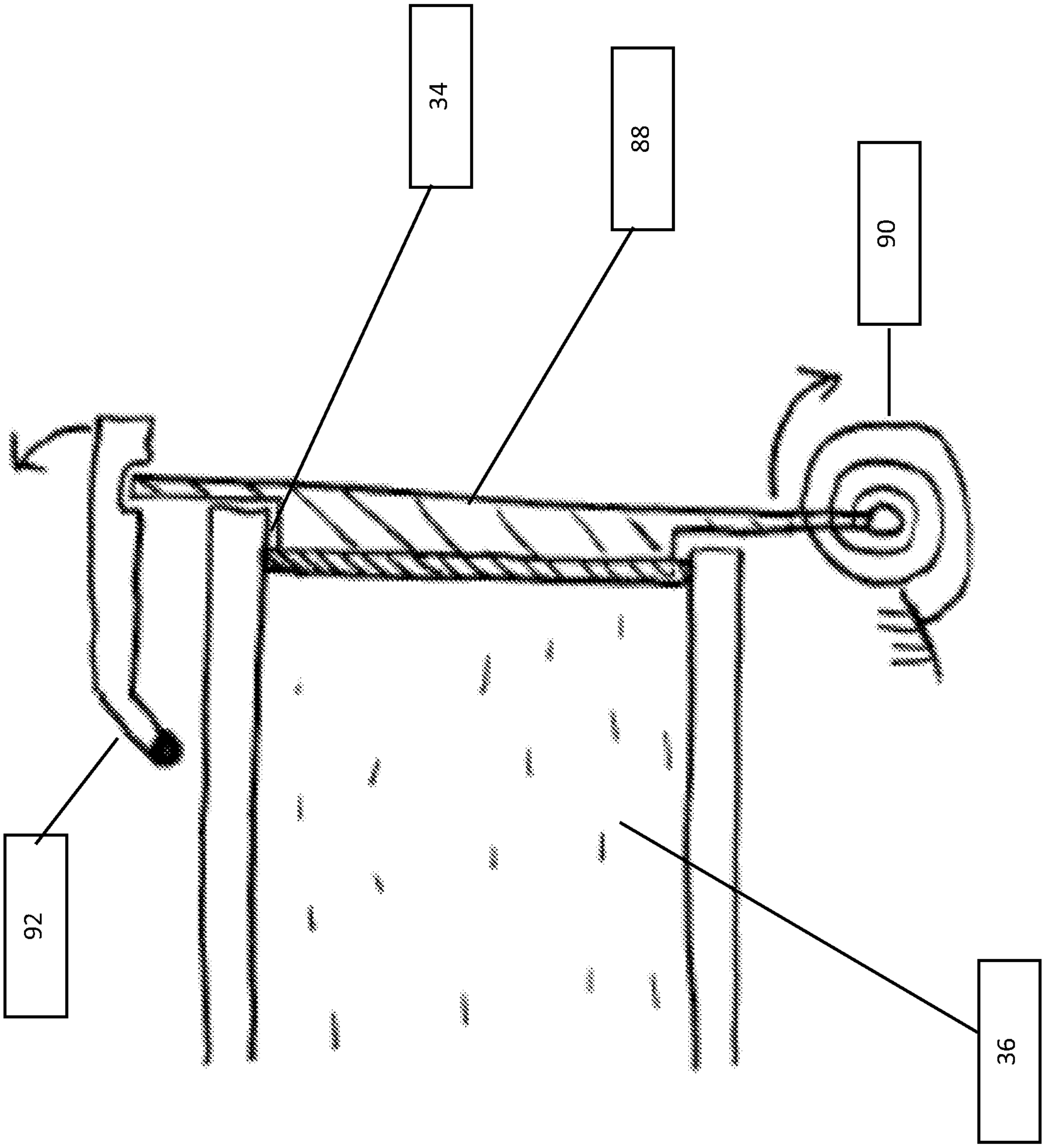
FIG. 36D shows a method of accessing a drug cartridge by opening a latch, in accordance with the subject invention.
Figure 36E:
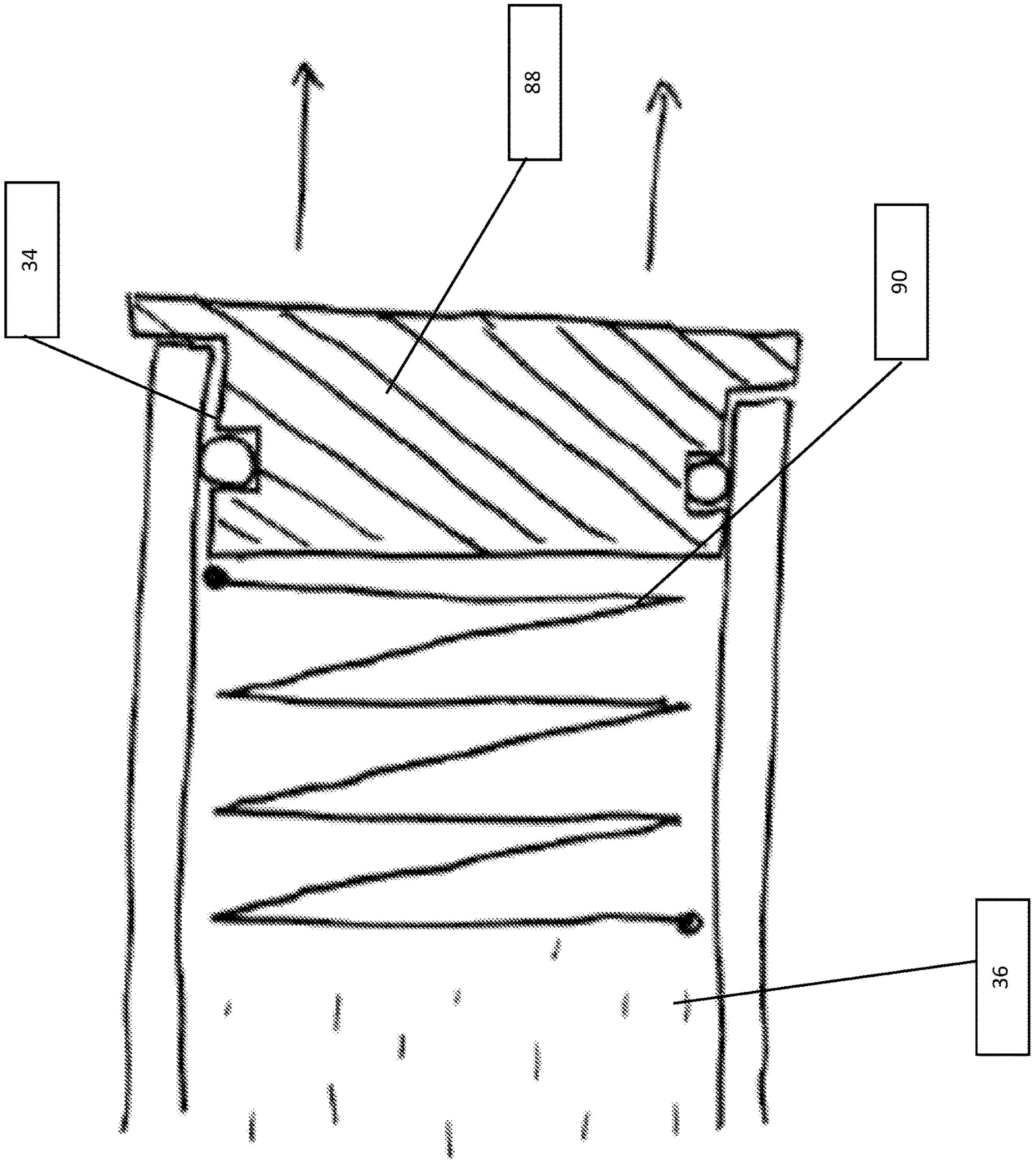
FIG. 36E shows a method of accessing a drug cartridge by translating a plug using an internal spring, in accordance with the subject invention.

FIGS. 36A-38B show different non-sterile connection seal arrangements useable with the subject invention as alternatives to the valve 80 or the delivery cannula 406. With reference to FIGS. 36A-36E, a removable cap or plug 88 may be provided, which may be formed to resiliently engage a portion of the fluid outlet 34 and/or the internal lumen 36 (FIGS. 36A and 36E). As shown in FIGS. 36B-36D, the cap or plug 88 may be removably mounted to portions of the plug adapter 14B about the fluid outlet 34 and/or the inner lumen 36. As shown in FIGS. 36D and 36E, a spring or other biasing mechanism 90 may be provided to assist in removal of the cap or plug 88. A latch 92 may be provided to resist the biasing force of the spring 90 in maintaining the cap or plug 88 in place until proper time for removal.

Figure 37A:
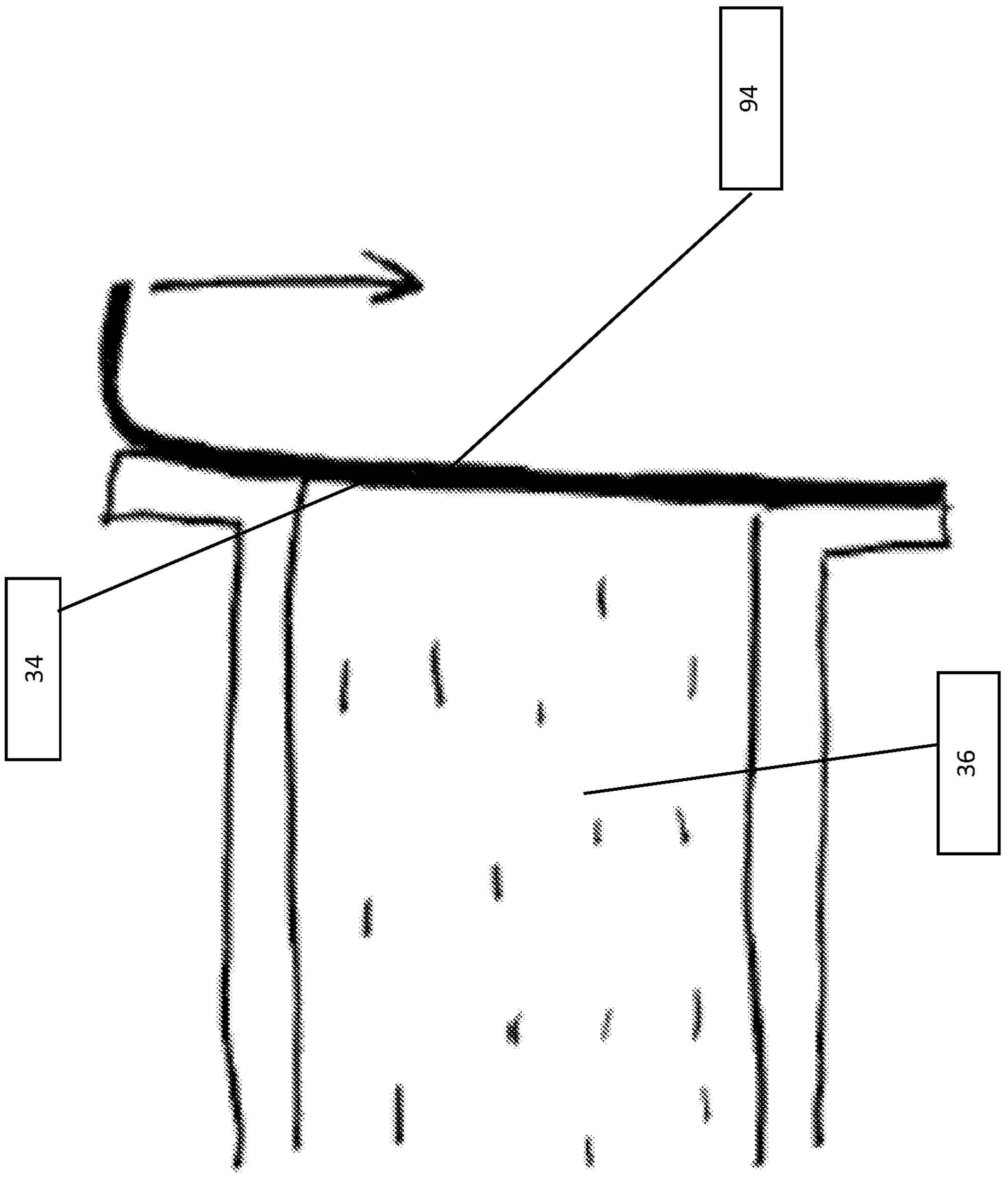
FIG. 37A shows a method of accessing a drug cartridge by peeling a film, in accordance with the subject invention.
Figure 37B:
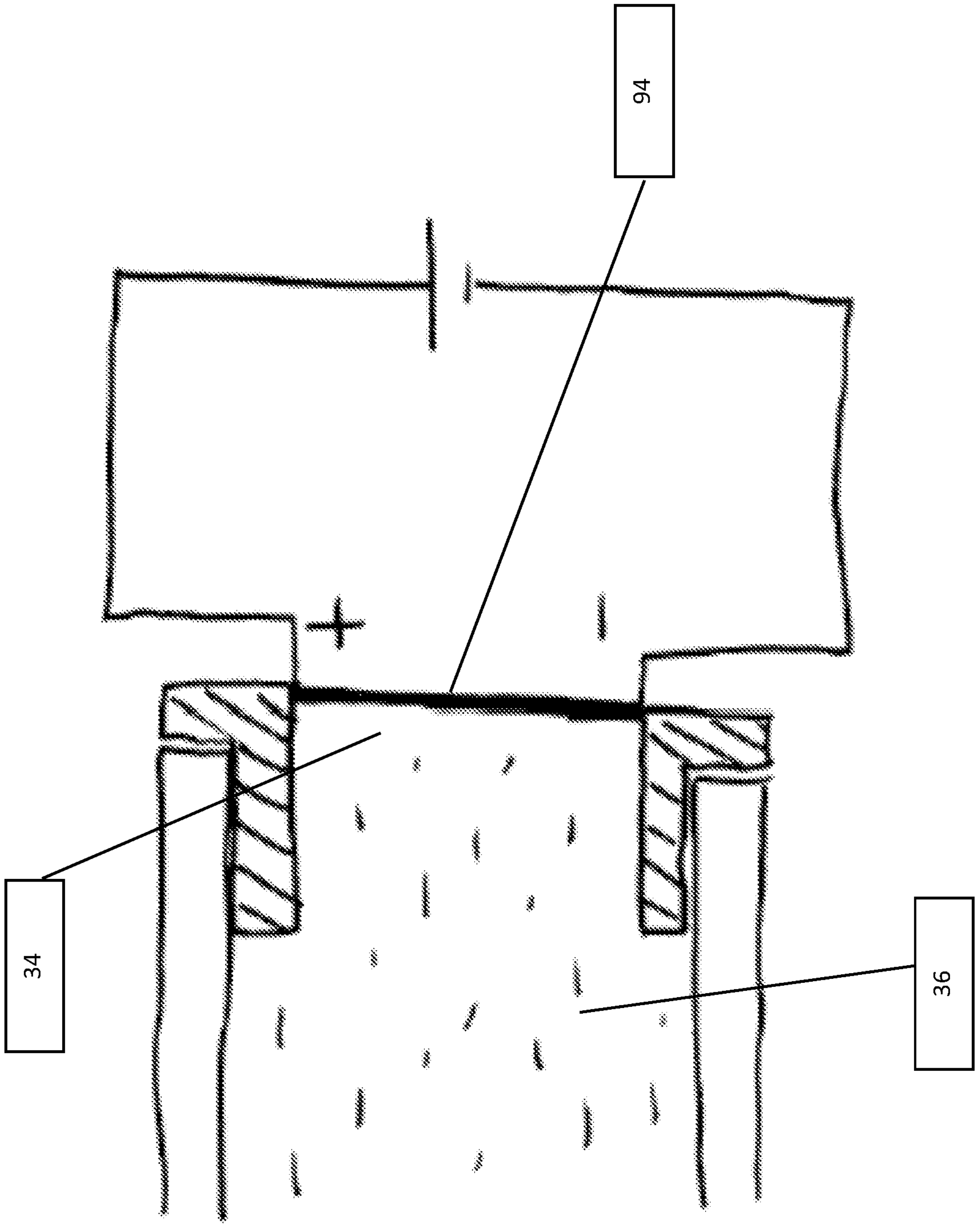
FIG. 37B shows a method of accessing a drug cartridge by rupturing a film with an electromotive force, in accordance with the subject invention.
Figure 37C:
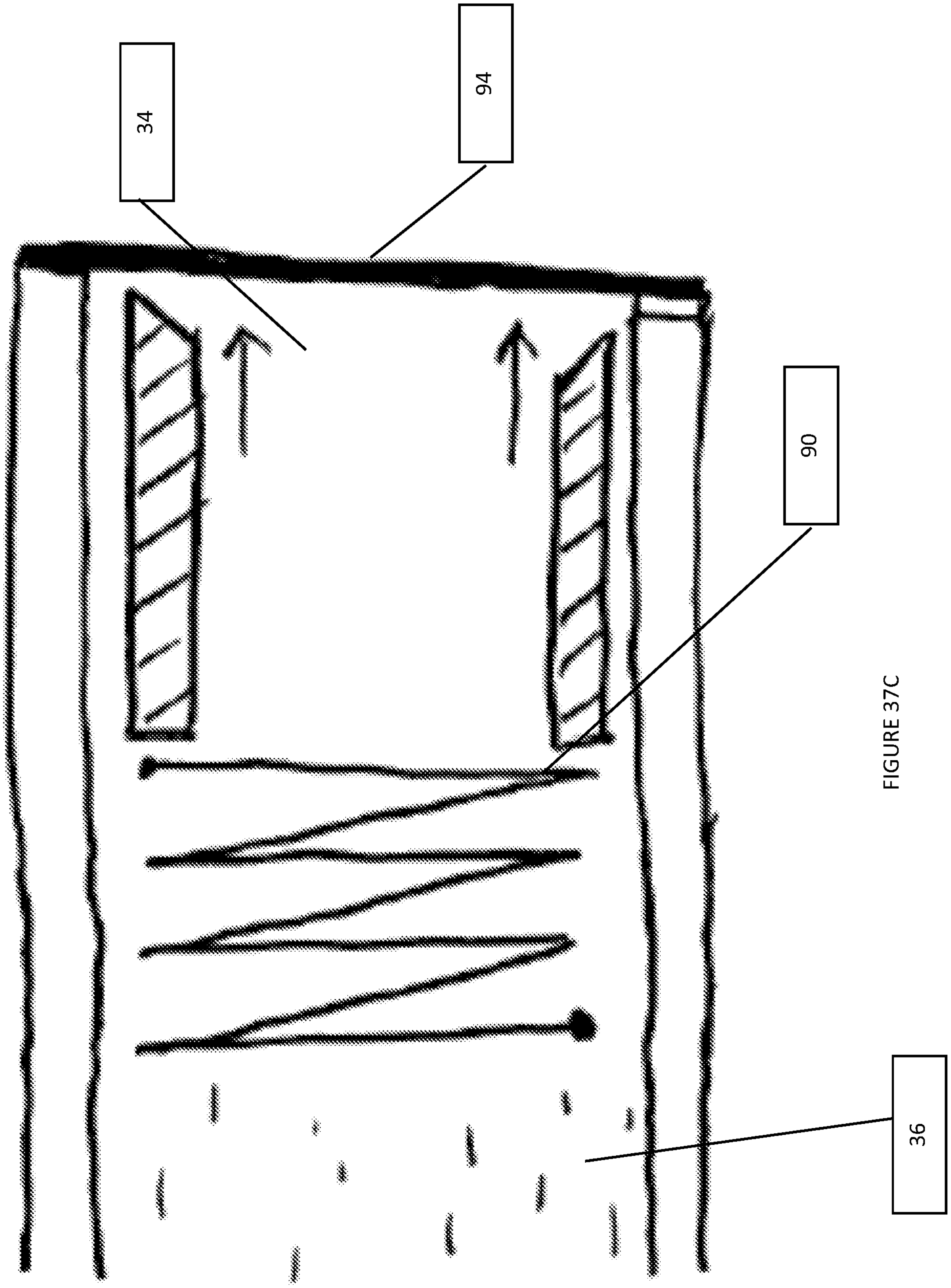
FIG. 37C shows a method of accessing a drug cartridge by rupturing a film using spring force, in accordance with the subject invention.
Figure 37D:
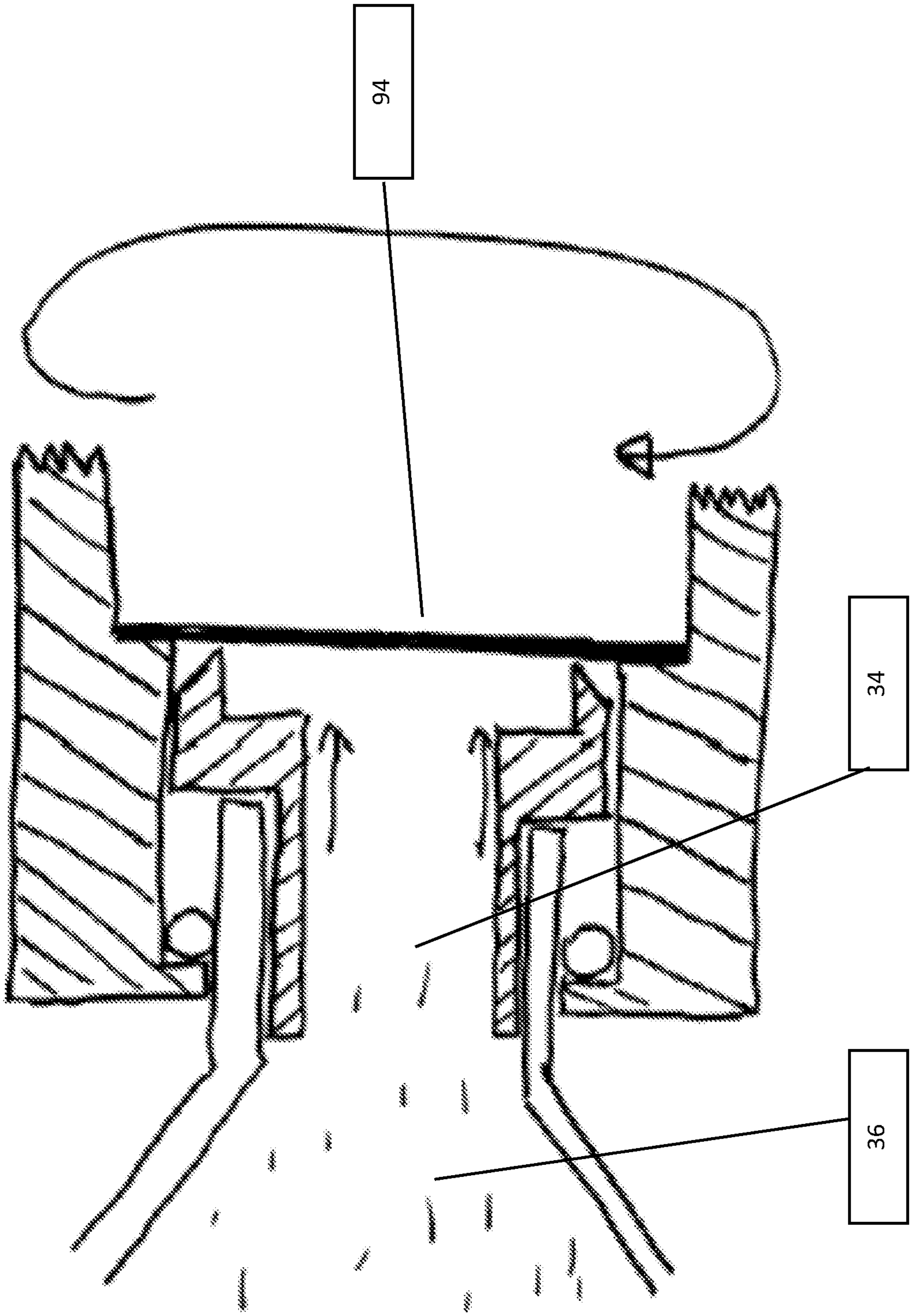
FIG. 37D shows a method of accessing a drug cartridge by cutting a film using rotational movement, in accordance with the subject invention.

Alternatively, as shown in FIGS. 37A-37D, a film 94 may be applied across portions of the plug adapter 14B to cover, and seal, the fluid outlet 34 and the internal lumen 36. As shown in FIG. 37A, the film 94 may be peelable. As shown in FIGS. 37B-37D, the film 94 may be rupturable, possibly using electromotive force (FIG. 37B), spring force (FIG. 37C), and/or mechanical force (FIG. 37D).

Figure 38A:
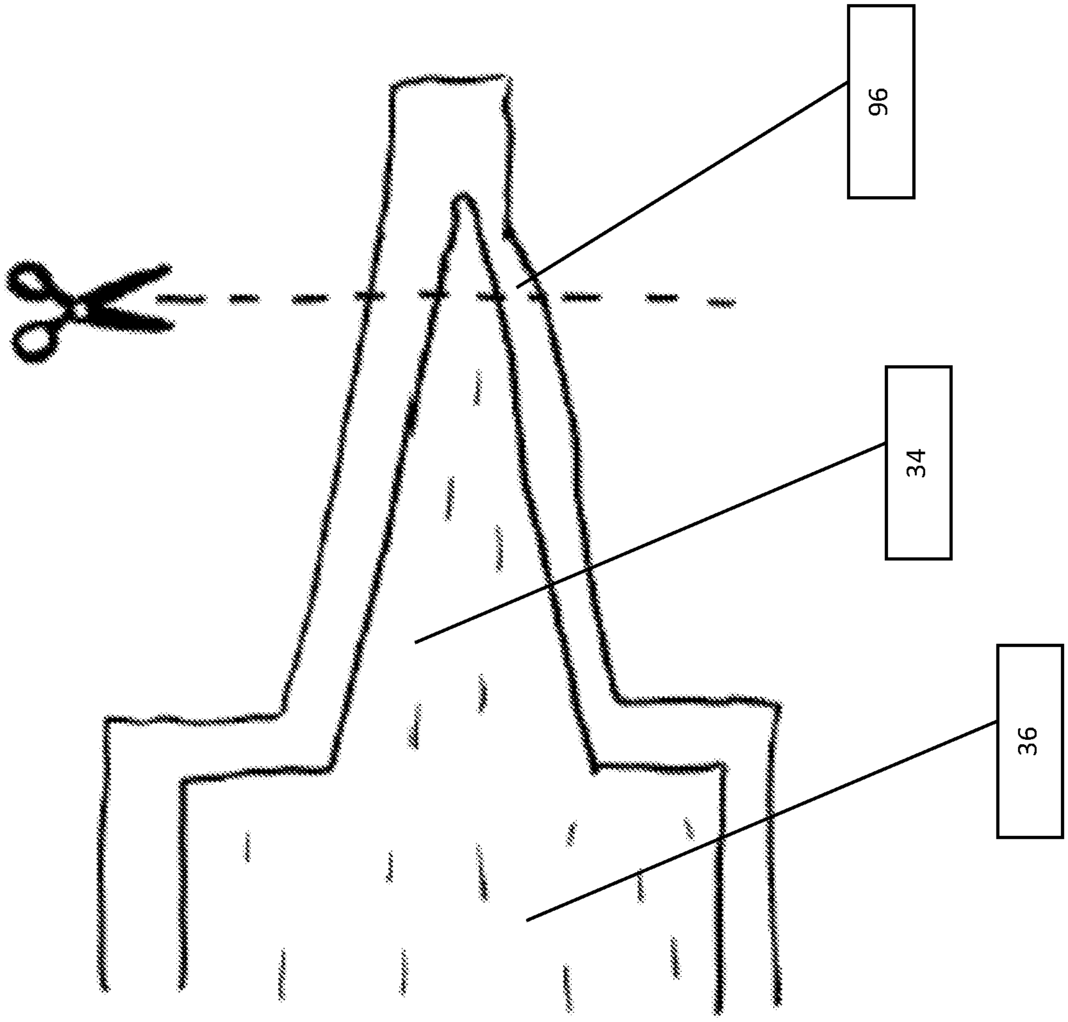
FIG. 38A shows a method of accessing a drug cartridge by cutting along a score line, in accordance with the subject invention.
Figure 38B:
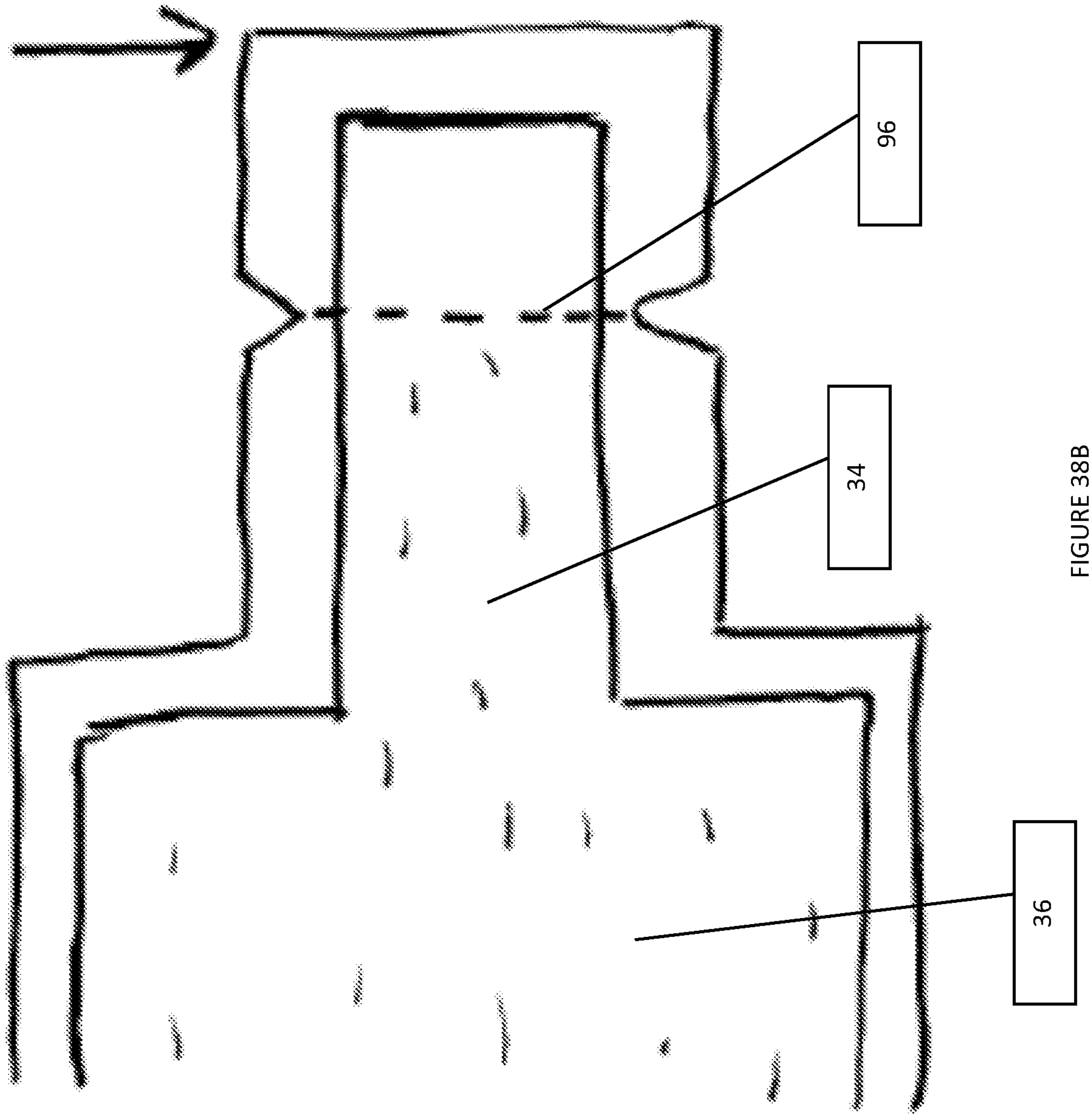
FIG. 38B shows a method of accessing a drug cartridge by shearing along a score line, in accordance with the subject invention.

Further, as shown in FIGS. 38A-38B, portions of the plug adaptor 14B may be heat sealed or otherwise joined to form a continuous seal across the fluid outlet 34 and the internal lumen 36. As shown in FIG. 38A, this seal may be cut or otherwise disrupted to open the seal and expose the fluid outlet 34. As an alternative, as shown in FIG. 38B, one or more score lines 96 may be provided to define line(s) of weakness allowing for removable of a portion of the seal to expose the fluid outlet 34.

Figure 39A:
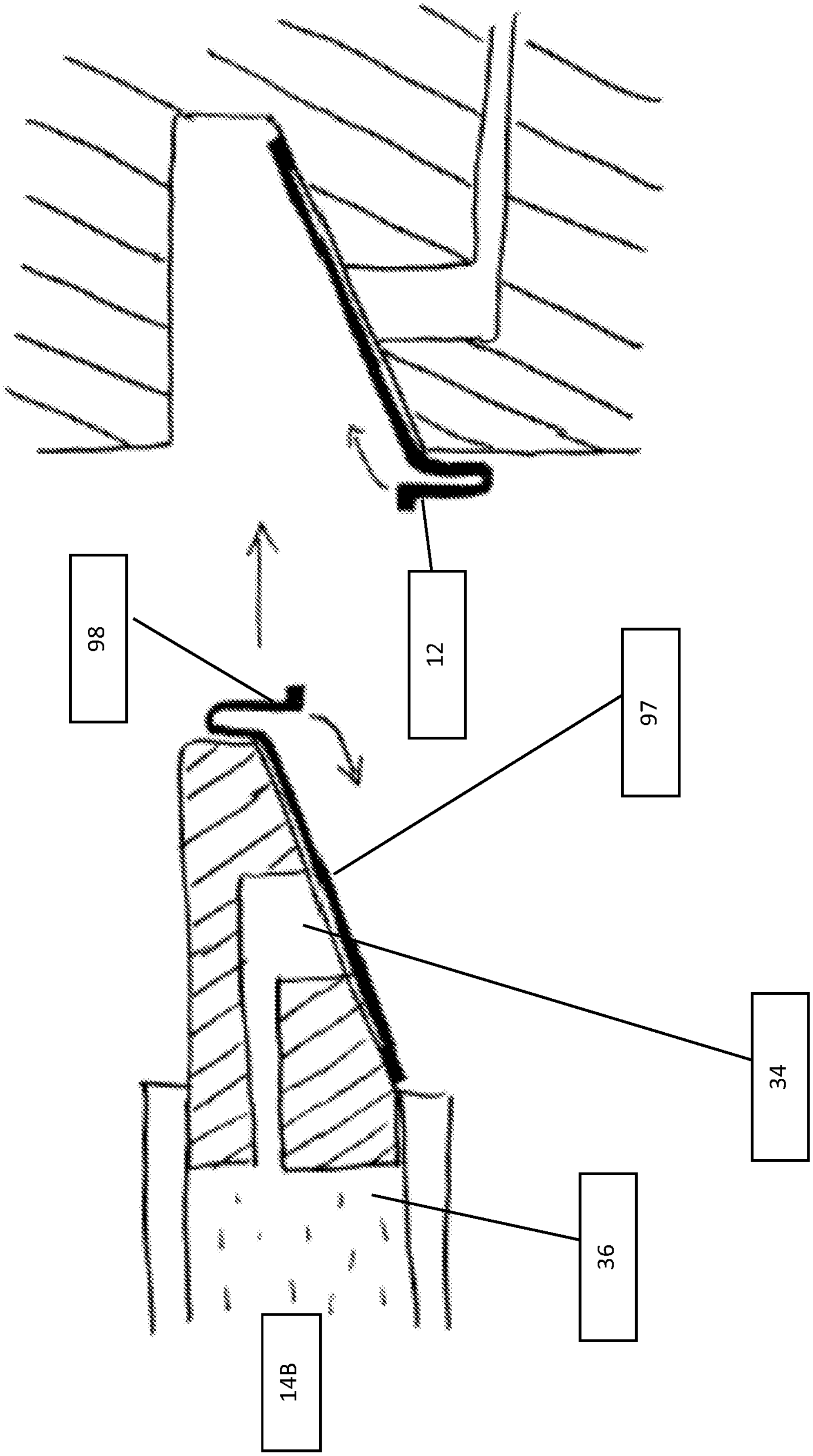
FIG. 39A shows a method of accessing a drug cartridge by engaging two edges of film covering the fluid path, in accordance with the subject invention. In this illustration, the film is mounted to flat surfaces.
Figure 39B:
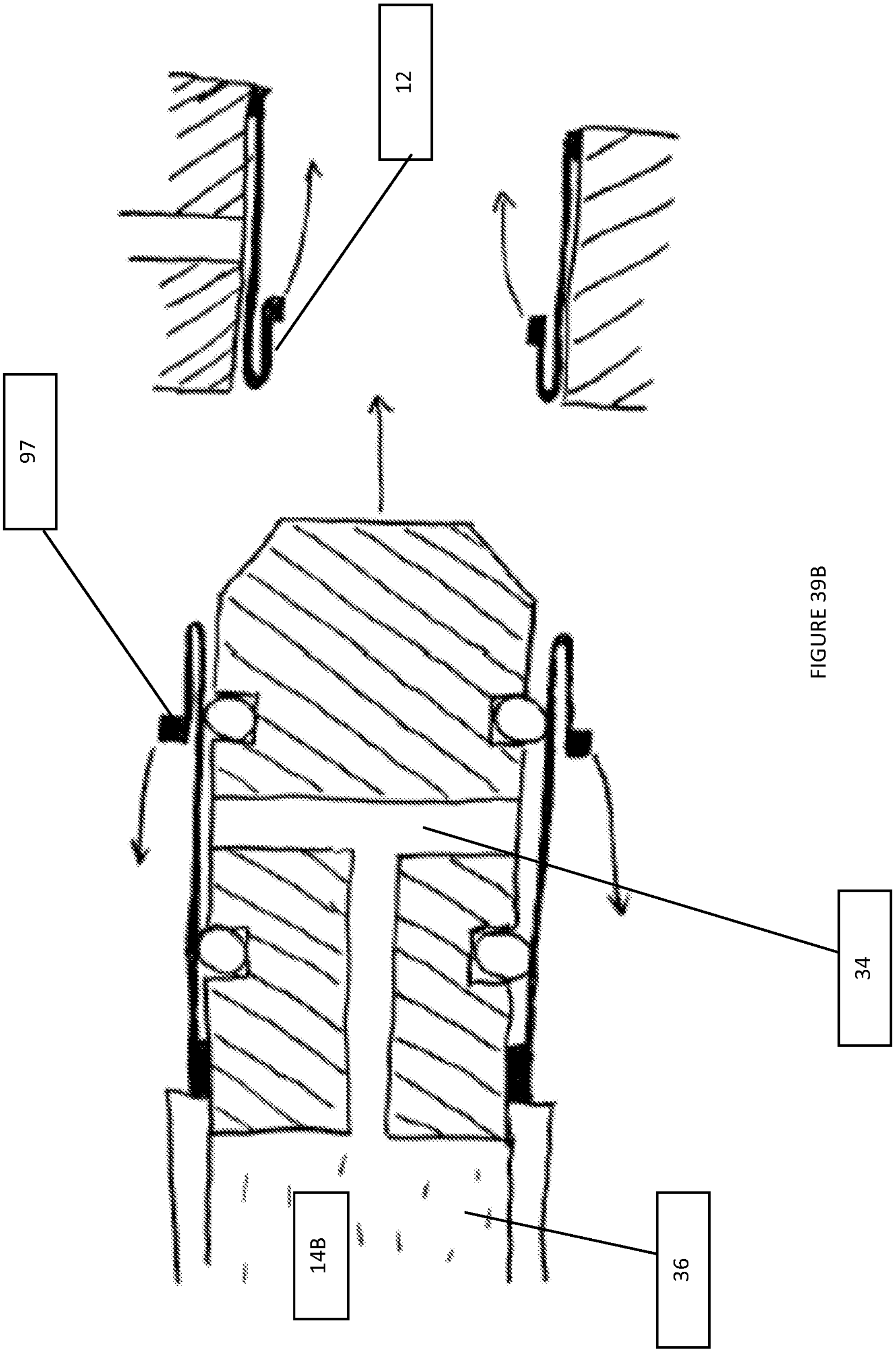
FIG. 39B shows a method of accessing a drug cartridge by engaging two edges of film covering the fluid path, in accordance with the subject invention. In this illustration, the film is mounted to cylindrical surfaces.
Figure 39C:
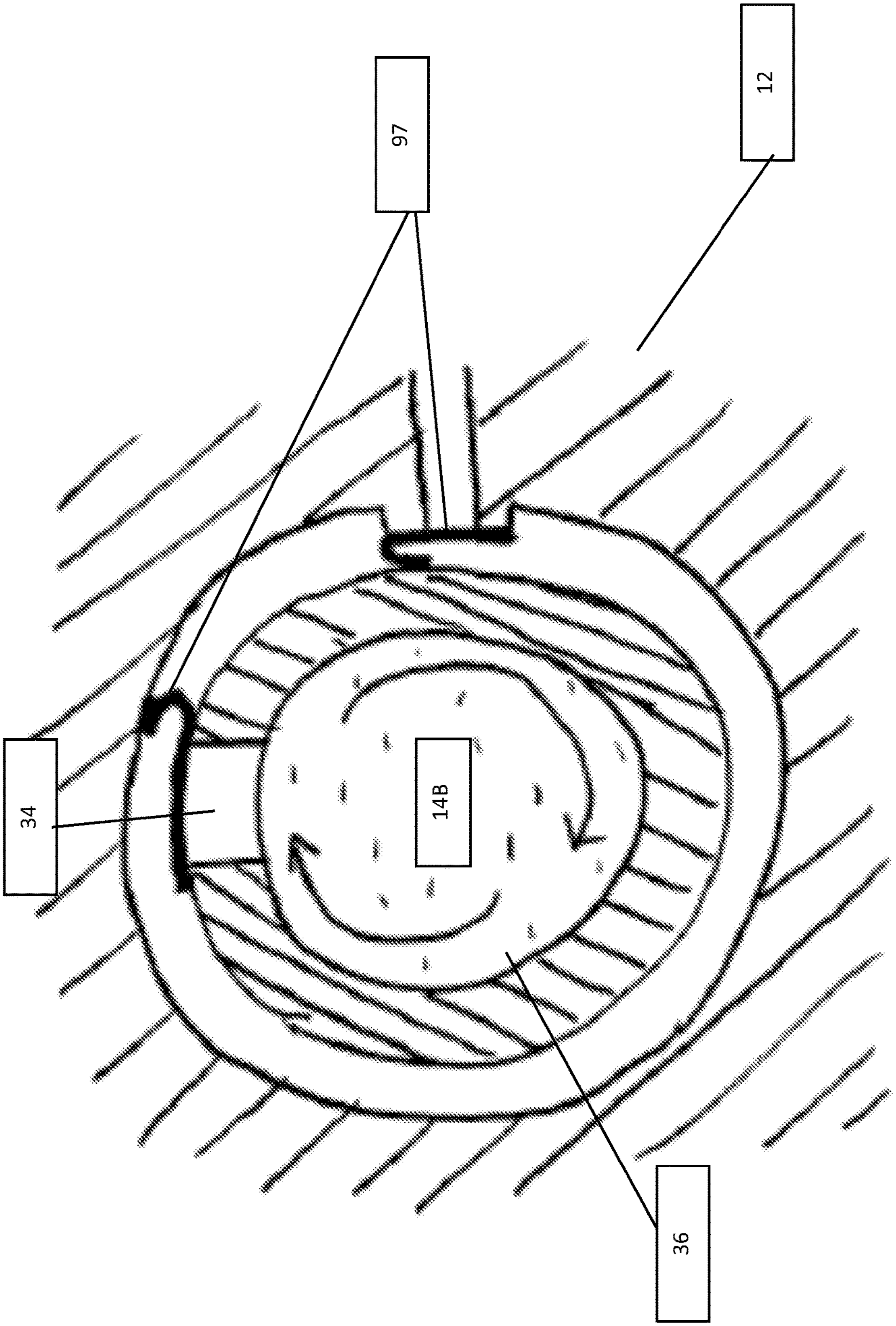
FIG. 39C shows a method of accessing a drug cartridge by peeling film via relative rotation of an internal component, in accordance with the subject invention.
Figure 39D:
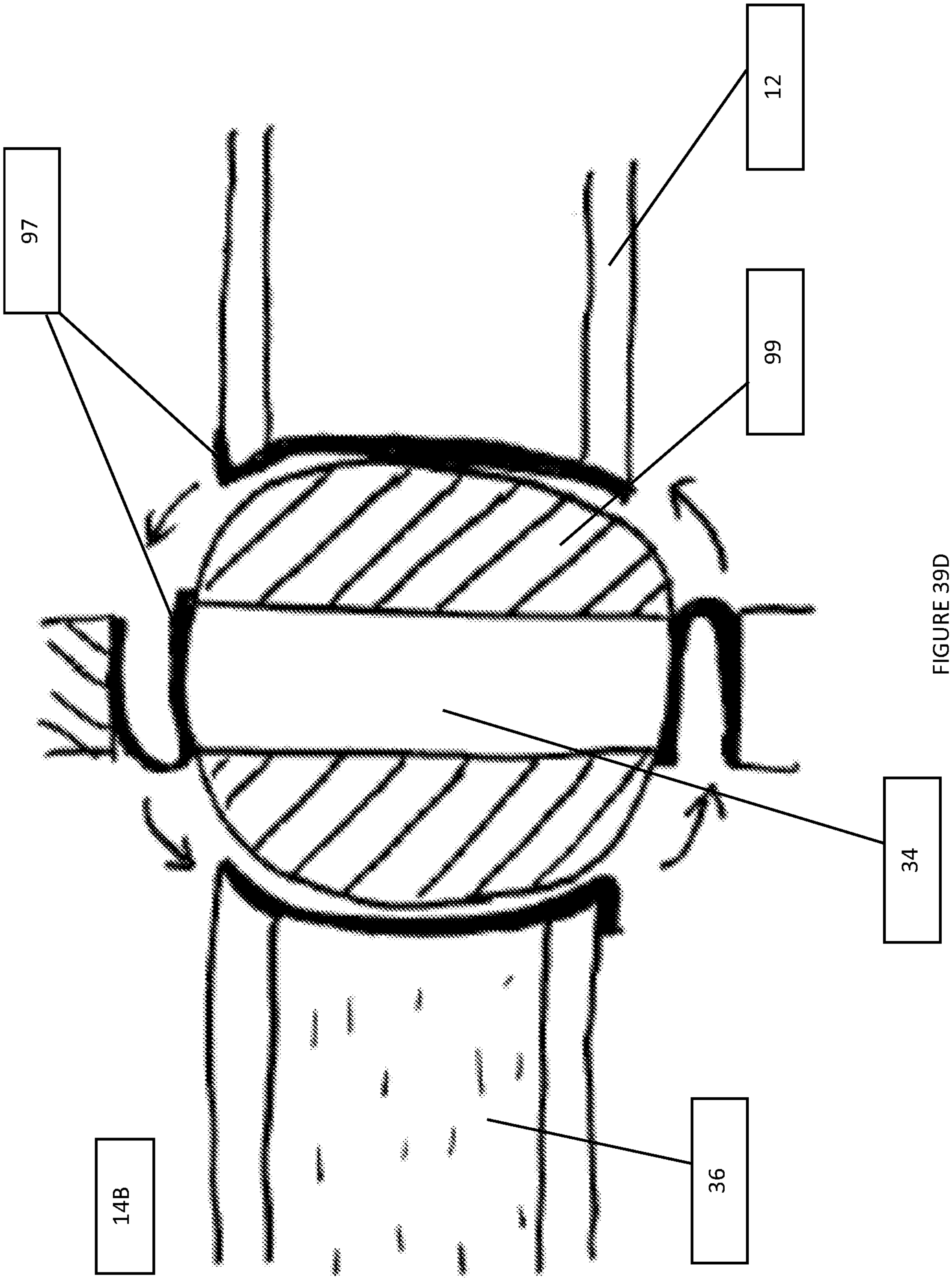
FIG. 39D shows a method of accessing a drug cartridge by peeling film via ball-valve type element, in accordance with the subject invention.

FIGS. 39A-41D show different sterile connection seal arrangements useable with the subject invention. For example, as shown in FIGS. 39A-39D, "rolling diaphragm" arrangements may be utilized where a sterile barrier 97 is provided on the plug adaptor 14B with an outward extending edge 98. The sterile barrier 97 seals the internal lumen 36. With attachment of the plug adaptor 14B to the body 12, the outward extending edge 98 may catch a portion of the body 12 and be rolled backward to expose the internal lumen 36. As shown in FIGS. 39A-39C, the plug adapter 14B and the body 12 may be formed with different cooperating surfaces to facilitate removal of the sterile barrier 97, including matching tapered surfaces (FIG. 39A) and matching cylindrical surfaces (FIG. 39B, removal with insertion; FIG. 39C, removal with rotation after insertion). FIG. 39D shows the use of a ball-valve type element 99 to connect the internal lumen 36 to the body 12, where adjustment of the ball-valve type element 99 causes removal of the sterile barriers 97 and allows for communication between the internal lumen 36 and the body 12.

Figures 2, 40A:
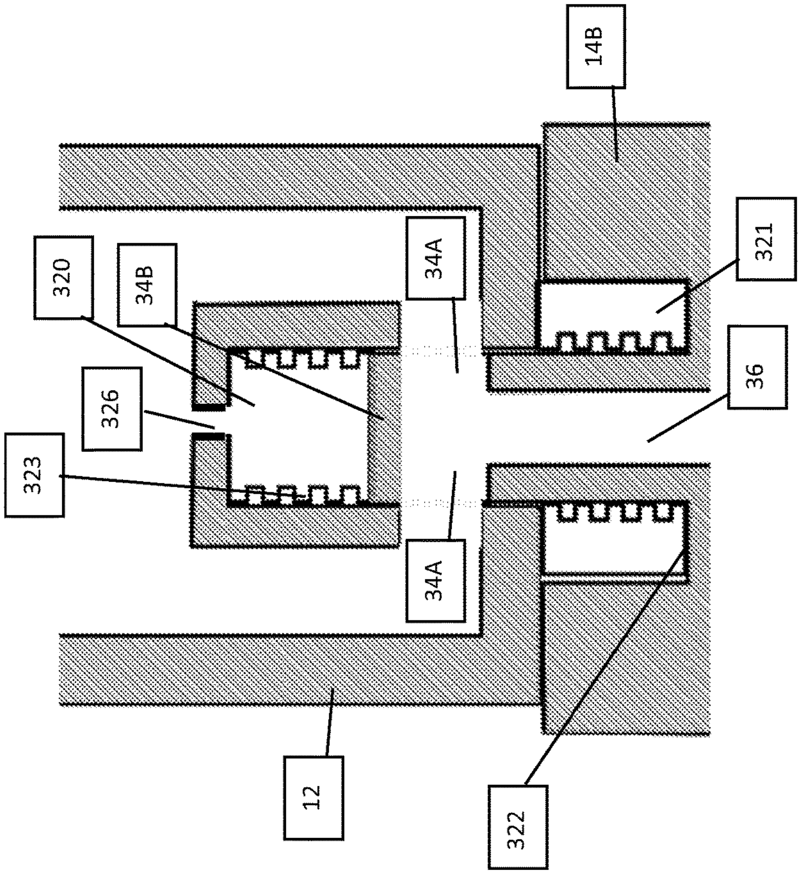
Figures 1, 40A:
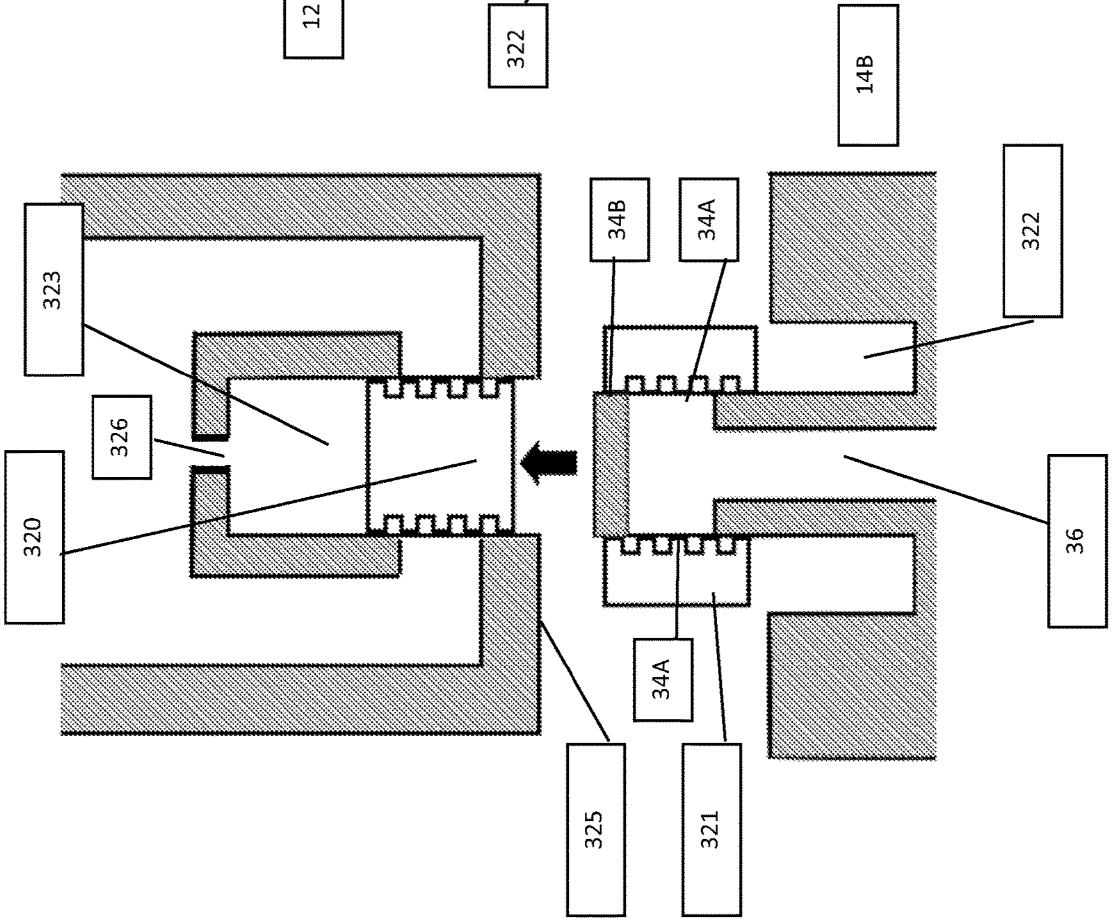
Figure 40B:
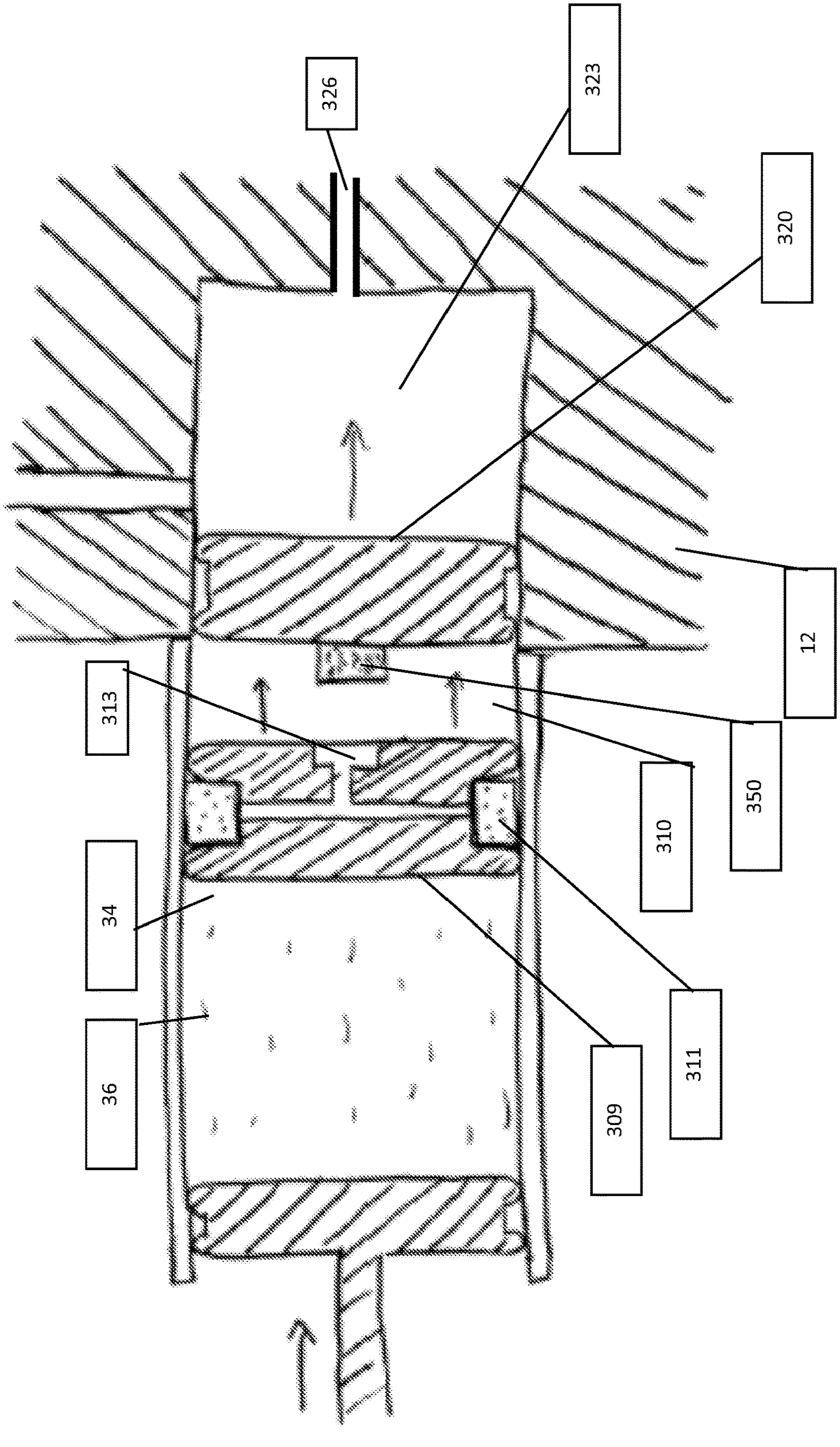
FIG. 40B shows a method of decontaminating the fluid path using a disinfectant reservoir and a slidable piston, in accordance with the subject invention.
Figure 40C:
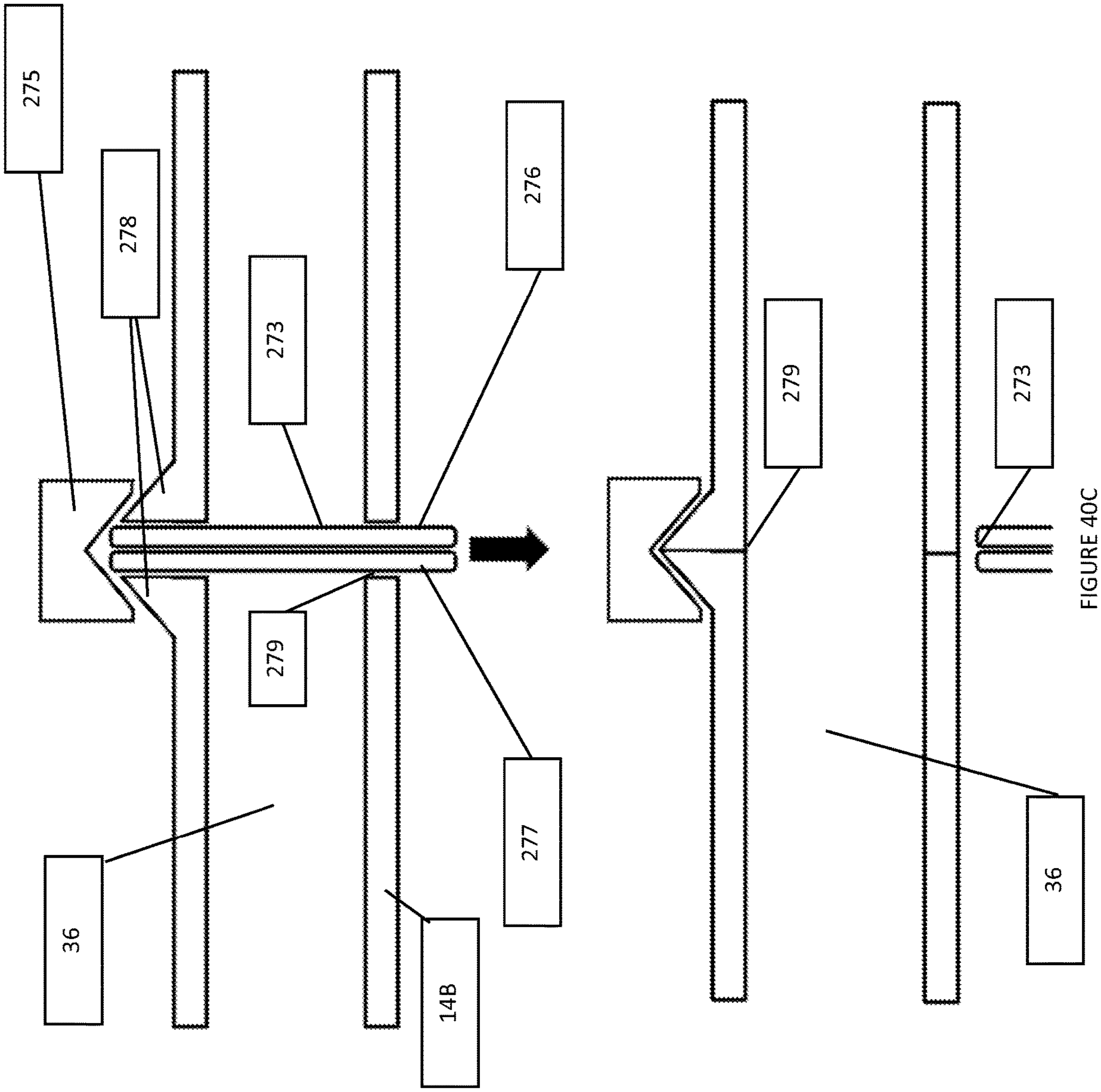
FIG. 40C shows a method for accessing a drug cartridge using removable lateral seals and a clamping mechanism, in accordance with the subject invention.

FIGS. 40A-40C show different shifting seal arrangements where adjustment of seals allows for flow of drug. For example, in FIG. 40A, plug seal 320 may be provided in a first channel 323 in the body 12. A second channel 322 may be formed in the plug adapter 14B about the internal lumen 36. The fluid outlet 34 may be formed with side ports 34A and a closed end 34B. An annular ring seal 321 is initially located about the fluid outlet 34 to seal the side ports 34A. As shown in FIG. 40A-1, with insertion of the fluid outlet 34 into the body 12, the plug seal 320 is caused to shift in the first channel 323 and the ring seal 321 is caused to shift into the second channel 322. Thus, as shown in FIG. 40A-2, the side ports 34A are exposed to allow communication between the internal lumen 36 and the body 12. One or more vent openings 326 may be provided in the first channel 323 to allow for air to escape with the shifting of the plug seal 320 into the first channel 323.

With reference to FIG. 40B, the plug seal 320 may be provided in the first channel 323 with a disinfectant reservoir 350. A slidable piston 309 may be provided in the fluid outlet 34 having an annular wiper 311. Disinfectant channels 313 are formed in the piston 309 to convey disinfectant to the wiper 311. To form a connection between the internal lumen 36 and the body 12, pressure is applied to the liquid drug (which is generally incompressible), resulting in forward movement of the piston 309. Disinfectant emitted from the disinfectant reservoir 350 is conveyed to the wiper 311, via the disinfectant channels 313, so that the inner surface of the fluid outlet 34 is sterilized with movement of the piston 309. With sufficient movement, the piston 309 engages the plug seal 323, causing movement into the first channel 323. With further sufficient movement, the piston 309 by-passes at least one fluid duct in the body, allowing for open communication with the internal lumen 36. The first channel 323 may be vented by one or more of the vent openings 326.

With reference to FIG. 40C, a lateral seal 273 may be provided, formed by multiple film layers 276, 277, to have a certain level of stiffness. The lateral seal 273 may be located through a slit 279 to span the fluid outlet 34 and/or the internal lumen 36 to provide a seal thereof. Flanges 278 may be formed about portions of the slit 279 with a clamping element 275 acting on the flanges 278 to maintain the slit 279 in close, seal contact with the lateral seal 273, which is retained in place. To allow open communication with the internal lumen 36, the lateral seal 273 is removable through the slit 279 with the slit 279 self-sealing. Sufficient resiliency must be provided in the materials about the slit 279 to allow for proper sealing against the lateral seal 273 and subsequent self-scaling.

Figure 41A:
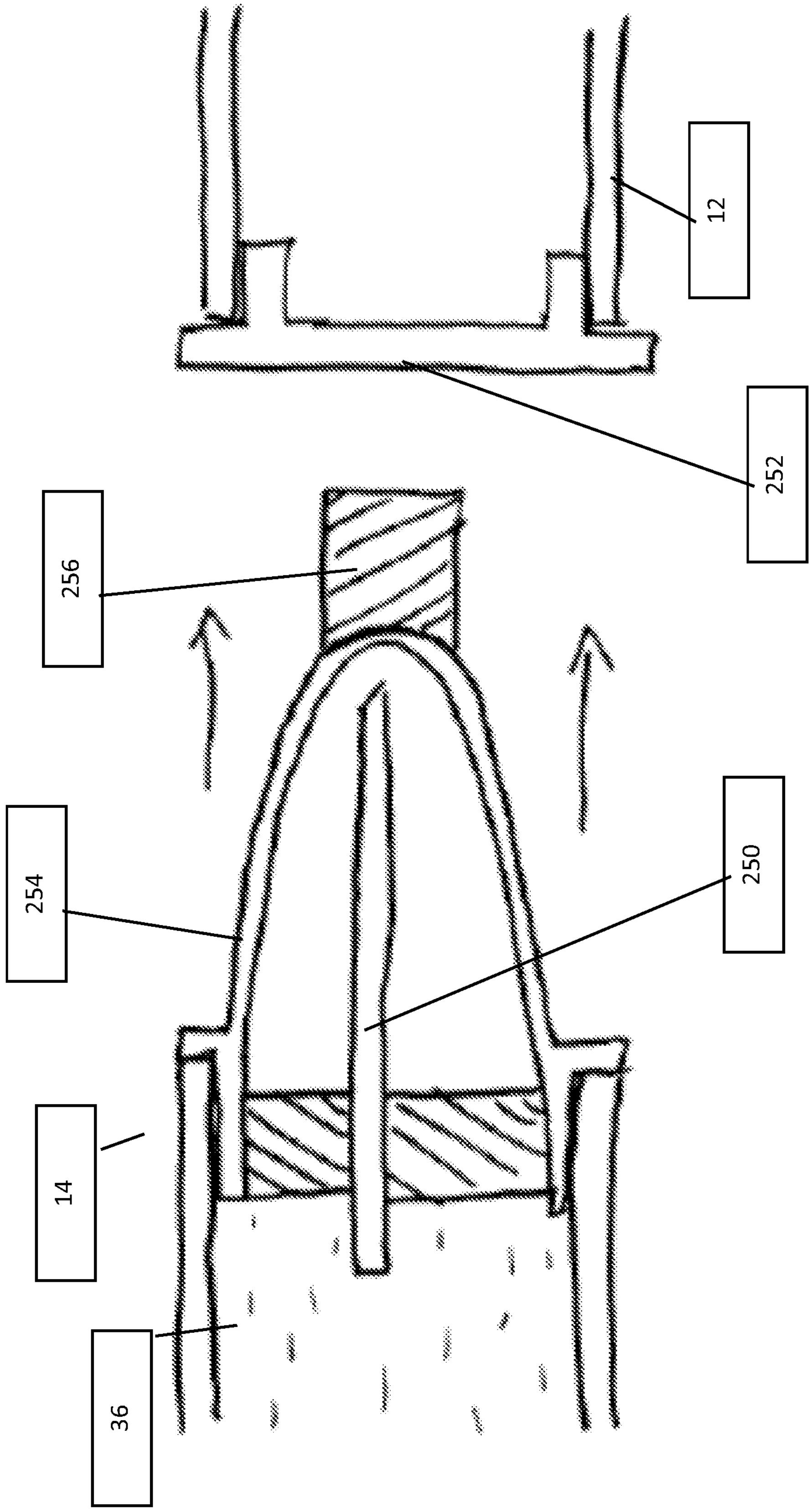
FIG. 41A shows a method of decontaminating the fluid path using a disinfectant reservoir which is pierced by a cannula, in accordance with the subject invention.
Figure 41B:
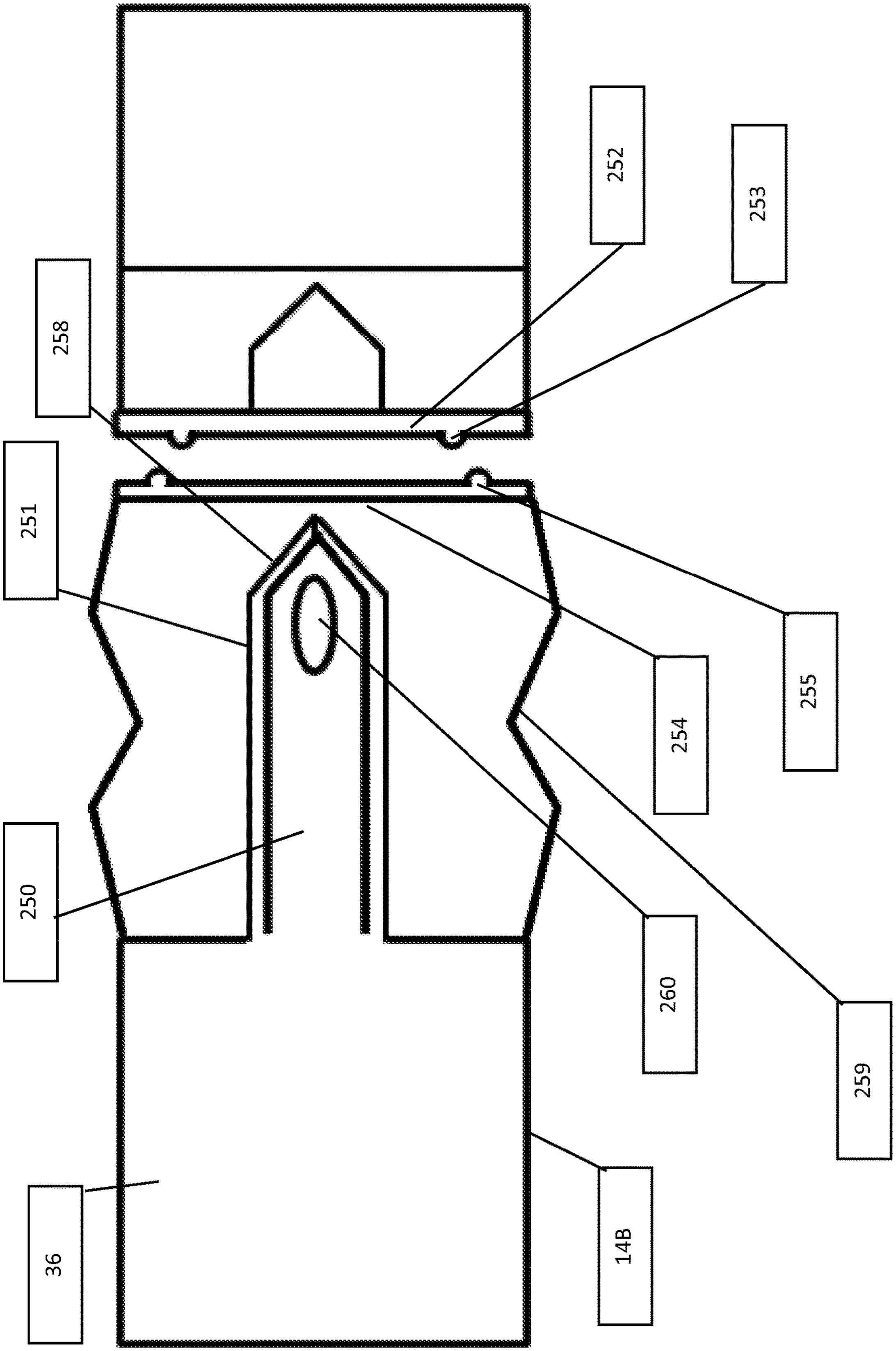
FIG. 41B shows a method for accessing a drug cartridge using a single-tip sheathed needle and septum, in accordance with the subject invention.
Figure 41C:
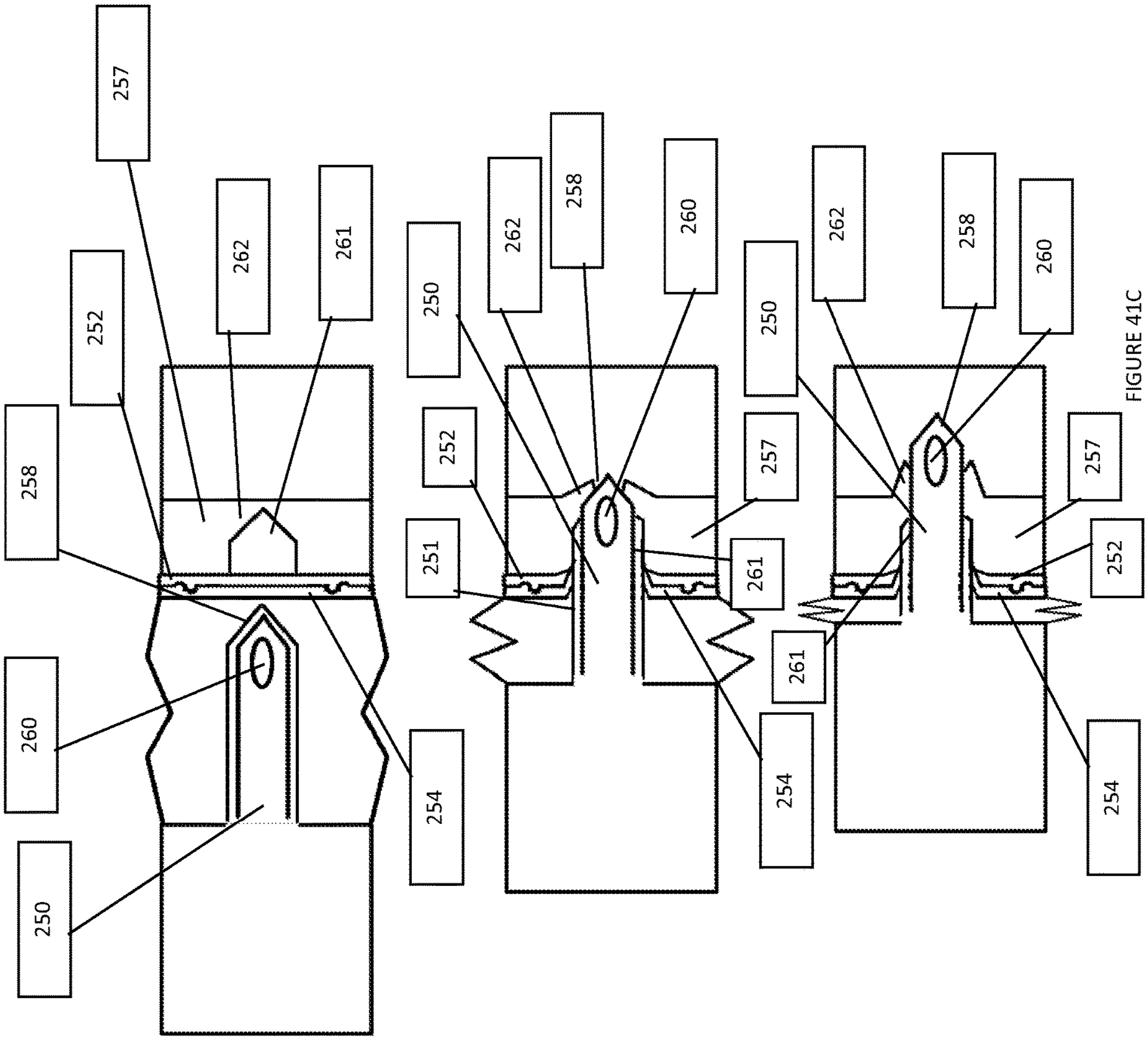
FIG. 41C shows the system of FIG. 41B in use.
Figure 41D:
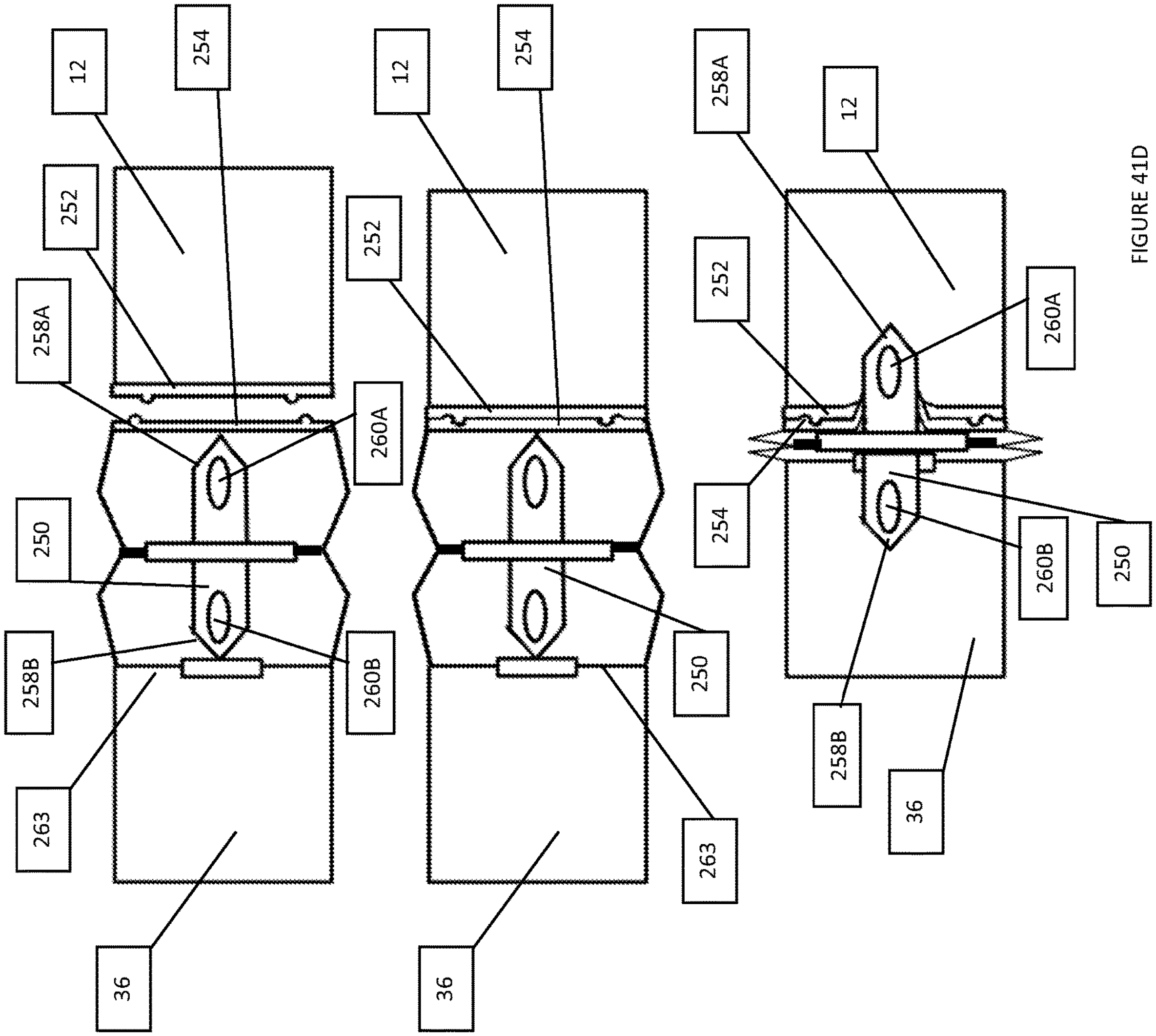
FIG. 41D shows a method for accessing a drug cartridge using a dual-tip sheathed needle and septa, in accordance with the subject invention.
Figure 41E:
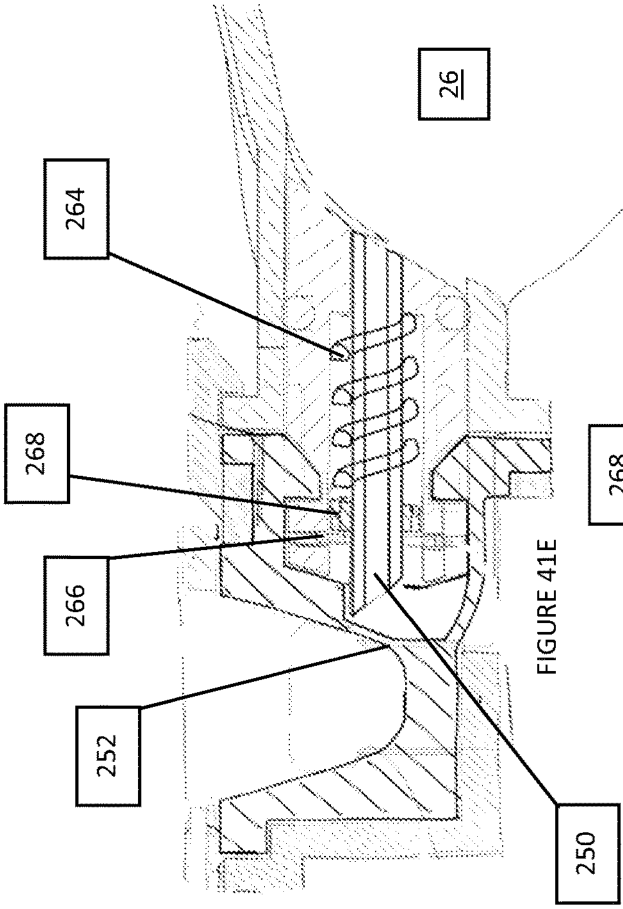
FIG. 41E shows a method for accessing a drug cartridge using a spring-loaded needle, in the pre-loaded state, within the drug cartridge outlet, in accordance with the subject invention.
Figure 41F:
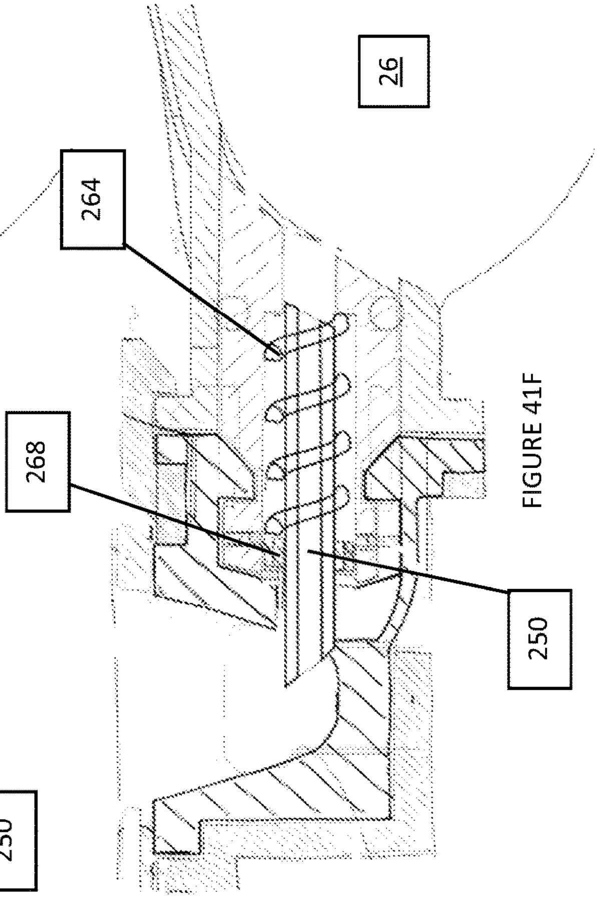
FIG. 41F shows a method for accessing a drug cartridge using a spring-loaded needle, in the extended state, within the drug cartridge outlet, in accordance with the subject invention.
Figure 42:
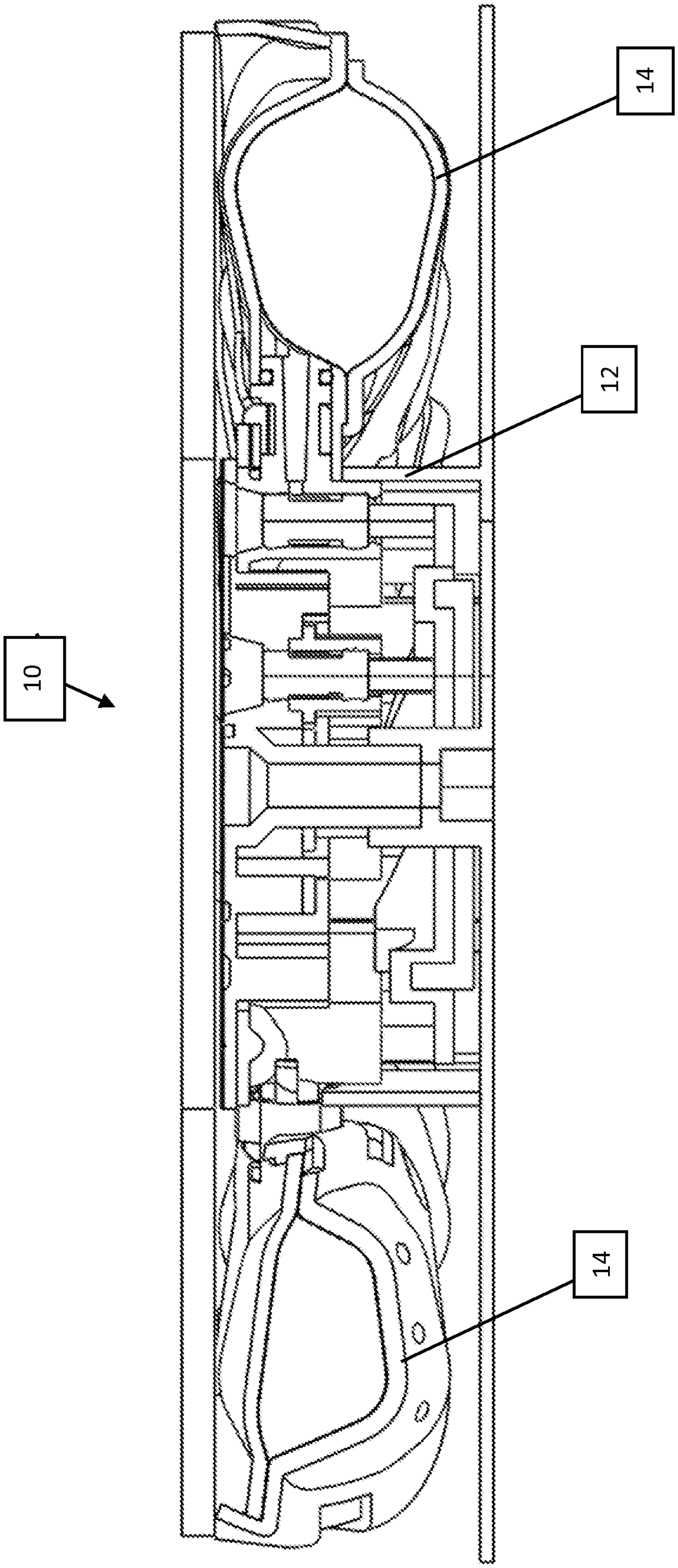
FIG. 42 is a section view of a drug delivery device, illustrating a useable fluid path, in accordance with the subject invention.
Figure 43:
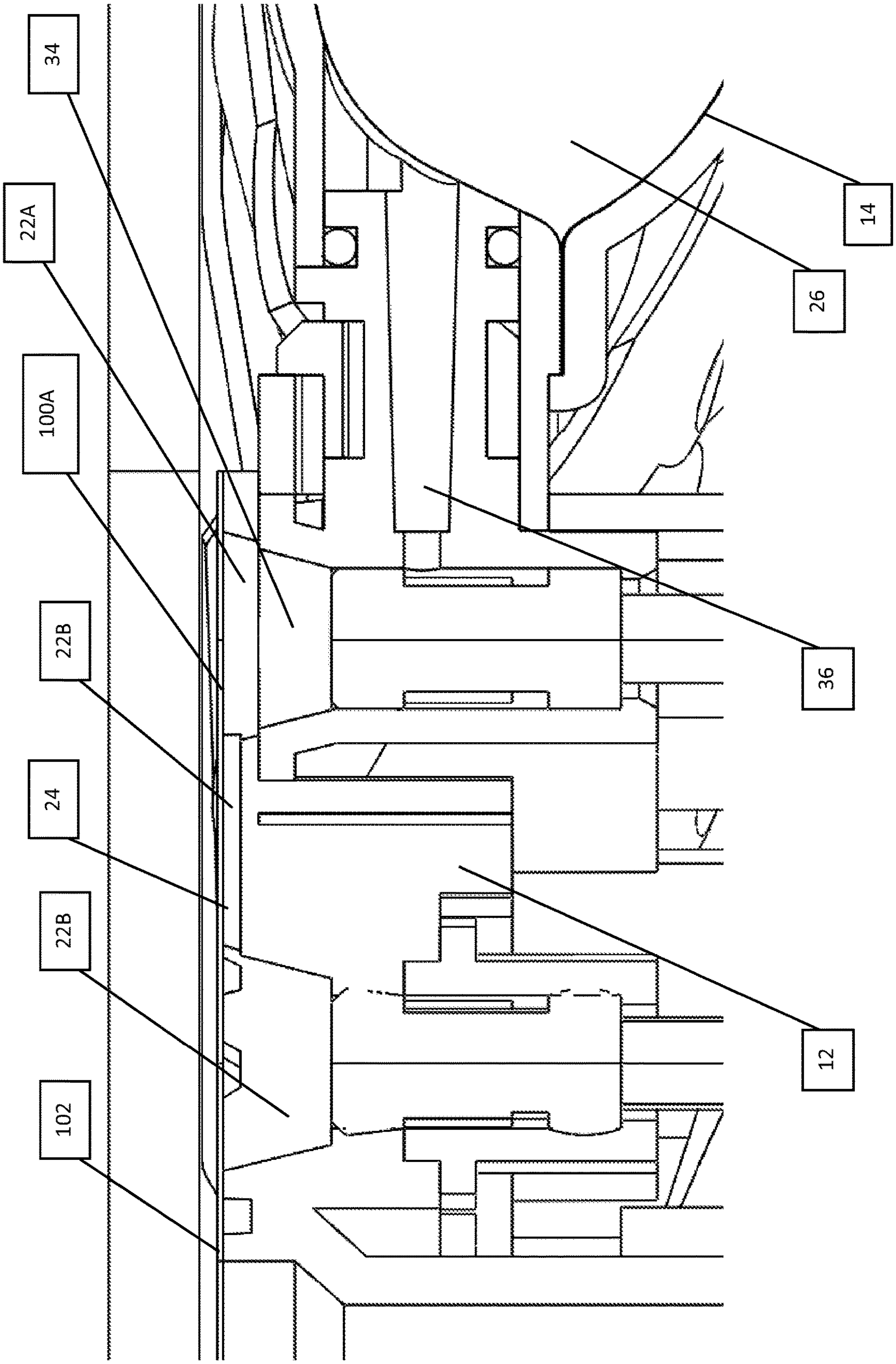
FIG. 43 is a detailed view of a section of FIG. 42.
Figure 44:
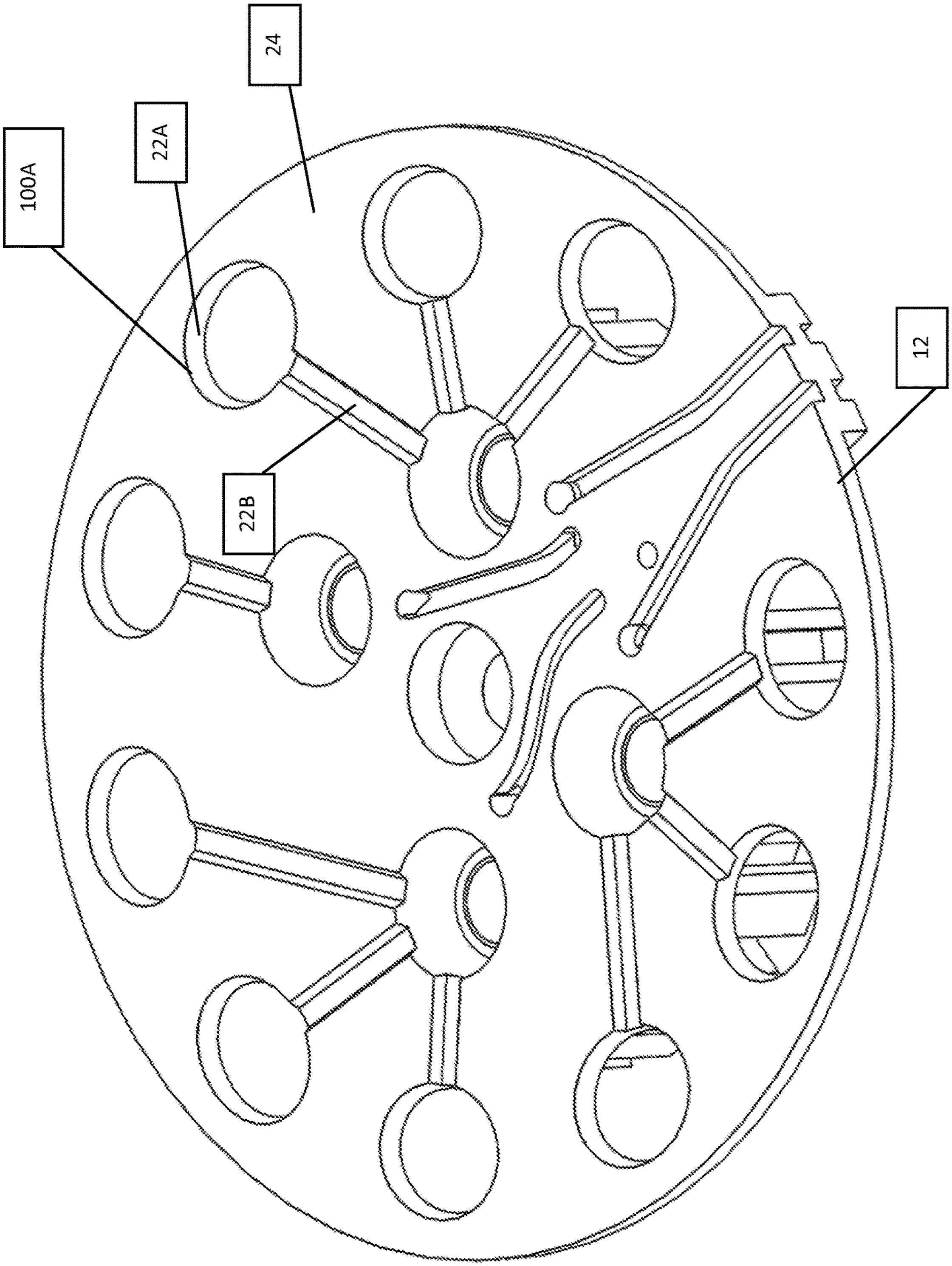
FIG. 44 is an isometric view of a body useable with the subject invention.
Figure 45:
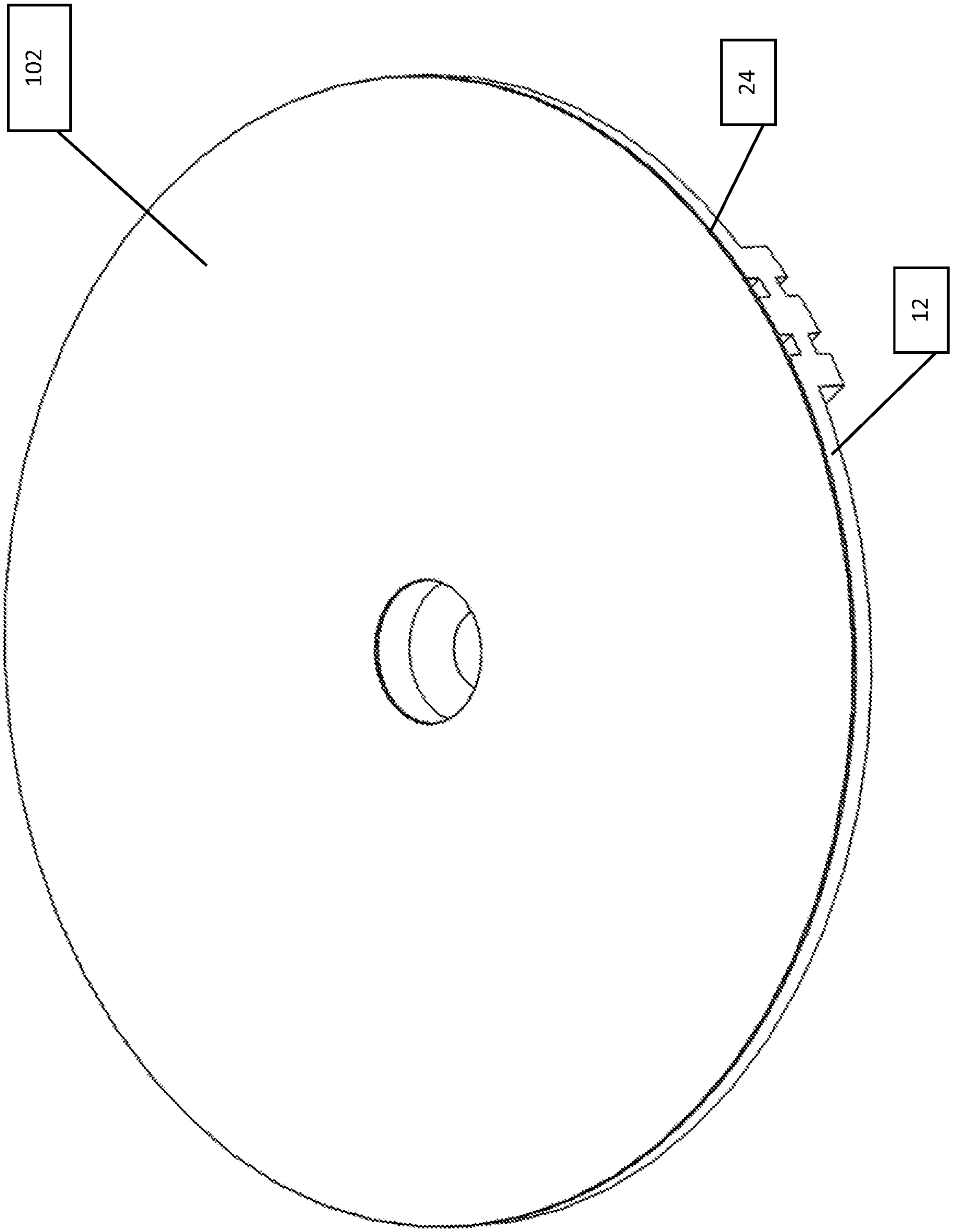
FIG. 45 shows the body of FIG. 44 with a barrier.

With reference to FIGS. 41A-41F, a cannula 250 may be provided with the internal lumen 36 configured for piercing through a septum 252 located on the body 12. The cannula 250 may be supported by a bulkhead or plug located within the fluid outlet 34. As shown in FIG. 41A, the cannula 250 may be encased in a sealed septum 254 with a disinfectant wiper 256 located on an exterior thereof. The cannula 250 is maintained in a sterile condition within the sealed septum 254. In use, the cannula 250 is caused to pierce the sealed septum 254, pass through the wiper 256 and pierce the septum 252. This allows for open communication between the internal lumen 36 and the body 12. FIGS. 41B and 41C show the cannula 250 encased in sheath 251 (e.g., an elastomeric sheath) and having a closed end 258 with side ports 260. Here, with the cannula 250 piercing the septum 252, open communication is provided through the side ports 260. As shown in FIG. 41B, a collapsible wall 259 (e.g., having bellows or pleats) may be provided about the cannula 250 sealed off by the septum 254. The wall 259 may be formed to collapse with the septum 254 pressing against the septum 252. With sufficient advancement, the cannula 250 pierces the septum 254. With piercing the septum 252, the cannula 250 is caused to advance through the septum 254, with the sheath 251 being restricted due to engagement with the septum 254. This allows for the cannula 250 to be exposed with further advancement through the septum 252 to allow communication between the internal lumen 36 and the body 12 via the side ports 260. Cooperating annular ribs 253, 255 may be formed on the septa 252, 254 which are concentrically aligned with the septa 252, 254 being in pressing engagement. The annular ribs 253, 255 co-act to maintain alignment between the septa 252, 254. FIG. 41C shows that a pierceable backing 257 may be provided behind the septum 252 to provide rigidity and support to the septum 252. A central open passage 261 may be provided in the backing 257 which leads to a thinned web 262 aligned to be pierced by the cannula 250. As shown in FIGS. 41E and 41F, a spring 264 may be provided for advancing the cannula 250. A locking ring 266 may be utilized to retain the cannula 250 in an initial state, as shown in FIG. 41E. The locking ring 266 may be displaced or disrupted to allow the spring 264 to advance the cannula 250 in piercing the septum 252. A seal collar 268 may be provided about the cannula 250 to advance therewith, to provide a seal about the cannula 250.

FIG. 41D provides the cannula 250 as double-ended with two closed ends 258A, 258B and two sets of side ports 260A, 260B. Here, a secondary septum 263 is provided located interiorly of the cannula 250. The cannula 250 may be partially embedded into the secondary septum 263 to be held in place. In use, the cannula 250 pierces both the septum 252, the sealed septum 254, and the secondary septum 263 to allow for open communication between the internal lumen 36 and the body 12 via the two sets of side ports 260A, 260B.

In any of the embodiments of FIGS. 41A-41F, any of the septum 252, 254, and/or the secondary septum 263 may include biocidal materials to promote sterility, including, but not limited to, antimicrobial silver.

With the reservoir section 14A of drug cartridge 14 sterilized, then aseptically filled and sealed by the plug adaptor 14B, the drug cartridge 14 may be stored and transported as needed. External portions of the drug cartridge 14, including the fluid outlet 34, may be open to atmosphere during storage and assembly to the body of the device, thus not being sterile.

As shown in FIGS. 42-56, the drug cartridge 14 may be mounted to the body 12 in any manner. For example, portions of the plug adaptor 14B and the body 12 may be joined by laser welding, adhesive, fusion, and so forth. The drug cartridge 14 is assembled to the body 12 to have the fluid outlet 34 be aligned with a first fluid duct 22A to define a continuous flow path for the drug from the reservoir 26. The first fluid duct 22A extends from the fluid outlet 34 to a first opening 100A formed in the first face 24 of the body 12. A secondary fluid duct 22B may extend from the first opening 100A to be in communication with the first fluid duct 22A. The secondary fluid duct 22B continues the flow path from the fluid outlet 34. The secondary fluid duct 22B is open along the first face 24. As shown in FIGS. 90-91, the drug cartridge 14 may be mounted to a second face 24A of the body 12 with the first fluid duct 22A extending from the fluid outlet 24 and through the thickness of the body 12 to the secondary fluid duct 22A.

A barrier 102 may be provided across the first face 24 to at least cover the first opening 100A. The barrier 102 closes the open side of the first opening 100A to contain the flow path within the fluid duct 22A and the first opening 100A. The barrier 102 is also selected to allow for passage therethrough of ultraviolet radiation, x-ray radiation, pulsed light or electron-beam, depending on the decontamination process selected. The barrier 102 may be, but not is required to be, transparent to the respective emission. The barrier 102 may be transmissive to the respective transmission to be effective, without requiring 100% of the respective emission to pass through.

The ultraviolet radiation, x-ray radiation, pulsed light or electron-beam may emanate from one or more sources which are stationary or mounted on moving fixtures. The body 12 may be stationary or moving when exposed to the ultraviolet radiation, x-ray radiation, the pulsed light or the electron-beam. The body 12 must be situated relative to the source(s) of the ultraviolet radiation, x-ray radiation, the pulsed light or the electron-beam to ensure sufficient exposure for the required level of decontamination. By way of non-limiting example, the one or more sources of ultraviolet radiation, x-ray radiation, pulsed light or electron-beam may be located inside a tunnel above a moving belt carrying the body 12. The rate of movement of the belt may be manipulated to control the rate of exposure of the body 12. In addition, multiple sources of ultraviolet radiation, x-ray radiation, pulsed light or electron-beam may be utilized in the tunnel which are spaced apart along a radius about the moving belt to provide semi- or hemi-spherical coverage of the body 12. Alternatively, the one or more sources of ultraviolet radiation, x-ray radiation, pulsed light or electron-beam may be mounted on rigid fixtures, movable arms, or the like, to provide coverage to the body 12, which may be stationary. Relative movement between the body 12 and the source(s) of ultraviolet radiation, x-ray radiation, pulsed light or electron-beam may be provided, with one or both elements moving. All elements may be also statically set in fixed, stationary positions with no relative movement therebetween.

Figure 57:
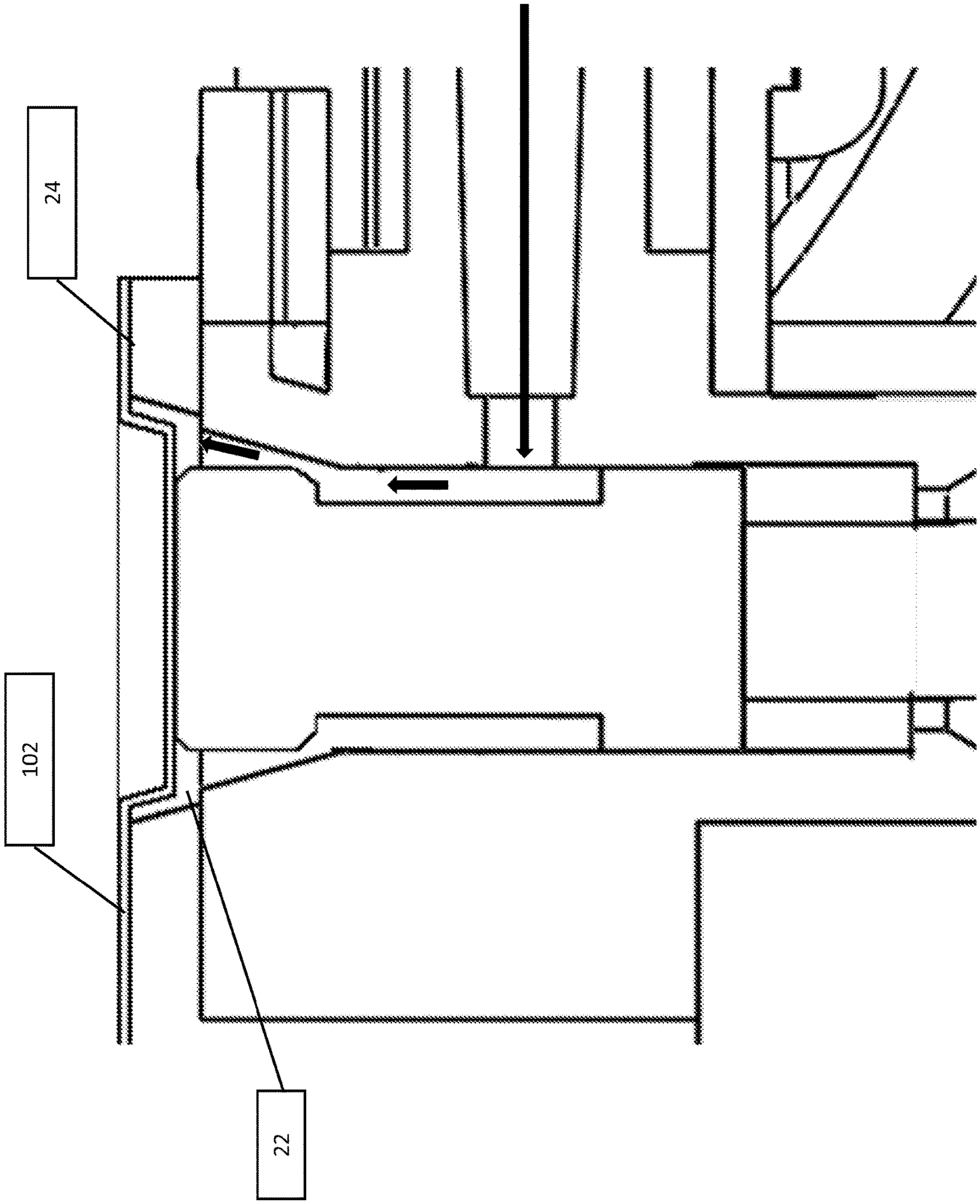
FIG. 57 is a detailed view of a section of FIG. 56.

The barrier 102 may be a single- or multi-ply polymeric film which includes one or more of: fluoropolymer; fluoropolymer copolymer; polyimide; polymethylepentine; silicone; cyclic olefin copolymer; and, cyclic olefin polymer. Alternatively, the barrier 102 may be molded, extruded, laminated and/or thermoformed from one or more of the listed materials. In addition, as shown in FIG. 57, the barrier 102 may be conformed to the topography of the first face 24 including extending into one or more of the fluid ducts 22. This reduces open volume therein.

The barrier 102 may be fixed to the first face 24 in any manner, including, but not limited to, heat scaling, adhesion, fusion, and so forth.

Figure 46:
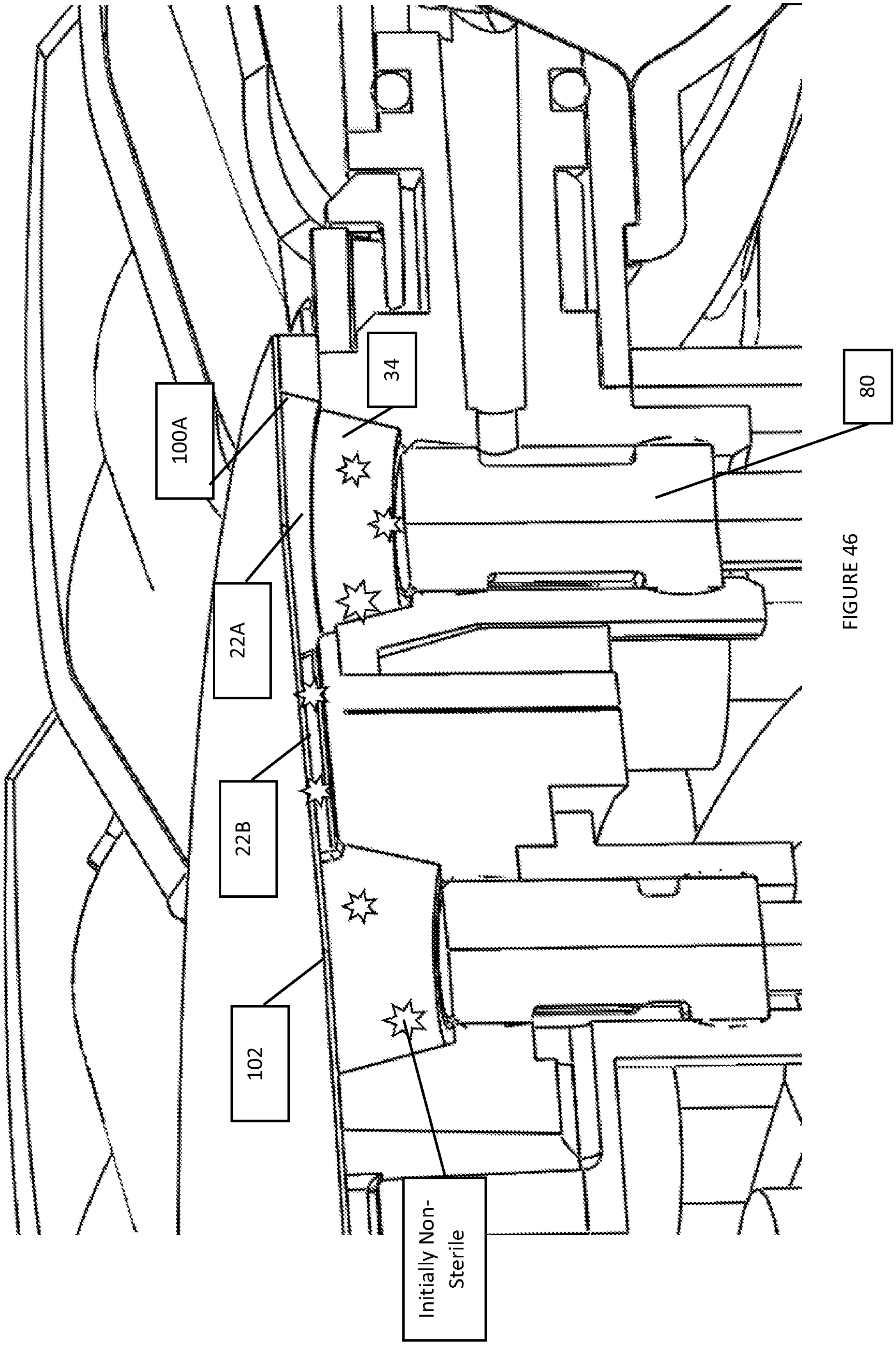
FIG. 46 is a section view showing potential non-sterile regions of a drug delivery device that require sterilization.
Figure 47:
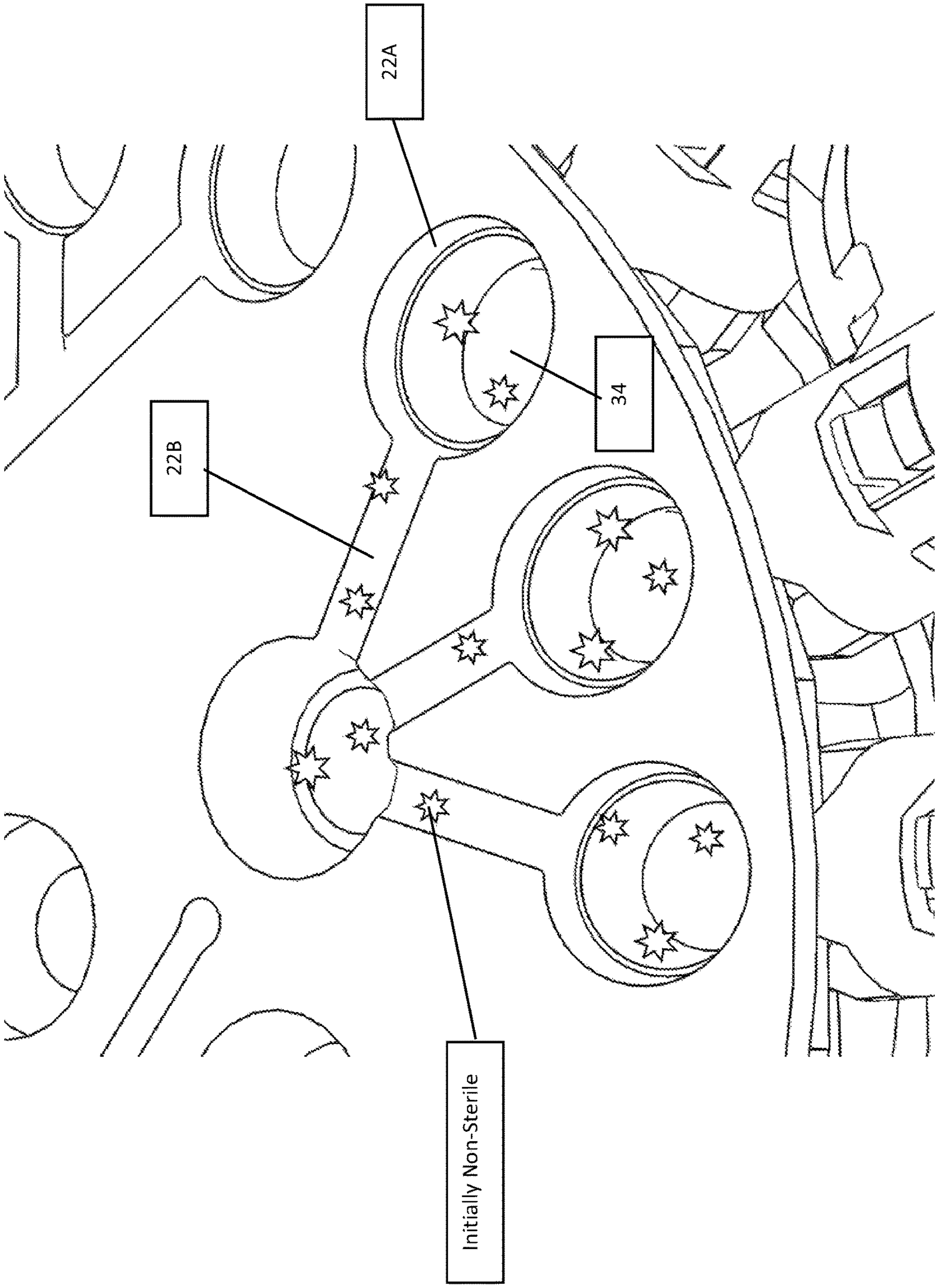
FIG. 47 is an isometric view showing potential non-sterile regions of a drug delivery device that require sterilization.

As shown in FIGS. 46 and 47, with the drug cartridges 14 being secured to the body 12, certain portions of the fluid path may be non-sterile, such non-sterile portions shown representatively by stars. This may occur where the drug cartridges 14 have non-sterile connection seal arrangements, such as with the use of valve 80. Thus, portions of the fluid outlet 34 may be non-sterile. Likewise, portions of the body 12 may be non-sterile, such as the first fluid duct 22A, the second fluid duct 22B, and the opening 100A.

The barrier 102 allows for decontamination, including sterilization, of the flow path along the first face 24. In this manner, the drug cartridge 14 may be separately prepared and assembled to the body 12, with the fluid ducts 22 and the fluid outlet 34 being decontaminated. As shown in FIGS. 48-52 and 69, with the fluid ducts 22 being open along the first face 24 and exposing the fluid outlet 34, the first face 24 may be exposed to ultraviolet radiation, x-ray radiation, pulsed light or an electron beam so that the ultraviolet radiation, x-ray radiation, pulsed light or electron-beam may pass through the barrier 102, to decontaminate exposed surfaces of the fluid ducts 22A, 22B and the fluid outlet 34. A sterile path may be provided, allowing for opening of the seal (FIGS. 55-56) to permit liquid flow. Negative pressure may be applied to the fluid ducts 22 to draw drug from the reservoirs 26 of the drug cartridges 14 simultaneously or in series (in various combinations). In addition, diluent may be pumped through the fluid ducts 22, as needed, to reconstitute dry drug components in one or more of the drug cartridges 14, with subsequent withdrawal of reconstituted liquid drug utilizing negative pressure.

Figure 48:
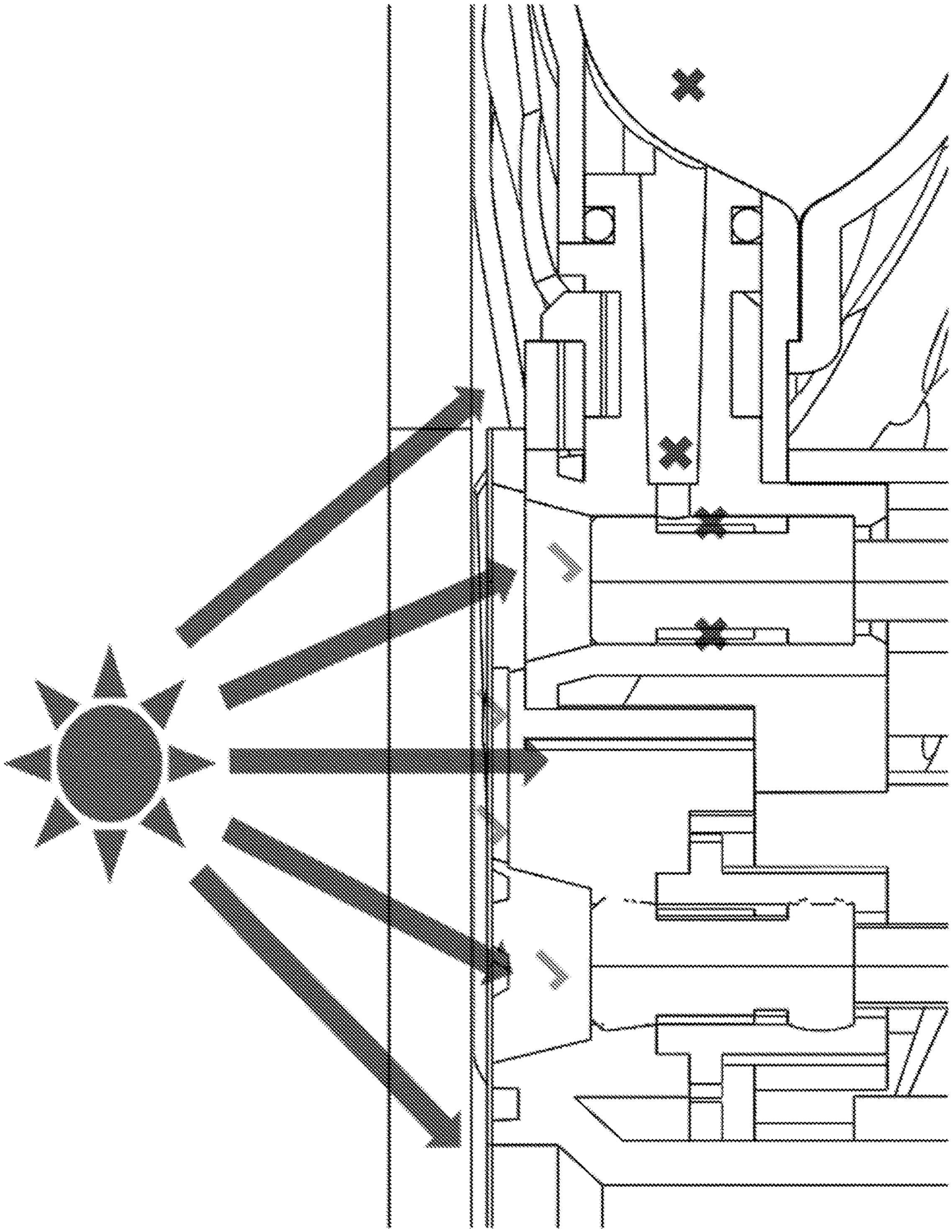
FIG. 48 is a section view showing regions of a drug delivery device which should be sterilized via ultraviolet radiation, pulsed light or electron-beam, and which should not.
Figure 49:
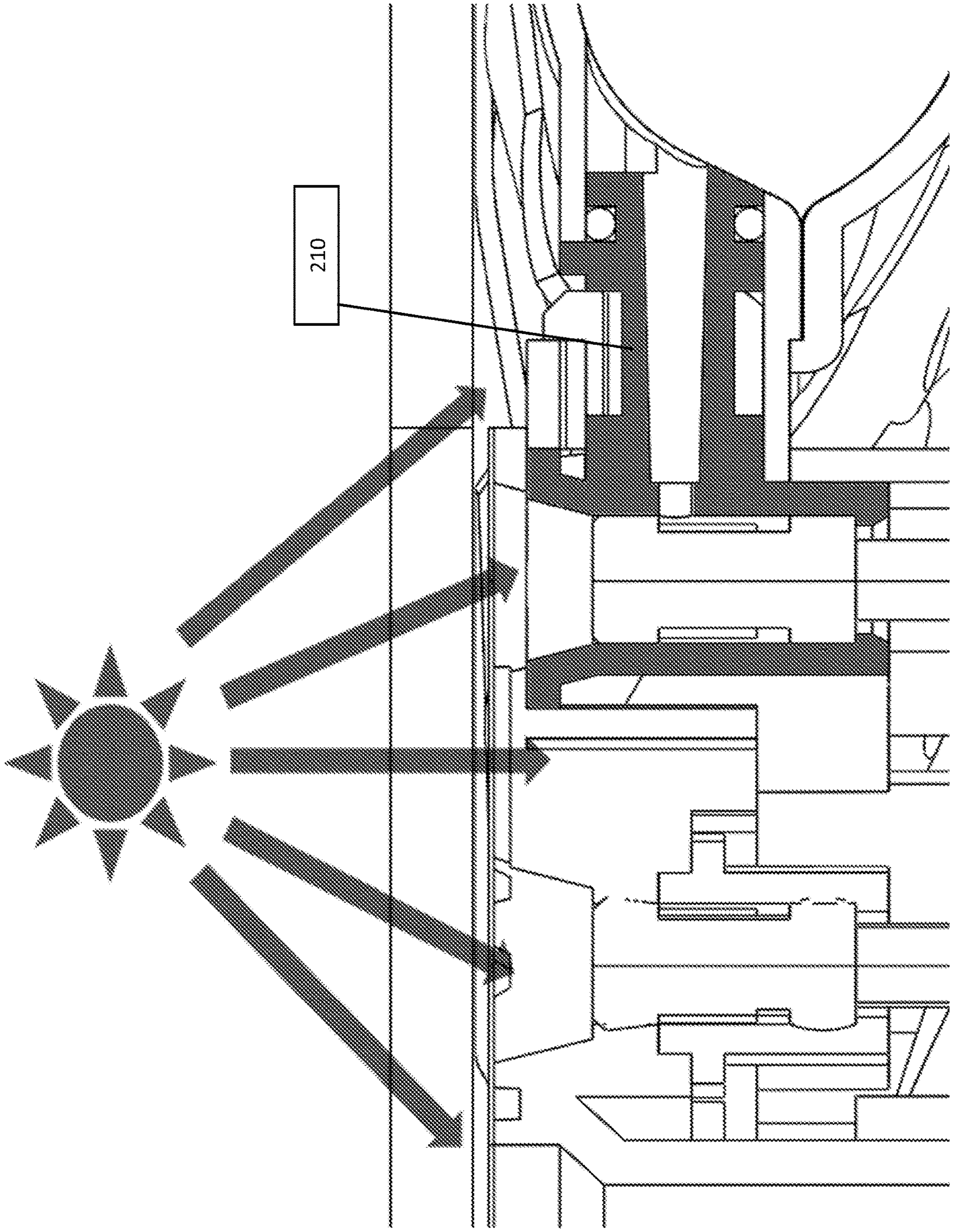
FIGS. 49-49C show locations where additives may be utilized in a drug delivery device to block penetration of ultraviolet radiation or pulsed light.
Figure 50:
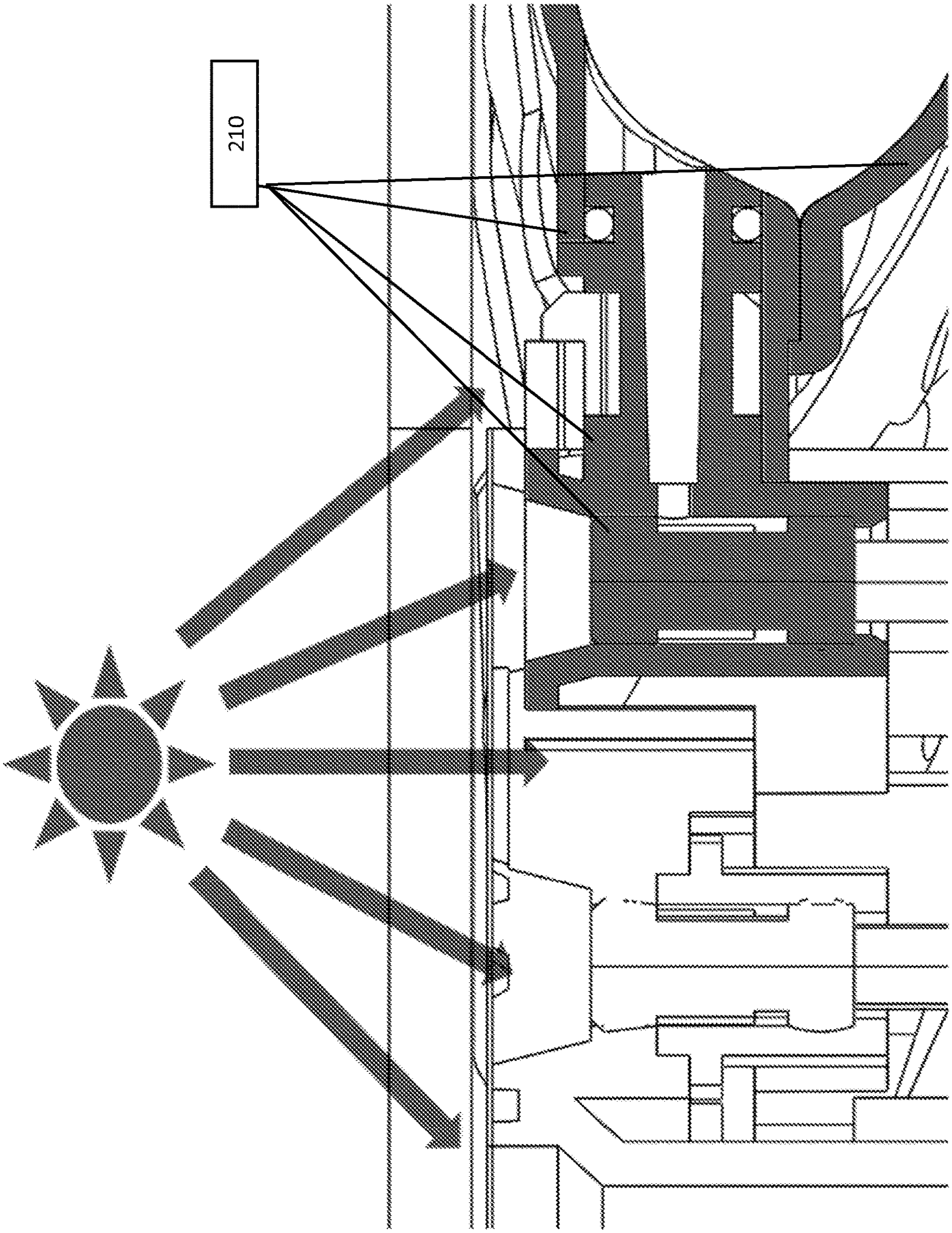
FIG. 50 shows additional locations, beyond the locations shown in FIG. 49, where additives may be utilized to block penetration of ultraviolet radiation or pulsed light.
Figure 51:
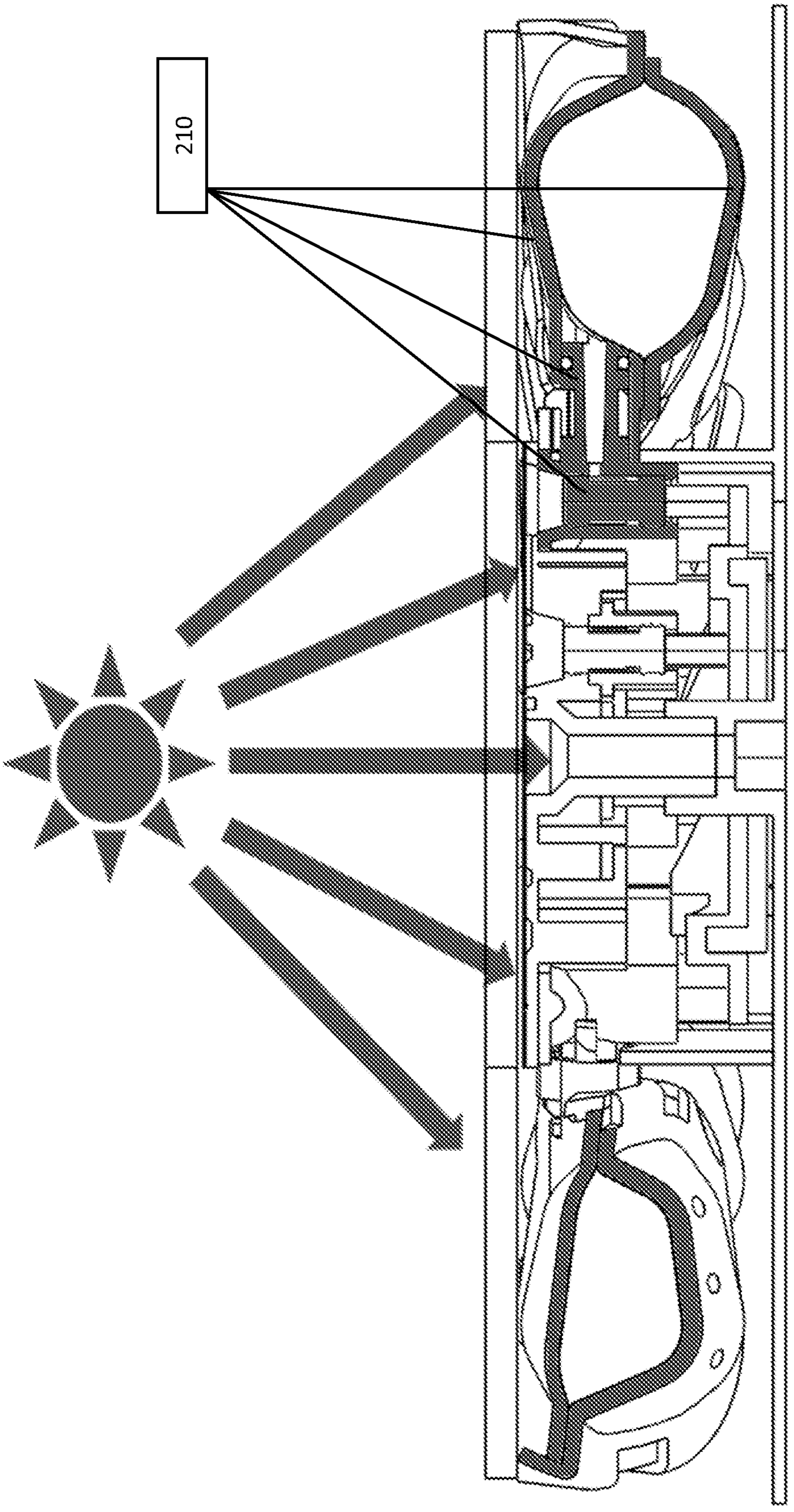
FIG. 51 is a full section view of a drug delivery device, illustrating the blocking components shown in FIG. 50.
Figure 52:
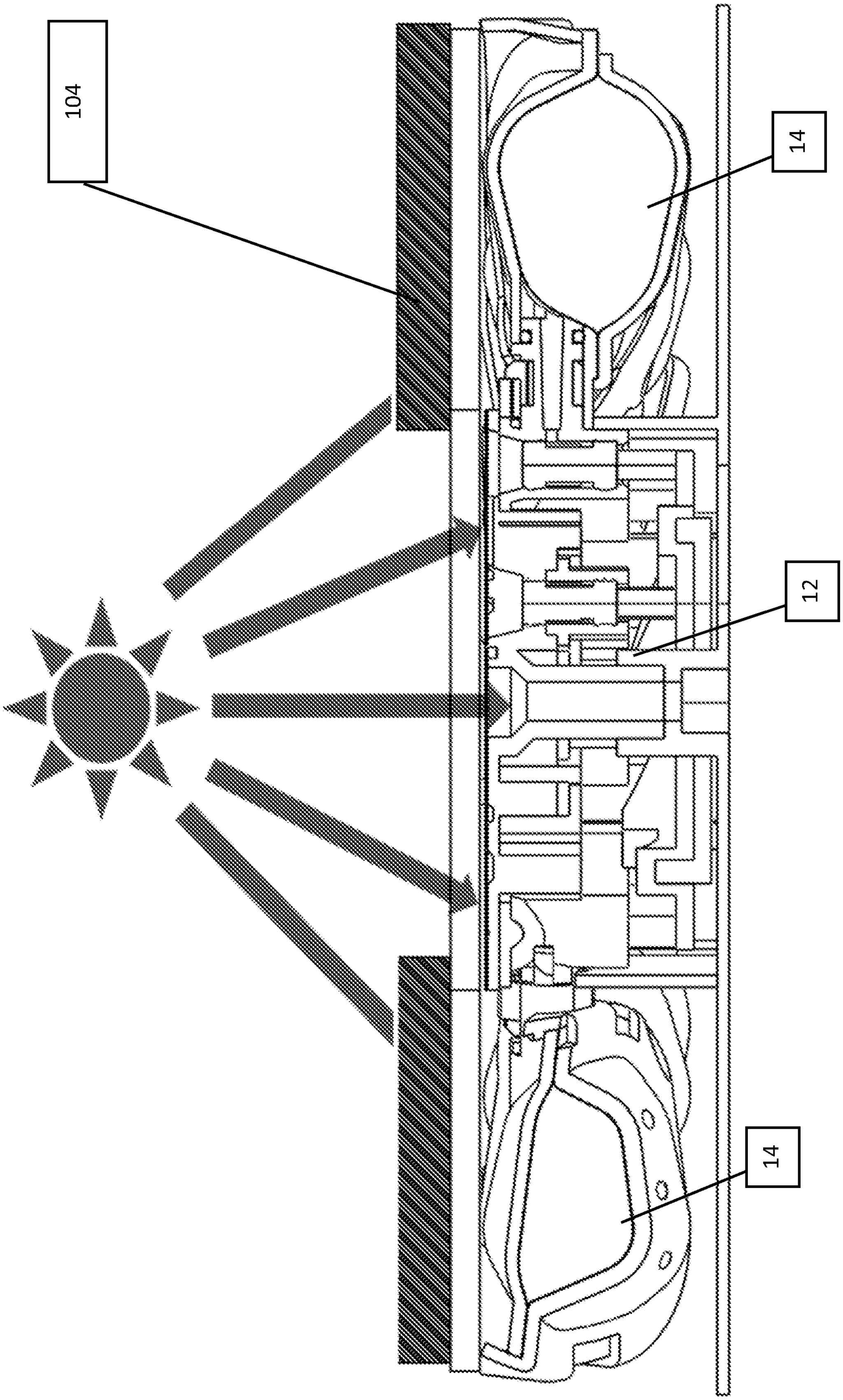
FIG. 52 is a section view of a drug delivery device, showing a shield to block ultraviolet radiation, pulsed light or electron-beam radiation.
Figure 52A:
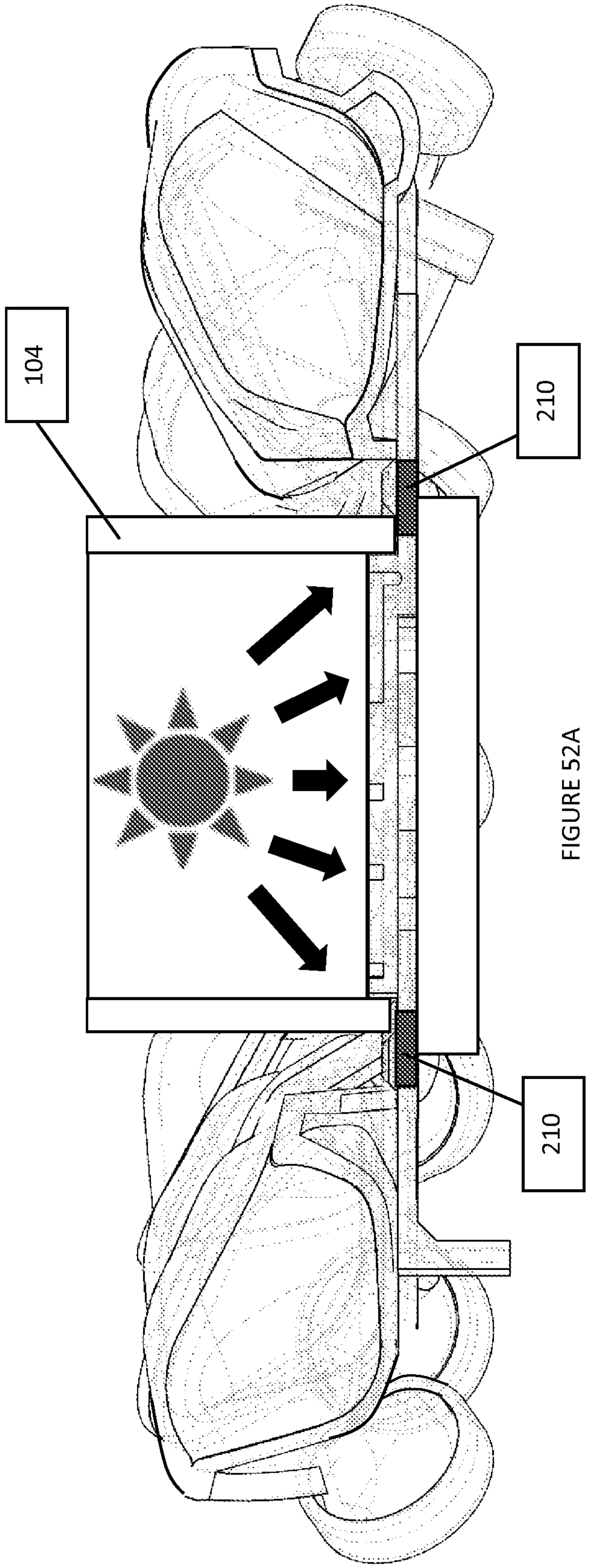
FIG. 52A is a section view of a drug delivery device, which shows an alternative shield for blocking ultraviolet radiation, pulsed light or electron-beam radiation.
Figure 52B:
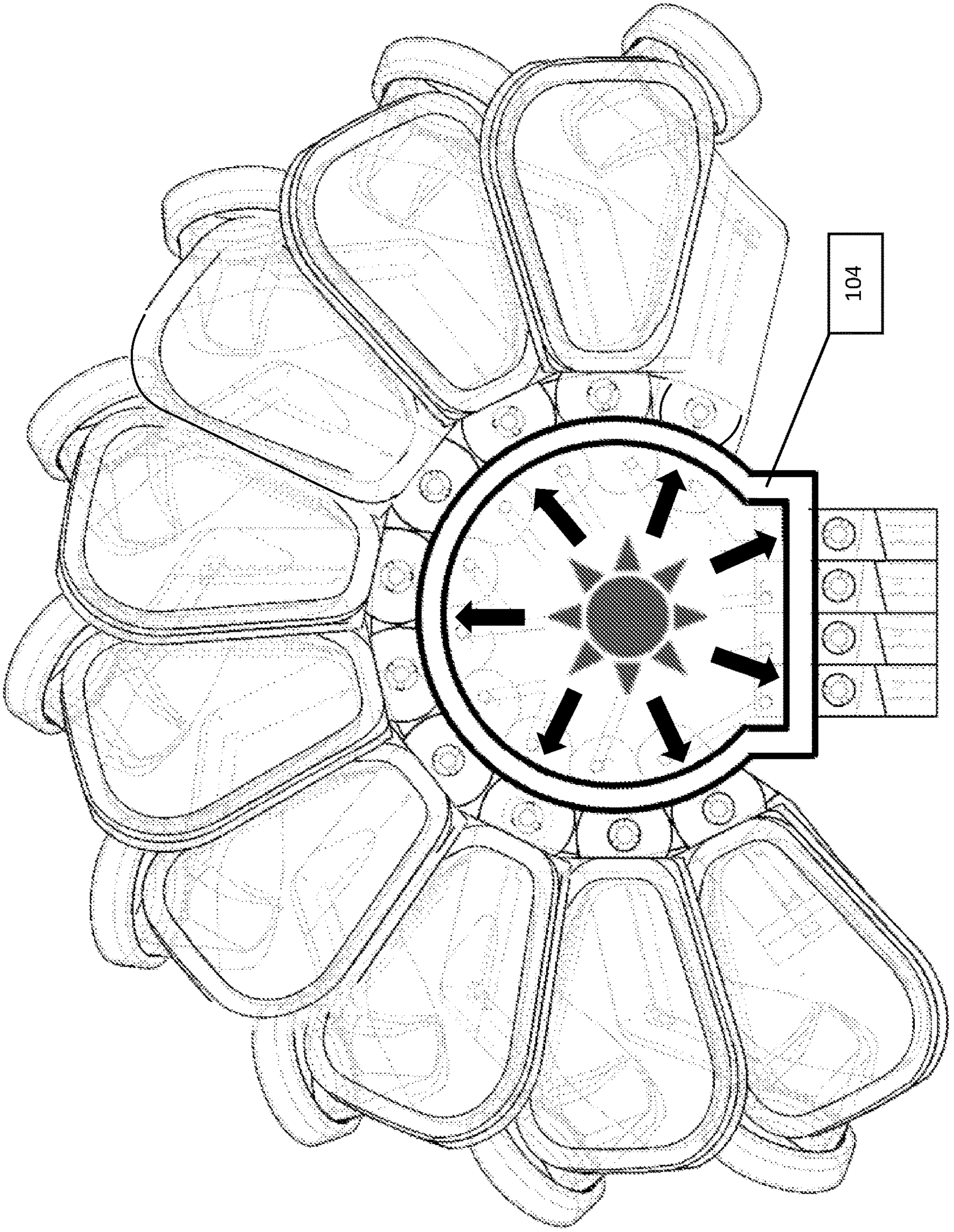
FIG. 52B is a top view of the shield shown in FIG. 52A.
Figure 53:
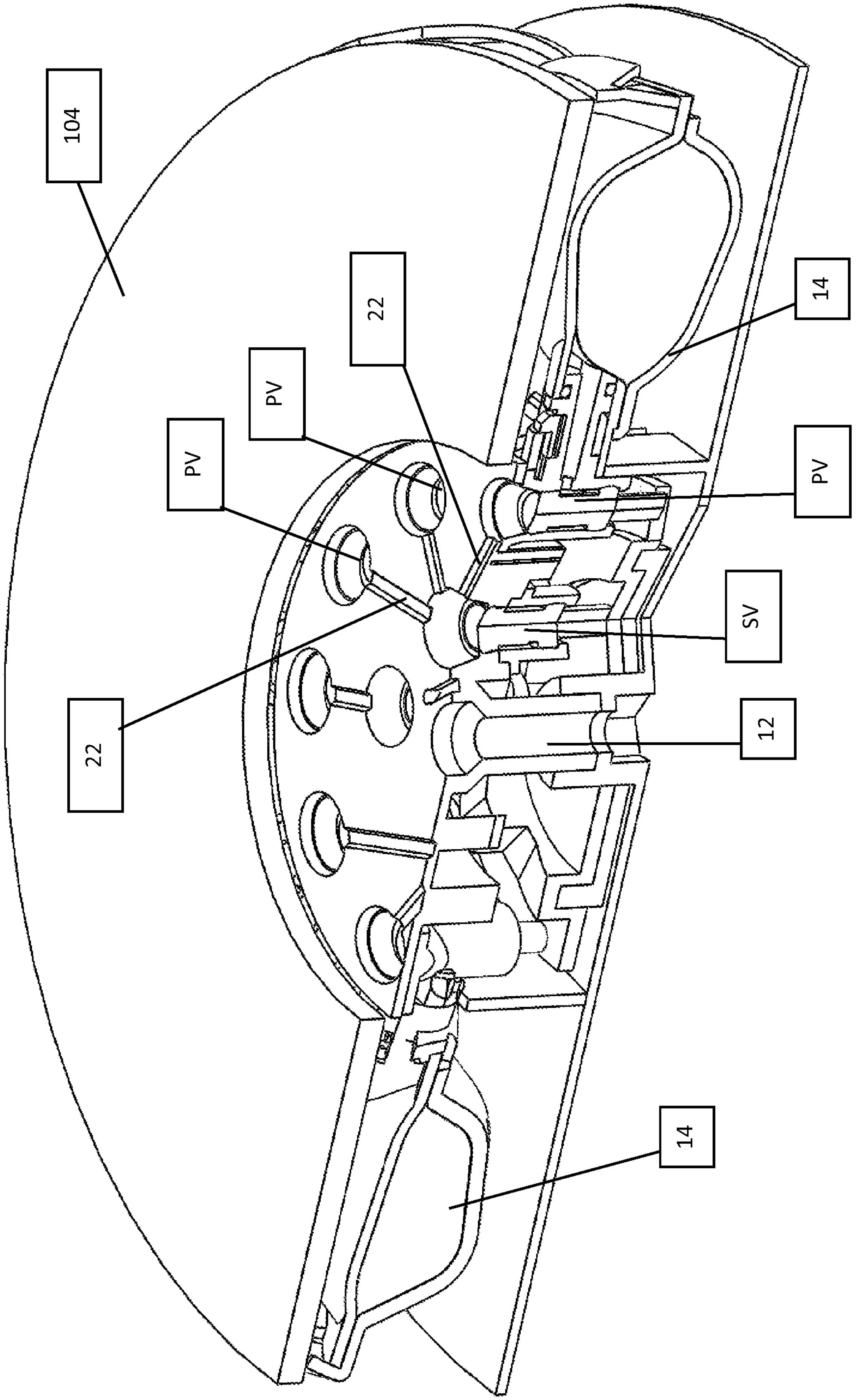
FIG. 53 is a section view of a drug delivery device, which shows a fluid path and valving configuration, in accordance with the subject invention.

As shown representatively in FIG. 48 with "x" markings, it is preferred to have certain portions of the drug cartridge 14 protected from ultraviolet radiation, x-ray radiation, pulsed light or electron-beam exposure. These areas may be sensitive to such exposure, resulting in harm to the contained drug components. As shown in FIGS. 52-53, to protect the sensitive areas of the drug cartridges 14, including the reservoirs 26, from deleterious effects due to exposure to ultraviolet radiation, x-ray radiation, pulsed light or electron-beam, one or more shields 104 may be provided which block ultraviolet radiation, x-ray radiation, pulsed light or electron-beam, depending which is being used. The shields 104 may be planar (as shown in FIG. 52) or tubular (as shown in FIGS. 52A-52B). The sensitive areas may include biocidal materials to promote sterility, including, but not limited to, antimicrobial silver. In addition, or alternatively, where ultraviolet radiation and/or x-ray radiation is utilized, ultraviolet-blocking and/or x-ray-blocking additives may be added to shaded portions 210 of the drug cartridge 14, as shown in FIGS. 49-51. The ultraviolet-blocking and/or x-ray-blocking additives may be any known additive which effectively blocks passage of ultraviolet radiation or x-ray radiation, including, but not limited to, inorganic materials, such as oxides (e.g., TiO2 and ZnO), and organic materials, such as amine light stabilizers (such as that sold under the tradename HALS_Chimassorb 2020), UV absorbers (such as those sold under the tradenames Tinuvin 326 and Uvinul 3034, by BASF), and carbon black. The ultraviolet-blocking and/or x-ray-blocking additives may be used on pulsed light, depending on constituent electromagnetic radiations included therein.

Figure 54:
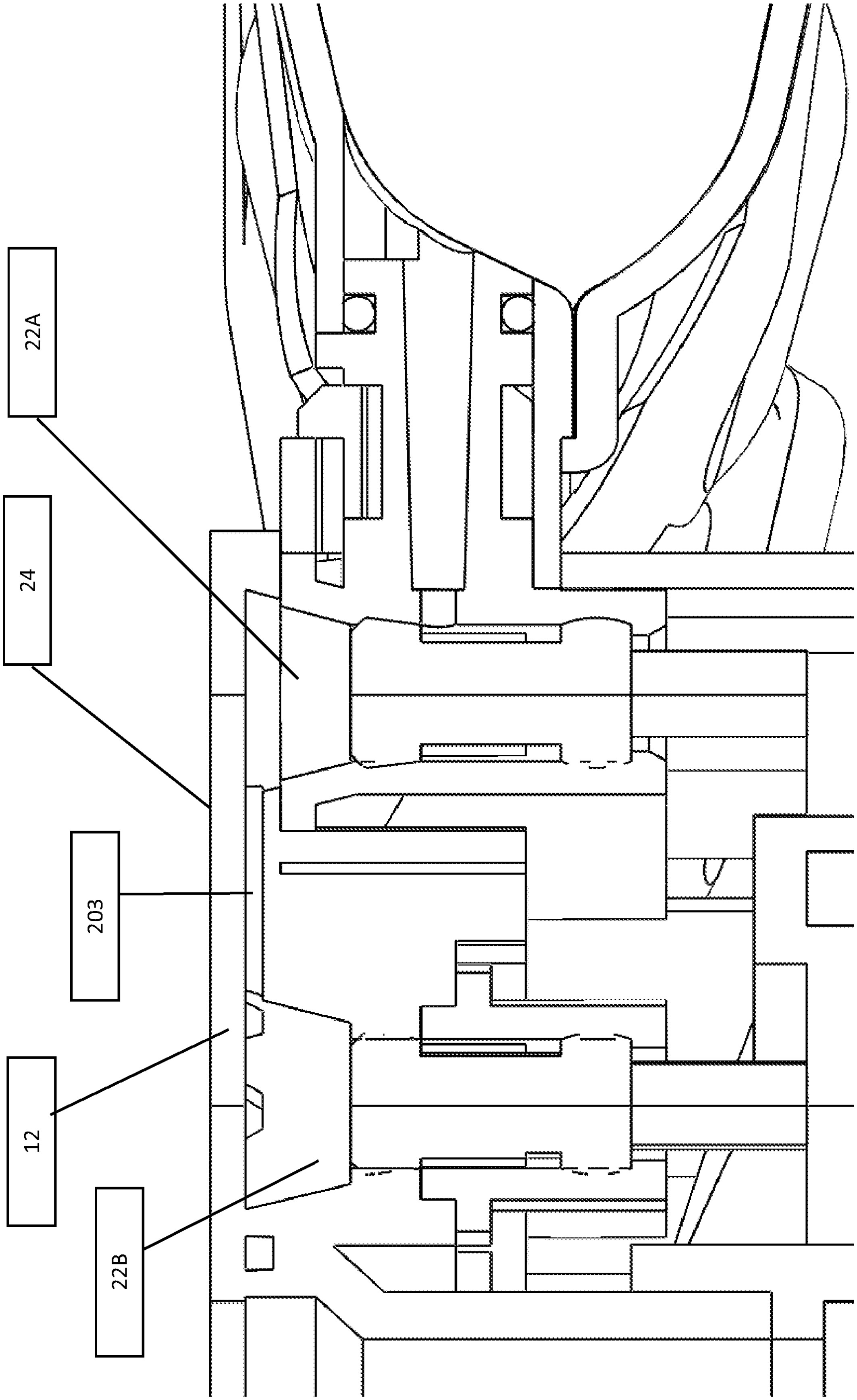
FIG. 54 is a detailed view of a section of FIG. 53, focusing on the body of the device.
Figure 55:
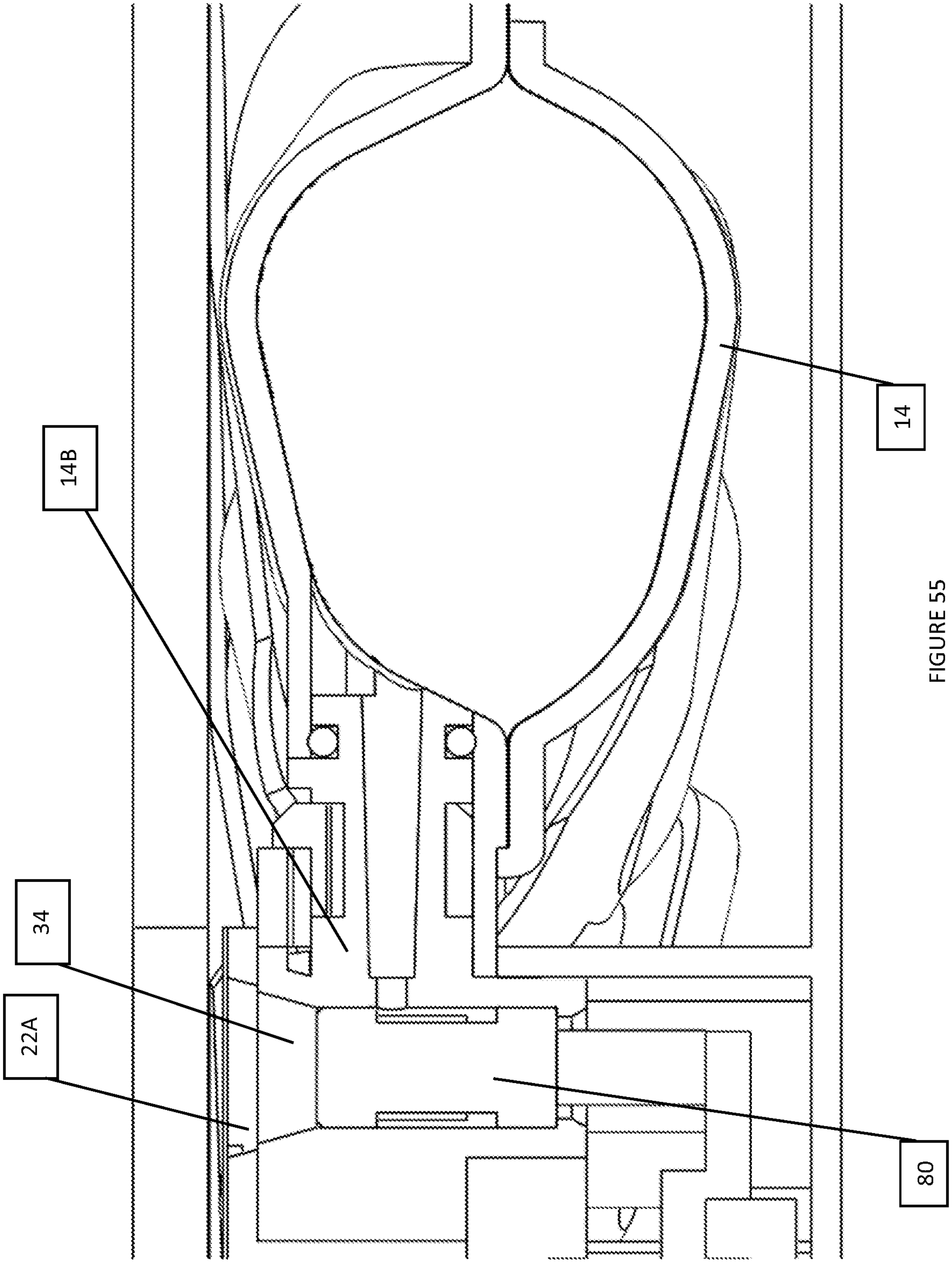
FIG. 55 shows a drug cartridge mounted to a body of a drug delivery device, having a valve in a closed state, in accordance with the subject invention.
Figure 56:
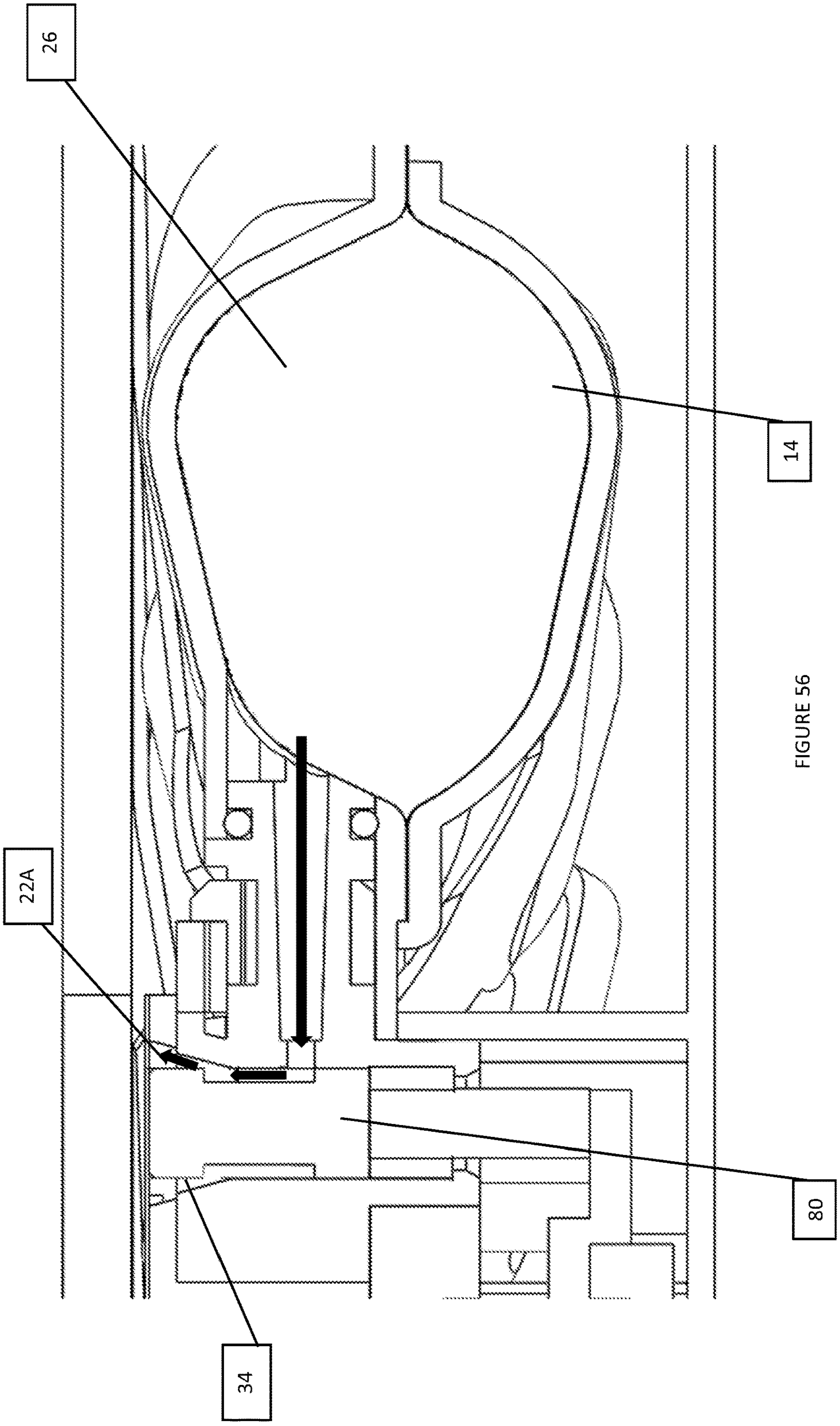
FIG. 56 shows the drug cartridge of FIG. 55, with the valve in an open state, defining a flow path.

As shown above, surfaces needing decontamination are exposed and generally facing the source of ultraviolet radiation, x-ray radiation, pulsed light or electron-beam radiation. With passage through the barrier 102, these surfaces are unobstructed to receive radiation. It is noted that ultraviolet radiation, x-ray radiation, pulsed light and electron-beam radiation have effectiveness to a certain depth of material. Thus, as shown in FIG. 54, one or more of ducts 22 may be provided as encased in the body 12 as encased duct 203. Any encased ducts 203 should be in sufficient proximity to the first face 24 to be properly decontaminated with exposure to ultraviolet radiation, x-ray radiation, pulsed light or electron-beam radiation. As shown in FIG. 54, with the use of encased ducts 203, the barrier 102 may not be omitted or applied to only where the ducts 22 are exposed.

Figure 49A:
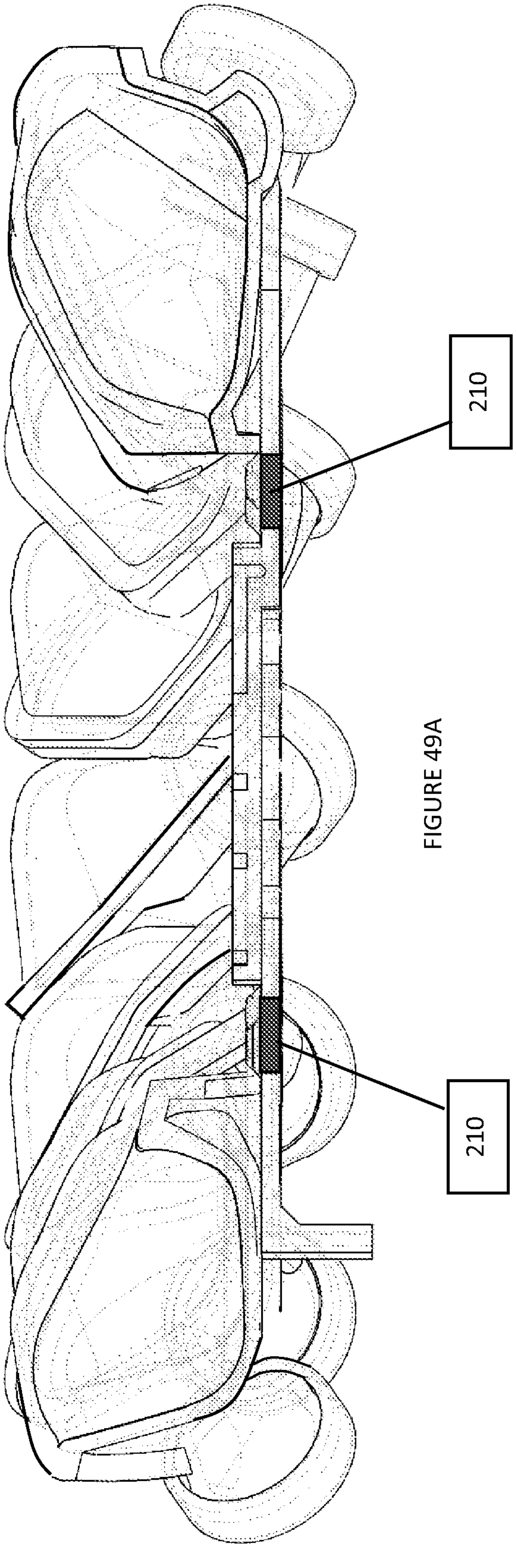
Figure 49B:
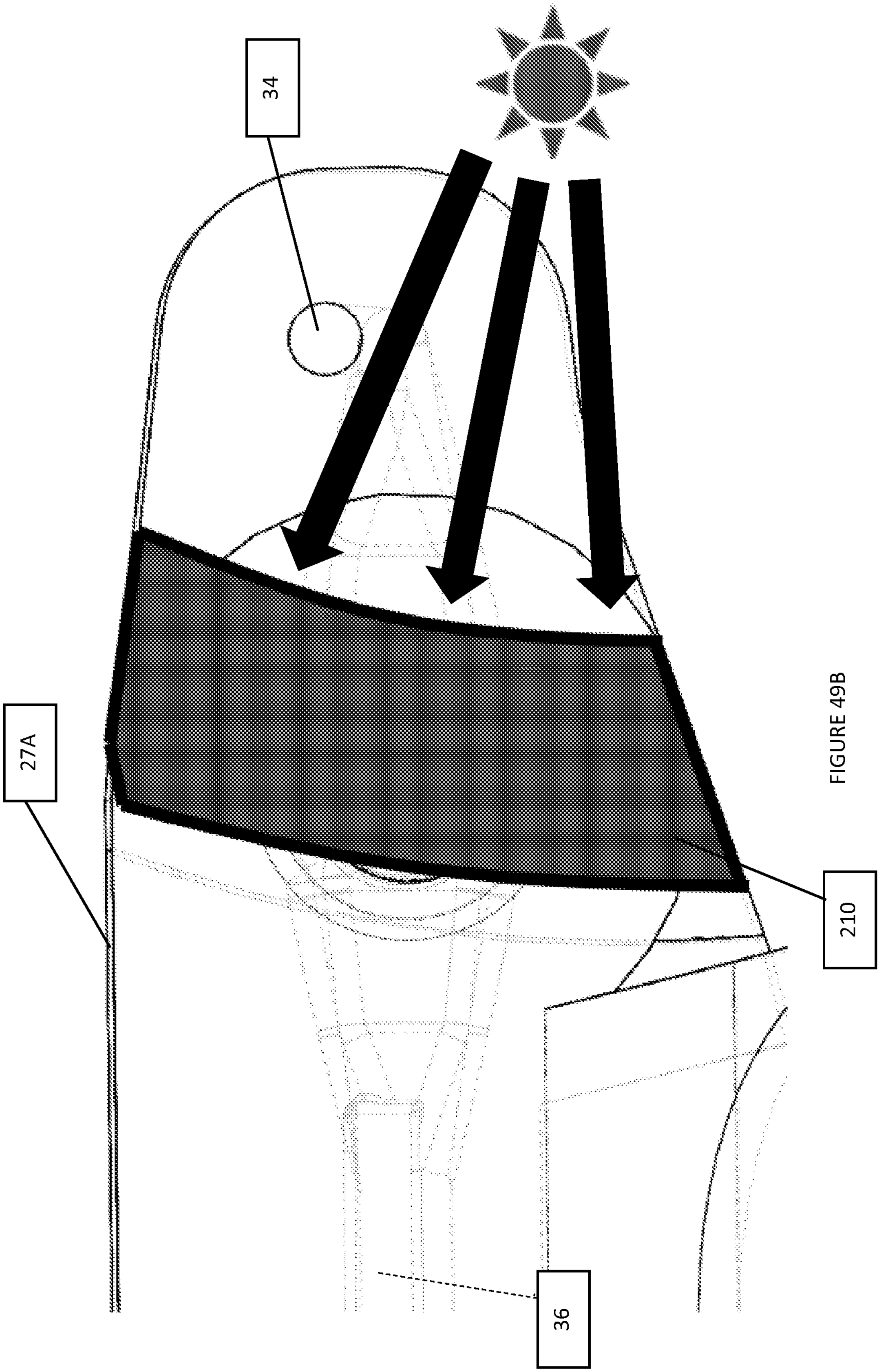
Figure 49C:
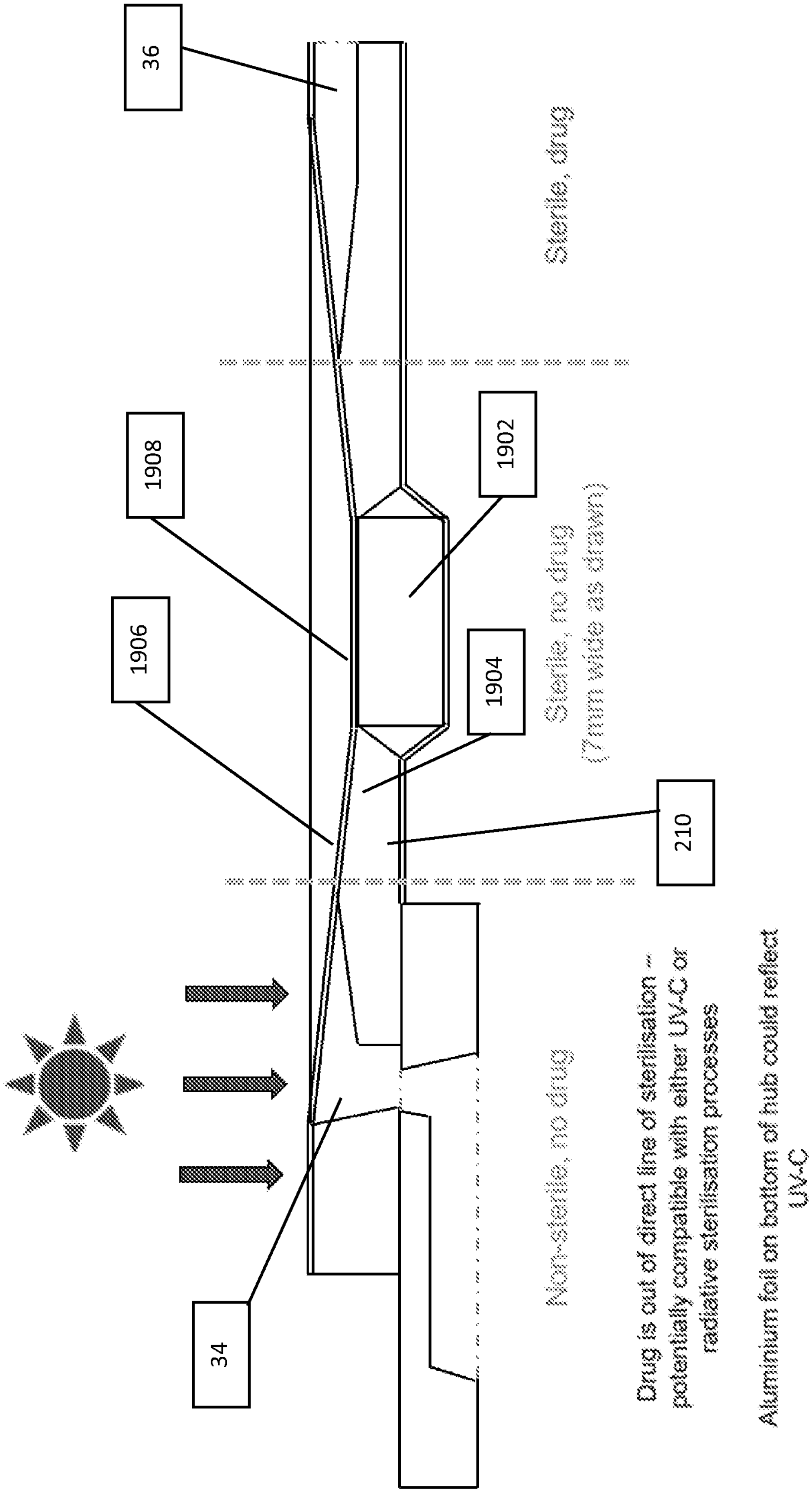

With the drug cartridge 14 being provided with the wing portion 27A, ultraviolet-blocking and/or x-ray blocking additives may be provided across the wing portion 27A to cross the well 1900, the additives being located between the fluid outlet 34 and portions of the internal lumen 36 upstream from the seal 1908, as shown by the shaded portions 210 in FIGS. 49A-49C. In this manner, the fluid outlet may be sterilized without deleterious effects on any drug contained within the internal lumen 36. Moreover, as shown in FIG. 52A, the shield 104, in tubular form, may be shaped to overlap the shaded portions 210, thus providing UV/x-ray blocking in both radial and vertical directions.

Figure 73A:
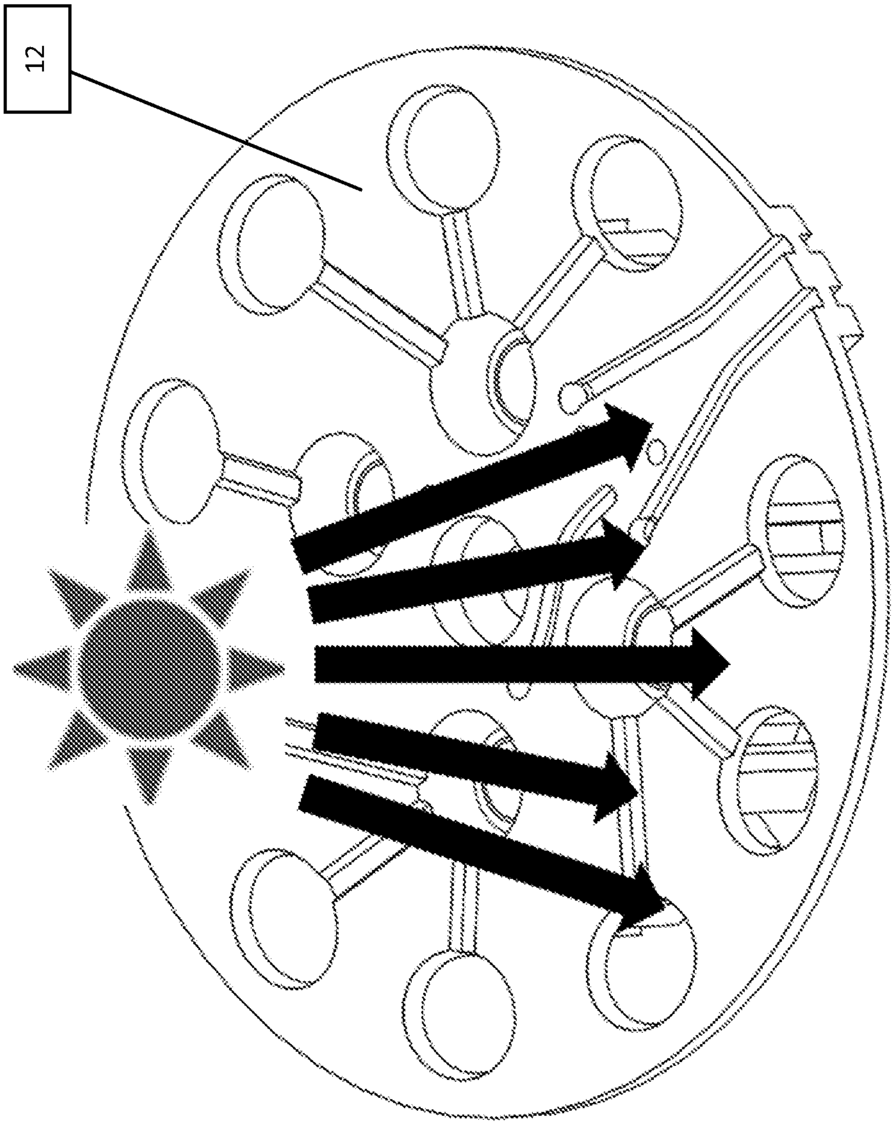
FIG. 73A shows schematically the location on a body of the drug delivery device for ultraviolet radiation exposure.
Figure 73B:
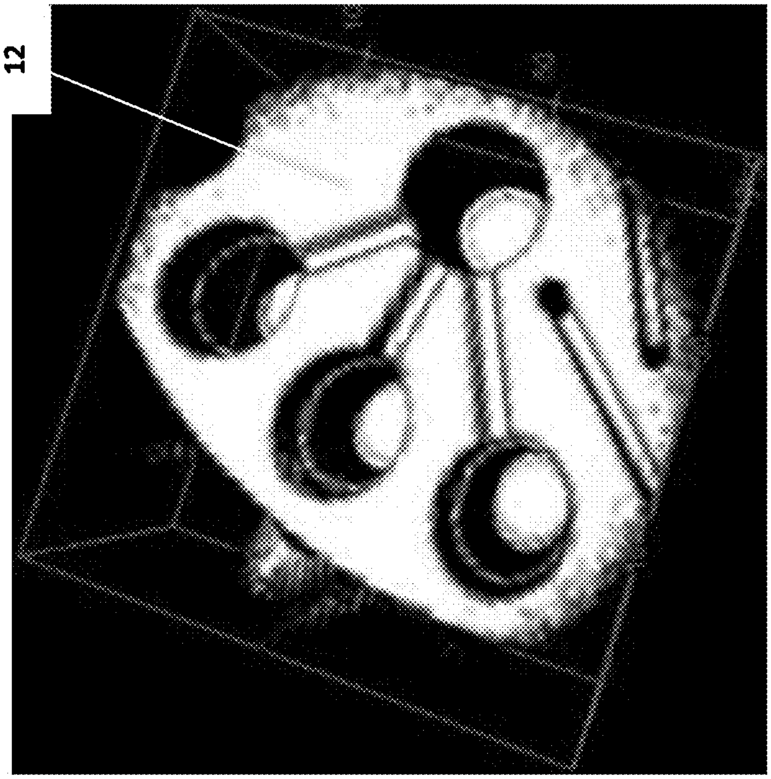
FIG. 73B shows the UV threshold dose achieved after three seconds of ultraviolet radiation exposure.
Figure 73C:
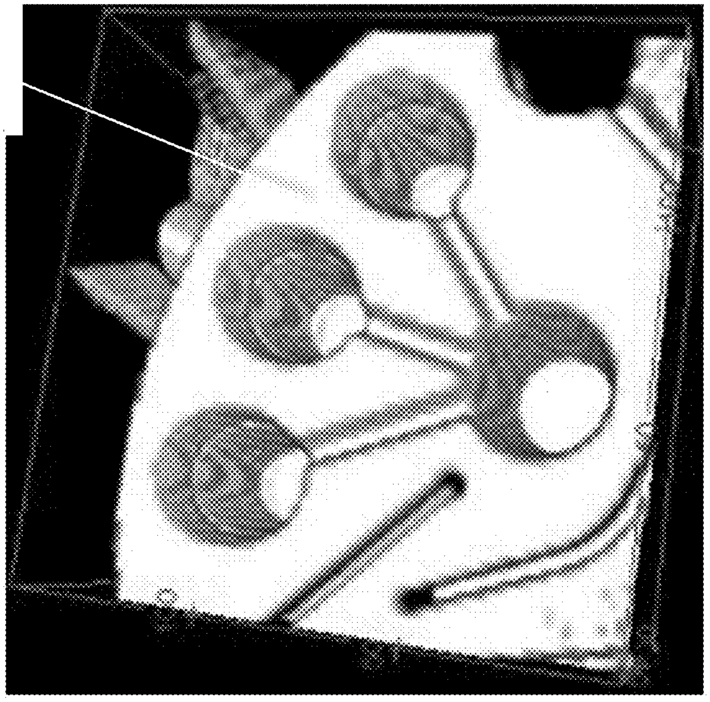
Figure 74:
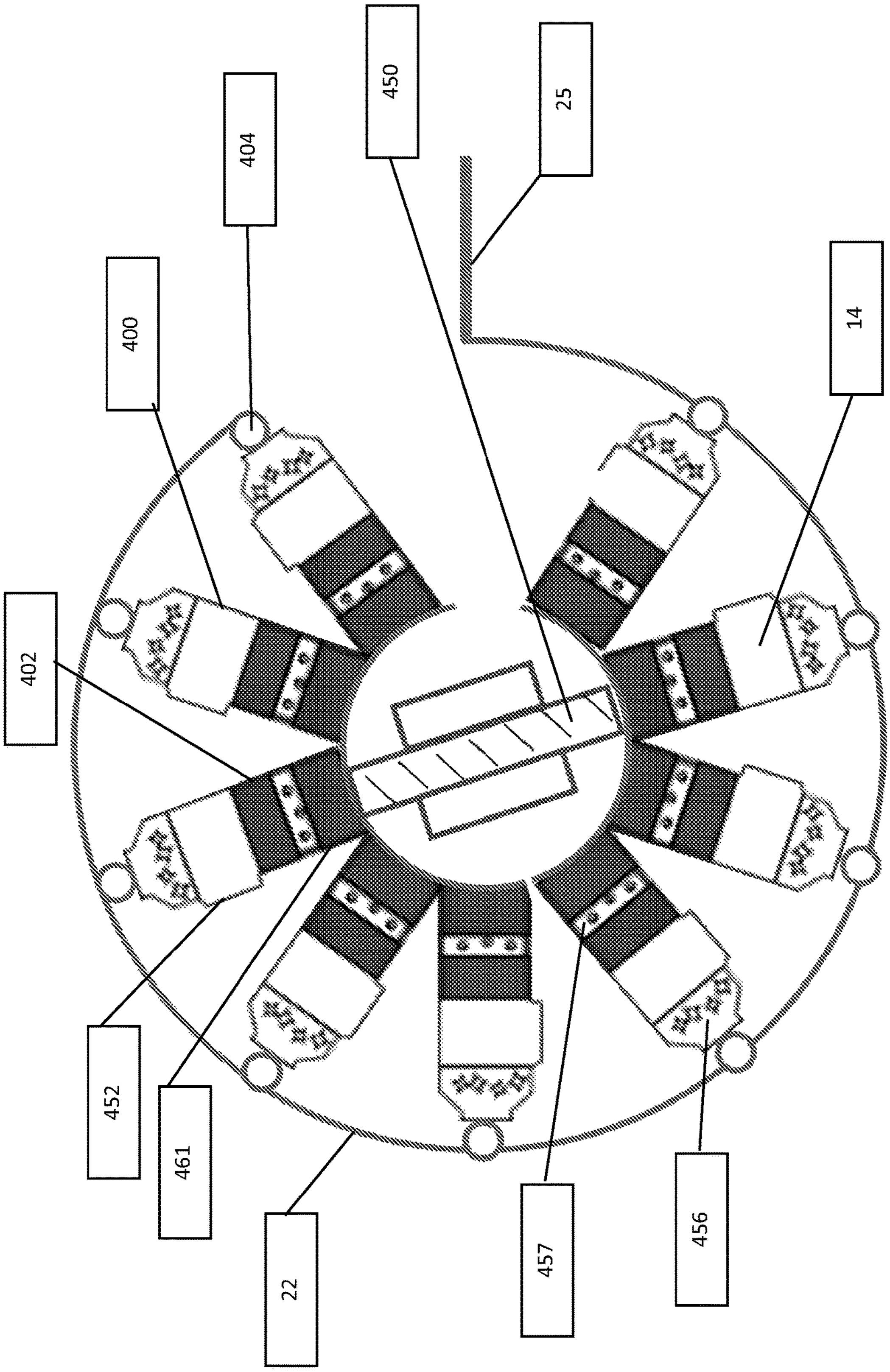
Figure 75:
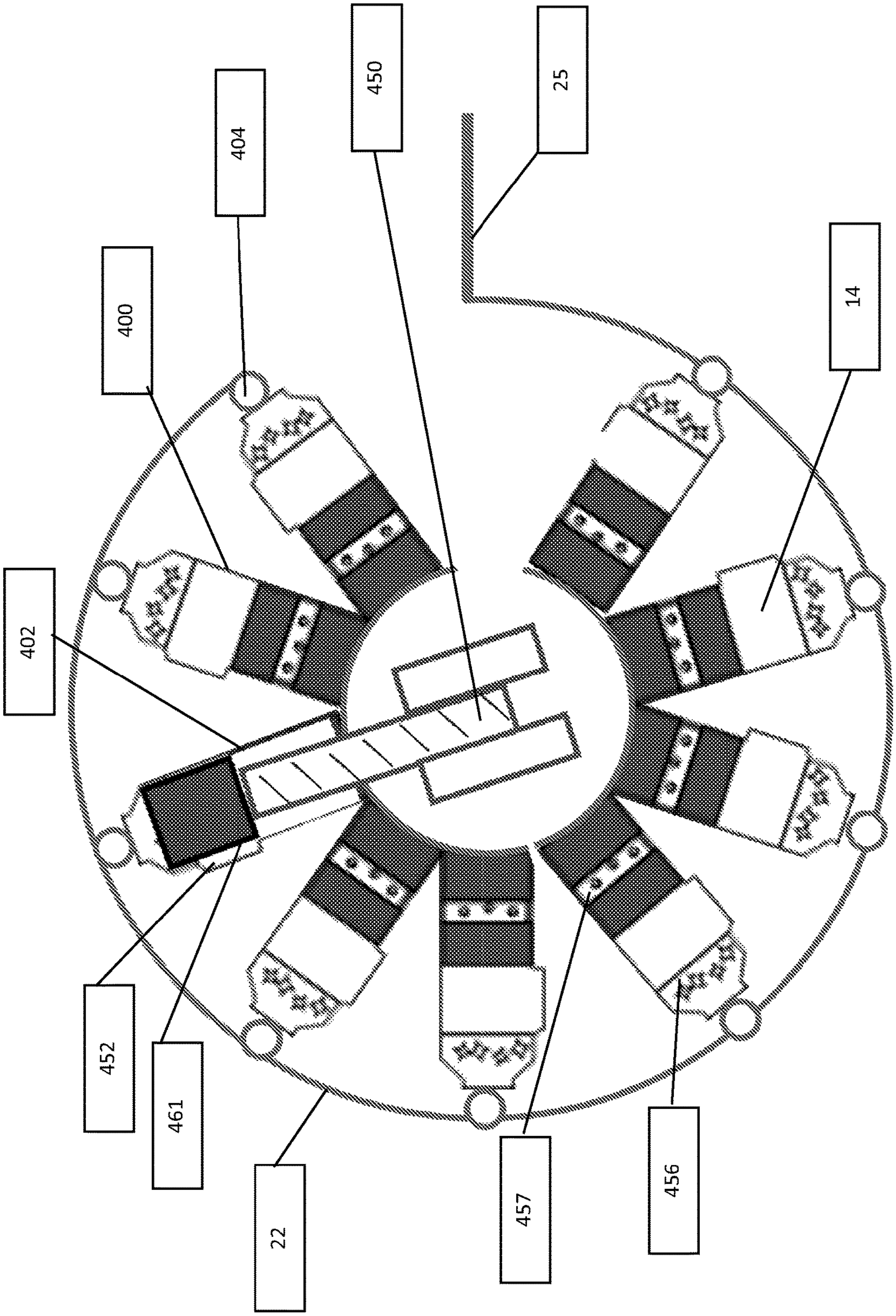
Figure 76:
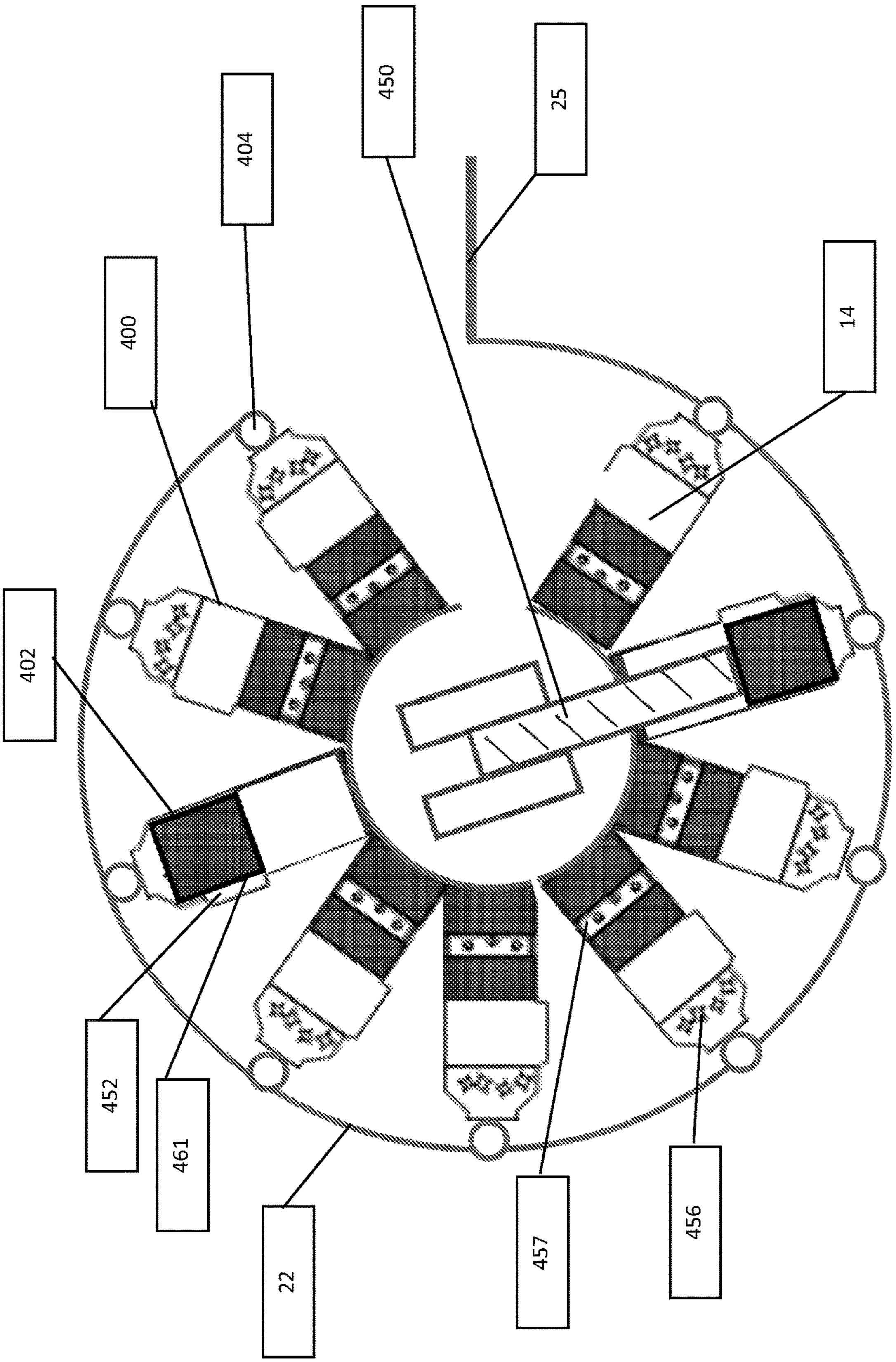
Figure 77:
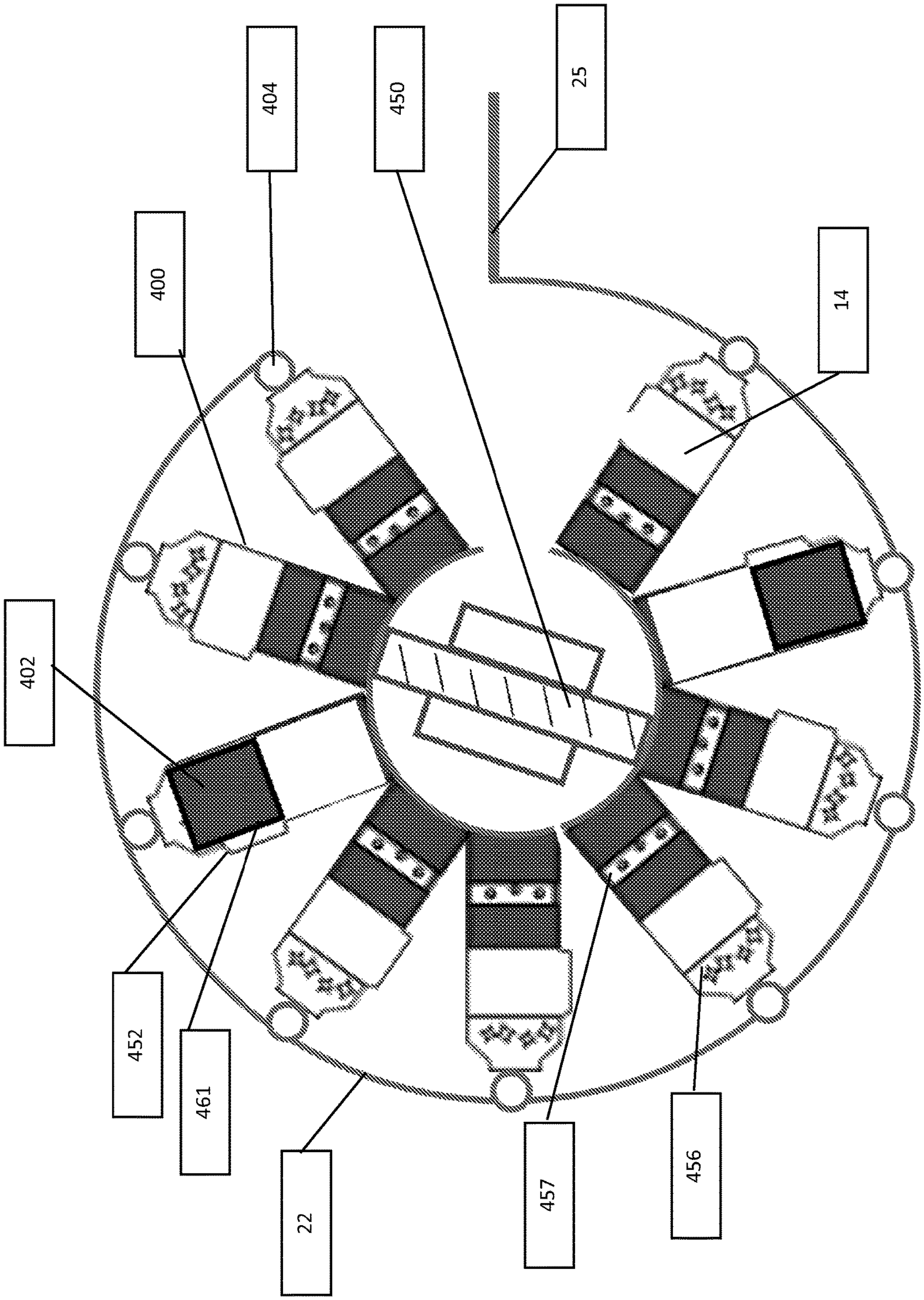
Figure 78:
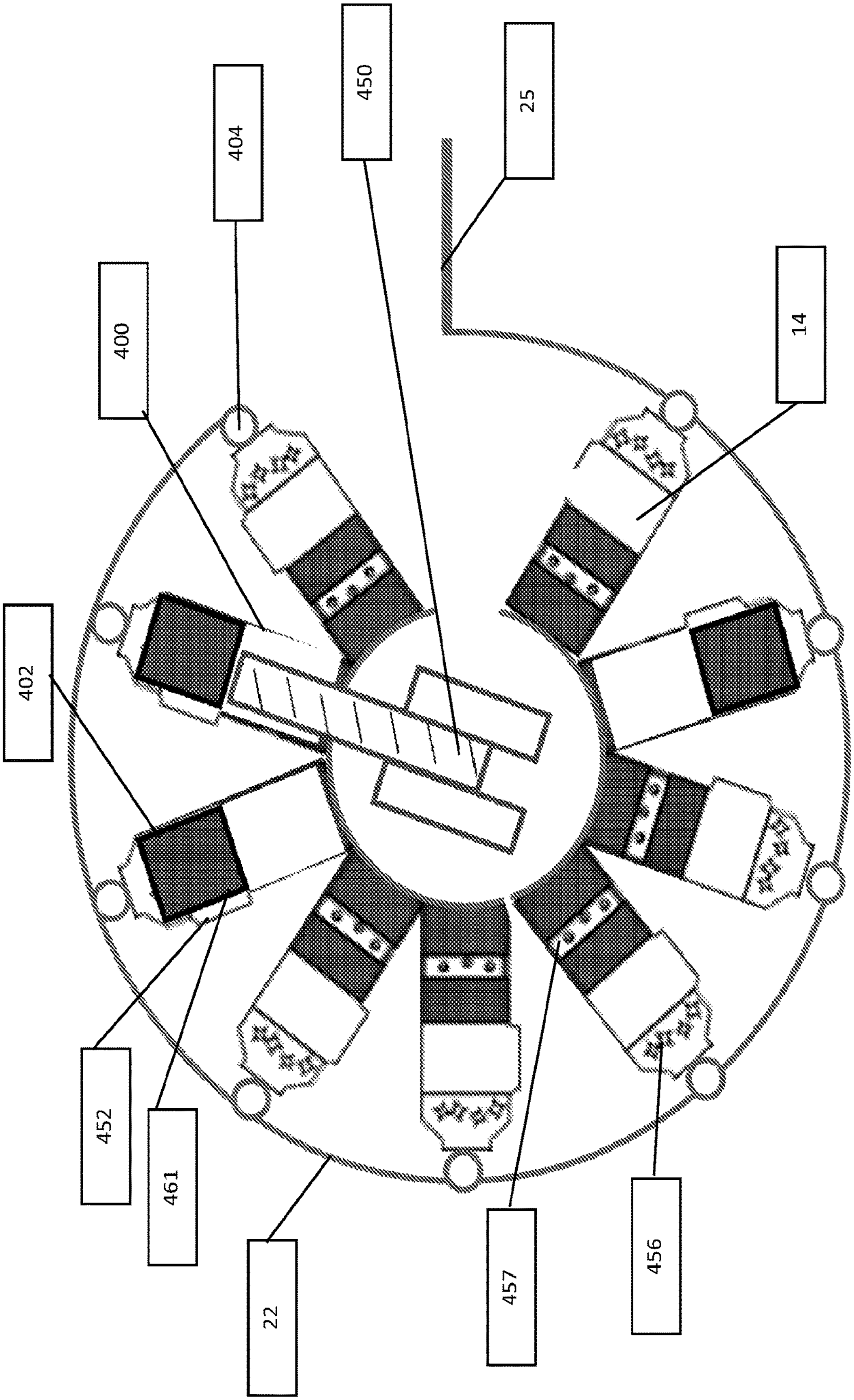

FIG. 73A shows a body 12 which may be decontaminated using ultraviolet radiation. FIGS. 73B-73C show the amount of ultraviolet radiation received on surfaces of the body 12 after certain time intervals. In FIGS. 73B-73C, black surfaces indicate ultraviolet radiation readings of less than 10 $mJ/cm^2$, which may be considered a threshold dose. White surfaces indicate ultraviolet radiation reading of at least 10 $mJ/cm^2$, i.e., of at least the threshold dose. FIG. 73B is an image captured of the body 12 having been exposed to ultraviolet radiation for 3 seconds, while FIG. 73C is an image captured of the body 12 having been exposed to ultraviolet radiation for 30 seconds. As can be seen in FIG. 73C, good distribution of ultraviolet radiation is achievable, even with differently directed surfaces. FIG. 73C shows that the body 12 may be sterilized with exposure to ultraviolet radiation. The same is expected with x-ray radiation, pulsed light and electron-beam radiation.

As will be appreciated by those skilled in the art, additional sterilization techniques, such as heat and gas sterilization (e.g., EtO ethylene oxide), may be used to supplement the application of ultraviolet radiation, x-ray radiation, pulsed light and/or electron-beam radiation. In addition, these sterilization techniques may be used in lieu of ultraviolet radiation, x-ray radiation, pulsed light and/or electron-beam radiation, e.g., where the barrier 102 is not provided or is not transmissive to such radiation. It is also possible to use decontamination techniques utilizing ultraviolet radiation, x-ray radiation, pulsed light and/or electron-beam radiation in varying combinations.

As will be appreciated by those skilled in the art, the decontamination methods described herein may be used with various drug delivery devices, including those having contained drug reservoirs (i.e., not separately provided). In addition, the decontamination methods may be used to sterilize related fluid path(s) prior to filling of drug to sterilize the related fluid path. The subject invention allows for the covering of open fluid ducts in the body of a drug delivery device which are covered by a barrier, and which may be decontaminated by exposure to ultraviolet radiation, x-ray radiation, pulsed light or electron-beam which passes through the barrier.

What is claimed is:

1. A method of preparing a drug delivery device, the method comprising:

providing at least one drug cartridge having a reservoir, a fluid outlet, and an internal lumen communicating the reservoir with the fluid outlet, wherein the internal lumen includes a first portion extending from the reservoir, and a second portion disposed transversely to the first portion, a valve seat being located at a first end of the second portion to define an interface between the fluid outlet and the internal lumen, a second end of the second portion being open;

sterilizing the internal lumen of the drug cartridge;

filling the reservoir with one or more drug components via the sterilized internal lumen;

forming a seal across the sterilized internal lumen to limit ingress therein of contaminants, wherein the seal is formed by an elastomeric valve which is spool shaped having first and second enlarged lands connected by an elongated core, wherein, with the elastomeric valve forming the seal, a majority of the elastomeric valve sits within the sterilized internal lumen with the first land being seated in the valve seat to form the seal, and, wherein the second land is seated in the second portion, between the first portion and the second end, so as to seal the sterilized internal lumen to limit ingress of contaminants therein from the second end;

assembling the filled drug cartridge to a body of the drug delivery device such that the fluid outlet is aligned with a fluid duct defined in the body, wherein the seal separates the sterilized internal lumen from the fluid outlet, the fluid duct extending from the fluid outlet to an opening in a first face of the body;

providing a continuous barrier across the first face of the body to at least cover the opening, wherein the barrier is ultraviolet transmissive; and, with the barrier uninterrupted across the first face of the body, and the filled drug cartridge assembled to the body of the drug delivery device, exposing the first face of the body to ultraviolet radiation so as to allow the ultraviolet radiation to pass through the barrier and decontaminate the fluid duct and the fluid outlet, wherein the elastomeric valve is shiftable within the internal lumen to un-seal the sterilized internal lumen to permit communication between the fluid duct and the reservoir.

2. A method as in claim 1, wherein, with the elastomeric valve shifting to un-seal the sterilized internal lumen, the second land continuously remains between the first portion and the second end.

3. A method as in claim 1, wherein the body defines a secondary fluid duct extending from, and in communication with, the opening, the secondary fluid duct being formed in the first face of the body and covered by the barrier.

4. A method as in claim 1, wherein the seal is formed by a removable film.

5. A method as in claim 1, wherein the seal is formed by a pierceable film.

6. A method as in claim 1, wherein the seal is formed by a sealing sheet joined to a sealing surface, the sealing sheet being separable from the sealing surface.

7. A method as in claim 1, wherein the barrier is a polymeric film.

8. A method as in claim 7, wherein the polymeric film includes a single layer.

9. A method as in claim 7, wherein the polymeric film includes multiple layers.

10. A method as in claim 7, wherein the polymeric film includes one of more of: fluoropolymer; fluoropolymer copolymer; polyimide; polymethylepentine; silicone; cyclic olefin copolymer; and, cyclic olefin polymer.

11. A method of preparing a drug delivery device, the method comprising:

providing at least one drug cartridge having a reservoir, a fluid outlet, and an internal lumen communicating the reservoir with the fluid outlet;

sterilizing the internal lumen of the drug cartridge;

filling the reservoir with one or more drug components via the sterilized internal lumen;

forming a seal across the sterilized internal lumen to limit ingress therein of contaminants;

assembling the filled drug cartridge to a body of the drug delivery device such that the fluid outlet is aligned with a fluid duct defined in the body, wherein the seal separates the sterilized internal lumen from the fluid outlet, the fluid duct extending from the fluid outlet to an opening in a first face of the body;

providing a barrier across the first face of the body to at least cover the opening, wherein the barrier is ultraviolet transmissive; and, exposing the first face of the body to ultraviolet radiation so as to allow the ultraviolet radiation to pass through the barrier and decontaminate the fluid duct and the fluid outlet, wherein the body defines a secondary fluid duct extending from, and in communication with, the opening, the secondary fluid duct being formed in the first face of the body and covered by the barrier.

12. A method as in claim 11, wherein the seal is formed by an elastomeric valve.

13. A method as in claim 12, wherein, with the elastomeric valve forming the seal, a majority of the elastomeric valve sits within the sterilized internal lumen.

14. A method as in claim 13, wherein the elastomeric valve is shiftable within the internal lumen to un-seal the sterilized internal lumen to permit communication between the fluid duct and the reservoir.

15. A method as in claim 14, wherein the elastomeric valve is spool shaped having first and second enlarged lands connected by an elongated core, and, wherein with the elastomeric valve forming the seal, the first land is seated in a valve seat defined at the interface of the fluid outlet and the internal lumen to form the seal.

16. A method as in claim 15, wherein the internal lumen includes a first portion extending from the reservoir, and a second portion disposed transversely to the first portion, the valve seat being located at a first end of the second portion, a second end of the second portion being open, and, wherein the second land is seated in the second portion, between the first portion and the second end, so as to seal the sterilized internal lumen to limit ingress of contaminants therein from the second end.

17. A method as in claim 16, wherein, with the elastomeric valve shifting to un-seal the sterilized internal lumen, the second land continuously remains between the first portion and the second end.

18. A method as in claim 11, wherein the seal is formed by a removable film.

19. A method as in claim 11, wherein the seal is formed by a pierceable film.

20. A method as in claim 11, wherein the seal is formed by a sealing sheet joined to a sealing surface, the sealing sheet being separable from the sealing surface.

21. A method as in claim 11, wherein the barrier is a polymeric film.

22. A method as in claim 21, wherein the polymeric film includes a single layer.

23. A method as in claim 21, wherein the polymeric film includes multiple layers.

24. A method as in claim 21, wherein the polymeric film includes one of more of: fluoropolymer; fluoropolymer copolymer; polyimide; polymethylepentine; silicone; cyclic olefin copolymer; and, cyclic olefin polymer.

* * * * *